(12) United States Patent
Lieu et al.

(10) Patent No.: US 12,247,204 B1
(45) Date of Patent: Mar. 11, 2025

(54) ADVANCED RNA TARGETING (ARNATAR) FOR ANGIOTENSINOGEN

(71) Applicant: Arnatar Therapeutics, Inc, San Diego, CA (US)

(72) Inventors: Yen Lieu, San Diego, CA (US); Lingdi Zhang, San Diego, CA (US); Xuehai Liang, San Diego, CA (US); Yanfeng Wang, San Diego, CA (US)

(73) Assignee: ARNATAR THERAPEUTICS, INC, San Diego, CA (US)

( * ) Notice: Subject to any disclaimer, the term of this patent is extended or adjusted under 35 U.S.C. 154(b) by 0 days.

(21) Appl. No.: 18/751,048

(22) Filed: Jun. 21, 2024

Related U.S. Application Data

(63) Continuation of application No. PCT/US2024/033852, filed on Jun. 13, 2024.

(60) Provisional application No. 63/472,727, filed on Jun. 13, 2023, provisional application No. 63/472,780, filed on Jun. 13, 2023, provisional application No. 63/533,283, filed on Aug. 17, 2023.

(51) Int. Cl.
*C12N 15/113* (2010.01)
*A61P 9/12* (2006.01)
*C07H 21/02* (2006.01)

(52) U.S. Cl.
CPC .............. *C12N 15/113* (2013.01); *A61P 9/12* (2018.01); *C07H 21/02* (2013.01); *C12N 2310/11* (2013.01); *C12N 2310/14* (2013.01); *C12N 2310/315* (2013.01); *C12N 2310/351* (2013.01)

(58) Field of Classification Search
CPC .............. C12N 15/113; C12N 2310/11; C12N 2310/14; C12N 2310/315; C12N 2310/351; A61P 9/12
USPC ...... 424/9.1; 435/6.1, 91.1, 91.31, 455, 458; 514/44 A; 536/23.1, 24.5
See application file for complete search history.

(56) References Cited

U.S. PATENT DOCUMENTS

| | | | |
|---|---|---|---|
| 7,015,315 B1 | 3/2006 | Cook et al. | |
| 7,582,744 B2 | 9/2009 | Manoharan et al. | |
| 7,732,593 B2 | 6/2010 | Zamore et al. | |
| 7,750,144 B2 | 7/2010 | Zamore et al. | |
| 8,389,490 B2 | 3/2013 | Jiménez et al. | |
| 8,420,799 B2 | 4/2013 | Manoharan | |
| 8,754,201 B2 | 6/2014 | Manoharan et al. | |
| 8,796,436 B2 | 8/2014 | Manoharan et al. | |
| 8,809,516 B2 | 8/2014 | Manoharan et al. | |
| 8,859,749 B2 | 10/2014 | Andreou et al. | |
| 9,181,549 B2 | 11/2015 | Prakash et al. | |
| 9,506,030 B2 | 11/2016 | Bhat | |
| 9,708,615 B2 | 7/2017 | Manoharan et al. | |
| 9,796,756 B2 | 10/2017 | Hadwiger et al. | |
| 9,796,974 B2 | 10/2017 | Rajeev et al. | |
| 10,087,208 B2 | 10/2018 | Guzaev et al. | |
| 10,233,448 B2 | 3/2019 | Maier et al. | |
| 10,273,477 B2 | 4/2019 | Manoharan et al. | |
| 10,344,275 B2 | 7/2019 | Wan et al. | |
| 10,570,169 B2 | 2/2020 | Seth et al. | |
| 10,612,024 B2 | 4/2020 | Maier et al. | |
| 10,612,027 B2 | 4/2020 | Maier et al. | |
| 10,668,170 B2 | 6/2020 | Rajeev et al. | |
| 10,669,544 B2 | 6/2020 | Manoharan et al. | |
| 10,709,728 B2 | 7/2020 | Hinkle | |
| 10,814,007 B2 | 10/2020 | Foster et al. | |
| 10,837,013 B2 | 11/2020 | Brown | |
| 10,870,849 B2 | 12/2020 | Brown | |
| 10,912,792 B2 | 2/2021 | Mullick et al. | |
| 11,015,201 B2 | 5/2021 | Foster et al. | |
| 11,110,174 B2 | 9/2021 | Manoharan et al. | |
| 11,203,755 B2 | 12/2021 | Higuchi et al. | |
| 11,401,517 B2 | 8/2022 | Maier et al. | |
| 11,406,716 B2 | 8/2022 | Rajeev et al. | |
| 2007/0031844 A1 | 2/2007 | Khvorova et al. | |
| 2011/0293725 A1 | 12/2011 | de los Rios et al. | |
| 2016/0272970 A1 | 9/2016 | Rozema et al. | |
| 2020/0031862 A1 | 1/2020 | Brown et al. | |

FOREIGN PATENT DOCUMENTS

| | | |
|---|---|---|
| CN | 117264948 | 6/2022 |
| CN | 117070517 | 7/2024 |
| EP | 0313219 | 4/1989 |
| EP | 1532248 | 4/2009 |
| EP | 2877579 | 6/2015 |
| EP | 3357507 | 8/2018 |
| WO | WO2009/002944 | 12/2008 |
| WO | WO2018/031933 | 2/2018 |
| WO | WO2019/222166 | 11/2019 |
| WO | WO2022/261005 | 12/2022 |
| WO | WO2023/014765 | 2/2023 |
| WO | WO2023/034719 | 3/2023 |

(Continued)

OTHER PUBLICATIONS

Roberts et al (Nature Rev., Drug Discovery, vol. 19, pp. 673-694 (2020)) (Year: 2020).*
And Kobelt et al.(Cancer Gene Therapy in Gene Therapy of Cancer: Methods and Protocols, Methods in Molecular Biology, vol. 2521, pp. 1-15 (Springer Nature 2022)) (Year: 2022).*
Damase et al (Frontiers in Bioengineering and Biotechnology, vol. 9, Article 628137, pp. 1-24 (2021)) (Year: 2021).*
Osborn et al (Nucleic Acid Therapeutics, vol. 28, No. 3, pp. 128-136 (2018)) (Year: 2018).*

(Continued)

*Primary Examiner* — Jane J Zara
(74) *Attorney, Agent, or Firm* — ADRIANO & ASSOCIATES

(57) ABSTRACT

Disclosed herein are Advanced RNA Targeting (ARNATAR) dsRNA compounds targeting angiotensinogen (AGT). Such compounds are useful in methods for reducing expression of AGT and for therapeutically treating RAAS associated diseases, disorders and/or conditions, or symptoms thereof in a subject.

22 Claims, 10 Drawing Sheets
Specification includes a Sequence Listing.

(56) References Cited

FOREIGN PATENT DOCUMENTS

| WO | WO2023/088227 | 5/2023 |
| WO | WO2024/013334 | 1/2024 |
| WO | WO2024/031101 | 2/2024 |
| WO | WO2024/137543 | 6/2024 |
| WO | WO2024/137545 | 6/2024 |
| WO | WO2024/187193 | 9/2024 |

OTHER PUBLICATIONS

Bost et al (ACS Nano, vol. 15, pp. 13993-14021 (2021)) (Year: 2021).*
Allerson et al., 2005. J Med Chem, 48:901-904 (Exhibit 52).
Amarzguioui et al., 2003, Nucleic Acids Res, 31(2):589-595 (Exhibit 53).
Braasch et al., 2003, Biochemistry, 42(26):7967-7975 (Exhibit 54).
Bramsen and Kjems, 2012, Frontiers in Genetics, 3(154):1-22 (Exhibit 55).
Bramsen et al., 2010, Nucleic Acids Res, 38(17):5761-5773 (Exhibit 56).
Chen et al., 2022, Molecular Therapy, Nucleic Acids, 29:150-160 (Exhibit 57).
Chiu and Rana, 2003, RNA, 9:1034-1048 (Exhibit 58).
Choung et al., Biochem Biophys Res Commun, 2006, 3 42:919-927 (Exhibit 59).
Cruz-López et al., Hypertension, 2022, 79:2115-2126 (Exhibit 60).
Czauderna et al., 2003, Nucleic Acids Res, 31(11);2705-2716 (Exhibit 61).
Debacker et al., 2020, Molecular Therapy, 28(8):1759-1771 (Exhibit 62).
Elbashir et al., Duplexes of 21-Nucleotide RNAs Mediate RNA Interference in Cultured Mammalian Cells, Nature, 2001, 411:494-498 (Exhibit 63).
Fire et al. (Potent and Specific Genetic Interference by Double-Stranded RNA in Caenorhabditis elegans, Nature, 1998. 391:806-811) (Exhibit 64).
Friedrich and Aigner, Therapeutic siRNA: State-of-the-Art and Future Perspectives, 2022, BioDrugs, 36(5):549-571 (Exhibit 65).
Hu et al., Therapeutic siRNA: State of the Art, Signal Transduction and Targeted Therapy, 2020, 5:101 (Exhibit 66).
Keam, 2022, Drugs, 82:1419-1425 (Exhibit 67).
Layzer et al., 2004, RNA, 10:766-771 (Exhibit 68).
Lima et al., Single-stranded siRNAs activate RNAi in animals, Cell. 2012, 150(5):883-94 (Exhibit 69).
Morgan et al., Clinical Res, 2021, 6(6):4865-96 (Exhibit 70).
Mubonen et al., 2007, Chem & Biodiversity, 4:858-873 (Exhibit 71).
Nair et al., J. Am. Chem. Soc. 2014, 136(49):16958-16961 (Exhibit 72).
Paunovska et al., Drug Delivery Systems for RNA Therapeutics, 2022, Nature Reviews Genetics, 23(S):265-280 (Exhibit 73).
Prakash et al., 2014, Nucleic Acids Res, 42(13):8796-807 (Exhibit 74).
Ranasinghe et al., J Am Heart Assoc, 2022, 11(20) (Exhibit 75).
Stephenson and Zamecnik (Inhibition of Rous Sarcoma Viral RNA Translation by a Specific Oligodeoxyribonucleotide, PNAS, 1978, 75:285-288 (Exhibit 76).
Ui-Tei, et al., 2008, Nucleic Acids Res, 36(7):2136-51 (Exhibit 77).
Campbell and Wengel, Chem Soc Rev, 2011, 40(12):5680-9 (Exhibit 78).
Sharma et al., 2018, Bioconjugate Chem, 29:2478-2488 (Exhibit 79).
Schikora et al., Inorganica Chimica Acta, 2016, 452:118-124 (Exhibit 80).
Desai et al., N Engl J Med, 2023;389:228-38 (Exhibit 81).
Haase et al., J Clin Invest. 2020, 130(6):2928-2942 (Exhibit 82).
Morgan et al., J Am Coll Cardiol Basic Trans Science, 2021;6(6):485-96 (Exhibit 83).
Mullick et al., Hypertension, 2017, 70(3):566-576 (Exhibit 84).
Olearczyk et al., Hypertension Research, 2014, 37:405-412 (Exhibit 85).
Peng et al., Hypertension, 1998, 31(6):1317-23 (Exhibit 86).
Schlaich et al., Lancet, 400(10367):1927-1937 (Exhibit 87).
Uijl et al., Hypertension, 2019, 73:1249-1257 (Exhibit 88); and.
Uijl et al., J Am Heart Assoc, 2022;11:e026426 (Exhibit 89).
Allerson et al., 2005, J Med Chem, 48:901-904.
Amarzguioui et al., 2003, Nucleic Acids Res, 31(2):589-595.
Braasch et al., 2003, Biochemistry, 42(26):7967-7975.
Bramsen and Kjems, 2012, Frontiers in Genetics, 3(154):1-22.
Bramsen et al., 2010, Nucleic Acids Res, 38(17):5761-5773.
Chen et al., 2022, Molecular Therapy, Nucleic Acids, 29:150-160.
Chiu and Rana, 2003, RNA, 9:1034-1048.
Choung et al., Biochem Biophys Res Commun, 2006, 342:919-927.
Cruz-López et al., Hypertension, 2022, 79:2115-2126.
Czauderna et al., 2003, Nucleic Acids Res, 31(11):2705-2716.
Debacker et al., 2020, Molecular Therapy, 28(8):1759-1771.
Elbashir et al., Duplexes of 21-Nucleotide RNAs Mediate RNA Interference in Cultured Mammalian Cells, Nature, 2001, 411:494-498.
Fire et al. (Potent and Specific Genetic Interference by Double-Stranded RNA in Caenorhabditis elegans, Nature, 1998. 391:806-811).
Friedrich and Aigner, Therapeutic siRNA: State-of-the-Art and Future Perspectives, 2022, BioDrugs, 36(5):549-571.
Hu et al., Therapeutic siRNA: State of the Art, Signal Transduction and Targeted Therapy, 2020, 5:101.
Keam, 2022, Drugs, 82:1419-1425.
Layzer et al., 2004, RNA, 10:766-771.
Lima et al., Single-stranded siRNAs activate RNAi in animals, Cell. 2012, 150(5):883-94.
Morgan et al., Clinical Res, 2021, 6(6):4865-96.
Muhonen et al., 2007, Chem & Biodiversity, 4:858-873.
Nair et al., J. Am. Chem. Soc. 2014, 136(49):16958-16961.
Paunovska et al., Drug Delivery Systems for RNA Therapeutics, 2022, Nature Reviews Genetics, 23(5):265-280.
Prakash et al., 2014, Nucleic Acids Res, 42(13):8796-807.
Ranasinghe et al., J Am Heart Assoc, 2022, 11(20).
Stephenson and Zamecnik (Inhibition of Rous Sarcoma Viral RNA Translation by a Specific Oligodeoxyribonucleotide, PNAS, 1978, 75:285-288.
Ui-Tei, et al., 2008, Nucleic Acids Res, 36(7):2136-51.
Campbell and Wengel, Chem Soc Rev, 2011, 40(12):5680-9.
Sharma et al., 2018, Bioconjugate Chem, 29:2478-2488.
Schikora et al., Inorganica Chimica Acta, 2016, 452:118-124.
Desai et al., N Engl J Med, 2023;389:228-38.
Haase et al., J Clin Invest. 2020, 130(6):2928-2942.
Morgan et al., J Am Coll Cardiol Basic Trans Science, 2021;6(6):485-96.
Mullick et al., Hypertension, 2017, 70(3):566-576.
Olearczyk et al., Hypertension Research, 2014, 37:405-412.
Peng et al., Hypertension, 1998, 31(6):1317-23.
Schlaich et al., Lancet, 400(10367):1927-1937.
Uijl et al., Hypertension, 2019, 73:1249-1257.
Uijl et al., J Am Heart Assoc, 2022;11:e026426.
International Search Report dated Nov. 7, 2024 in connection International Application No. PCT/US2024/33852 filed Jun. 13, 2024—Exhibit 97 (provided herein);.
Written Opinion of the International Searching Authority dated Nov. 7, 2024 in connection International Application No. PCT/US2024/33852 filed Jun. 13, 2024—Exhibit 98 (provided herein);.
WO2023/014765 (Alnylam Pharmaceuticals Inc) Feb. 9, 2023, p. 137; claims 1-63, 78-80; examples 1-3; tables 3,8; sequences 646 and 948—Exhibit 99 (provided herein);.
Jeffrey Olearczyk et al., Targeting of hepatic angiotensinogen using chemically modified siRNAs results in significant and sustained blood pressure lowering in a rat model of hypertension, Hypertension Research, Dec. 12, 2013, vol. 37 No. 5, pp. 405-412; see figures 2 and 3—Exhibit 100 (provided herein).
International Search Report dated Nov. 7, 2024 in connection International Application No. PCT/US2024/33852 filed Jun. 13, 2024.
Written Opinion of the International Searching Authority dated Nov. 7, 2024 in connection International Application No. PCT/US2024/33852 filed Jun. 13, 2024.
Jeffrey Olearczyk et al., Targeting of hepatic angiotensinogen using chemically modified siRNAs results in significant and sustained blood pressure lowering in a rat model of hypertension, Hypertension Research, Dec. 12, 2013, vol. 37 No. 5, pp. 405-412; see figures 2 and 3.

* cited by examiner

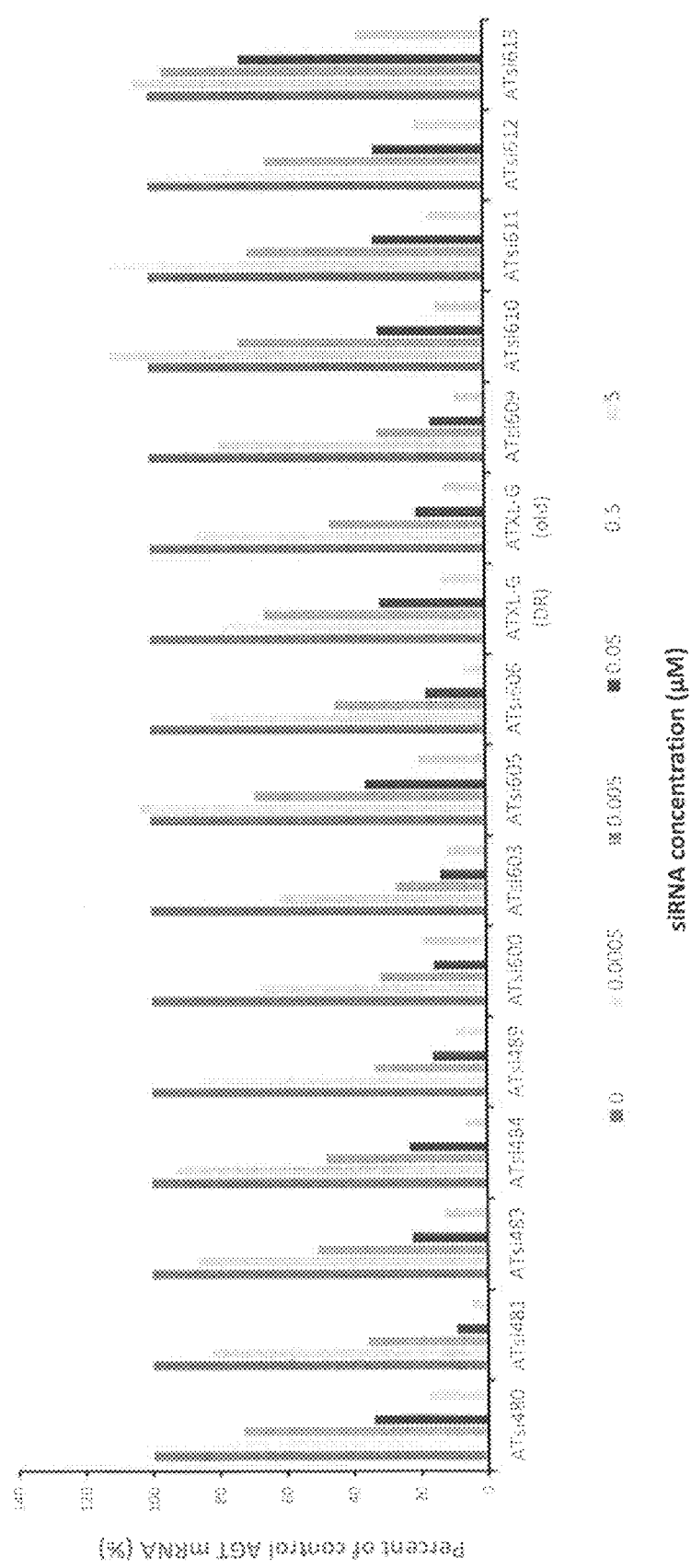
Figure 1. siRNA Activity Screen in Human Primary Hepatocytes by Free Uptake for 48h

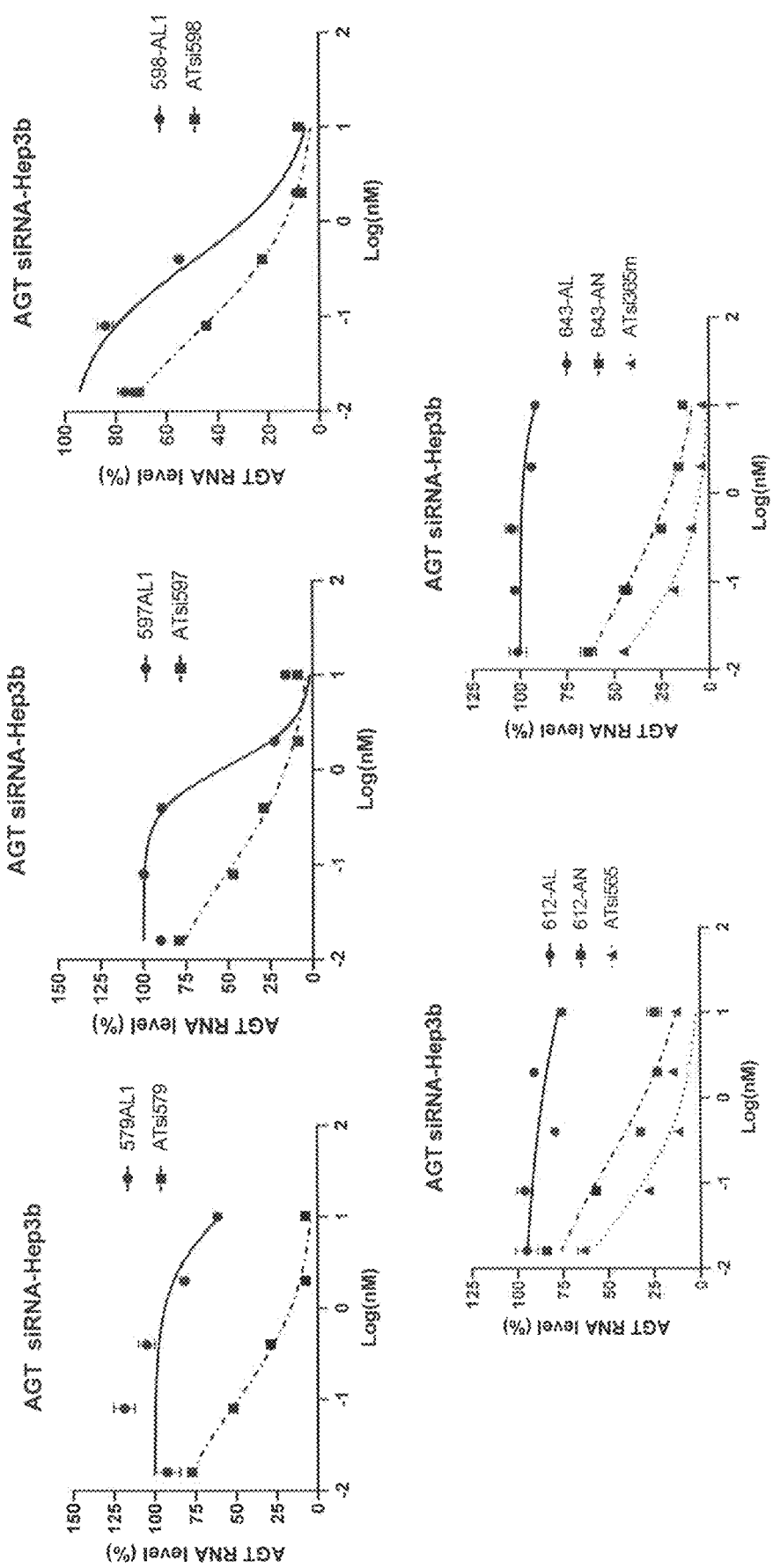
Figure 2. Comparison of ARNATAR Motifs to Third Party Motifs

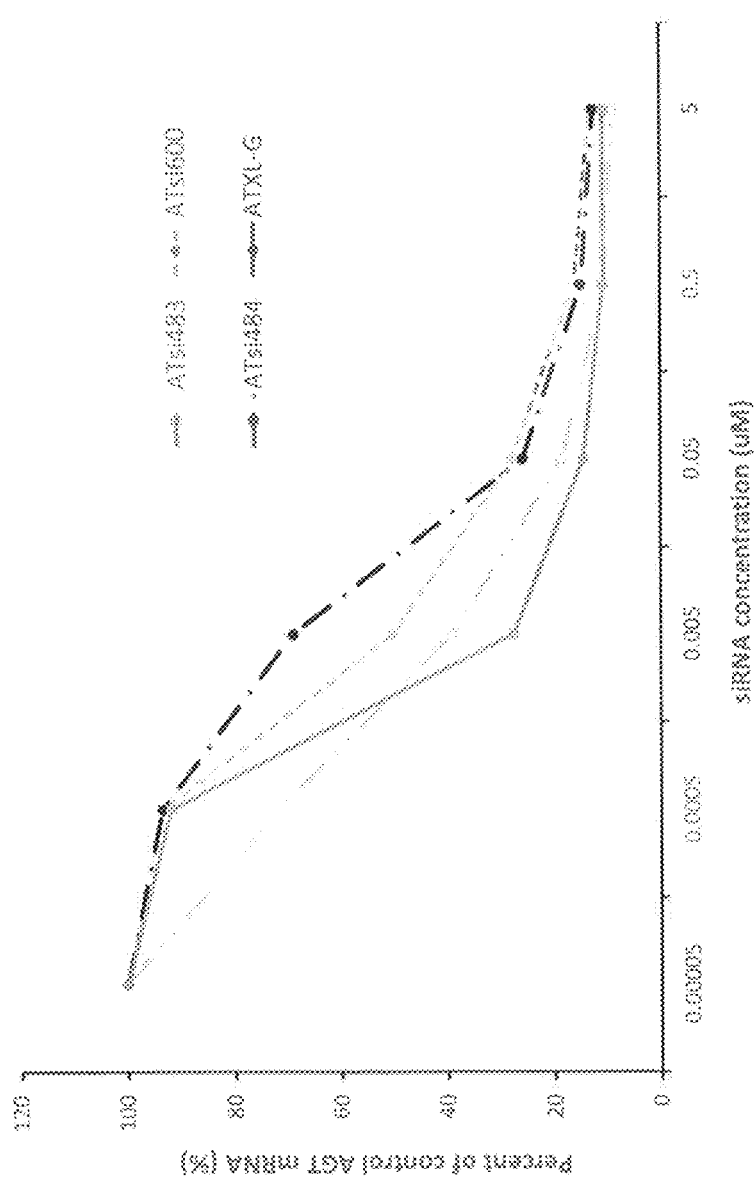
Figure 3. AGT mRNA Levels in Human Primary Hepatocytes by Free Uptake of siRNAs for 42 hr

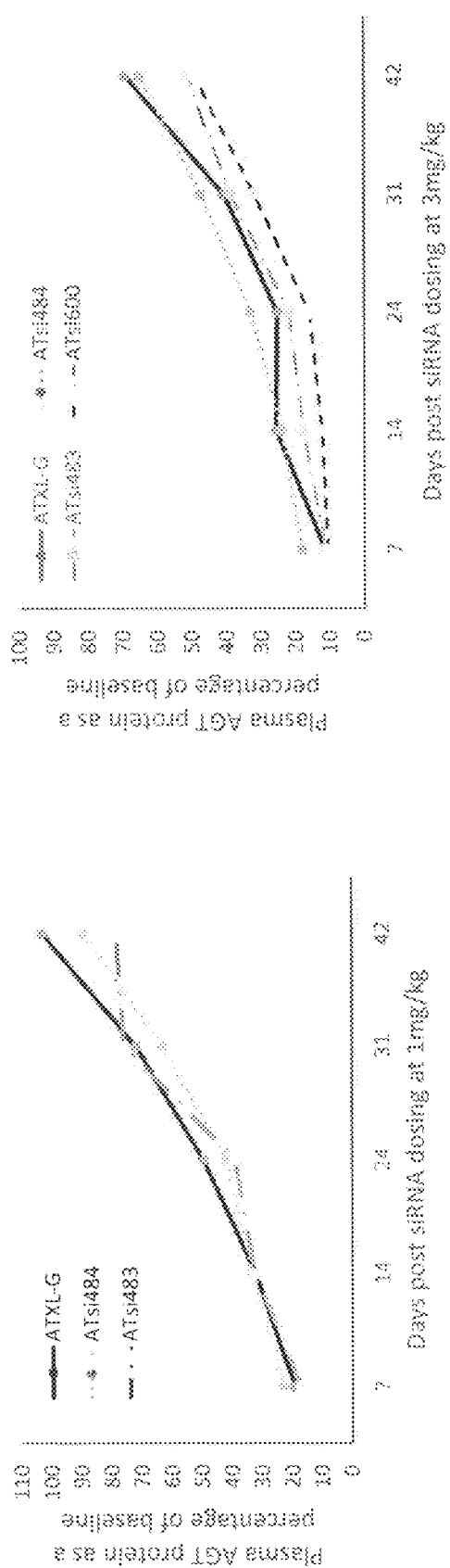
Figure 4. *In Vivo* Percent AGT Protein Levels in Mouse Plasma at Different Times after siRNA Dosing at 1 mg/kg or 3mg/kg

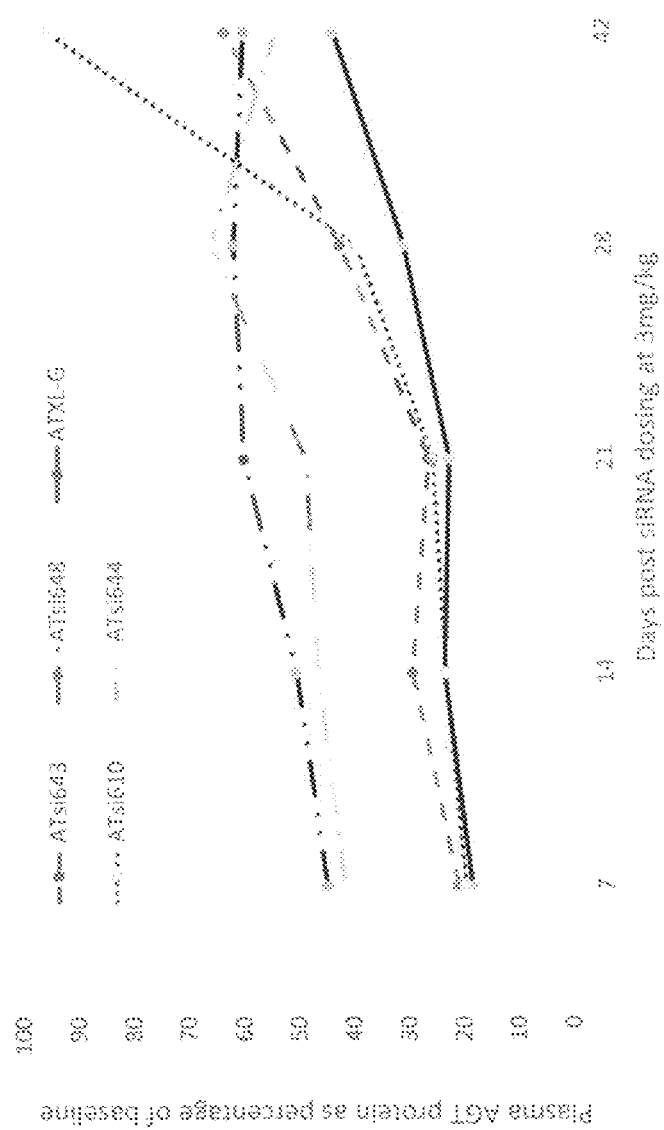
Figure 5. *In Vivo* AGT Protein Levels in Mouse Serum at Different Times after siRNA Dosing at 3 mg/kg

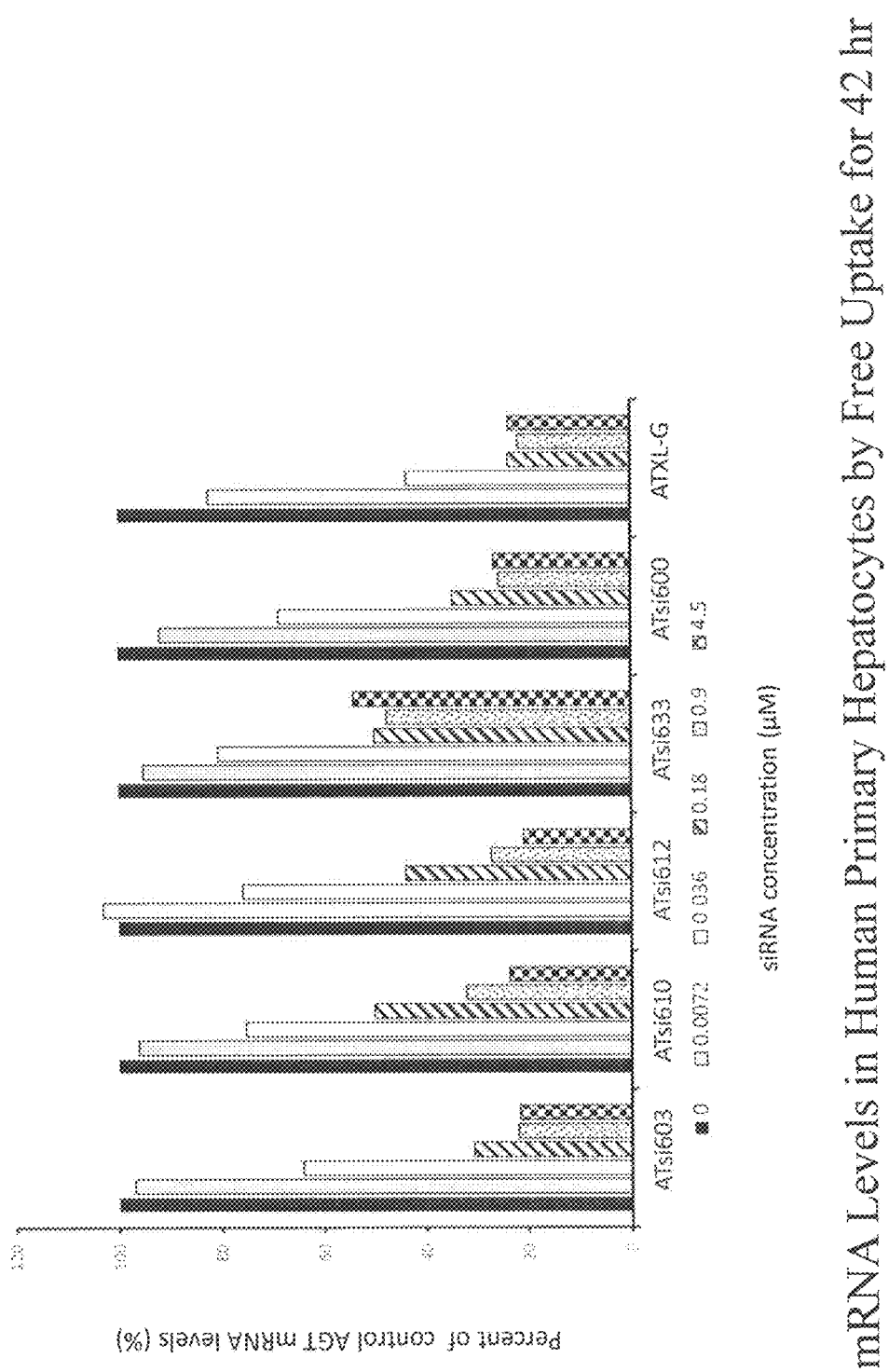
Figure 6. AGT mRNA Levels in Human Primary Hepatocytes by Free Uptake for 42 hr

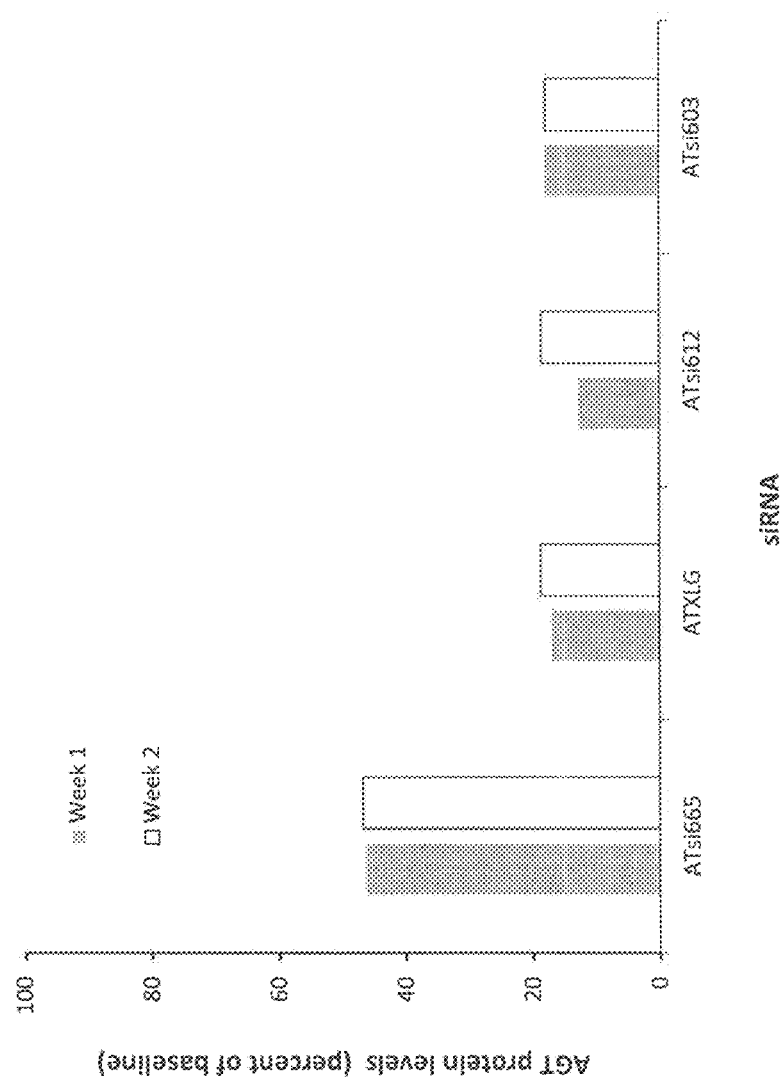
Figure 7. *In Vivo* AGT Protein Levels in Mouse Serum after siRNA Dosing at 3 mg/kg

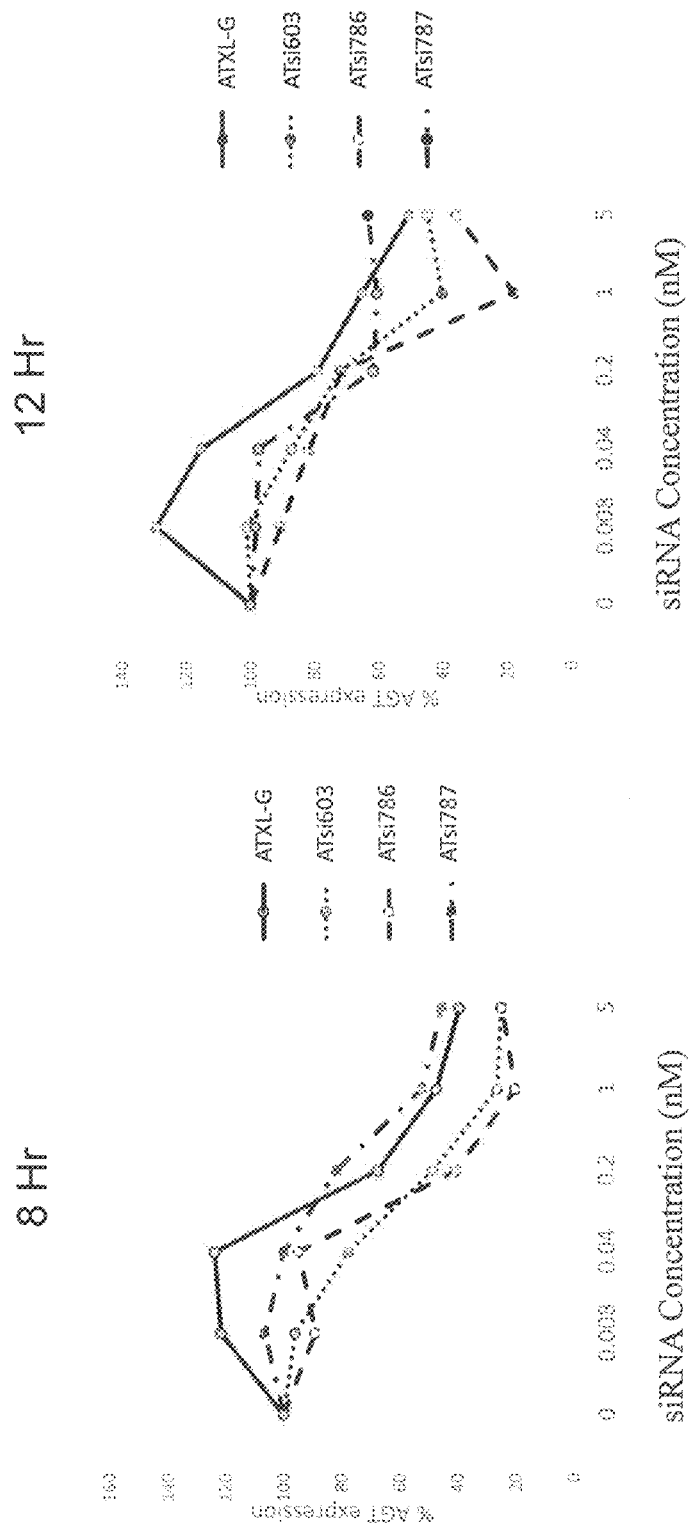
Figure 8. Transfection of ATXL-G, ATsi603, ATsi786 and ATsi787 into Hep3B Cells

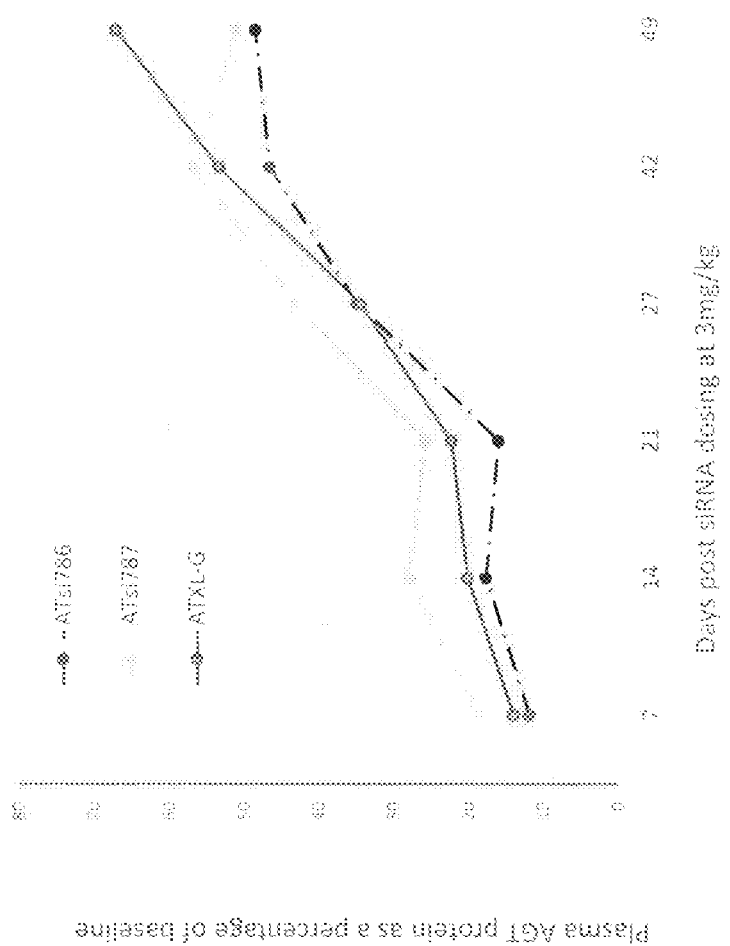
Figure 9. Percent AGT Protein Levels in Mouse Plasma at Different Times After siRNA Dosing at 3 mg/kg

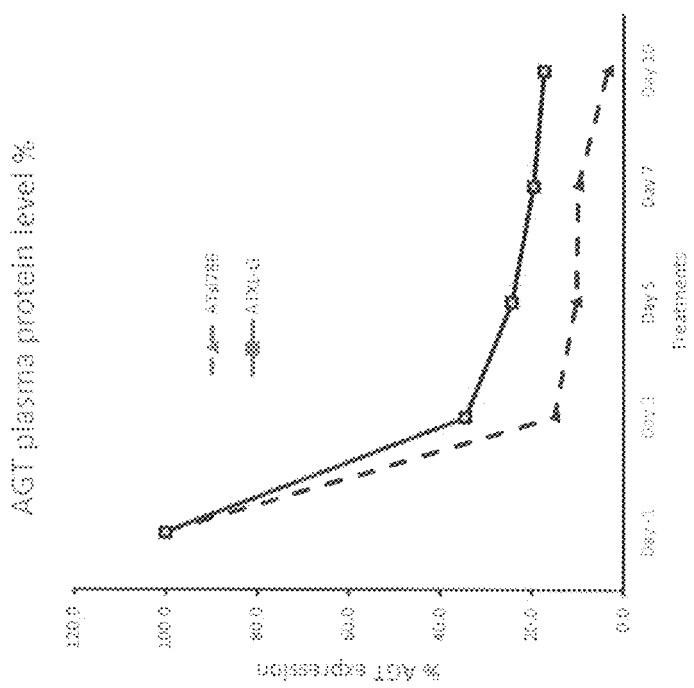
Figure 10: Percent AGT Protein Levels in Transgenic Mouse Plasma at Different Times After siRNA Dosing at 3 mg/kg

ADVANCED RNA TARGETING (ARNATAR) FOR ANGIOTENSINOGEN

This subject application claims priority under 35 U.S.C. § 111a to PCT Application No. PCT/US24/33852 filed Jun. 13, 2024, which claims the benefit of U.S. Provisional Application Ser. No. 63/472,727, filed Jun. 13, 2023, 63/472,780, filed Jun. 13, 2023 and 63/533,283, filed Aug. 17, 2023, the entireties of which are hereby incorporated by reference herein.

This application contains a Sequence Listing that has been filed electronically in the form of a XML filed, created Jun. 13, 2024 and named 2024_06_13_Seq_Listing, the entirety of which is hereby incorporated by reference herein

FIELD

Certain embodiments are directed to methods and compounds for modulating angiotensinogen (AGT) gene expression by Advanced RNA Targeting (ARNATAR). Such methods and compounds are useful for reducing expression of AGT, thereby treating diseases, disorders and/or conditions related to AGT in a subject.

BACKGROUND

Angiotensinogen (also known as AGT, SERPINA8 or ANHU), a member of the serpin family, is a component of the renin-angiotensin system (RAS) pathway (also known as the renin-angiotensin-aldosterone system (RAAS)). It is primarily produced in the liver and is released into the circulation where renin converts it into angiotensin I. Angiotensin converting enzyme (ACE) then converts angiotensin I into angiotensin II.

Angiotensin II, a peptide hormone, has multiple effects on the circulatory system that controls blood pressure and may contribute to hypertension. Angiotensin II causes vasoconstriction which, in turn, can increase blood pressure. Angiotensin II stimulates secretion of the hormone aldosterone from the adrenal cortex. Aldosterone causes the kidneys to increase reabsorption of sodium and modulation of the glomerular filtration rate which can lead to an increase of fluid volume in a body which, in turn, can increase blood pressure. Excess angiotensin II can lead to dysregulation of the RAAS pathway and high blood pressure.

Chronic high blood pressure is known as hypertension. High blood pressure in a hypertensive subject requires the heart to work harder to circulate blood through the blood vessels. Hypertension can lead to many deleterious conditions in a body such as increased oxidative stress, increased inflammation, hypertrophy, fibrosis in the heart, fibrosis in the kidneys, and fibrosis in the arteries, and result in, e.g., left ventricular fibrosis, arterial remodeling, and glomerulosclerosis.

Hypertension is known as a major risk factor for various diseases, disorders and conditions such as shortened life expectancy due to, for example, cardiovascular morbidity, chronic kidney disease, stroke, myocardial infarction, heart failure, aneurysms of the blood vessels (e.g. aortic aneurysm), peripheral artery disease, heart damage (e.g., heart enlargement or hypertrophy) and other cardiovascular related diseases, disorders and/or conditions.

The prevalence of resistant hypertension (RHTN), hypertension resistant to drug treatment, has steadily increased in number likely due to an ageing population and an ever-increasing incidence of obesity despite the number of anti-hypertensive drugs commercially available. Also, commercially available anti-hypertensive therapies targeting various RAAS pathway components have been ineffective in completely inhibiting or blocking the RAAS pathway. The mechanism(s) for this ineffective inhibition has not been fully elucidated, but may occur by ACE escape and/or aldosterone escape pathways. Thus, there is a need for new therapeutics.

The use of therapeutic oligomeric compounds (e.g., oligonucleotides) was first proposed over forty years ago by Stephenson and Zamecnik (Inhibition of Rous Sarcoma Viral RNA Translation by a Specific Oligodeoxyribonucleotide, PNAS, 1978, 75:285-288).

Sequence-specific silencing of gene expression, RNA interference (RNAi), was discovered in 1998 by Fire et al. (Potent and Specific Genetic Interference by Double-Stranded RNA in *Caenorhabditis elegans*, Nature, 1998, 391:806-811). RNAi utilizes double-stranded RNA (dsRNA) to inhibit gene expression via the RNA-induced silencing complex (RISC).

RISC comprises a complex of multiple proteins interacting with an oligomeric compound to inhibit gene expression. The oligomeric compound acts as a template for RISC to recognize complementary messenger RNA (mRNA) transcripts to target a specific mRNA transcript for cleavage. Cleavage of the target mRNA blocks translation of the target mRNA and silences the target gene. Oligomeric compounds utilized by RISC include, but are not limited to: single stranded oligomeric compounds such as microRNAs (miR-NAs), certain oligonucleotides, and single strand siRNAs (Lima et al., Single-stranded siRNAs activate RNAi in animals. Cell. 2012, 150(5):883-94), and double stranded RNA (dsRNA) compounds such as short hairpin RNAs (shRNAs) and small interfering RNAs (siRNAs).

In 2001, Elbashir et al., showed that 21-nucleotide long siRNA duplexes specifically suppress expression of endogenous and heterologous genes in mammalian cell lines and theorized that siRNA may eventually be used as a gene-specific therapeutic (Duplexes of 21-Nucleotide RNAs Mediate RNA Interference in Cultured Mammalian Cells, Nature, 2001, 411:494-498).

The field of oligomeric therapeutic compounds is still maturing and improvements in delivery, stability, specificity, safety and potency are still being sought to improve the therapeutic efficacy of the oligomeric compound.

Currently, several clinical trials are underway assessing nucleic acid-based therapeutics targeting AGT to treat hypertension. In clinical trials, both an siRNA therapeutic and an antisense oligonucleotide (ASO) therapeutic are being assessed (Ranasinghe et al., J Am Heart Assoc, 2022, 11(20); Cruz-López et al., Hypertension, 2022, 79:2115-2126; Morgan et al., Clinical Res, 2021, 6(6):4865-96), however, neither type of nucleic acid therapeutic has been given regulatory approval for patient treatment. Thus, there is still an unmet need for nucleic acid-based therapeutics targeting AGT. Disclosed herein are dsRNA compounds targeting AGT improved with Advanced RNA Targeting (ARNATAR) abilities that enhance their gene silencing activity.

SUMMARY

Several embodiments provided herein relate to the discovery of certain ARNATAR design dsRNA compounds targeting AGT transcripts that can enhance their effectiveness in modulating AGT gene expression. In several aspects, the dsRNA compound is a modified shRNA or siRNA compound. The double-stranded RNA compound comprises a sense strand and an antisense strand. The antisense strands can be fully or substantially complementary to a target nucleic acid.

In some embodiments, a double stranded ribonucleic acid (dsRNA) compound for inhibiting expression of angiotensinogen (AGT) in a cell comprises a sense strand and an antisense strand forming a double stranded portion, wherein the antisense strand comprises any one of the antisense strand sequences in any one of Tables 2, 5, 7, 9, 10 or 13.

In some embodiments, a double-stranded ribonucleic acid (dsRNA) compound for inhibiting expression of angiotensinogen (AGT) in a cell comprises a sense strand and an antisense strand forming a double stranded portion, wherein the sense strand comprises any one of the sense strand sequences in any one of Tables 2, 5, 7, 9, 10 or 13.

In some embodiments, a double-stranded ribonucleic acid (dsRNA) compound for inhibiting expression of angiotensinogen (AGT) in a cell comprises a sense strand and an antisense strand forming a double stranded portion, wherein the sense strand comprises any one of the sense strand sequences in any one of Tables 2, 5, 7, 9, 10 or 13, and wherein the antisense strand comprises the corresponding antisense strand sequences in any one of Tables 2, 5, 7, 9, 10 or 13.

In one embodiment, a double-stranded ribonucleic acid (dsRNA) compound for inhibiting expression of angiotensinogen (AGT) in a cell comprises a sense strand and an antisense strand forming a double stranded portion, wherein the antisense strand comprises any one of the antisense strand sequences of Table 13, and wherein the sense strand comprises the corresponding sense strand sequence of Table 13.

In one embodiment, a double-stranded ribonucleic acid (dsRNA) compound for inhibiting expression of angiotensinogen (AGT) in a cell comprises a sense strand and an antisense strand forming a double stranded (duplex) portion, wherein the sense strand comprises the nucleotide sequence of SEQ ID NO: 61, and wherein the antisense strand comprises the nucleotide sequence of SEQ ID NO: 62. In certain embodiments, the dsRNA compound comprises a conjugate. In certain embodiments, the conjugate is N-Acetylgalactosamine (GalNAc). In certain embodiments, the conjugate is attached to the 3' end of the sense strand of a dsRNA compound targeting AGT. In certain embodiments, the conjugate is attached to the 3' end of the sense strand of a siRNA compound targeting AGT.

Certain embodiments provide a method for inhibiting the expression of angiotensinogen (AGT) in a subject comprising the step of administering a dsRNA compound described herein to the subject, in an amount sufficient to inhibit expression of AGT. In certain embodiments, the dsRNA compound inhibits expression of AGT by at least about 70%, 75%, 80%, 85%, 90%, 95%, 98% or 99%. In certain embodiments, the dsRNA compound comprises an siRNA.

In certain embodiments, a pharmaceutical composition for inhibiting expression of angiotensinogen (AGT) in a cell is provided comprising a double-stranded ribonucleic acid (dsRNA) compound described herein, alone or in combination with a pharmaceutically acceptable carrier or excipient.

Certain embodiments provide a method of inhibiting expression of angiotensinogen (AGT) in a cell comprising contacting the cell with a dsRNA compound or a pharmaceutical composition described herein in an amount sufficient to inhibit expression of AGT, thereby inhibiting expression of AGT in the cell.

Certain embodiments provide a method of treating a RAAS associated disease, disorder and/or condition in a subject, comprising administering to the subject in need thereof a therapeutically effective amount of a dsRNA compound or a pharmaceutical composition described herein, thereby treating the RAAS associated disease, disorder and/or condition in the subject.

Certain embodiments provide a method of treating a subject having a disease, disorder and/or condition that would benefit from reduction in angiotensinogen (AGT) expression, comprising administering to the subject in need thereof a therapeutically effective amount of a dsRNA compound or a pharmaceutical composition described herein, thereby treating the subject having the disorder that would benefit from reduction in AGT expression.

Certain embodiments provide a method of preventing at least one symptom in a subject having a disorder that would benefit from reduction in angiotensinogen (AGT) expression, comprising administering to the subject in need thereof a prophylactically effective amount of a dsRNA compound or a pharmaceutical composition described herein, thereby preventing at least one symptom in the subject having the disorder that would benefit from reduction in AGT expression.

In certain embodiments, a kit comprising a dsRNA compound or a pharmaceutical composition described herein, and optionally, a label, is provided.

In one embodiment, a process for preparing a sense and/or antisense strand of a double stranded ribonucleic acid (dsRNA) compound is provided, wherein the process comprises the steps of: a) preparing the sense and/or antisense strand by sequential coupling of modified and/or unmodified nucleotides via the phosphoramidite oligonucleotide synthesis on a solid support; b) optionally, coupling a GalNAc-comprising moiety to the sense and/or antisense strand on the solid support via the phosphoramidite oligonucleotide synthesis; c) detaching the sense and/or antisense strand from the solid support and removing the solid support; and d) optionally, further purifying the sense and/or antisense strand, optionally using chromatography.

In one embodiment, a process for preparing a sense and/or antisense strand of a double stranded ribonucleic acid (dsRNA) compound is provided, wherein the process comprises the steps of: a) coupling a GalNAc-comprising moiety to a solid support via the phosphoramidite oligonucleotide synthesis, b) coupling a modified and/or unmodified nucleotide via the phosphoramidite oligonucleotide synthesis to the GalNAc-comprising moiety on the solid support; c) sequentially coupling additional modified and/or unmodified nucleotides via the phosphoramidite oligonucleotide synthesis to prepare the sense and/or antisense strand; d) detaching the sense and/or antisense strand from the solid support and removing the solid support; and e) optionally, further purifying the sense and/or antisense strand, optionally using chromatography.

In one embodiment, a process of preparing a double stranded ribonucleic acid (dsRNA) compound is provided, comprising: a) contacting the sense strand prepared according any one of the processes described herein with the antisense strand prepared according any one of the processes described herein in equimolar concentrations in a solution; b) optionally heating the solution to a temperature of about 94° C.; and c) optionally reducing the temperature of the solution to about 25° C.

Certain embodiments provide a double stranded ribonucleic acid (dsRNA) compound for use in medicine.

Certain embodiments provide a double stranded ribonucleic acid (dsRNA) compound for use in treating or preventing a RAAS associated disease, disorder and/or condition in a subject.

BRIEF DESCRIPTION OF THE DRAWINGS

FIG. 1: shows AGT siRNA inhibition screen in human primary hepatocyte cells after 48 hours free uptake.

FIG. 2: shows the dose response curves of AGT siRNAs on AGT expression (percent) after transfection of AGT siRNAs into Hep3B for 24 hours to compare ARNATAR modifications to Third Party modifications of the same sequences without GalNAc.

FIG. 3: shows ARNATAR AGT siRNA ATsi483 with comparable inhibition activity as reference AGT siRNA ATXL-G in human primary hepatocyte cells after 42 hours free uptake.

FIG. 4: shows in vivo AGT protein levels via ELISA in blood plasma after siRNA dosing, illustrating comparable activity and durability of ARNATAR AGT siRNAs compared to reference AGT siRNA ATXL-G over a >4-week time period.

FIG. 5: shows in vivo plasma AGT protein levels after dosing with further modifications of ARNATAR AGT siRNAs, demonstrating comparable activity and durability as reference AGT siRNA ATXL-G over a time course of 4 weeks.

FIG. 6: shows in vitro inhibition activity via 42 hours free uptake by human primary hepatocytes of ARNATAR modified AGT siRNAs and reference ATXL-G.

FIG. 7: shows in vivo plasma AGT protein levels of some of ARNATAR AGT siRNAs that have lower activity in vitro but comparable or better activity than reference ATXL-G in vivo.

FIG. 8: shows dose response curves of AGT siRNAs on AGT expression (percent) after transfection of ARNATAR AGT siRNAs into Hep3B for 8 or 12 hours, demonstrating better activity than reference ATXL-G for some ARNATAR siRNAs.

FIG. 9: shows percent AGT protein levels in mouse plasma at different times after siRNA dosing at 3 mg/kg, showing similar or better activity at several time points than reference ATXL-G.

FIG. 10: shows percent AGT protein levels in mouse plasma of AGT-AAV transgenic mice at different times after siRNA dosing at 3 mg/kg with compound ATsi786 showing more potent knockdown than reference ATXL-G.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated-by-reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well-known and commonly used in the art. Standard techniques may be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout in the disclosure herein are incorporated-by-reference for the portions of the document discussed herein, as well as in their entirety.

Unless otherwise indicated, the following terms have the following meanings:

"2'-O-methoxyethyl" (also 2'-MOE and 2'-O(CH$_2$)$_2$—OCH$_3$) refers to an O-methoxy-ethyl modification at the 2' position of a furanose ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety. "2'-MOE nucleotide" (also 2'-O-methoxyethyl nucleotide) means a nucleotide comprising a 2'-MOE modified sugar moiety.

"2'-O-methyl" (also 2'-OCH$_3$ and 2'-OMe) refers to an O-methyl modification at the 2' position of a furanose ring. A 2'-O-methyl modified sugar is a modified sugar.

"2'-OMe nucleoside" (also 2'-O-methyl nucleoside) means a nucleoside comprising a 2'-OMe modified sugar moiety. "2'-OMe nucleotide" (also 2'-O-methyl nucleotide) means a nucleotide comprising a 2'-OMe modified sugar moiety.

"2'-substituted nucleoside" means a nucleoside comprising a substituent at the 2'-position of the furanose ring other than H or OH. In certain embodiments, 2' substituted nucleosides include nucleosides with a fluoro (2'-F), O-methyl (2'-OMe), O-methoxyethyl (2'-MOE) or bicyclic sugar modifications.

"5-methylcytosine" means a cytosine modified with a methyl group attached to the 5 position. A 5-methylcytosine is a modified nucleobase.

"About" means within +7% of a value. For example, if it is stated, "the compounds affected at least about 70% inhibition of mRNA", it is implied that the mRNA levels are inhibited within a range of 63% and 77%.

"Animal" refers to a human or non-human animal, including, but not limited to, mice, rats, rabbits, dogs, cats, pigs, and non-human primates, including, but not limited to, monkeys and chimpanzees.

"Antibody" refers to a complete antibody molecule or any fragment or portion thereof, such as the heavy chain, the light chain, F$_{ab}$ portion, and F$_c$ portion.

"Antisense oligonucleotide" or "ASO" means a single-stranded oligonucleotide having a nucleobase sequence that permits hybridization to a corresponding region or segment of a target nucleic acid. In certain embodiments, the antisense oligonucleotide comprises one or more ribonucleoside (RNA) residues and/or deoxyribonucleoside (DNA) residues.

"Base complementarity" refers to the capacity for the base pairing of nucleobases of an oligonucleotide with corresponding nucleobases in a target nucleic acid (i.e., hybridization), and is mediated by Watson-Crick, Hoogsteen or reversed Hoogsteen hydrogen binding between corresponding nucleobases. Base complementarity also refers to canonical (e.g., A:U, A:T, C:G) or non-canonical base pairings (e.g., A:G, A:U, G:U, I:U, I:A, I:C).

"Bicyclic sugar" means a furanose ring modified by the bridging of two non-geminal carbon atoms. A bicyclic sugar is a modified sugar.

"Cap structure" or "terminal cap moiety" means chemical modifications, which have been incorporated at either terminus of an oligomeric compound.

"Chemical modification" means modification of molecular structure or element from naturally occurring molecules. For example, siRNA compounds are composed of linked ribonucleosides (also sometimes referred to herein as RNA), therefore, substitution of a deoxyribonucleoside (also sometimes referred to herein as DNA) for a ribonucleoside is considered a chemical modification of the siRNA compound.

"Chemically distinct portion" refers to a portion of an oligomeric compound that is in some way chemically different than another portion of the same oligomeric compound. For example, a portion having 2'-OMe nucleotides is chemically distinct from a portion having nucleotides without 2'-OMe modifications.

"Chimeric oligomeric compounds" means oligomeric compounds that have at least 2 chemically distinct portions, each portion having a plurality of subunits. For example, as disclosed herein, siRNA can comprise a peripheral portion and a central portion. The peripheral portion comprises motifs with various modified or unmodified nucleobases so as to confer increased stability, specificity, safety and potency, while the central portion comprises various modified or unmodified nucleobases to serve as substrate for RISC mediated degradation.

"Complementarity" means the capacity for pairing between nucleobases of a first nucleic acid and a second nucleic acid.

"Comply" in the context of a therapy means the adherence with a recommended therapy by a subject.

"Comprise", "comprises" and "comprising" will be understood to imply the inclusion of a stated member without the exclusion of other (e.g., non-stated) members. For example, the inclusion of a stated step or element or group of steps or elements but not the exclusion of any other step or element or group of steps or elements, respectively.

"Contiguous nucleobases" means nucleobases adjacent to each other.

"Deoxyribonucleotide" means a nucleotide having a hydrogen at the 2' position of the sugar portion of the nucleotide. A sequence of deoxyribonucleotides is sometimes referred to as "DNA" herein. A deoxyribonucleotide is sometimes referred to as "DNA nucleotide", "d nucleotide" or "D" herein. Deoxyribonucleotides may be modified with any of a variety of substituents.

"Designing" or "designed" in the context of an oligomeric compound refer to the process of making/engineering an oligomeric compound that specifically hybridizes with a target nucleic acid molecule. Designing generally encompasses providing mutations and/or modifications to a e.g., natural sequence.

"Efficacy" means the ability to produce a desired effect.

"Expression" generally includes all the functions by which a gene's coded information is converted into structures present and operating in a cell. Such structures include, but are not limited to the products of transcription and/or translation. Within the present disclosure, expression refers to protein as the products of expression.

"Fully complementary" or "100% complementary" means each nucleobase of a first nucleic acid molecule has a complementary nucleobase in a second nucleic acid molecule. In certain embodiments, a first nucleic acid molecule is an oligomeric compound and a target nucleic acid molecule is a second nucleic acid molecule.

"Fully modified motif" refers to an oligomeric compound comprising a contiguous sequence of nucleosides wherein each nucleoside has a chemical modification.

"GalNAc" refers to the compound N-Acetylgalactosamine or to a compound comprising a N-Acetylgalactosamine compound. A GalNAc-comprising moiety (or sometimes only "GalNAc" or "GalNAc moiety" used herein) describes a compound comprising at least one N-Acetylgalactosamine compound usually attached to one or more spacers and/or linkers for the attachment to an oligonucleotide compound.

"Hybridization" means the annealing of complementary nucleic acid molecules. In certain embodiments, complementary nucleic acid molecules include, but are not limited to, a combination of an oligomeric compound and a nucleic acid molecule target. In certain embodiments, complementary nucleic acid molecules include, but are not limited to, a combination of an siRNA and a nucleic acid molecule target, particularly an mRNA target molecule.

"Induce", "inhibit", "potentiate", "elevate", "increase", "decrease" or the like, generally denotes an action to obtain quantitative differences between two states.

"Inhibiting the expression or activity" refers to a reduction or blockade of the expression or activity and does not necessarily indicate a total elimination of expression or activity.

"Internucleoside linkage" refers to the chemical bond between two adjacent nucleosides. The linkage may be a naturally occurring linkage, i.e., a phosphate linkage, or an artificial linkage, such as a phosphorothioate (also known as thiophosphate or PS) linkage.

"Linked nucleosides" means adjacent nucleosides (e.g., A, G, C, T, U, and I) linked together by an internucleoside linkage. Examples of linked nucleosides include a sequence of deoxyribonucleosides (sometimes referred to as DNA herein) or a sequence of ribonucleosides (sometimes referred to as RNA herein).

"Mismatch" or "non-complementary nucleobase" refers to the case when a nucleobase of a first nucleic acid is not capable of pairing with the corresponding nucleobase of a second or target nucleic acid through Watson-Crick basepairing (e.g., A:T, A:U, C:G).

"Modified internucleoside linkage" refers to a substitution or any change from a naturally occurring internucleoside bond (i.e., a phosphodiester internucleoside bond).

"Modified nucleobase" means any nucleobase other than adenine, cytosine, guanine, thymidine, or uracil. An "unmodified nucleobase" means the purine bases adenine (A) and guanine (G), and the pyrimidine bases thymine (T), cytosine (C) and uracil (U).

"Modified nucleoside" means a nucleoside having a modified sugar moiety and/or a modified nucleobase. As used herein, where the oligomeric compound is RNA-based, a substitution of a deoxyribonucleoside (sometimes referred to as DNA nucleoside herein) for a ribonucleoside is considered a modification of the oligomeric compound. Also, where the oligomeric compound is DNA-based, a substitution of a ribonucleoside (sometimes referred to as RNA nucleoside herein) for a deoxyribonucleoside is considered a modification of the oligomeric compound.

"Modified nucleotide" means a nucleotide having at least one of a modified sugar moiety, a modified internucleoside linkage, a deoxyribonucleoside (sometimes referred to as DNA nucleotide herein) for a ribonucleoside (sometimes referred to as RNA nucleotide herein) substitution, a ribonucleoside (sometimes referred to as RNA nucleoside herein) for a deoxyribonucleoside (sometimes referred to as DNA nucleoside herein) substitution, and a modified nucleobase.

"Modified oligonucleotide" means an oligonucleotide comprising at least one of a modified internucleoside linkage, a modified sugar, a deoxyribonucleoside (sometimes referred to as DNA nucleoside herein) for a ribonucleoside (sometimes referred to as RNA nucleoside herein) substitution, a ribonucleoside (sometimes referred to as RNA nucleoside herein) for a deoxyribonucleoside (sometimes referred to as DNA nucleoside herein) substitution, and/or a modified nucleobase.

"Modified sugar" means substitution and/or any change from a natural sugar moiety of a nucleotide found in DNA or RNA.

"Moiety" means one of the portions into which something is divided i.e., a part or component of something. For example, a sugar moiety of a nucleotide is the sugar component of the nucleotide.

"Monomer" refers to a single unit of an oligomer or a single unit for forming an oligomer.

Monomers include, but are not limited to, nucleosides and nucleotides, whether naturally occurring or modified.

"Motif" means a pattern of modification in an oligomeric compound. For example, as disclosed herein, ARNATAR designed oligomeric compounds comprising motifs with various modified nucleobases and internucleoside linkages in order to improve delivery, stability, specificity, safety and potency of the compounds.

"Natural sugar (moiety)" or generally "sugar (moiety)" means a sugar (moiety) found in DNA (2'-H) or RNA (2'-OH), i.e., 2-deoxy-beta-D-ribofuranose or beta-D-ribofuranose, respectively.

"Naturally occurring internucleoside linkage" means a 3' to 5' phosphodiester linkage.

"Non-complementary nucleobase" refers to a pair of nucleobases that do not form hydrogen bonds with one another or otherwise support hybridization.

"Nucleic acid (molecule)" refers to a sequence of monomeric nucleotides. A nucleic acid molecule includes, but is not limited to, ribonucleic acids (RNA), messenger RNA (mRNA), deoxyribonucleic acids (DNA), single-stranded nucleic acids, double-stranded nucleic acids, small interfering ribonucleic acids (siRNA), hairpin ribonucleic acids (shRNA) and microRNAs (miRNA).

"Nucleobase" means any unmodified nucleobase as defined above, any modified nucleobase and/or any artificial nucleobase that may generally be any heterocyclic moiety capable of pairing with a base of a nucleic acid molecule.

"Nucleobase complementarity" refers to the ability of a nucleobase of base pairing (also known as being complementary) with another nucleobase. If a nucleobase at a certain position of an oligomeric compound is capable of hydrogen bonding with a nucleobase at a certain position of a target nucleic acid molecule, then the position of hydrogen bonding between the oligomeric compound and the target nucleic acid molecule is considered to be complementary at that nucleobase pair. For example, in DNA, adenine (A) is complementary to thymine (T); in RNA, adenine (A) is complementary to uracil (U); and, guanine (G) is complementary to cytosine (C) in both DNA and RNA. Base pairs, or complementary nucleobases, are usually canonical Watson-Crick base pairs (C:G, A:U, A:T), but, non-canonical base pairs such as Hoogsteen base pairs (e.g., A:G, A:U), Wobble base pairs (e.g., G:U, I:U, I:A, I:C, wherein I is hypoxanthine) and the like are also included. Nucleobase complementarity facilitates hybridization of the oligomeric compounds described herein to their target nucleic acids.

"Nucleobase sequence" means the order of contiguous nucleobases independent of any sugar, linkage, and/or nucleobase modification.

"Nucleoside" means a nucleobase linked to the natural or modified sugar as defined above.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system. "Mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target.

"Nucleotide" means a nucleoside having a linkage group (e.g., a phosphate (p) or phosphorothioate (PS) group) covalently linked to the sugar portion of the nucleoside. Nucleotides include ribonucleotides and deoxyribonucleotides with phosphate and/or phosphorothioate linkages. A sequence of linked nucleotides, e.g., ribonucleotides, deoxyribonucleotides and/or a mixture thereof, form an oligonucleotide.

"Off-target effect" refers to an unwanted or deleterious biological effect associated with modulation of RNA or protein expression of a gene other than the intended target nucleic acid.

"Oligomeric activity" means any detectable or measurable activity attributable to the hybridization of an oligomeric compound to its target nucleic acid. In certain embodiments, oligomeric activity is measured as a decrease in the amount or expression of a target nucleic acid. Oligomeric activity can be modulated by an oligomeric compound such as a dsRNA. Oligomeric activity can be modulated by an oligomeric compound such as an siRNA.

"Oligomeric compound" means a compound of linked monomeric subunits (also known as "subunits" herein) that is capable of undergoing hybridization to at least a region of a target nucleic acid through hydrogen bonding. The monomeric subunits are particularly modified or unmodified nucleotides or nucleosides, and the oligomeric compound is particularly an oligonucleotide. The oligomeric compound acts as a template for RISC to recognize complementary messenger RNA (mRNA) transcripts to target a specific mRNA transcript for cleavage. Cleavage of the target mRNA blocks translation of the target mRNA and silences the target gene. Examples of oligomeric compounds include single-stranded and double-stranded compounds, such as, antisense oligonucleotides, ssRNAs, siRNAs, shRNAs and miRNAs. Generally, oligomeric compounds are distinguished from polymeric compounds based on their number of monomers, wherein an oligomer often has about 5 to about 100 monomeric units.

"Oligomeric inhibition" means reduction of target nucleic acid (e.g., mRNA) levels in the presence of an oligomeric compound complementary to a target nucleic acid compared to target nucleic acid levels in the absence of the oligomeric compound.

"Oligomeric mechanisms" include RISC or RNase H related mechanisms involving hybridization of an oligomeric compound with target nucleic acid (e.g., mRNA), wherein the outcome or effect of the hybridization is target degradation and inhibition of gene expression.

"Oligonucleotide" as used herein means a sequence of linked nucleosides and/or nucleotides, each of which can be modified or unmodified, independently from each other. Oligonucleotides can have a linking group other than a phosphate group (e.g., a phosphorothioate group) used as a linking moiety between nucleosides. In certain embodiments, an oligonucleotide comprises one or more ribonucleoside (RNA) residues and/or deoxyribonucleoside (DNA) residues.

"Phosphorothioate linkage" or "PS" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an oligomeric compound.

"Region" is defined as a portion of the target nucleic acid having at least one identifiable structure, function, or characteristic.

"RNA" or "ribonucleic acid" consists of ribose nucleotides or ribonucleotides (nitrogenous bases attached to a ribose sugar) linked by phosphodiester bonds, forming sequences of varying lengths. The nitrogenous bases in RNA are adenine, guanine, cytosine, and uracil.

"Ribonucleotide" means a nucleotide having a hydroxy at the 2' position of the sugar portion of the nucleotide. Ribonucleotides can be modified with any of a variety of substituents and may be connected by covalent linkages other than naturally occurring phosphodiester such as phosphorothioate. A ribonucleotide is sometimes referred to as RNA, "R" or "r" herein.

"Segments" are defined as smaller or sub-portions of regions within a nucleic acid molecule, particularly a target nucleic acid.

"Sites" as used herein are defined as unique nucleobase positions within a nucleic acid, particularly a target nucleic acid.

"Specifically hybridizable" refers to an oligomeric compound having a sufficient degree of complementarity between an oligomeric compound (e.g., siRNA) and a target nucleic acid (e.g., mRNA) to induce a desired effect, while exhibiting minimal or no effects on non-target nucleic acids under conditions in which specific binding is desired, i.e., under physiological conditions in the case of in vivo assays and therapeutic treatments.

"Stringent hybridization conditions" or "stringent conditions" refer to conditions under which an oligomeric compound will hybridize to its target nucleic acid, with minimal hybridization to other nucleic acid molecules.

"Subject" means a human or non-human animal, particularly a human or non-human animal selected for treatment or therapy.

"Target" generally refers to a protein or nucleic acid molecule, the modulation of which is desired. As used herein, "target" particularly refers to a nucleic acid molecule (e.g., mRNA), the modulation of which is desired.

"Target gene" refers to a gene encoding a target.

"Targeting" means the process of design and selection of an oligomeric compound that will specifically hybridize to a target nucleic acid and induce a desired effect.

"Target nucleic acid," "target RNA," "target RNA transcript" and "nucleic acid target" all mean a nucleic acid capable of being targeted by oligomeric compounds.

"Target region" means a portion of a target nucleic acid to which one or more oligomeric compounds is targeted.

"Target segment" means the sequence of nucleotides of a target nucleic acid to which an oligomeric compound is targeted. "5' target site" refers to the 5'-most nucleotide of a target segment. "3' target site" refers to the 3'-most nucleotide of a target segment. In an embodiment, a target segment is at least a 13-nucleobase portion (i.e. at least 13 consecutive nucleobases) of a target region to which an oligomeric compound is targeted.

"Therapeutic efficacy" or "therapeutically effective" refers to the effectiveness of a compound or composition such as an oligomeric compound described herein in a therapeutic application. Therapeutic efficacy can be increased by improvements in delivery, stability, specificity, safety and/or potency of the therapeutic compound.

"Unmodified" RNA nucleobases mean the purine bases adenine (A) and guanine (G), and the pyrimidine bases cytosine (C) and uracil (U). "Unmodified" DNA nucleobases mean the purine bases adenine (A) and guanine (G), and the pyrimidine bases thymine (T) and cytosine (C). In certain embodiments, an unmodified RNA nucleobase is considered modified when a DNA nucleobase is substituted for the RNA nucleobase in an oligomeric compound such as an siRNA compound. In certain embodiments, an unmodified DNA nucleobase is considered modified when an RNA nucleobase is substituted for the DNA nucleobase in a DNA sequence.

"Unmodified nucleoside" means herein a nucleoside composed of a naturally occurring nucleobase and a naturally occurring sugar moiety. In certain embodiments, an unmodified nucleoside is an RNA nucleoside in an oligomeric compound such as an siRNA compound.

"Unmodified nucleotide" means herein a nucleotide composed of a naturally occurring nucleobase, a naturally occurring sugar moiety, and an internucleoside linkage, wherein the internucleotide linkage may be a naturally occurring linkage (i.e., a phosphate linkage) or an artificial linkage (e.g., a phosphorothioate linkage). In certain embodiments, an unmodified nucleotide is an RNA nucleotide in an oligomeric compound such as an siRNA compound.

Disclosed herein are improved compounds targeting a nucleic acid encoding angiotensinogen (AGT) with Advanced RNA Targeting (ARNATAR) designs that enhance their gene silencing activity. In certain embodiments, the compound is a double stranded ribonucleic acid (dsRNA) compound. In an embodiment, the dsRNA compound is an shRNA or an siRNA compound.

In some embodiments, a double stranded ribonucleic acid (dsRNA) compound for inhibiting expression of angiotensinogen (AGT) in a cell comprises a sense strand and an antisense strand forming a double stranded portion, wherein the antisense strand comprises any one of the antisense nucleotide sequences in any one of Tables 2, 5, 7, 9, 10 or 13. In certain embodiments, the dsRNA compound is an siRNA compound, wherein the antisense strand comprises any one of the antisense nucleotide sequences in any one of Tables 2, 5, 7, 9, 10 or 13. In certain embodiments, the siRNA compound comprises oligomeric sequences as shown in Tables 2, 5, 7, 9, 10 or 13. In certain embodiments, the oligomeric sequences comprise a 13, 14, 15, 16, 17, 18, 19, 20 or 21 nucleoside long portion of any sequence shown in Tables 2, 5, 7, 9, 10 or 13. In some embodiments, the dsRNA (e.g. siRNA) compound comprises the antisense strand of any one of the antisense nucleotide sequences of Table 13. In some embodiments, the dsRNA (e.g. siRNA) compound comprises the antisense strand of any one of the antisense nucleotides of SEQ ID NOs: 3, 5, 7, 9, 11, 13, 15, 17, 19, 21, 23, 28, 30, 32, 35, 37, 39, 42, 44, 46, 47, 50, 52 and 54. In a particular embodiment, the dsRNA (e.g. siRNA) compound comprises the antisense strand of the nucleotide sequence of SEQ ID NO: 62. In one embodiment, the dsRNA (e.g. siRNA) compound comprises a 13, 14, 15, 16, 17, 18, 19 or 20 nucleoside long portion of the sequence of SEQ ID NO: 62. In a preferred embodiment, the dsRNA (e.g., siRNA) compound comprises the antisense strand of sequence of SEQ ID NOs: 9 or 19, or a 13, 14, 15, 16, 17, 18, 19 or 20 nucleoside long portion thereof.

In one embodiment, a double-stranded ribonucleic acid (dsRNA) compound for inhibiting expression of angiotensinogen (AGT) in a cell comprises a sense strand and an antisense strand forming a double stranded portion, wherein the sense strand comprises any one of the sense nucleotide sequences in any one of Tables 2, 5, 7, 9, 10 or 13. In certain embodiments, the dsRNA compound is an siRNA compound, wherein the sense strand comprises any one of the sense nucleotide sequences in any one of Tables 2, 5, 7, 9, 10 or 13. In certain embodiments, the siRNA compound comprises oligomeric sequences as shown in Tables 2, 5, 7, 9, 10 or 13. In certain embodiments, the oligomeric sequences comprise a 13, 14, 15, 16, 17, 18, 19, 20 or 21 nucleoside long portion of any sequence shown in Tables 2, 5, 7, 9, 10 or 13. In some embodiments, the dsRNA (e.g. siRNA) compound comprises the sense strand nucleotide sequence in Table 13. In some embodiments, the dsRNA (e.g. siRNA) compound comprises the sense strand of any one of the sense nucleotides of SEQ ID NOs: 2, 4, 6, 8, 10, 12, 14, 16, 18, 20, 22, 27, 29, 31, 33, 34, 36, 38, 40, 41, 43, 45, 48, 49, 51, 53 and 55. In a particular embodiment, the dsRNA (e.g. siRNA) compound comprises the sense strand nucleotide sequence of SEQ ID NO: 61. In one embodiment, the dsRNA (e.g. siRNA) compound comprises a 13, 14, 15, 16, 17, 18, 19 or 20 nucleoside long portion of the sequence of SEQ ID NO: 61. In a preferred embodiment, the siRNA compound comprises the sense strand of the sequence of SEQ ID NO: 8, 33 or 55, preferably 55, or a 13, 14, 15, 16, 17, 18, 19 or 20 nucleoside long portion thereof.

In one embodiment, a double-stranded ribonucleic acid (dsRNA) compound for inhibiting expression of angiotensinogen (AGT) in a cell comprises a sense strand and an antisense strand forming a double stranded portion, wherein the sense strand comprises any one of the sense nucleotide sequences in any one of Tables 2, 5, 7, 9, 10 or 13, and wherein the antisense strand comprises any one of the antisense nucleotide sequences in any one of Tables 2, 5, 7, 9, 10 or 13. In certain embodiments, the dsRNA compound is an siRNA compound, wherein the sense strand comprises any one of the sense nucleotide sequences in any one of Tables 2, 5, 7, 9, 10 or 13, and wherein the antisense strand comprises any of the antisense nucleotide sequences in any one of Tables 2, 5, 7, 9, 10 or 13. In certain embodiments, the sense strand or antisense strand comprises a 13, 14, 15, 16, 17, 18, 19, 20 or 21 nucleoside long portion of any sequence shown in Tables 2, 5, 7, 9, 10 or 13. In a particular embodiment, the dsRNA (e.g. siRNA) compound comprises the sense strand of the nucleotide sequence of SEQ ID NO: 61 and the antisense strand of the nucleotide sequence of SEQ ID NO: 62. In one embodiment, the dsRNA (e.g. siRNA) compound comprises a 13, 14, 15, 16, 17, 18, 19 or 20 nucleoside long portion of the sequences of SEQ ID NO: 61 and/or 62. In a preferred embodiment, the dsRNA (e.g., siRNA) compound comprises the antisense sequence of SEQ ID NOs: 9 or 19, and the sense sequence of SEQ ID NOs: 8, 33 or 55, or a 13, 14, 15, 16, 17, 18, 19 or 20 nucleoside long portion thereof. In a preferred embodiment, the sense strand comprises the sequence of SEQ ID NO: 55, or a 13, 14, 15, 16, 17, 18, 19 or 20 nucleoside long portion thereof, and the antisense strand comprises the sequence of SEQ ID NOs: 9 or 19, or a 13, 14, 15, 16, 17, 18, 19 or 20 nucleoside long portion thereof.

In certain embodiments, the dsRNA comprises at least one modified nucleotide. In another embodiment, substantially all of the nucleotides of the sense strand are modified nucleotides; substantially all of the nucleotides of the antisense strand are modified nucleotides; or substantially all of the nucleotides of the sense strand and substantially all of the nucleotides of the antisense strand are modified nucleotides. Substantially all refers to at least about 70%, 75%, 80%, 85%, 90% or 95% of the nucleosides being modified. In a further embodiment, all of the nucleotides of the sense strand are modified nucleotides; all of the nucleotides of the antisense strand are modified nucleotides; or all of the nucleotides of the sense strand and all of the nucleotides of the antisense strand are modified nucleotides. Modifications are preferably selected from the group consisting of phosphorothioate internucleotide (PS) linkage, modifications of the furanose ring (e.g., 2' substituted nucleosides including nucleosides with a fluoro (2'-F), O-methyl (2'-OMe), O-methoxyethyl (2'-MOE), H (deoxyribonucleotide) or bicyclic sugar modifications), and combinations thereof.

In certain embodiments, the dsRNA comprises a strand comprising at least one phosphorothioate internucleotide (PS) linkage. In certain embodiments, the dsRNA comprises a strand comprising a phosphorothioate internucleotide (PS) linkage adjacent to a deoxyribonucleoside (D) or ribonucleoside (R). In certain embodiments, the dsRNA comprises a phosphorothioate internucleotide (PS) linkage adjacent to the deoxyribonucleoside (D) or ribonucleoside (R) on the 5' side, the 3' side or both sides. In certain embodiments, the dsRNA comprises a strand comprising a phosphorothioate internucleotide (PS) linkage adjacent to 2 nucleosides at the 5' end of the strand and/or 2 nucleosides at the 3' end of the strand.

In certain embodiments, the dsRNA comprises an siRNA. In a preferred embodiment, the siRNA comprises any one of the ARNATAR designed siRNAs listed in any one of Tables 2, 5, 7, 9, 10 or 13. In a preferred embodiment, the dsRNA comprises the nucleotide sequence and chemical modifications of ATsi786 (SEQ ID NOs: 9 and 55) or ATsi787 (SEQ ID NOs: 19 and 55). In a preferred embodiment, the siRNA comprises the nucleotide sequence and chemical modifications of ATsi786 (SEQ ID NOs: 9 and 55) or ATsi787 (SEQ ID NOs: 19 and 55).

dsRNA can be trafficked into target cells by a variety of modalities. In certain embodiments, dsRNA compounds enter cells via viral delivery vectors, lipid-based delivery, polymer-based delivery, and/or conjugate-based delivery.

In certain embodiments, the dsRNA compound described herein further comprises a conjugate moiety. In certain embodiments, the siRNA listed in any one of Tables 2, 5, 7, 9, 10 or 13 comprises a conjugate moiety. The conjugate can be selected from cholesterols, lipids, carbohydrates, phospholipids, biotin, phenazine, folate, phenanthridine, anthraquinone, acridine, fluoresceins, rhodamines, coumarins, and dyes. In a preferred embodiment, the conjugate moiety is an N-Acetylgalactosamine (GalNAc)-comprising moiety. It is to be understood that the GalNAc-comprising moiety will usually contain at least one GalNAc compound and a linker for attachment to the dsRNA. In an embodiment, the conjugate can be attached to the 3' end of a sense strand. In a preferred embodiment, the dsRNA compound is an siRNA conjugated to a GalNAc-comprising moiety.

Certain embodiments disclosed herein provide a compound comprising an siRNA for inhibiting expression of AGT in a cell, wherein the siRNA comprises a sense strand and an antisense strand forming a duplex, wherein the sense strand (ATs786 or ATs787 as shown in Table 13, SEQ ID NO: 55) comprises the formula:

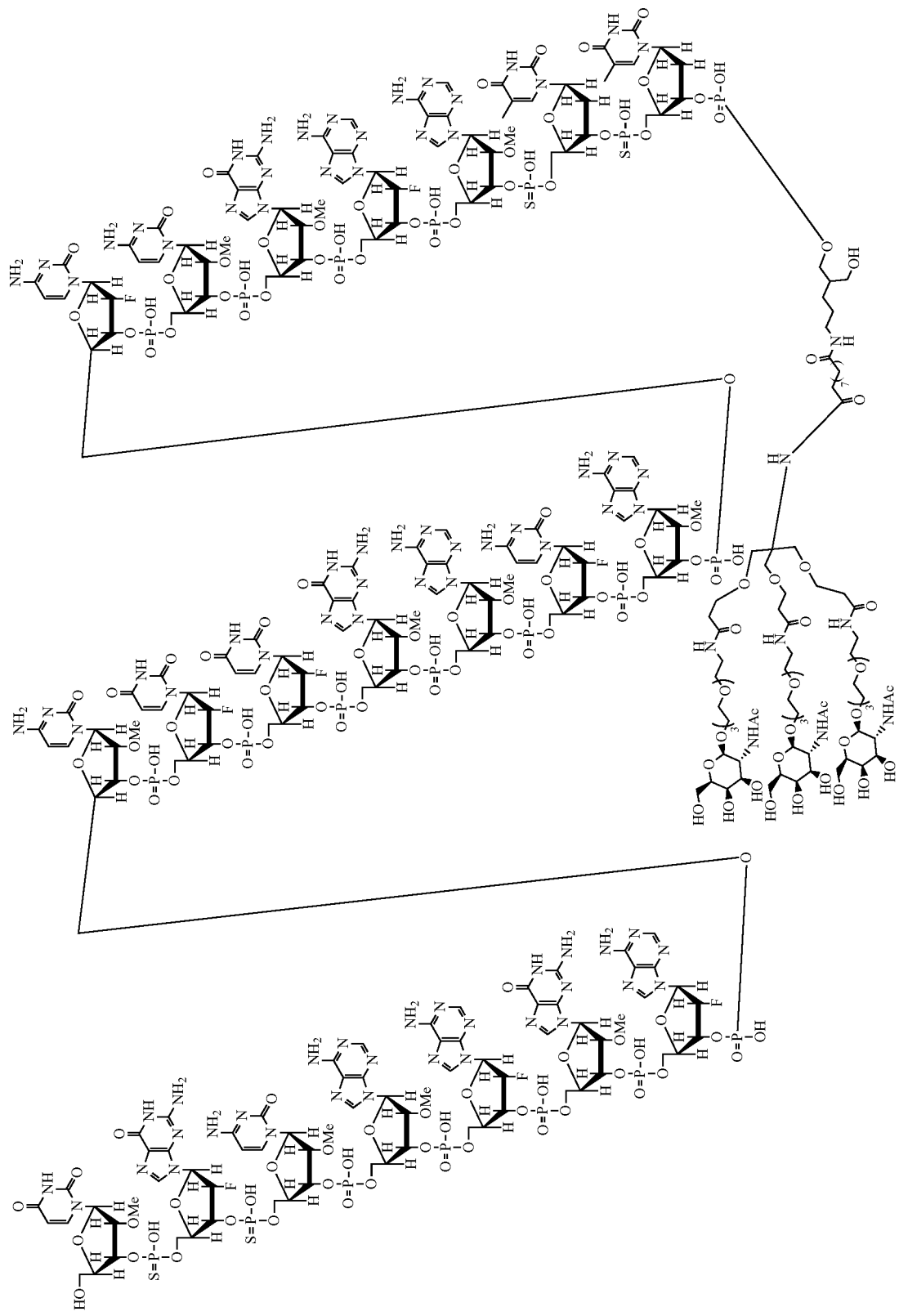

Certain embodiments disclosed herein provide a compound comprising an siRNA for inhibiting expression of AGT in a cell, wherein the siRNA comprises an antisense strand and an antisense strand forming a duplex, wherein the antisense strand (ATa786 as shown in Table 13, SEQ ID NO: 9) comprises the formula:

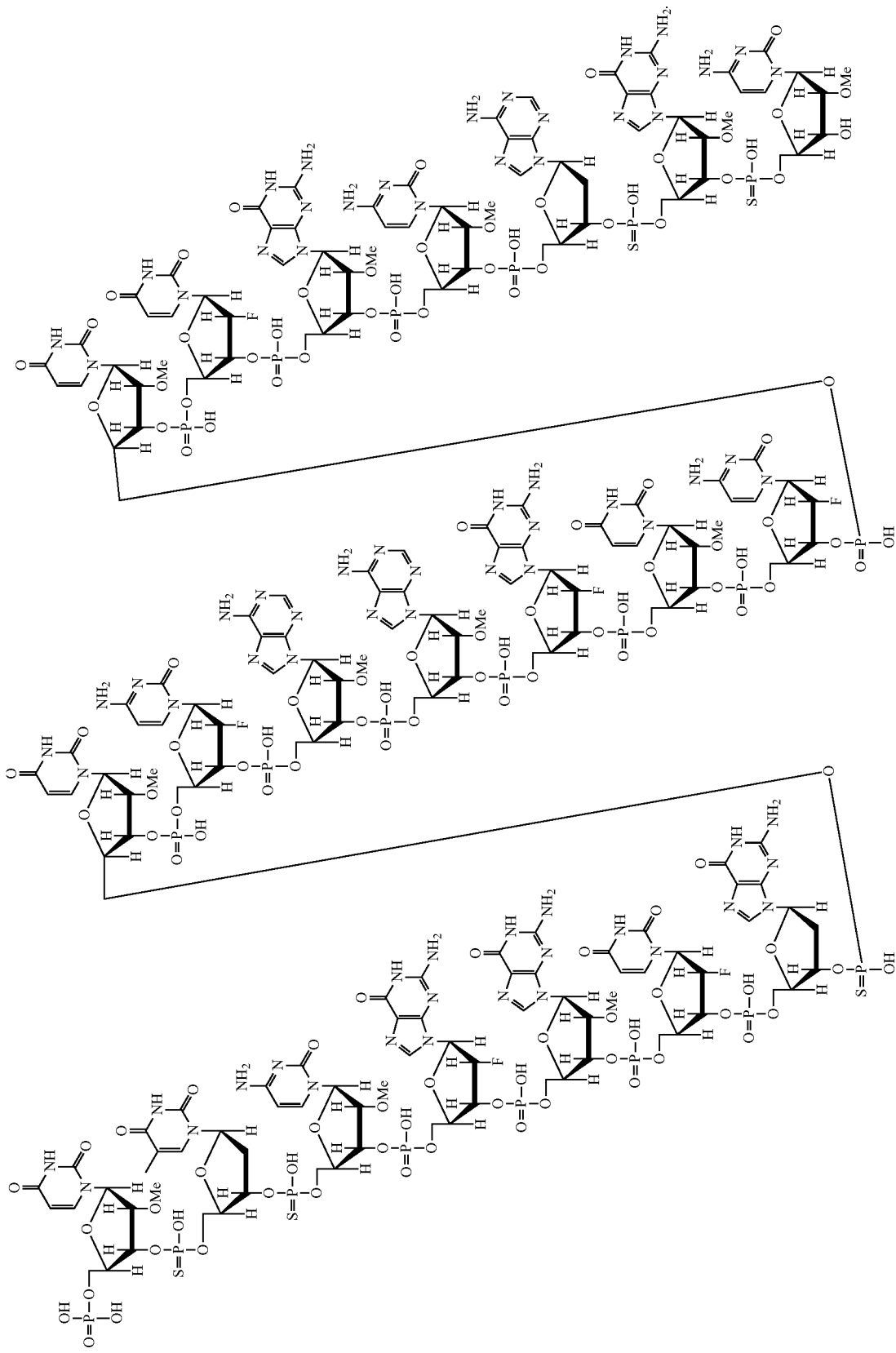

Certain embodiments disclosed herein provide a compound comprising an siRNA for inhibiting expression of AGT in a cell, wherein the siRNA comprises an antisense strand and an antisense strand forming a duplex, wherein the antisense strand (ATa787 as shown in Table 13, SEQ ID NO: 19) comprises the formula:

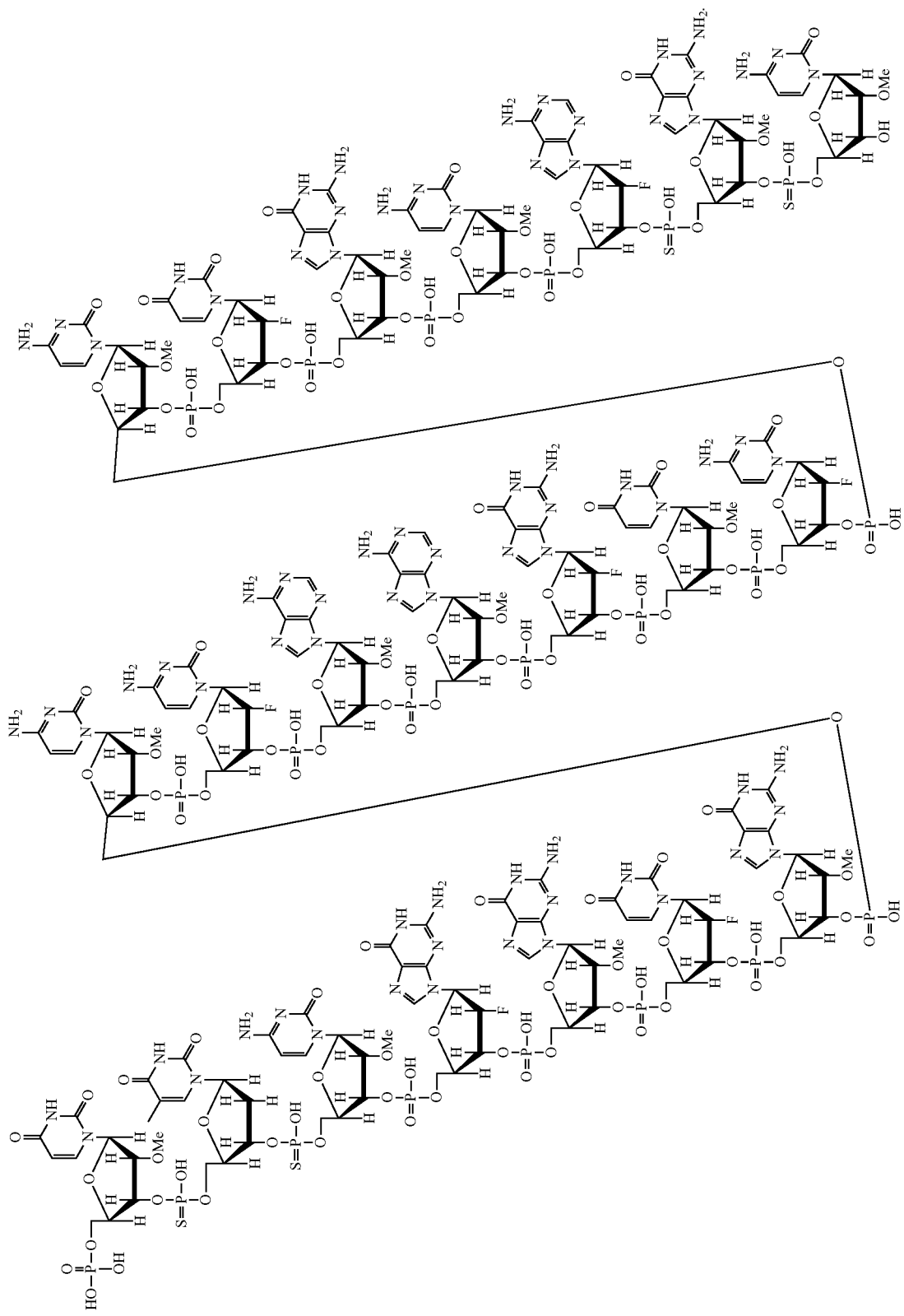

Certain embodiments disclosed herein provide a compound comprising an siRNA for inhibiting expression of AGT in a cell, wherein the siRNA comprises a sense strand and an antisense strand forming a duplex, wherein the sense strand (ATs786 as shown in Table 13, SEQ ID NO: 55) comprises the formula:

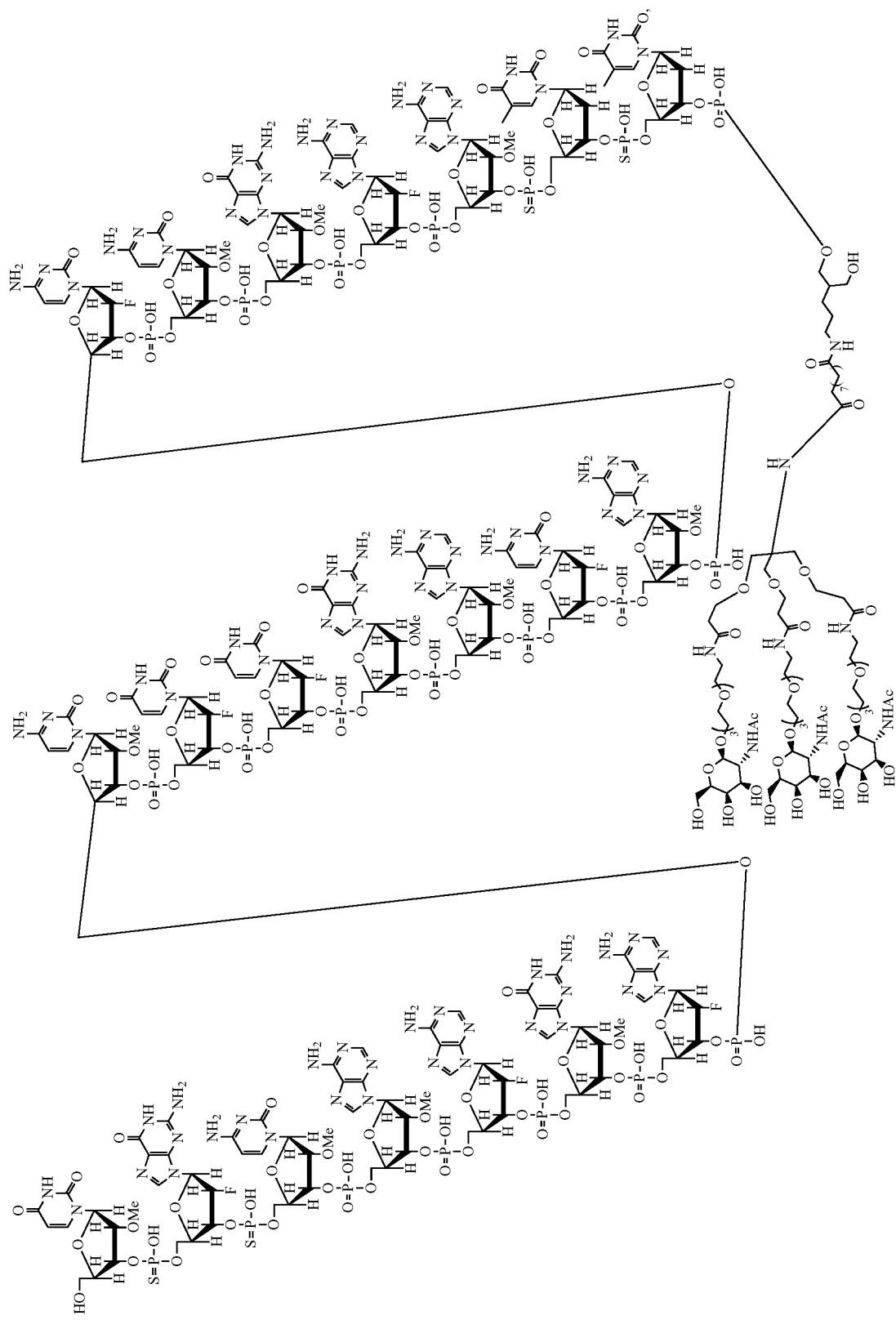

and the antisense strand (ATa786 as shown in Table 13, SEQ ID NO: 9) comprises the formula:

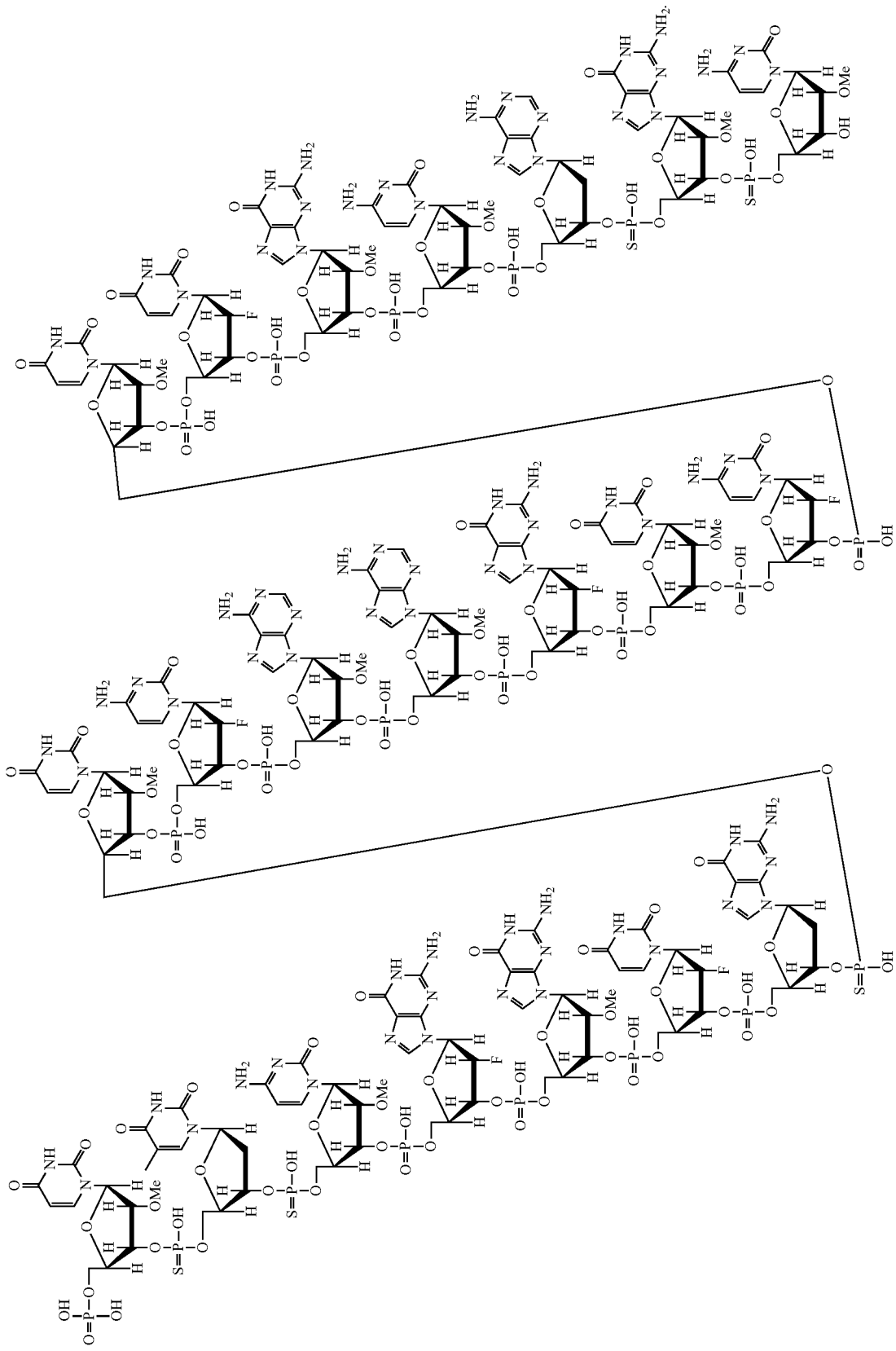

Certain embodiments disclosed herein provide a compound comprising an siRNA for inhibiting expression of AGT in a cell, wherein the siRNA comprises a sense strand and an antisense strand forming a duplex, wherein the sense strand (ATs787 as shown in Table 13, SEQ ID NO: 55) comprises the formula:

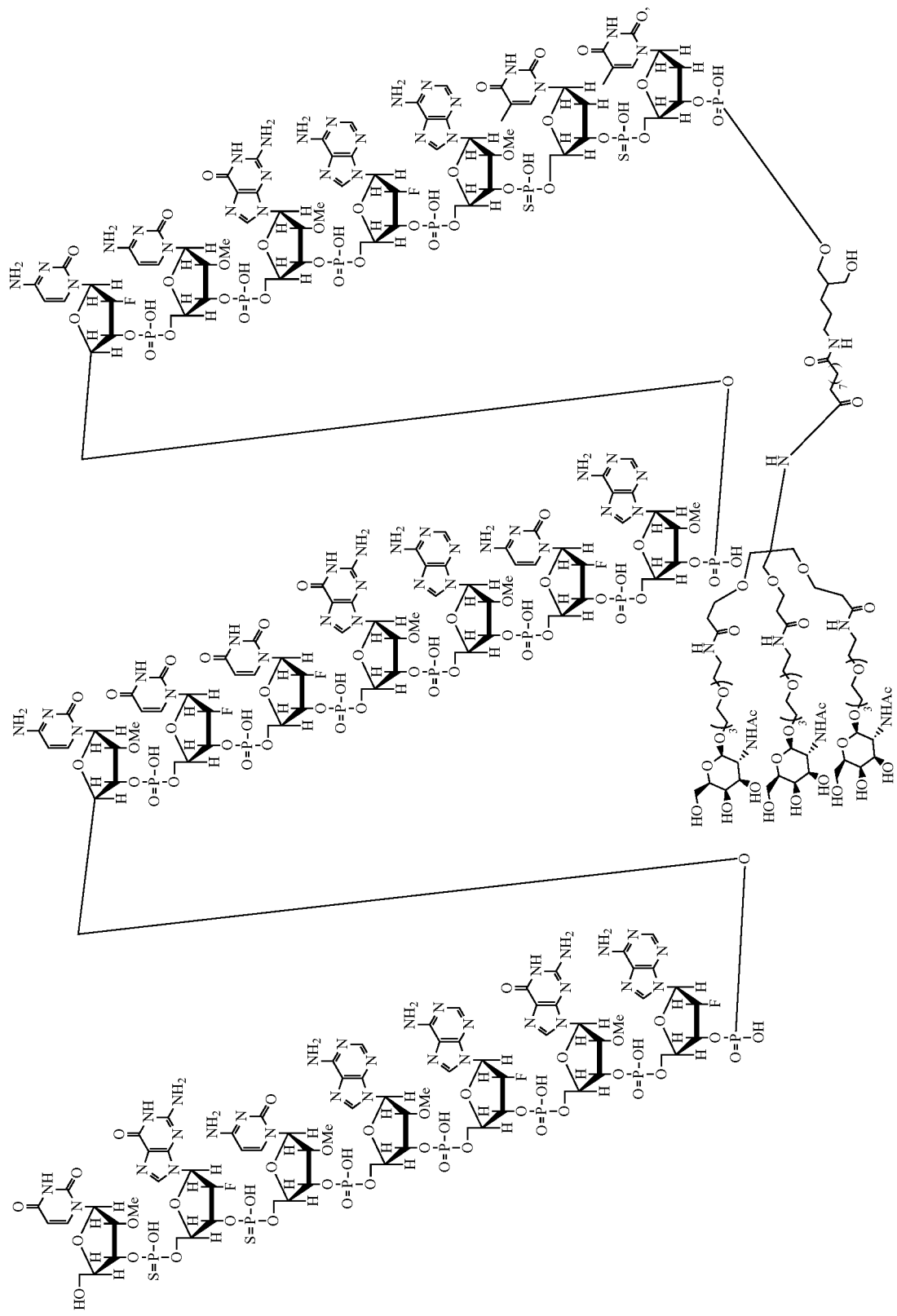

and the antisense strand (ATa787 as shown in Table 13, SEQ ID NO: 19) comprises the formula:

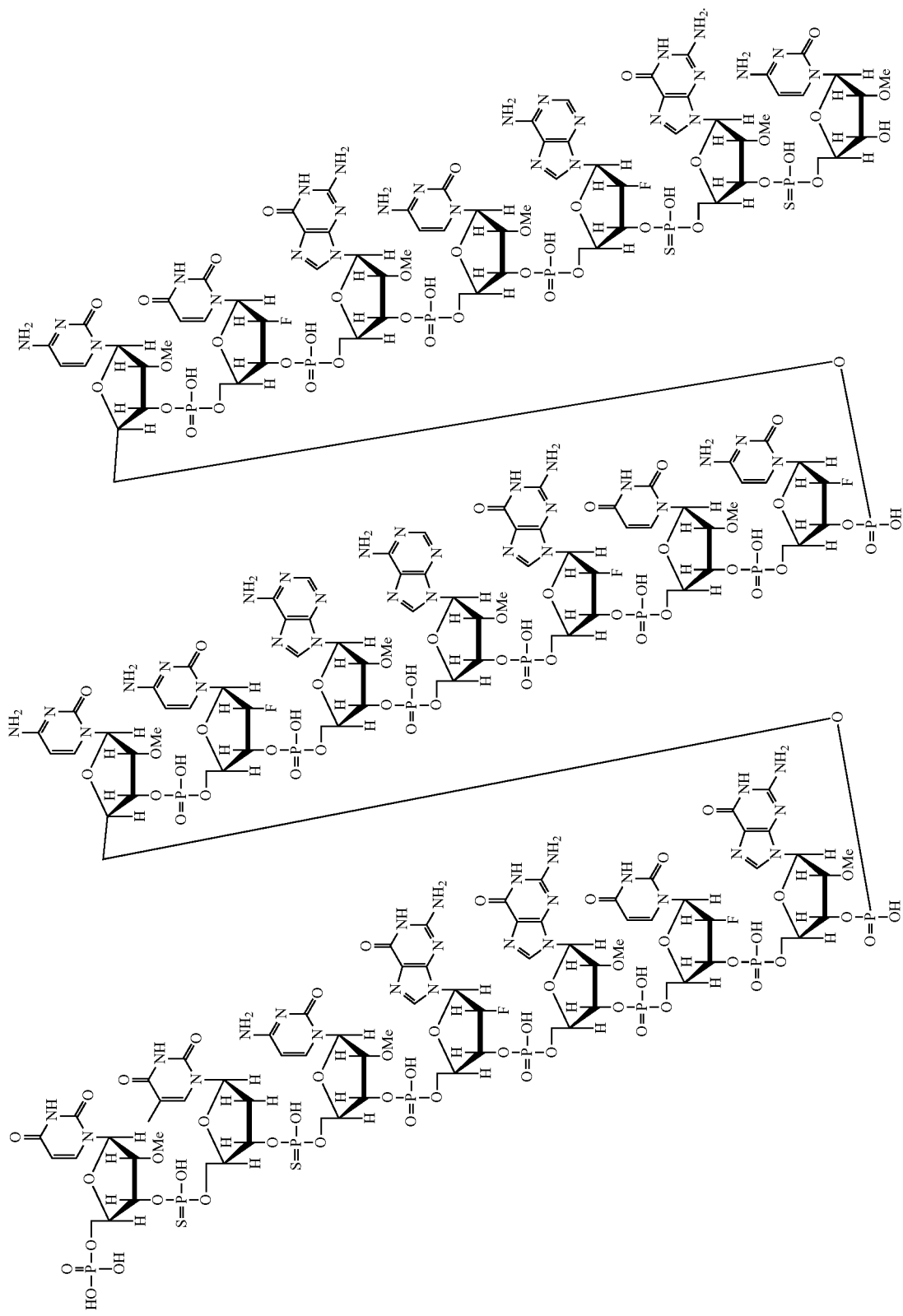

In certain embodiments, the compounds or compositions disclosed herein comprise a salt of the dsRNA. In certain embodiments, the compounds or compositions disclosed herein comprise a salt of the siRNAs disclosed in Tables 2, 5, 7, 9, 10 and 13.

Certain embodiments provide a method of inhibiting expression of angiotensinogen (AGT) in a cell comprising contacting the cell with a dsRNA compound or a pharmaceutical composition described herein in an amount sufficient to inhibit expression of AGT, thereby inhibiting expression of AGT in the cell. In certain embodiments, the compounds or compositions comprise a dsRNA that inhibits expression of angiotensinogen (AGT) in a cell by at least about 70%, 75%, 80%, 85%, 90%, 95%, 98% or 99%. In certain embodiments, the dsRNA is an siRNA that inhibits expression of angiotensinogen (AGT) by at least about 70%, 75%, 80%, 85%, 90%, 95%, 98% or 99%. In certain embodiments, the compound or composition that inhibits expression of AGT is provided in Tables 2, 5, 7, 9, 10 or 13. In a preferred embodiment, the sense strand of the siRNA comprises the nucleotide sequence and chemical modification of SEQ ID NOs: 8, 33 or 55). In a preferred embodiment, the antisense strand of the siRNA comprises the nucleotide sequence and chemical modification of SEQ ID NOs: 9 or 19). In a further preferred embodiment, the siRNA comprises the nucleotide sequence and chemical modifications of ATsi786 (SEQ ID NOs: 9 and 55) or ATsi787 (SEQ ID NOs: 19 and 55). The amount of angiotensinogen (AGT) expression inhibition can be generally measured by assessing the mRNA and/or protein levels in a cell after contacting the cells with a dsRNA compound or a pharmaceutical composition and comparing the mRNA or protein levels to cells which did not contact the dsRNA.

In certain embodiments, the siRNA compound that inhibits expression of angiotensinogen (AGT) is provided in Tables 2, 5, 7, 9, 10 or 13 and inhibits expression of AGT by at least about 85%. In a preferred embodiment, the siRNA comprises the nucleotide sequence and chemical modifications of ATsi786 (SEQ ID NOs: 9 and 55) or ATsi787 (SEQ ID NOs: 19 and 55). The amount of angiotensinogen (AGT) expression inhibition can be generally measured by assessing the mRNA and/or protein levels in a cell after contacting the cells with a dsRNA compound or a pharmaceutical composition and comparing the mRNA or protein levels to cells which did not contact the dsRNA.

In certain embodiments, the siRNA compound that inhibits expression of angiotensinogen (AGT) is provided in Tables 2, 5, 7, 9, 10 or 13 and inhibits expression of AGT by at least about 90%. In a preferred embodiment, the siRNA comprises the nucleotide sequence and chemical modifications of ATsi786 (SEQ ID NOs: 9 and 55) or ATsi787 (SEQ ID NOs: 19 and 55). The amount of angiotensinogen (AGT) expression inhibition can be generally measured by assessing the mRNA and/or protein levels in a cell after contacting the cells with a dsRNA compound or a pharmaceutical composition and comparing the mRNA or protein levels to cells which did not contact the dsRNA.

Certain embodiments of the invention provide an assay to determine the level of AGT inhibition in a sample from a subject. In certain embodiments, the AGT assay comprises: a) administering a compound or composition disclosed herein to a subject in an amount sufficient to inhibit expression of AGT; b) removing a sample from a subject; c) determining the amount of AGT protein present in the sample; thereby determining the amount of AGT inhibition by the compound or composition. In certain embodiments, the sample is from blood, serum, urine and/or liver. In certain embodiments, the amount of AGT protein present in the sample is determined by isolating the AGT protein from the sample, Western Blotting the protein and probing with an AGT specific monoclonal antibody to assess the amount of AGT protein present. In certain embodiments, the amount of AGT protein present in the sample is determined using ELISA.

In certain embodiments, a pharmaceutical composition for inhibiting expression of angiotensinogen (AGT) in a cell comprises a dsRNA, alone or in combination with a pharmaceutically acceptable carrier, diluent and/or excipient. In certain embodiments, the dsRNA is in a buffer solution. The buffer solution can comprise acetate, citrate, prolamine, carbonate, or phosphate or any combination thereof. In one embodiment, the buffer solution is phosphate buffered saline (PBS). In certain embodiments, the dsRNA in the pharmaceutical composition is an siRNA. In certain embodiments, the siRNA sequence is as provided in Tables 2, 5, 7, 9, 10 or 13. In a preferred embodiment, the siRNA comprises the nucleotide sequence and chemical modifications of ATsi786 (SEQ ID NOs: 9 and 55) or ATsi787 (SEQ ID NOs: 19 and 55).

Certain embodiments of the invention provide a method for treating a RAAS associated disease, disorder and/or condition in a subject, comprising administering to the subject in need thereof a therapeutically effective amount of a compound or composition disclosed herein in an amount sufficient to inhibit expression of AGT, whereby inhibiting expression of AGT in the subject treats the RAAS associated disease, disorder and/or condition in the subject. In certain embodiments, the compound or composition that inhibits expression of an AGT is as provided in Tables 2, 5, 7, 9, 10 or 13. In a preferred embodiment, the siRNA comprises the nucleotide sequences of SEQ ID NOs: 61 and 62. In a further preferred embodiment, the siRNA comprises the nucleotide sequence and chemical modifications of ATsi786 (SEQ ID NOs: 9 and 55) or ATsi787 (SEQ ID NOs: 19 and 55).

Certain embodiments of the invention provide a method for treating a RAAS associated disease, disorder and/or condition in a subject, comprising administering to the subject in need thereof a therapeutically effective amount of a compound comprising the ARNATAR designed dsRNA listed in Tables 2, 5, 7, 9, 10 or 13, or a pharmaceutical composition comprising the dsRNA listed in Tables 2, 5, 7, 9, 10 or 13, in an amount sufficient to inhibit expression of AGT whereby inhibiting expression of AGT in the subject treats the RAAS associated disease, disorder and/or condition in the subject. In certain embodiments, the dsRNA for treating a RAAS associated disease, disorder and/or condition in the subject is an siRNA listed in Tables 2, 5, 7, 9, 10 or 13. In a preferred embodiment, the siRNA comprises the nucleotide sequence of SEQ ID NOs: 61 and 62. In a further preferred embodiment, the siRNA comprises the nucleotide sequence and chemical modifications of ATsi786 (SEQ ID NOs: 9 and 55) or ATsi787 (SEQ ID NOs: 19 and 55).

In certain embodiments, a symptom of a RAAS associated disease, disorder and/or condition is treated in a subject comprising administering to the subject in need thereof a therapeutically effective amount of a compound comprising the ARNATAR designed dsRNA listed in Tables 2, 5, 7, 9, 10 or 13, or a pharmaceutical composition comprising the dsRNA listed in Tables 2, 5, 7, 9, 10 or 13 in an amount sufficient to inhibit expression of AGT whereby inhibiting expression of AGT in the subject treats the symptom of the RAAS associated disease, disorder and/or condition. In certain embodiments, the dsRNA for treating the symptom in the subject is an siRNA listed in Tables 2, 5, 7, 9, 10 or 13. In a preferred embodiment, the siRNA comprises the nucleotide sequence of SEQ ID NOs: 61 and 62. In a further preferred embodiment, the siRNA comprises the nucleotide sequence and chemical modifications of ATsi786 (SEQ ID NOs: 9 and 55) or ATsi787 (SEQ ID NOs: 19 and 55).

In certain embodiments, the RAAS associated disease, disorder and/or condition is selected from the group consisting of high blood pressure, hypertension, borderline hypertension, primary hypertension, secondary hypertension isolated systolic or diastolic hypertension, pregnancy-associated hypertension, diabetic hypertension, resistant hypertension, refractory hypertension, paroxysmal hypertension, renovascular hypertension, Goldblatt hypertension, hypertension associated with low plasma renin activity or plasma renin concentration, ocular hypertension, glaucoma, pulmonary hypertension, portal hypertension, systemic venous hypertension, systolic hypertension, labile hypertension; hypertensive heart disease, hypertensive nephropathy, atherosclerosis, arteriosclerosis, vasculopathy, diabetic nephropathy, diabetic retinopathy, chronic heart failure, cardiomyopathy, diabetic cardiac myopathy, glomerulosclerosis, coarctation of the aorta, aortic aneurism, ventricular fibrosis, heart failure, myocardial infarction, angina, stroke, renal disease, renal failure, systemic sclerosis, intrauterine growth restriction (IUGR), fetal growth restriction, obesity, liver steatosis/fatty liver, non-alcoholic steatohepatitis (NASH), non-alcoholic fatty liver disease (NAFLD), glucose intolerance, type 2 diabetes (non-insulin dependent diabetes), and metabolic syndrome. In a preferred embodiment, the RAAS associated disease, disorder and/or condition is hypertension.

Certain embodiments of the invention provide a method for treating hypertension in a subject, comprising administering to the subject in need thereof a therapeutically effective amount of a compound comprising the ARNATAR designed dsRNA listed in Tables 2, 5, 7, 9, 10 or 13, or a pharmaceutical composition comprising the dsRNA listed in Tables 2, 5, 7, 9, 10 or 13, in an amount sufficient to inhibit expression of AGT whereby inhibiting expression of AGT in the subject treats the hypertension in the subject. In certain embodiments, the dsRNA for treating hypertension in the subject is an siRNA listed in Tables 2, 5, 7, 9, 10 or 13. In a preferred embodiment, the siRNA comprises the nucleotide sequence of SEQ ID NOs: 61 and 62. In a further preferred embodiment, the siRNA comprises the nucleotide sequence and chemical modifications of ATsi786 (SEQ ID NOs: 9 and 55) or ATsi787 (SEQ ID NOs: 19 and 55). Types of hypertension include primary, secondary, resistant, malignant and isolated hypertension.

In certain embodiments, the subject in need of therapeutic treatment with a compound or composition disclosed herein is a human subject. In certain embodiments, the subject has: a systolic blood pressure of at least 130 mm Hg and a diastolic blood pressure of at least 80 mm Hg; or, a systolic blood pressure of at least 140 mm Hg and a diastolic blood pressure of at least 80 mm Hg. In certain embodiments, the subject has systolic blood pressure above about 120 mm Hg, 125 mm Hg, 130 mm Hg, 135 mmHg or 140 mmHg. In certain embodiments, the subject has systolic blood pressure between 130-160 mm Hg, 130-165 mm Hg, 130-170 mm Hg, 130-180 mm Hg, 135-160 mm Hg, 135-165 mm Hg, 135-170 mm Hg, 140-170 mm Hg, 145-180 mm Hg, 155-180 mm Hg. In certain embodiments, the subject is part of a group susceptible to salt sensitivity, is overweight, is obese, and/or is pregnant.

Certain embodiments of the invention provide a method for treating a subject having a disease, disorder and/or condition that would benefit from reduction in angiotensinogen (AGT) expression, comprising administering to the subject in need thereof a therapeutically effective amount of a compound comprising the dsRNA listed in Tables 2, 5, 7, 9, 10 or 13, or a pharmaceutical composition comprising any of the dsRNA listed in Tables 2, 5, 7, 9, 10 or 13, in an amount sufficient to inhibit expression of AGT whereby inhibiting expression of AGT in the subject treats the subject having the disorder that would benefit from reduction in AGT expression. In certain embodiments, the dsRNA is an siRNA listed in Tables 2, 5, 7, 9, 10 or 13. In a preferred embodiment, the siRNA comprises the nucleotide sequence of SEQ ID NOs: 61 and 62. In a further preferred embodiment, the siRNA comprises the nucleotide sequence and chemical modifications of ATsi786 (SEQ ID NOs: 9 and 55) or ATsi787 (SEQ ID NOs: 19 and 55). In certain embodiments, the disease, disorder and/or condition is a RAAS associated disease, disorder and/or condition.

Certain embodiments of the invention provide a method of preventing or reducing at least one symptom in a subject having a disorder that would benefit from reduction in angiotensinogen (AGT) expression, comprising administering to the subject in need thereof a prophylactically effective amount of a compound comprising the dsRNA listed in Tables 2, 5, 7, 9, 10 or 13, or a pharmaceutical composition comprising any of the dsRNA listed in Tables 2, 5, 7, 9, 10 or 13, in an amount sufficient to inhibit expression of AGT whereby inhibiting expression of AGT in the subject prevents or reduces at least one symptom in the subject having the disorder that would benefit from reduction in AGT expression. In certain embodiments, the dsRNA is an siRNA listed in Tables 2, 5, 7, 9, 10 or 13. In a preferred embodiment, the siRNA comprises the nucleotide sequence of SEQ ID NOs: 61 and 62. In a further preferred embodiment, the siRNA comprises the nucleotide sequence and chemical modifications of ATsi786 (SEQ ID NOs: 9 and 55) or ATsi787 (SEQ ID NOs: 19 and 55). In certain embodiments, the at least one symptom is a RAAS associated symptom.

Certain embodiments provide a method for inhibiting AGT expression in a subject comprising the step of administering the compound or composition comprising the dsRNA described herein to the subject, in an amount sufficient to inhibit expression of AGT. The dsRNA compound is administered subcutaneously or intravenously to the subject. In certain embodiments, the dsRNA inhibits expression of angiotensinogen (AGT) by at least about 70%, 75%, 80%, 85%, 90%, 95%, 98% or 99%.

Certain embodiments provide a double stranded ribonucleic acid (dsRNA) compound described herein for use in medicine. Certain embodiments provide the double stranded ribonucleic acid (dsRNA) compound described herein for use in treating or preventing a RAAS associated disease, disorder and/or condition in a subject. In certain embodiments, the RAAS associated disease, disorder and/or condition is as described above.

In certain embodiments, the dsRNA is administered to the subject at a dose of about 0.01 mg/kg to about 50 mg/kg. In certain embodiments, the dsRNA is an siRNA that inhibits expression of angiotensinogen (AGT) by at least about 70%, 75%, 80%, 85%, 90%, 95%, 98% or 99%. In certain embodiments, the dsRNA is an siRNA that is administered to the subject at a dose of about 0.01 mg/kg to about 50 mg/kg. In certain embodiments, a preferred dose is selected from 700 mg, 800 mg and 900 mg. In certain embodiments, a therapeutically effective amount of the compound or composition comprising the dsRNA described herein is dosed at about 150 mg, 300 mg or 600 mg once every 3 months. In certain embodiments, a therapeutically effective amount of the compound or composition comprising the dsRNA described herein is dosed at about 150 mg, 300 mg or 600 mg once every 6 months.

In certain embodiments, after administration of the compound or composition comprising dsRNA to a subject, the level of AGT in a sample(s) from the subject is determined. In certain embodiments, the level of AGT in the subject sample(s) is an AGT nucleic acid (e.g., mRNA) level or protein level in a blood, plasma, urine or liver tissue sample (s). In certain embodiments, the dsRNA is an siRNA.

In certain embodiments, after administration of the compound or composition comprising dsRNA to a subject, additional factors are assessed. In certain embodiments, the level of bradykinin, prekallikrein, or blood pressure in the subject is determined. In certain embodiments, the dsRNA is an siRNA.

In certain embodiments, the compound or composition comprising dsRNA is administered alone or in combination with additional therapeutic agent(s) to a subject for treatment of a RAAS associated disease, disorder and/or condition, or symptom thereof. In certain embodiments, the dsRNA is an siRNA listed in Tables 2, 5, 7, 9, 10 or 13. In a preferred embodiment, the siRNA comprises the nucleotide sequence of SEQ ID NOs: 61 and 62. In a further preferred embodiment, the siRNA comprises the nucleotide sequence and chemical modifications of ATsi786 (SEQ ID NOs: 9 and 55) or ATsi787 (SEQ ID NOs: 19 and 55). In certain embodiments, the additional therapeutic agent is selected from the group consisting of a diuretic, an angiotensin converting enzyme (ACE) inhibitor, an angiotensin II receptor antagonist (also known as an angiotensin II receptor blocker (ARB)), a beta-blocker, a vasodilator, a calcium channel blocker, an aldosterone antagonist, an alpha2-agonist, a renin inhibitor, an alpha-blocker, a peripheral acting adrenergic agent, a selective DI receptor partial agonist, a nonselective alpha-adrenergic antagonist, a synthetic, a steroidal antimineralocorticoid agent, an angiotensin receptor-neprilysin inhibitors (ARNi), Entresto®, sacubitril/valsartan; or an endothelin receptor antagonist (ERA), sitaxentan, ambrisentan, atrasentan, BQ-123, zibotentan, bosentan, macitentan, and tezosentan; a combination of any of the foregoing; and a hypertension therapeutic agent formulated as a combination of agents. In certain embodiments, the additional therapeutic agent comprises an angiotensin II receptor antagonist. In certain embodiments, the angiotensin II receptor antagonist is selected from the group consisting of losartan, valsartan, olmesartan, eprosartan, and azilsartan. In certain embodiments, the additional therapeutic agent(s), when used in combination with the compounds or compositions comprising a dsRNA described herein, may provide a synergistic or additive effect in lowering blood pressure in a subject.

In one embodiments, a process for preparing the sense and/or antisense strand of the double stranded ribonucleic acid (dsRNA) compound is provided, wherein the process comprises the steps of: (a) preparing the sense and/or antisense strand by sequential coupling of modified and/or unmodified nucleotides via the phosphoramidite oligonucleotide synthesis on a solid support; (b) optionally, coupling a GalNAc-comprising moiety to the sense and/or antisense strand on the solid support via the phosphoramidite oligonucleotide synthesis; (c) detaching the sense and/or antisense strand from the solid support and removing the solid support; and (d) optionally, further purifying the sense and/or antisense strand, optionally using chromatography. Phosphoramidite oligonucleotide synthesis is generally known in the art. By this process a sense or antisense strand may be prepared that may contain a GalNAc-comprising moiety as conjugate at its 5' end. Preferably, this process is used to prepare the antisense strand that does not contain any conjugate (e.g., the antisense strand of SEQ ID NO: 9 or 19).

In one embodiments, a process for preparing the sense and/or anisense strand of the double stranded ribonucleic acid (dsRNA) compound is provided, wherein the process comprises the steps of: (a) coupling a GalNAc-comprising moiety to a solid support via the phosphoramidite oligonucleotide synthesis, (b) coupling a modified and/or unmodified nucleotide via the phosphoramidite oligonucleotide synthesis to the GalNAc-comprising moiety on the solid support; (c) sequentially coupling additional modified and/or unmodified nucleotides via the phosphoramidite oligonucleotide synthesis to prepare the sense and/or anisense strand; (d) detaching the sense and/or antisense strand from the solid support and removing the solid support; and (e) optionally, further purifying the sense and/or antisense strand, optionally using chromatography. By this process a sense or antisense strand is prepared that contains a GalNAc-comprising moiety as conjugate at its 3' end. Preferably, this process is used to prepare the sense strand containing a 3' end GalNAc conjugate (e.g., the sense strand of SEQ ID NO: 55).

In one embodiments, a process of preparing the double stranded ribonucleic acid (dsRNA) compound is provided, comprising: (a) contacting the sense prepared according any one of the above processes with the antisense strand prepared according any one of the above processes in equimolar concentrations in a solution; (b) optionally heating the solution to a temperature of about 94° C.; and (c) optionally reducing the temperature of the solution to about 25° C. Preferably, the sense strand is a sense strand containing a 3' end GalNAc conjugate and the antisense strand is an antisense strand that does not contain any conjugate. Certain embodiments provide a process for preparing an oligonucleotide (of the sense or antisense strand) for use in forming a compound or composition described herein comprising synthesizing an oligonucleotide on solid support by: (a) attaching a modified or unmodified nucleotide to the solid support by phosphoramidite chemistry; (b) removing excess phosphoramidite reaction solution; (c) removing an acid labile protecting group from the nucleotide with an acid solution; (d) removing the acid solution; (e) coupling a modified or unmodified nucleotide, GalNAc-comprising moiety, or lipophilic moiety by phosphoramidite chemistry to the unprotected nucleotide attached to the solid support to form an elongating oligonucleotide attached to the solid support; (f) removing excess phosphoramidite reaction solution; (g) capping unreacted amines or alcohols on the oligonucleotide attached to the solid support with an acetic anhydride solution to reduce branching and truncation; (h) removing the acetic anhydride solution; (i) introducing a phosphodiester linkage by an oxidizing reagent and/or a phosphorothioate linkage by a sulfurizing reagent; (j) removing the oxidizing and/or sulfurizing reagent; (k) repeating steps (c)-(j) until the desired length of the oligonucleotide is achieved; (l) removing the oligonucleotide from the solid support with an alkaline solution; (m) removing the solid support from the oligonucleotide solution; and (n) optionally, purifying the oligonucleotide using chromatography.

Certain embodiments provide a process for preparing an oligonucleotide (of the sense or antisense strand) for use in forming a compound or composition described herein comprising synthesizing an oligonucleotide on a moiety loaded solid support by: (a) attaching a modified or unmodified nucleotide to the moiety on the solid support by phosphoramidite chemistry; (b) removing excess phosphoramidite reaction solution; (c) removing an acid labile protecting group from the nucleotide with an acid solution; (d) removing the acid solution; (e) coupling a modified or unmodified nucleotide by phosphoramidite chemistry to the unprotected nucleotide attached to the solid support to form an elongating oligonucleotide attached to the solid support; (f) removing excess phosphoramidite reaction solution; (g) capping unreacted amines or alcohols on the oligonucleotide attached to the solid support with an acetic anhydride solution to reduce branching and truncation; (h) removing the acetic anhydride solution; (i) introducing a phosphodiester linkage by an oxidizing reagent and/or a phosphorothioate linkage by a sulfurizing reagent; (j) removing the oxidizing and/or sulfurizing reagent; (k) repeating steps (c)-(j) until the desired length of the oligonucleotide is achieved; (l) removing the oligonucleotide from the solid support with an alkaline solution; (m) removing the solid support from the oligonucleotide solution; and (n) optionally, purifying the oligonucleotide using chromatography. In certain embodiments, the moiety loaded on the solid support is selected from a GalNAc-comprising moiety, cholesterol, lipid, carbohydrate, phospholipid, biotin, phenazine, folate, phenanthridine, anthraquinone, acridine, fluorescein, rhodamine, coumarin, dye, and the like. In a preferred embodiment, the moiety loaded on the solid support is a GalNAc-comprising moiety.

The present invention also provides kits comprising any of the compounds or any of the pharmaceutical compositions disclosed herein, and optionally, a label (e.g., instructions for use). The present invention provides a vial comprising any of the compounds or any of the pharmaceutical compositions disclosed herein. The present invention provides a syringe comprising any of the compounds or any of the pharmaceutical compositions disclosed herein. In one embodiment, the invention provides a kit for performing a method of inhibiting expression of AGT in a subject by administering to the subject in need thereof an amount effective to inhibit expression of the AGT in the subject. The kit comprises a dsRNA compound and instructions for use and, optionally, means for administering the dsRNA to a subject. In certain embodiments, the compound or pharmaceutical composition is a dsRNA listed in Tables 2, 5, 7, 9, 10 or 13. In certain embodiments, the dsRNA is an siRNA listed in Tables 2, 5, 7, 9, 10 or 13. In a preferred embodiment, the siRNA of the kit comprises the nucleotide sequence and chemical modifications of ATsi786 (SEQ ID NOs: 9 and 55) or ATsi787 (SEQ ID NOs: 19 and 55).

The following description applies to all of the above embodiments.

Oligomeric Compounds

Oligomeric compounds of the invention include, but are not limited to, double stranded RNA (dsRNA) compounds such as short hairpin RNAs (shRNAs) and small interfering RNAs (siRNAs) target the AGT gene by targeting the AGT mRNA. An oligomeric compound of the invention comprises an "antisense strand" to a target nucleic acid, meaning that is is capable of undergoing hybridization to a target nucleic acid through hydrogen bonding.

In certain embodiments, an oligomeric compound has a nucleobase sequence that, when written in the 5' to 3' direction, comprises the reverse complement of the target segment of a target nucleic acid to which it is targeted. For example, in certain such embodiments, an siRNA compound comprises an antisense strand which has a nucleobase sequence that, when written in the 5' to 3' direction, comprises the reverse complement of the target segment of a target nucleic acid to which it is targeted.

In certain embodiments, an oligomeric compound is 12-30 subunits in length. In certain embodiments, an oligomeric compound is 18 to 30 subunits in length. In certain embodiments, an oligomeric compound is 12 to 22 subunits in length. In certain embodiments, an oligomeric compound is 14 to 30 subunits in length. In certain embodiments, an oligomeric compound is 14 to 21 subunits in length. In certain embodiments, an oligomeric compound is 15 to 30 subunits in length. In certain embodiments, an oligomeric compound is 15 to 21 subunits in length. In certain embodiments, an oligomeric compound is 16 to 30 subunits in length. In certain embodiments, an oligomeric compound is 16 to 21 subunits in length. In certain embodiments, an oligomeric compound is 17 to 30 subunits in length. In certain embodiments, an oligomeric compound is 17 to 21 subunits in length. In certain embodiments, an oligomeric compound is 18 to 30 subunits in length. In certain embodiments, an oligomeric compound is 18 to 21 subunits in length. In certain embodiments, an oligomeric compound is 20 to 30 subunits in length. In certain embodiments, an oligomeric compound is 15 subunits in length. In certain embodiments, an oligomeric compound is 16 subunits in length. In certain embodiments, an oligomeric compound is 17 subunits in length. In certain embodiments, an oligomeric compound is 18 subunits in length. In certain embodiments, an oligomeric compound is 20 subunits in length. In certain embodiments, an oligomeric compound is 21 subunits in length. In certain embodiments, an oligomeric compound is 22 subunits in length. In certain embodiments, an oligomeric compound is 23 subunits in length. In certain embodiments, an oligomeric compound is 25 subunits in length. In certain embodiments, an oligomeric compound is 25 subunits in length. In other embodiments, the oligomeric compound is 8 to 80, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked subunits. In certain such embodiments, the oligomeric compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments, the oligomeric compound is an siRNA.

It is possible to increase or decrease the length of an oligomeric compound, such as an siRNA compound, and/or introduce base mismatch(es) without eliminating activity (U.S. Pat. No. 7,772,203, incorporated-by-reference herein). For example, it is possible to introduce non-canonical base pairings (e.g., A:G, A:C, G:U, I:U, I:A, I:C) into an oligomeric compound without eliminating activity. In certain embodiments, designing oligomeric compounds with one or more non-canonical base pairings, i.e., mismatch(es), enhances the activity of the oligomeric compound.

The oligomeric compound can comprise a mismatch(es) with the target, between the oligomeric strands within the duplex, or combinations thereof. The mismatch may occur throughout the siRNA such as in the overhang (a portion of the sense or antisense strand at the 5' and/or 3' end of a duplexed siRNA that has no complementary strand) or the duplex portion.

Oligomeric Compound Motifs

A motif refers to a pattern of modification of an oligomeric compound. Various motifs have been described in the art and are incorporated-by-reference herein (e.g., U.S. Pat. Nos. 11,203,755; 10,870,849; EP Patent 1,532,248; U.S. Pat. Nos. 11,406,716; 10,668,170; 9,796,974; 8,754,201; 10,837, 013; 7,732,593; 7,015,315; 7,750,144; 8,420,799; 8,809, 516; 8,796,436; 8,859,749; 9,708,615; 10,233,448; 10,273, 477; 10,612,024; 10,612,027; 10,669,544; 11,401,517; USSN 2020/0031862; USSN 2016/0272970). However, new and improved motifs are constantly being sought.

In certain embodiments, oligomeric compounds disclosed herein, such as siRNAs, have chemically modified subunits arranged into motifs to confer on to the oligomeric compounds beneficial properties including, but not limited to: enhanced inhibitory activity to increase potency; increased binding affinity to increase specificity for a target nucleic acid, thereby limiting off-target effects and increasing safety; or enhanced resistance to degradation by in vivo nucleases thereby increasing stability and durability. In certain embodiments, the oligomeric compounds are chimeras where the peripheral nucleobases of the oligomeric compounds comprise motifs with various modified or unmodified nucleobases so as to confer increased stability, specificity, safety and potency, while the central portion of the compound comprises various modified or unmodified nucleobases to serve as substrates for RISC mediated degradation. Each distinct portion can comprise uniform sugar moieties, modified, or alternating sugar moieties. Each portion can comprise a varied pattern of phosphate and phosphorothioate linkages.

In certain embodiments, the oligomeric compounds targeted to an AGT nucleic acid comprises a sense strand with sequence and chemical modification motif as shown in Tables 2, 5, 7, 9, 10 or 13. In certain embodiments, the oligomeric compounds targeted to an AGT nucleic acid comprises an antisense strand with sequence and chemical modification motif as shown in Tables 2, 5, 7, 9, 10 or 13.

Target Nucleic Acids, Target Regions and Nucleotide Sequences

Several embodiments are directed to methods of modulating gene expression by dsRNA inhibition.

In certain embodiments, a method of inhibiting angiotensinogen (AGT) gene expression in a cell comprises administering to the cell a dsRNA compound targeted to an mRNA (or its corresponding cDNA) transcript of AGT (GenBank NM_001382817.3, incorporated herein as SEQ ID NO:1).

The nucleic acid sequence and chemical modification motifs of dsRNA targeting the AGT transcript are shown in Tables 2, 5, 7, 9, 10 and 13. It is understood that the sequence set forth in each SEQ ID NO in the examples contained herein is independent of any modification to a sugar moiety, an internucleoside linkage, or a nucleobase. As such, siRNA compounds defined by a SEQ ID NO may comprise, independently, one or more modifications to a sugar moiety, an internucleoside linkage, or a nucleobase. siRNA compounds denoted by ARNATAR designations indicate a combination of sequence and motif.

Hybridization

In some embodiments, hybridization occurs between an oligomeric compound disclosed herein and an mRNA. The most common mechanism of hybridization involves hydrogen bonding (e.g., Watson-Crick, Hoogsteen or reversed Hoogsteen hydrogen bonding) between complementary nucleobases of the nucleic acid molecules.

In Watson-Crick canonical base pairings, adenine (A) is complementary to thymine (T) in DNA, adenine (A) is complementary to uracil (U) in RNA, and guanine (G) is complementary to cytosine (C) in both DNA and RNA. Base pairs, or complementary nucleobases, are usually Watson-Crick base pairs (C:G, A:U, A:T), but, non-canonical base pairs such as Hoogsteen base pairs (e.g., A:G, A:U), Wobble base pairs (e.g., G:U, I:U, I:A, I:C, wherein I is hypoxanthine) and the like are also permitted during hybridization of the oligomeric compound to a target nucleic acid or target region. Wobble base pairs in RNAi agents have previously been described (see e.g., U.S. Pat. Nos. 7,732,593; 7,750, 144).

Nucleobase complementarity facilitates hybridization of the oligomeric compounds described herein to their target nucleic acids with the stronger the pairing (e.g., the more base pairs and/or the stronger the hydrogen bond), the stronger the hybridization of the oligomeric compound to the target. Hybridization can occur under varying conditions. Stringent conditions are sequence-dependent and are determined by the nature and composition of the oligomeric compound to be hybridized.

Methods of determining whether a sequence is specifically hybridizable to a target nucleic acid are well known in the art. In certain embodiments, the oligomeric compounds provided herein are specifically hybridizable with a target mRNA with little to no off-target binding.

Complementarity

An oligomeric compound and a target nucleic acid are complementary to each other when a sufficient number of nucleobases of the oligomeric compound can hybridize with the corresponding nucleobases of the target nucleic acid, such that a desired effect will occur (e.g., inhibition of a target nucleic acid, such as an mRNA nucleic acid).

Non-complementary nucleobases between an oligomeric compound and an mRNA nucleic acid may be tolerated provided that the oligomeric compound remains able to specifically hybridize to a target nucleic acid. Moreover, an oligomeric compound may hybridize over one or more segments of an mRNA nucleic acid such that intervening or adjacent segments is not involved in the hybridization event (e.g., a loop structure, mismatch or hairpin structure).

In certain embodiments, the oligomeric compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to an mRNA nucleic acid, a target region, target segment, or specified portion thereof. Percent complementarity of an oligomeric compound with a target nucleic acid can be determined using routine methods.

For example, an oligomeric compound in which 18 of 20 nucleobases of the antisense strand of the oligomeric compound are complementary to a target region, and would therefore specifically hybridize, would represent 90 percent complementarity. In this example, the remaining non-complementary nucleobases may be clustered or interspersed with complementary nucleobases and need not be contiguous to each other or to complementary nucleobases. Percent complementarity of an oligomeric compound with a region of a target nucleic acid can be determined routinely using BLAST programs (basic local alignment search tools) and PowerBLAST programs known in the art (Altschul et al., 1990, J. Mol. Biol., 215:403-410; Zhang and Madden, 1997, Genome Res., 7:649-656) and available through the website for the National Center for Biotechnology Information (NCBI, https://blast.ncbi.nlm.nih.gov/Blast.cgi). Percent homology, sequence identity or complementarity, can be determined by, for example, NCBI Blast (Johnson et al., Nucleic Acids Res. 2008, 36 (Web Server issue): W5-W9).

In certain embodiments, the oligomeric compounds provided herein, or specified portions thereof, are fully complementary (i.e. 100% complementary) to a target nucleic acid, or specified portion thereof. For example, an oligomeric compound may be fully complementary to an mRNA nucleic acid, or a target region, or a target segment or target sequence thereof. As used herein, "fully complementary" means each nucleobase of an oligomeric compound is capable of precise base pairing with the corresponding nucleobases of a target nucleic acid. For example, a 20-nucleobase oligomeric compound is fully complementary to a target sequence that is 400 nucleobases long, so long as there is a corresponding 20 nucleobase portion of the target nucleic acid that is fully complementary to the oligomeric compound.

Fully complementary can also be used in reference to a specified portion of the oligomeric compound or the nucleic acid target. For example, a 20-nucleobase portion of a 30-nucleobase oligomeric compound can be "fully complementary" to a target sequence that is 400 nucleobases long. The 20-nucleobase portion of the 30-nucleobase oligomer is fully complementary to the target sequence, if the target sequence has a corresponding 20 nucleobase portion wherein each nucleobase is complementary to the 20-nucleobase portion of the oligomeric compound. At the same time, the entire 30 nucleobase oligomeric compound may or may not be fully complementary to the target sequence, depending on whether the remaining 10 nucleobases of the oligomeric compound are also complementary to the target sequence.

The location of a non-complementary nucleobase may be at the 5' end or 3' end of the oligomeric compound. Alternatively, the non-complementary nucleobase or nucleobases may be at an internal position of the oligomeric compound. When two or more non-complementary nucleobases are present, they may be contiguous (i.e. linked) or non-contiguous.

In certain embodiments, oligomeric compounds that are, or are up to 12, 13, 14, 15, 16, 17, 18, 19, 20 or 21 nucleobases in length comprise no more than 6, no more than 5, no more than 4, no more than 3, no more than 2, or no more than 1 non-complementary nucleobase(s) relative to a target nucleic acid, such as an mRNA nucleic acid, or specified portion thereof.

In certain embodiments, oligomeric compounds that are, or are up to 12, 13, 14, 15, 16, 17, 18, 19, 20, 21, 22, 23, 24, 25, 26, 27, 28, 29, or 30 nucleobases in length comprise no more than 8, no more than 7, no more than 6, no more than 5, no more than 4, no more than 3, no more than 2, or no more than 1 non-complementary nucleobase(s) relative to a target nucleic acid, such as an mRNA nucleic acid, or specified portion thereof.

The oligomeric compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an oligomeric compound. In certain embodiments, the oligomeric compounds, are complementary to at least an 8-nucleobase portion of a target segment. In certain embodiments, the oligomeric compounds are complementary to at least a 9-nucleobase portion of a target segment. In certain embodiments, the oligomeric compounds are complementary to at least a 10-nucleobase portion of a target segment. In certain embodiments, the oligomeric compounds are complementary to at least an 11-nucleobase portion of a target segment. In certain embodiments, the oligomeric compounds are complementary to at least a 12-nucleobase portion of a target segment. In certain embodiments, the oligomeric compounds are complementary to at least a 13-nucleobase portion of a target segment. In certain embodiments, the oligomeric compounds are complementary to at least a 14-nucleobase portion of a target segment. In certain embodiments, the oligomeric compounds are complementary to at least a 15-nucleobase portion of a target segment. Also contemplated are oligomeric compounds that are complementary to at least a 9, 10, 11, 12, 13, 14, 15, 16, 17, 18, 19, 20, or more nucleobase portion of a target segment, or a range defined by any two of these values.

Identity

The oligomeric compounds provided herein may also have a defined percent identity to a particular nucleotide sequence, SEQ ID NO, or compound represented by a specific ARNATAR number, or portion thereof. As used herein, an oligomeric compound is identical to the sequence disclosed herein if it has the same nucleobase pairing ability. For example, an RNA which contains uracil in place of thymidine in a disclosed DNA sequence would be considered identical to the DNA sequence since both uracil and thymidine pair with adenine. Shortened and lengthened versions of the oligomeric compounds described herein as well as compounds having non-identical bases relative to the oligomeric compounds provided herein also are contemplated. The non-identical bases may be adjacent to each other or dispersed throughout the oligomeric compound. Percent identity of an oligomeric compound is calculated according to the number of bases that have identical base pairing relative to the sequence to which it is being compared.

In certain embodiments, a portion of the oligomeric compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion of the oligomeric compound is compared to an equal length portion of the target nucleic acid.

Chemical Modifications

A nucleoside is a base-sugar combination. The nucleobase (also known as base) portion of the nucleoside is normally a heterocyclic base moiety. Nucleotides are nucleosides that further include a covalent linkage (e.g., phosphate group or a chemically modified linkage as described infra) to the sugar portion of the nucleoside. Oligonucleotides are formed through the covalent linkage of adjacent nucleotides to one another, to form a linear sequence of linked nucleotides. Within the oligonucleotide structure, the linkage groups are commonly referred to as forming the internucleoside linkages of the oligonucleotide. Oligomeric compounds are made up of one (e.g., ssRNAs, antisense oligonucleotides or miRNAs) or more oligonucleotides (e.g., dsRNAs such as siRNAs or shRNAs)

Modifications to oligomeric compounds encompass substitutions or changes to nucleobases, internucleoside linkages or sugar moieties. Modified oligomeric compounds as disclosed herein are often preferred over native or unmodified forms because of desirable properties such as, for example, enhanced delivery (e.g., increased cellular uptake), enhanced specificity or affinity for a nucleic acid target, increased stability in the presence of nucleases, enhanced safety (e.g., fewer side effects after administration of the compound to a subject) or increased potency (e.g., inhibitory activity).

Nucleobase Modifications

A nucleobase is a heterocyclic moiety capable of base pairing with a nucleobase of another nucleic acid. Modifications to nucleobases can be advantageous to an oligomeric compound for various reasons including, but not limited to, increase stability of the oligomeric compound, increase specificity, decreased immunogenicity of the oligomeric compound, increase affinity of the oligomeric compound, increase potency of the oligomeric compound and other desirable features.

Examples of nucleobase modifications and their advantages are well known in the art (Friedrich and Aigner, Therapeutic siRNA: State-of-the-Art and Future Perspectives, 2022, BioDrugs, 36(5):549-571; Hu et al., Therapeutic siRNA: State of the Art, Signal Transduction and Targeted Therapy, 2020, 5:101). Nucleobase modifications can comprise substituting nucleobases with nucleobase analogs or modification of a part of the nucleobase. Examples of nucleobase modifications include, but are not limited to, pseudouridine, 2'-thiouridine, N6'-methyladenosine, and 5'-methylcytidine, 5'-fluoro-2'-deoxyuridine, N-ethylpiperidine 5' triazole-modified adenosine, 5'-nitroindole, 2',4'-difluorotolylribonucleoside, N-ethylpiperidine 7'-EAA triazole-modified adenosine, 6'-phenylpyrrolocytosine and the like.

In certain embodiments, oligomeric compounds targeted to an mRNA nucleic acid comprise one or more modified nucleobases. In certain embodiments, the modified nucleobases are, for example, deoxyribonucleosides (D) substituted for ribonucleosides (R). In certain embodiments, a modified nucleobase can be a thymine substitution for a uracil. In certain embodiments, multiple nucleobases of an oligomeric compound are modified. In certain embodiments, each nucleobase of an oligomeric compound is modified.

Internucleoside Linkage Modifications

The naturally occurring internucleoside linkage of RNA and DNA is a 3' to 5' phosphodiester linkage. For nucleosides that include a furanose sugar, the phosphate group can be linked to the 2', 3' or 5' hydroxyl moiety of the sugar. Oligomeric compounds having one or more modified, i.e., non-naturally occurring, internucleoside linkages are often selected over oligomeric compounds having naturally occurring internucleoside linkages because of desirable properties such as, for example, enhanced cellular uptake, enhanced affinity for target nucleic acids, decrease toxicity, increased stability and durability, decreased degradation and other desirable features for an oligomeric compound. Modified internucleoside linkages and their advantages are well known in the art (Friedrich and Aigner, Therapeutic siRNA: State-of-the-Art and Future Perspectives, 2022, BioDrugs, 36(5):549-571; Hu et al., Therapeutic siRNA: State of the Art, Signal Transduction and Targeted Therapy, 2020, 5:101).

Oligomeric compounds having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates (e.g., 5'-methylphosphonate (5'-MP)), phosphoramidate, and phosphorothioates (e.g., phosphorodithioate Rp isomer (PS, Rp), phosphorodithioate Rp isomer (PS,Sp), 5'-phosphorothioate (5'-PS)), methoxypropylphosphonate, (S)-5'-C-methyl with Phosphate, peptide nucleic acid (PNA), 5'-(E)-vinylphosphonate.

In certain embodiments, oligomeric compounds targeted to an mRNA nucleic acid comprise one or more modified internucleoside linkages. In certain embodiments, the modified internucleoside linkages are phosphorothioate (PS) linkages. In certain embodiments, one or more internucleoside linkage of an oligomeric compound is a phosphorothioate internucleoside linkage. In certain embodiments, the PS linkage is adjacent to a deoxyribonucleoside (sometimes referred to as DNA or "D" herein) or a ribonucleoside (sometimes referred to as RNA, "R" or "r" herein). In certain embodiments, each internucleoside linkage of an oligomeric compound is a phosphorothioate internucleoside linkage.

Sugar Modifications

Natural sugars are sugar moieties found in DNA (2'-H) or RNA (2'-OH), i.e., 2-deoxy-beta-D-ribofuranose or beta-D-ribofuranose, respectively. Oligomeric compounds provided herein can contain one or more nucleosides wherein the natural sugar moiety has been modified. Such sugar modified nucleosides may impart desirable features such as increased stability, increased durability (e.g., increased half-life), increased binding affinity, decreased off-target effects, decreased immunogenicity, decreased toxicity, increased potency, or some other beneficial biological property to the oligomeric compounds. Sugar modifications and their advantages are known in the art (Friedrich and Aigner, 2022, BioDrugs, 36(5):549-571; Hu et al., Therapeutic siRNA: State of the Art, Signal Transduction and Targeted Therapy, 2020, 5:101; Chiu and Rana, 2003, RNA, 9:1034-1048; Choung et al., Biochem Biophys Res Commun, 2006, 342: 919-927; Amarzguioui et al., 2003, Nucleic Acids Res, 31(2):589-595; Braasch et al., 2003, Biochemistry, 42(26): 7967-7975; Czauderna et al., 2003, Nucleic Acids Res, 31(11):2705-2716; Allerson et al., 2005, J Med Chem, 48:901-904; Layzer et al., 2004, RNA, 10:766-771; Ui-Tei, et al., 2008, Nucleic Acids Res, 36(7):2136-51; Bramsen and Kjems, 2012, Frontiers in Genetics, 3(154):1-22; Bramsen et al., 2010, Nucleic Acids Res, 38(17):5761-5773; Muhonen et al., 2007, Chem & Biodiversity, 4:858-873; which are incorporated-by-reference herein).

In certain embodiments, nucleosides comprise a chemically modified ribofuranose ring moiety. Examples of chemically modified ribofuranose rings can include, without limitation, addition of substituent groups (e.g., 5' sugar modifications, 2' sugar modifications); bridging of non-geminal ring atoms to form bicyclic nucleic acids (BNA); replacement of the ribosyl ring oxygen atom with S, N(R), or C(R) (R=H, $C_1$-$C_{12}$ alkyl or a protecting group); nucleoside mimetic; and combinations thereof.

A 2'-modified sugar refers to a furanosyl sugar modified at the 2' position. A 2'-modified nucleoside refers to a nucleoside comprising a sugar modified at the 2' position of a furanose ring. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: $O[(CH_2)_nO]_mCH_3$, $O(CH_2)_nNH_2$, $O(CH_2)_nCH_3$, $O(CH_2)_nONH_2$, $OCH_2C(=O)N(H)CH_3$, and $O(CH_2)_nON[(CH_2)_nCH_3]_2$, where n and m are from 1 to about 10. Other 2'-substituent groups can also be selected from: $C_1$-$C_{12}$ alkyl, substituted alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving pharmacokinetic properties, and a group for improving the pharmacodynamic properties of an oligomeric compound, and other substituents having similar properties.

Further examples of nucleosides having modified sugar moieties include, without limitation, nucleosides comprising 5'-vinyl, 5'-methyl (R or S), 2'-F-5'-methyl, 4'-S, 2'-deoxy-2'-fluoro (2'-F), 2'-$OCH_3$ (2'-O-methyl, 2'-OMe), 2'-$O(CH_2)_2$ $OCH_3$ (2'-O-methoxyethyl, 2'-O-MOE, 2'-MOE), 2'-O-methyl-4-pyridine, phosphorodiamidate morpholino (PMO), tricyclo-DNA (tcDNA), 2'-arabino-fluoro, 2'-O-benzyl, glycol nucleic acid (GNA), and unlocked nucleic acid (UNA) substituent groups. The substituent at the 2' position can also be selected from allyl, amino, azido, thio, O-allyl, O—$C_1$-$C_{10}$ alkyl, $OCF_3$, $O(CH_2)_2SCH_3$, $O(CH_2)_2$—O—N(Rm)(Rn), and O—$CH_2$—C(=O)—N(Rm)(Rn), where each Rm and Rn is, independently, H or substituted or unsubstituted $C_1$-$C_{10}$ alkyl. 2'-OMe or 2'-$OCH_3$ or 2'-O-methyl each refers to a nucleoside comprising a sugar comprising an —$OCH_3$ group at the 2' position of the sugar ring. 2'-F refers to a sugar comprising a fluoro group at the 2' position. 2'-O-methoxyethyl or 2'-O-MOE or 2'-MOE each refers to a nucleoside comprising a sugar comprising an —$O(CH_2)_2OCH_3$ group at the 2' position of the sugar ring.

BNAs refer to modified nucleosides comprising a bicyclic sugar moiety wherein a bridge connecting two carbon atoms of the sugar ring connects the 2' carbon and another carbon of the sugar ring. Examples of bicyclic nucleosides include, without limitation, nucleosides comprising a bridge between the 4' and the 2' ribosyl ring atoms such as in locked nucleic acid (LNA). In certain embodiments, oligomeric compounds provided herein include one or more bicyclic nucleosides wherein the bridge comprises a 4' to 2' bicyclic nucleoside. LNAs and UNAs have been described by Campbell and Wengel (Chem Soc Rev, 2011, 40(12):5680-9) and are incorporated-by-reference herein.

In certain embodiments, oligomeric compounds comprise one or more nucleotides having modified sugar moieties. In certain embodiments, the modified sugar moiety has a 2'-OMe modification. In certain embodiments, the modified sugar moiety has a 2'-F modification. In certain embodiments, the 2'-OMe and/or 2'-F modified nucleotides are arranged in a motif. In a preferred embodiment, the modifications are arranged in Arnatar motifs as disclosed in PCT/US2023/084688, which is incorporated-by-reference herein.

In certain embodiments, the oligomeric compounds targeted to a nucleic acid comprises a sense strand with motif described by the one of the following formulas:

5'M-(Y)n—Z—(Y)r-D-D3', Formula (I):

5'Y—Z—(Y)q-FFNM-(Y)q-M-(Y)v-D-D3', Formula (II):

5'M*F*MMN*MN*MFFNMN*MN*MMFM*D*D3', Formula (III):

5'MFMMNMNMFFNMNMNMMNMDD3', or Formula (X):

5'MFMMNMNMFFMMNMNMMFMDD3', Formula (XI):

wherein
each D is a deoxyribonucleoside (D is a modification of R),
each R is a ribonucleoside,
each N is a nucleoside, modified or unmodified (e.g., D, R, M, F, UNA modified, or LNA modified),
each M is a 2'-OMe modified nucleoside,
each F is a 2'-F modified nucleoside,
each * is a phosphorothioate (PS) linkage,
each Y is two adjacent nucleosides with different modifications (e.g., MD, DM, DF, FD, MF or FM) or a modified nucleoside adjacent to an unmodified nucleoside (e.g., DR, RD, MR or RM),
each Z is two adjacent unmodified nucleosides or two adjacent nucleosides with the same modification or two adjacent unmodified nucleosides (e.g., MM, DD, RR, or FF),
each n is 6-8,
each q is 2-3,
each r is 1-2,
each v is 0-1, and
wherein no single modification type modifies more than two consecutive nucleotides. In certain embodiments, the FFNM is FFRM or FFMM.

In certain embodiments, the oligomeric compounds targeted to a nucleic acid comprises an antisense strand with motif described by one of the following formulas:

5'-L-M-(D)v—(Y)s—(Z)t—(Y)u—Z—N—(Z)r3', Formula (IV):

5'L-(Y)p-NM-(FMM)r—(Y)p—(Z)r3', Formula (V):

5'L-M*N*MNMFNMFMMNMFMFMMN*M*M3', Formula (VI):

5'L-M*D*MFMFNMFMMFMFMFMMN*M*M3', Formula (VII):

5'L-MNMNMFNMFMMNMFMFMMNMM3', Formula (VIII):

5'L-M-(Y)p—Z—(Y)p—(Z)r3', or Formula (IX):

5'L-MDMFMFNMFMMFMFMFMMNMM3', Formula (XII):

wherein
each D is a deoxyribonucleoside (D is a modification of R),
each R is a ribonucleoside, each N is a nucleoside, modified or unmodified (e.g., D, R, M, F, UNA modified, or LNA modified),
each M is a 2'-OMe modified nucleoside,
each F is a 2'-F modified nucleoside,
each L is a 5' phosphate, 5' vinyl phosphonate or 5' OH
each * is a phosphorothioate (PS) linkage,
each Y is two adjacent nucleosides with different modifications (e.g., MD, DM, DF, FD, MF or FM) or a modified nucleoside adjacent to an unmodified nucleoside (e.g., DR, RD, MR or RM),
each Z is two adjacent unmodified nucleosides or two adjacent nucleosides with the same modification or two adjacent unmodified nucleosides (e.g., MM, DD, RR, or FF),
each (5p) is 5'-phosphate,
each n is 6-8,
each p is 3-5,
each r is 1-2,
each v is 0-1,
each s is 2-7,
each t is 0-2, and
wherein no single modification type modifies more than two consecutive nucleotides. In certain embodiments, the FNM is FMM.

Oligomeric Compound Delivery Systems

Oligomeric compounds require entry into target cells to become active. A variety of modalities have been used to traffic oligomeric compounds into target cells including viral delivery vectors, lipid-based delivery, polymer-based delivery, and conjugate-based delivery (Paunovska et al., Drug Delivery Systems for RNA Therapeutics, 2022, Nature Reviews Genetics, 23(5):265-280; Chen et al., 2022, Molecular Therapy, Nucleic Acids, 29:150-160).

Lipid-based particles can form specific structures such as micelles, liposomes and lipid nanoparticles (LPNs) to carry oligomeric compounds into cells. To form these particles, LPNs can include one or more of a cationic or ionizable lipid (e.g., DLin-MC3-DMA, SM-102, ALC-0315), cholesterol, a helper lipid, 1,2-distearoyl-sn-glycero-3-phosphocholine (DSPC), poly(ethylene glycol) (PEG) modified lipid (e.g., PEG-2000-C-DMG, PEG-2000-DMG, ALC-0159), C12-200, cKK-E12 and the like. Different combinations of lipids can be formulated to affect the delivery of the oligomeric compound to different types of cells. In one example, therapeutic siRNA patisiran was formulated in cationic ionizable lipid DLin-MC3-DMA, cholesterol, polar phospholipid DSPC, and PEG-2000-C-DMG for delivery to hepatocytes.

Polymer-based particles are also used in oligomeric compound delivery systems. Such polymers include poly(lacticco-glycolic acid) (PLGA), polyethylenimine (PEI), poly(l-lysine) (PLL), poly(beta-amino ester) (PBAE), dendrimers (e.g., poly(amidoamine) (PAMAM) or PLL), and other polymers or modified polymers thereof. The polymer composition can be varied depending on the traits desired for delivery of the oligomeric compound.

The oligomeric compounds disclosed herein may be covalently linked to one or more moieties or conjugates which enhance the activity, cellular distribution or cellular uptake of the resulting compound. Conjugate groups can include cholesterols, lipids, carbohydrates, phospholipids, biotin, phenazine, folate, phenanthridine, anthraquinone, acridine, fluoresceins, rhodamines, coumarins, dyes, etc. Conjugate-based delivery can actively deliver oligomeric compounds to specific cell types.

In an example, an N-Acetylgalactosamine (GalNAc)-comprising moiety is conjugated to an oligomeric compound and delivers it into hepatocytes. Various GalNAc conjugates can be found in several publications including the following, all of which are incorporated-by-reference herein: Sharma et al., 2018, Bioconjugate Chem, 29:2478-2488; Nair et al., J. Am. Chem. Soc. 2014, 136(49):16958-16961; Keam, 2022, Drugs, 82:1419-1425; U.S. Pat. No. 10,087,208; Prakash et al., 2014, Nucleic Acids Res, 42(13): 8796-807; Debacker et al., 2020, Molecular Therapy, 28(8): 1759-1771; PCT/US2023/084692; U.S. Pat. Nos. 11,110, 174; 9,796,756; 9,181,549; 10,344,275; 10,570,169; 9,506, 030; and, U.S. Pat. No. 7,582,744.

In certain embodiments, the following GalNAc conjugate precursor with solid support can be used to conjugate an AGT dsRNA at the 3' end of the sense strand. In a preferred embodiment, the dsRNA is an ARNATAR designed siRNA selected from Tables 2, 5, 7, 9, 10 or 13.

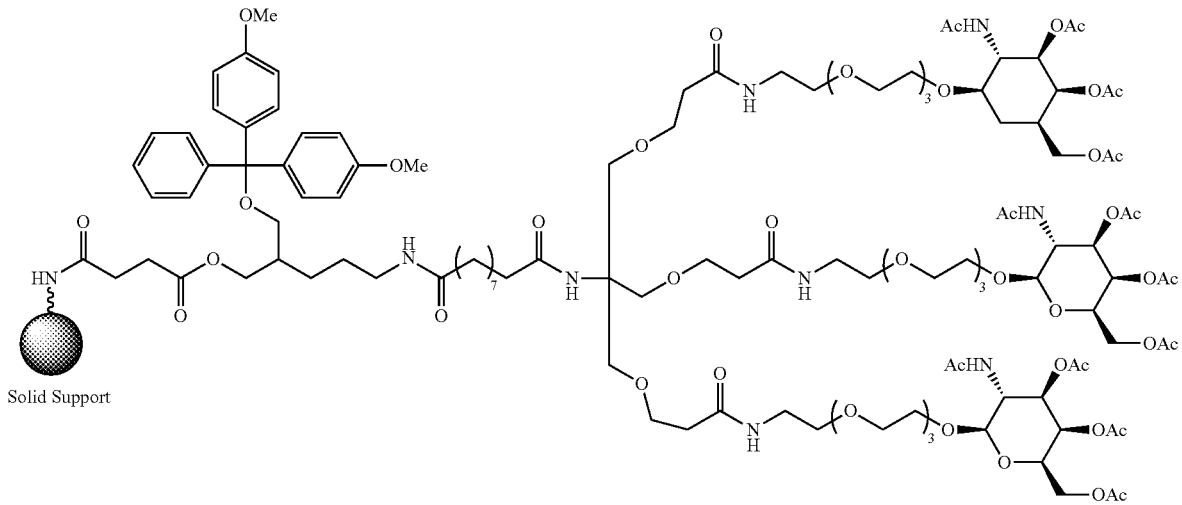

In a preferred embodiment, the GalNAc-comprising moiety conjugated to an oligonucleotide is GalNAc-AN (also known as GA4 or GA-AN) shown as follows:

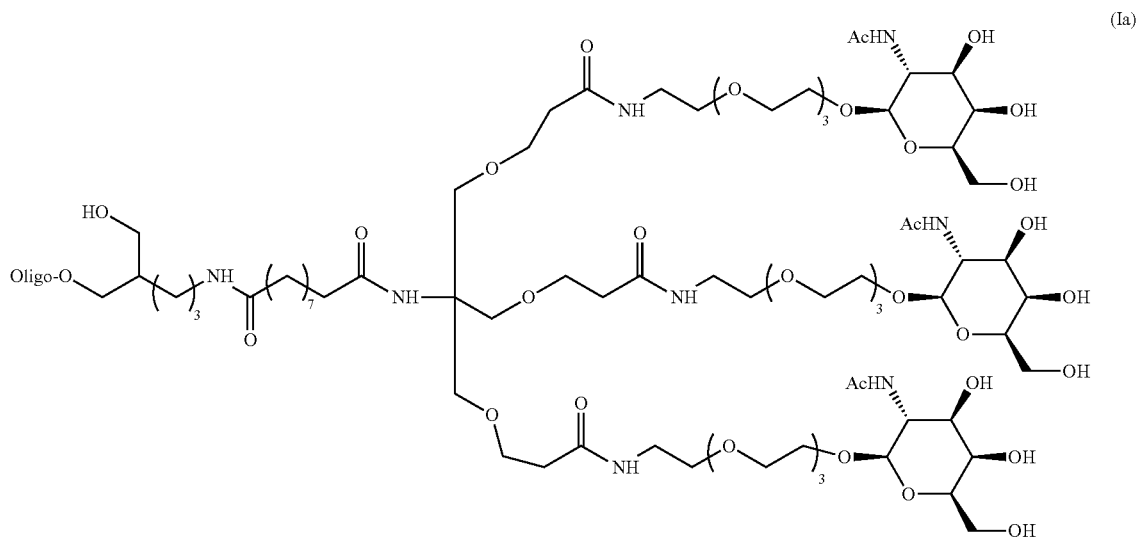

(Ia)

In one embodiment, GalNAc-AN is conjugated to a sense strand of a dsRNA compound.

In a preferred embodiment, GalNAc-AN conjugated to a dsRNA compound selected from any of the compounds in Tables 2, 5, 7, 9, 10 or 13.

Oligomeric Compound Synthesis siRNAs were designed, synthesized, and prepared using methods known in the art.

Solid phase syntheses of oligonucleotides were done on a MerMade™ 48× synthesizer (BioAutomation, LGC, Biosearch Technologies, Hoddesdon, UK), which can make up to 48 1 µMole or 5 µMole scale oligonucleotides per run using standard phosphoramidite chemistry. Phosphoramidite synthesis of oligonucleotides on a solid support is well known in the art (e.g., Beaucage and Caruthers, 1981, Tetrahedron Letters, 22(20): 1859-1862; Roy and Caruthers, 2013, Molecules, 18:14268-14284; and Sandahl et al., 2021, Nature Communications, 12:2760). Solid support is controlled pore glass (500-1400 Å) loaded with universal linkers or loaded with 3'-GalNAc conjugates (e.g., AM Chemicals, Vista, CA, USA; Primetech ALC, Minsk, Belarus; Gene Link, Elmsford, NY, USA; or any GalNAc conjugate disclosed herein) or universal solid support (AM Chemicals, Vista, CA, USA). Ancillary synthesis reagents and standard 2'-cyanoethyl phosphoramidite monomers (2'-fluoro, 2'-O-methyl, RNA, DNA) were obtained from various sources (Hongene Biotech, Shanghai, China; Sigma-Aldrich, St. Louis, MO, USA; Glen Research, Sterling, VA, USA; ThermoFisher Scientific, Waltham, MA, USA; LGC Biosearch Technologies, Hoddesdon, UK). Phosphoramidite mixtures were prepared in anhydrous acetonitrile or 30% DMF: acetonitrile and were coupled using 0.25M 4,5-dicyanoimidazole (DCI) (Sigma-Aldrich, St. Louis, MO, USA) with coupling times ranging from 120-360 seconds. Standard phosphodiester linkages were achieved using 0.02M iodine mixture in Tetrahydrofuran (THF), pyridine and water. Phosphorothiate linkages were generated using 0.05M sulfurizing Reagent II (3-((Dimethylamino-methylidene) amino)-3H-1,2,4-dithiazole-3-thione, DDTT) (40:60,Pyridine/Acetonitrile) (LGC Biosearch Technologies, Hoddesdon, UK) with an oxidation time of 6 minutes. All sequences were synthesized with Dimethoxy Trityl (DMT) protecting group removed.

Upon completion of solid phase synthesis, the oligonucleotides were cleaved from the solid support and deprotection of base labile groups performed by incubation in ammonium hydroxide at 55° C. for 6 hours. Ammonium hydroxide was removed using a centrifugal vacuum concentrator to dryness at room temperature. For sequences containing natural ribonucleotides (2'-OH) protected with tert-butyl dimethyl silyl (TBDMS), a second deprotection was performed using triethylamine; trihydrofluoride (TEA:3HF). To each TBDMS protected oligonucleotide 100 µL DMSO and 125 µL TEA:3HF was added and incubated at 65° C. for 2.5 hours. After incubation 25 µL of 3M sodium acetate was added to the solution which was subsequently precipitated in butanol at −20° C. for 30 minutes. The cloudy solution was centrifuged to a cake at which time the supernatant was carefully decanted with a pipette. The standard precipitation process was then completed with 75% ethanol:water then 100% ethanol as supernatant solutions. The oligonucleotide cake was dried for 30 minutes in a centrifugal vacuum concentrator.

Desalting without HPLC purification was performed after precipitation with 3M sodium acetate with a follow on G25 Sephadex® column (Sigma-Aldrich, St. Louis, MO, USA) elution. Purification of oligonucleotides was afforded by anion exchange chromatography on a Gilson GX271 prep HPLC system (Middleton, WI, USA) using BioWorks Q40 resin (Uppsala, Sweden). Final desalt was performed by Sephadex© G25 column. All oligonucleotides were analyzed by ion pairing reverse phase HPLC for purity an Agilent 1200 analytical HPLC (Santa Clara, CA, USA), negative ion mass spectrometry for intact mass on an Agilent 6130 single quad mass spectrometer (Santa Clara, CA, USA), and A260 quantification by UV/Vis on a Tecan Infinite® M Plex plate reader (Zurich, Switzerland).

Double Stranded Oligomeric Compound Duplex Formation

In general, for a double stranded oligomeric compound such as an siRNA compound, a sense and antisense oligonucleotide is annealed together to form a duplex. The duplex is formed by contacting the sense strand prepared according any one of the processes described herein with the antisense strand prepared according any one of the processes described herein in equimolar concentrations in a solution. Optionally, the solution is heated to a temperature of about 94° C. then the temperature is reduced to about 25° C. In an example, duplex formation of 50-300 mM can be achieved by heating samples at 94° C. for 4 mins in 1× phosphate-buffered saline in a block heater, followed by removal of the heating block containing the samples from the block heater, and allowing it to gradually cool down to room temperature over a time course of 1 hr.

Compositions and Methods for Formulating Pharmaceutical Compositions

The dsRNA compounds, such as siRNAs targeting AGT described herein, can be combined with pharmaceutically acceptable active or inert substances, such as a diluent, excipient or carrier, for the preparation of pharmaceutical compositions or formulations.

Compositions and methods for the formulation of pharmaceutical compositions are dependent upon a number of criteria, including, but not limited to, route of administration, extent of disease, or dose to be administered.

In certain embodiments, the pharmaceutical carrier or excipient is a pharmaceutically acceptable solvent, suspending agent or any other pharmacologically inert vehicle for delivering one or more nucleic acid compounds to an animal. The excipient can be liquid or solid and can be selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipients, which do not deleteriously react with nucleic acid compounds, suitable for parenteral or non-parenteral administration can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising a dsRNA compound targeted to an AGT nucleic acid and a pharmaceutically acceptable diluent. In certain embodiments, the pharmaceutically acceptable diluent is PBS. In certain embodiments, the dsRNA compound is an siRNA.

Pharmaceutical compositions comprising dsRNA compounds such as siRNAs can encompass any pharmaceutically acceptable salts, esters, or salts of such esters, or any other dsRNA which, upon administration to an animal, including a human, is capable of providing (directly or indirectly) the biologically active metabolite or residue thereof. Accordingly, for example, the disclosure is also drawn to pharmaceutically acceptable salts of dsRNA compounds, prodrugs, pharmaceutically acceptable salts of such prodrugs, and other bioequivalents. Suitable pharmaceutically acceptable salts include, but are not limited to, sodium and potassium salts.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer (e.g., PBS). In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers.

Dosages

For purposes of the disclosure, the amount or dose of the active agent (oligomeric compound of the invention) administered should be sufficient to e.g., inhibit the expression of AGT in an animal. In the animal (e.g., human), dose will be determined by the efficacy of the particular active agent and the condition of the animal, as well as the body weight of the animal to be treated.

Many assays for determining an administered dose are known in the art.

The dose of the active agent of the present disclosure also will be determined by the existence, nature and extent of any adverse side effects that might accompany the administration of a particular active agent of the present disclosure. Typically, the attending physician will decide the dosage of the active agent of the present disclosure with which to treat each individual subject, taking into consideration a variety of factors, such as age, body weight, general health, diet, sex, active agent of the present disclosure to be administered, route of administration, and the severity of the condition being treated.

Dosing

In certain embodiments, pharmaceutical compositions are administered according to a dosing regimen (e.g., dose, dose frequency, and duration) wherein the dosing regimen can be selected to achieve a desired effect i.e., is therapeutically effective in a subject. The desired effect can be, for example, reduction of AGT or the prevention, reduction, amelioration or slowing the progression of a disease, disorder and/or condition, or symptom thereof, associated with AGT or the RAAS pathway in a subject. In certain embodiments, the variables of the dosing regimen are adjusted to result in a desired concentration of pharmaceutical composition in a subject. "Concentration of pharmaceutical composition" as used with regard to dose regimen can refer to the dsRNA compound or active ingredient(s) of the pharmaceutical composition. For example, in certain embodiments, dose and dose frequency are adjusted to provide a tissue concentration or plasma concentration of a pharmaceutical composition at an amount sufficient to achieve a desired effect.

Dosing is dependent on severity and responsiveness of the disease state to be treated, with the course of treatment lasting from several days to several months, or until a cure is effected or a diminution of the disease state is achieved. Dosing is also dependent on drug potency and metabolism differences between subjects. In certain embodiments, a therapeutically effective dosage in a subject is from 0.01 µg to 50 mg per kg of body weight, 0.01 µg to 100 mg per kg of body weight, or within a range of 0.001 mg to 1000 mg dosing, and may be given once or more daily, weekly, monthly, quarterly or yearly, or even once every 2 to 20 years. Following successful treatment, it may be desirable to have the subject undergo maintenance therapy to prevent the recurrence of the disease state, wherein the dsRNA is administered in maintenance doses, ranging from 0.01 µg to 100 mg per kg of body weight, once or more daily, once or more weekly, once or more monthly, once or more quarterly, once or more yearly, to once every 20 years or ranging from 0.001 mg to 1000 mg dosing. In certain embodiments, it may be desirable to administer the dsRNA compound from at most once daily, once weekly, once monthly, once quarterly, once yearly, once every two years, once every three years, once every four years, once every five years, once every ten year, to once every 20 years.

In certain embodiments, the range of therapeutically effective dosing is between any of 1 mg-1500 mg, 100 mg-1400 mg, 100 mg-1300 mg, 100 mg-1200 mg, 100 mg-1100 mg, 100 mg-1000 mg, 100 mg-900 mg, 200 mg-800 mg, 300 mg-700 mg, 400 mg-600 mg, 100 mg-400 mg, 200 mg-500 mg, 300 mg-600 mg, and 400 mg-700 mg. In certain embodiments, a therapeutically effective dose is about 100 mg, 150 mg, 200 mg, 250 mg, 300 mg, 350 mg, 400 mg, 450 mg, 500 mg, 550 mg, 600 mg, 650 mg, 700 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, or 1500 mg. In certain embodiments, a preferred dose is selected from 700 mg, 800 mg and 900 mg.

In certain embodiments, a therapeutically effective amoung of the dsRNA is dosed at any of about 150 mg, 200 mg, 300 mg, 400 mg, 500 mg, 600 mg, 700 mg, 800 mg, or 900 mg twice a year.

In certain embodiments, a therapeutically effective amoung of the dsRNA is dosed at about 150 mg, 200 mg, 300 mg, 400 mg, 500 mg, 600 mg, 700 mg, 800 mg, or 900 mg quarterly. In certain embodiments, a therapeutically effective amount of the dsRNA is dosed at about 150 mg, 300 mg or 600 mg once every 3 months. In certain embodiments, a therapeutically effective amount of the dsRNA is dosed at about 150 mg, 300 mg or 600 mg once every 6 months.

Administration

The dsRNA compounds such as siRNAs or pharmaceutical compositions of the present invention can be administered in a number of ways depending upon whether local or systemic treatment is desired and upon the area to be treated. Administration can be oral, inhaled or parenteral.

In certain embodiments, the compounds and compositions as described herein are administered parenterally. Parenteral administration includes intravenous, intra-arterial, subcutaneous, intraperitoneal or intramuscular injection or infusion;

or intracranial, e.g., intrathecal or intraventricular, administration. In certain embodiments, parenteral administration is by infusion. Infusion can be chronic or continuous or short or intermittent. In certain embodiments, infused pharmaceutical agents are delivered with a pump.

In certain embodiments, parenteral administration is by injection. The injection can be delivered with a syringe or a pump. In certain embodiments, the injection is a bolus injection. In certain embodiments, the injection is administered directly to a tissue or organ.

In certain embodiments, formulations for parenteral, intrathecal or intraventricular administration can include sterile aqueous solutions which can also contain buffers, diluents and other suitable additives such as, but not limited to, penetration enhancers, carrier compounds and other pharmaceutically acceptable carriers or excipients.

In certain embodiments, formulations for oral administration of the compounds or compositions can include, but is not limited to, pharmaceutical carriers, excipients, powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders can be desirable. In certain embodiments, oral formulations are those in which compounds provided herein are administered in conjunction with one or more penetration enhancers, surfactants and chelators.

In Vitro Testing of dsRNAs

Described herein are methods for treatment of cells with dsRNAs, for example siRNAs, which can be modified appropriately for treatment with other oligomeric compounds.

Cells may be treated with siRNAs when the cells reach approximately 60-80% confluency in culture.

One reagent commonly used to introduce siRNAs into cultured cells includes the cationic lipid transfection reagent Lipofectamine™ RNAiMAX (Invitrogen, Waltham, MA). siRNAs may be mixed with Lipofectamine™ RNAiMAX in OPTI-MEM 1 (Thermo Fisher Scientific, Waltham, MA) to achieve the desired final concentration of siRNA and a Lipofectamine™ RNAiMAX concentration that may range from 0.001 to 300 nM siRNAs. Transfection procedures are done according to the manufacturer's recommended protocols.

Another technique used to introduce siRNAs into cultured cells includes electroporation.

siRNAs conjugated with a GalNAc-comprising moiety can be introduced to cells through incubation of the siRNAs with cells without transfection reagents, referenced herein as "free uptake". The siRNA-GalNAc conjugates are transported into asialoglycoprotein receptor (ASGR) positive cells such as hepatocytes via endocytosis.

Cells are treated with siRNAs by routine methods. Cells may be harvested 4-144 hours after siRNAs treatment, at which time mRNA (harvested at 4-144 hrs) or protein levels (extracted at 24-96 hrs) of target nucleic acids are measured by methods known in the art and described herein. In general, treatments are performed in multiple replicates, and the data are presented as the average of the replicate treatments plus the standard deviation.

The concentration of siRNAs used varies from cell line to cell line and target to target. Methods to determine the optimal siRNAs concentration for a particular target in a particular cell line are well known in the art. In general, cells are treated with siRNAs in a dose dependent manner to allow for the calculation of the half-maximal inhibitory concentration value (IC50). siRNAs are typically used at concentrations ranging from 0.001 nM to 300 nM when transfected with Lipofectamine™ RNAiMAX. siRNAs are used at higher concentrations ranging from 625 to 20,000 nM when transfected using electroporation or free uptake.

RNA Isolation

RNA analysis of AGT mRNA levels can be performed on total cellular RNA or poly(A)+ mRNA. Methods of RNA isolation are well known in the art. RNA is prepared using methods well known in the art, for example, using the TRIZOL Reagent (Thermo Fisher Scientific, Waltham, MA), Qiagen RNeasy kit (Qiagen, Hilden, Germany), or AcroPrep Advance 96-well Filter Plates (Pall Corporation, Port Washington, New York) using Qiagen's RLT, RWI and RPE buffers. RNA extraction procedures are done according to the manufacturer's recommended protocols.

In Vivo Testing of dsRNA Compounds dsRNA compounds, for example, siRNAs, are tested in animals to assess their ability to inhibit expression of AGT and/or the RAAS pathway and produce phenotypic changes such as a decrease in one or more RAAS pathway related diseases. Testing may be performed in normal animals, or in experimental disease models. For administration to animals, dsRNA are formulated in a pharmaceutically acceptable diluent, such as phosphate-buffered saline. Administration includes parenteral routes of administration, such as intraperitoneal, intravenous, and subcutaneous. Calculation of dsRNA dosage and dosing frequency depends upon factors such as route of administration and animal body weight. In one embodiment, following a period of treatment with dsRNAs, mRNA encoding AGT is isolated from liver tissue and changes in AGT expression are measured. Changes in AGT protein levels can also be measured. Changes in AGT expression can also be measured by determining the level of inhibition of the RAAS pathway in the animal. RAAS pathway related diseases, disorders and/or conditions may be used as markers for determining the level of AGT inhibition in the animal.

Certain Indications

In certain embodiments, the invention provides methods of treating a subject comprising administering one or more compounds and/or pharmaceutical compositions of the present invention to the subject. In certain embodiments, the subject has, or is at risk for, a RAAS pathway related disease, disorder and/or condition, or symptom thereof. In certain embodiments the invention provides methods for prophylactically reducing AGT expression in a subject. Certain embodiments include treating a subject in need thereof by administering to the subject a therapeutically effective amount of a dsRNA compound such as an siRNA targeted to an AGT nucleic acid.

In certain embodiments, administration to a subject of a therapeutically effective amount of a dsRNA compound targeted to an AGT nucleic acid is accompanied by monitoring of AGT levels in the blood plasma or tissue of the subject, to determine a subject's response to administration of the dsRNA compound. A subject's response to administration of the dsRNA compound is used by a physician to determine the amount and duration of therapeutic intervention.

In certain embodiments, administration to a subject of a dsRNA compound targeted to an AGT nucleic acid results in reduction of AGT expression by at least 15%, 20%, 25%, 30%, 35%, 40%, 45%, 50%, 55%, 60%, 65%, 70%, 75%, 80%, 85%, 90%, 95%, 99% or 100% or a range defined by any two of these values. In certain embodiments, administration to a subject of a dsRNA compound targeted to an AGT nucleic acid results in inhibition of the RAAS pathway by at least 15%, 20%, 25%, 30%, 35%, 40%, 45%, 50%, 55%, 60%, 65%, 70%, 75%, 80%, 85%, 90%, 95%, 99% or 100% or a range defined by any two of these values. In certain embodiments, administration to a subject of a dsRNA compound targeted to an AGT nucleic acid results in a change the RAAS pathway related disease, disorder, condition, symptom or marker (e.g., hypertension or organ damage) in the subject. In certain embodiments, administration to a subject of an AGT dsRNA compound increases or decreases the RAAS related disease, disorder, condition, symptom or marker by at least 15%, 20%, 25%, 30%, 35%, 40%, 45%, 50%, 55%, 60%, 65%, 70%, 75%, 80%, 85%, 90%, 95%, 99% or 100% or a range defined by any two of these values in the subject.

In certain embodiments, pharmaceutical compositions comprising a dsRNA compound targeted to AGT are used for the preparation of a medicament for treating a subject suffering or susceptible to a RAAS related disease, disorder or condition.

In certain embodiments, the dsRNA compound is an ARNATAR designed siRNA targeting AGT as listed in Tables 2, 5, 7, 9, 10 or 13.

Certain Combination Therapies

In certain embodiments, a first agent comprising a dsRNA compound provided herein is co-administered with one or more secondary agents to a subject. In certain embodiments, the dsRNA compound is an ARNATAR siRNA listed in Tables 2, 5, 7, 9, 10 or 13.

In certain embodiments, such second agents are designed to treat the same RAAS pathway related disease, disorder or condition as the first agent described herein. In certain embodiments, such second agents are designed to treat a different disease, disorder, or condition as the first agent described herein. In certain embodiments, such second agents are designed to treat an undesired side effect of one or more pharmaceutical compositions as described herein. In certain embodiments, such first agents are designed to treat an undesired side effect of a second agent. In certain embodiments, second agents are co-administered with the first agent to treat an undesired effect of the first agent. In certain embodiments, second agents are co-administered with the first agent to produce a combinational or additive effect. In certain embodiments, second agents are co-administered with the first agent to produce a synergistic effect.

In certain embodiments, the co-administration of the first and second agents permits use of lower dosages than would be required to achieve a therapeutic or prophylactic effect if the agents were administered as independent therapy. In certain embodiments the dose of a co-administered second agent is the same as the dose that would be administered if the second agent was administered alone. In certain embodiments the dose of a co-administered second agent is greater than the dose that would be administered if the second agent was administered alone.

In certain embodiments, a first agent and one or more second agents are administered at the same time. In certain embodiments, the first agent and one or more second agents are administered at different times. In certain embodiments, the first agent and one or more second agents are prepared together in a single pharmaceutical formulation. In certain embodiments, the first agent and one or more second agents are prepared separately.

In certain embodiments, second agents include, but are not limited to, certain procedures to reduce hypertension, diet changes, lifestyle changes, anti-fibrotic drugs and anti-hypertensive drugs such as RAAS inhibitors, diuretics, calcium channel blockers, adrenergic receptor antagonists, adrenergic agonists and vasodilators.

Examples of procedures that can reduce hypertension include, but are not limited to, renal denervation and baroreceptor activation therapy.

Examples of RAAS inhibitors include, but are not limited to ACE inhibitors (e.g., captopril, enalapril, fosinopril, lisinopril, perindopril, quinapril, ramipril, trandolapril and benazepril), angiotensin II receptor antagonists (e.g., candesartan, eprosartan, irbesartan, losartan, olmesartan, telmisartan and valsartan), renin inhibitors (e.g., aliskiren), and aldosterone receptor antagonists (e.g., eplerenone and spironolactone).

Examples of diuretics include loop diuretics (e.g., bumetanide, ethacrynic acid, furosemide, torsemide), thiazide diuretics (e.g., epitizide, hydrochlorothiazide, chlorothiazide and bendroflumethiazide), thiazide-like diuretics (e.g., indapamide, chlorthalidone and metolazone) and potassium-sparing diuretics (e.g., amiloride, triamterene and spironolactone).

Examples of calcium channel blockers include dihydropyridines (e.g., amlodipine, felodipine, isradipine, lercanidipine, nicardipine, nifedipine, nimodipine and nitrendipine) and non-dihydropyridines (e.g., diltiazem and verapamil).

Examples of adrenergic receptor antagonists include Beta blockers (e.g., atenolol, metoprolol, nadolol, oxprenolol, pindolol, propranolol and timolol), Alpha blockers (e.g., doxazosin, phentolamine, indoramin, phenoxybenzamine, prazosin, terazosin and tolazoline) and mixed Alpha+Beta blockers (e.g., bucindolol, carvedilol and labetalol).

Examples of vasodilators include sodium nitroprusside and hydralazine and its derivatives.

Examples of adrenergic agonists include alpha-2 agonists (e.g., clonidine, guanabenz, methyldopa and moxonidine).

Additional examples of anti-hypertensive drugs include guanethidine, reserpine and the like.

The second agents can be used in combination with the therapeutic compounds described herein to decrease a RAAS pathway related disease, disorder and/or condition such as hypertension, organ damage and the like in the subject.

Kits of the Invention

According to another aspect of the invention, kits are provided. Kits according to the invention include package(s) comprising any of the compositions of the invention or oligomeric compound of the invention. In various aspects, the kit comprises any of the compositions of the invention as a unit dose. For purposes herein "unit dose" refers to a discrete amount dispersed in a suitable carrier.

The phrase "package" means any vessel containing compositions presented herein. In preferred embodiments, the package can be a box or wrapping. Packaging materials for use in packaging pharmaceutical products are well known to those of skill in the art. Examples of pharmaceutical packaging materials include, but are not limited to, blister packs, bottles, tubes, inhalers, pumps, bags, vials, containers, syringes (including pre-filled syringes), bottles, and any packaging material suitable for a selected formulation and intended mode of administration and treatment.

The kit can also contain items that are not contained within the package but are attached to the outside of the package, for example, pipettes.

Kits may optionally contain instructions for administering compositions of the present invention to a subject having a condition in need of treatment. Kits may also comprise instructions for approved uses of components of the composition herein by regulatory agencies, such as the United States Food and Drug Administration. Kits may optionally contain labeling or product inserts for the present compositions. The package(s) and/or any product insert(s) may themselves be approved by regulatory agencies. The kits can include compositions in the solid phase or in a liquid phase (such as buffers provided) in a package. The kits also can include buffers for preparing solutions for conducting the methods, and pipettes for transferring liquids from one container to another.

The kit may optionally also contain one or more other compositions for use in combination therapies as described herein. In certain embodiments, the package(s) is a container for any of the means for administration such as intravitreal delivery, intraocular delivery, intratumoral delivery, peritumoral delivery, intraperitoneal delivery, intrathecal delivery, intramuscular injection, subcutaneous injection, intravenous delivery, intra-arterial delivery, intraventricular delivery, intrasternal delivery, intracranial delivery, or intradermal injection.

Methods of Use and Compounds for Use

The invention provides methods for inhibiting the expression of AGT in a subject and methods of treating a RAAS associated disease, disorder and/or condition or the symptoms thereof in a subject comprising administering an effective amount of a dsRNA compound of the invention or a pharmaceutical composition of the invention, so as to inhibit the expression of AGT in the subject. The invention also provides the compounds for use in the treatment use in treating or preventing a RAAS associated disease, disorder and/or condition in a subject.

In some embodiments of the present disclosure, the subject is a mammal, including, but not limited to, mammals of the order Rodentia, such as mice and hamsters, and mammals of the order Logomorpha, such as rabbits, mammals from the order Carnivora, including Felines (cats) and Canines (dogs), mammals from the order Artiodactyla, including Bovines (cows) and Swines (pigs) or of the order Perissodactyla, including Equines (horses). In some aspects, the mammals are of the order Primates, Ceboids, or Simoids (monkeys) or of the order Anthropoids (humans and apes). In a preferred aspect, the mammal is a human.

Advantages of the Invention

Disclosed herein are dsRNA compounds (e.g., siRNAs) targeting AGT improved with Advanced RNA Targeting (ARNATAR) abilities that enhance their gene silencing activity. The dsRNA compounds utilize ARNATAR motifs in conjunction with AGT targeting sequences to produce stable and durable therapeutic compounds allowing longer lasting benefits for acute and chronic diseases and/or less frequent dosing of the therapeutic compound. In addition to stability and durability, the dsRNA compounds utilizing ARNATAR motifs may have a quicker mode of action (for example, by knocking down AGT expression at an earlier time than the reference compound), which would be beneficial for acute diseases. In some instances, ARNATAR dsRNAs have been found to be more potent than a reference compound.

Another benefit of ARNATAR designed dsRNAs targeting AGT is a shortness of length. This shortness of length allows a shorter synthesis protocol and shorter synthesis time and decreases the cost of manufacturing the compounds.

Additionally, ARNATAR designed dsRNA compounds are very potent inhibitors of AGT. The high potency allows AGT reduction in tissues other than liver.

Accordingly, there is a need for improved dsRNA compounds to treat diseases. ARNATAR dsRNA compounds targeting AGT have been designed to improve speed, stability, specificity, safety and potency in order to produce an improved therapeutic.

EXAMPLES

While certain compounds, compositions and methods described herein have been described with specificity in accordance with certain embodiments, the following examples serve only to illustrate the compounds described herein and are not intended to limit the same. Each of the references recited in the present application is herein incorporated-by-reference in its entirety.

Example 1: Designing AGT siRNA with Varying Chemical Motifs

An angiotensinogen (AGT) transcript (Table 1) was targeted by siRNAs designed with ARNATAR motifs.

TABLE 1

| AGT Target Sequence | |
|---|---|
| Name | SEQ ID NO: |
| GenBank NM_001382817.3 | 1 |

AGT targeting siRNAs (also known as AGT siRNAs) were designed as shown in Table 2.

The following applies to all modified sequences disclosed herein:

A notation is made before each nucleotide indicating the type of chemical modification, if any, made to the nucleotide. If no modification notation is made before a letter designating a nucleotide, the nucleotide is a deoxyribonucleotide. Notations for the chemical modifications to the strands can be found as follows:

(5p)=5'-phosphate
r=ribonucleotide
d (or no notation made before a nucleotide)=deoxyribonucleotide which has been substituted for a ribonucleotide
f=2'-F
m=2'-OMe
*=phosphorothioate (PS) linkage which has been substituted for a phosphate (PO) linkage
gna=glycol nucleic acid If more than one sequence is disclosed in one row of the tables, the SEQ ID NO applies to the modified sequence ("Sequence+Chemistry").

Each ARNATAR sense strand is conjugated with a GalNAc-comprising moiety as described by Sharma (Sharma et al., 2018, Bioconjugate Chem, 29:2478-2488, herein incorporated-by-reference; also known as GalNAc3 or GA3 herein; Gene Link, Elmsford, NY, USA) or a GalNAc from AM Chemicals (U.S. Pat. No. 10,087,208, herein incorporated-by-reference; also known herein as GalNAc2 or GA2). As a control, a reference siRNA (also known as ATXL-G or benchmark siRNA herein) was synthesized and included in the studies described herein. This reference siRNA ATXL-G (Table 2A) mirrors a compound known as AD85481 in the prior art (WO2019/222166, incorporated-by-reference herein) and is believed to be Zilebesiran which is currently in clinical trials.

TABLE 2

AGT siRNAs with Modifications to Both Strands

| siRNA Name | Sense or Antisense | Strand Name | Sequence + Chemistry (5' to 3') | Sequence | SEQ ID NO: |
|---|---|---|---|---|---|
| ATsi480 | sense | ATs480 | mC*fC*mAmArC*mArG*mCfUfUmAmCrC*mArA*mGmCfCmU*T*T-GA2 | CCAACAGCUUACCAAGCCUTT | 2 |
|  | Antisense | ATa480 | (5p)mA*G*mGCmUfUmGmGfUmAmAfGmCfUmGfUmUmGfG*mG*mU | AGGCUUGUUAAGCUGUUGGGU | 3 |
| ATsi481 | sense | ATs481 | mU*fU*mAmA*rC*mA*rA*mGfCfCmUmA*rA*mG*rG*mUmCfUmU*T*T-GA3 | UUAACAAGCCUAAGGUCUUTT | 4 |
|  | Antisense | ATa481 | (5p)mA*A*mGfAmCfCmUfAmGmGfCmUfUmGfUmUmAfA*mG*mC | AAGACCUUAGGCUUGUUAAGC | 5 |
| ATsi489 | sense | ATs489 | mU*fU*mAmAfCmAmAfGfCfCmUmAfAmGfGmUfCmU*T*T-GA3 | UUAACAAGCCUAAGGUCUUTT | 6 |
|  | Antisense | ATa489 or ATa597 | (5p)mA*A*mGfAmCfCT*mUfAmGmGfCmUfUmGfUmUmAfA*mG*mC | AAGACCUAGGCUUGUUAAGC | 7 |
| ATsi603 | sense | ATs603 or ATs612 | mU*fG*mCmAfAmGfAmCfUfUmGmAfCmAfCmCmGfAmA*T*T-GA3 | UGCAAGACUUGACACCGAATT | 8 |
|  | Antisense | ATa603, ATa565 or ATa786 | (5p)mU*T*mCfGmGfUG*mUfCmAmAfGmUfCmUfUmGmCfA*mG*mC | UCGGUGUCAAGUCUUGCAGC | 9 |
| ATsi605 | sense | ATs605 | mU*fG*mCmAfAmAfAmCfUfUmGmAfCmAfCmCmGfAmA*T*T-GA3 | UGCAAAACUUGACACCGAATT | 10 |
|  | Antisense | ATa605 | (5p)mU*T*mCfGmGfUG*mUfCmAmAfGmUfUmUfUmGmCfA*mG*mC | UCGGUGUCAAGUUUUGCAGC | 11 |
| ATsi606 | sense | ATs606 | mC*fC*mAmAfCmAfGmCfUfUmAmAfCmAfAmGmCfCmU*T*T-GA3 | CCAACAGCUUAACAAGCCUTT | 12 |
|  | Antisense | ATa606 | (5p)mA*G*mGfCmUfUG*mUfUmAmAfGmCfUmGfUmUmGfGG*mG*mU | AGGCUUGUUAAGCUGUUGGGU | 13 |
| ATsi609 | sense | ATs600 or ATs484 | mC*fC*mAmAfUmAmGfCfUfUmAmAfCmAfAmGmCfCmU*T*T-GA3 | CCAAUAGCUUAACAAGCCUTT | 14 |
|  | Antisense | ATa609 | (5p)mA*G*mGfCmUfUmGmUfUmAmAfGmCfUmUmAfUmUmGfG*mG*mU | AGGCUUGUUAAGCUAUUGGUU | 15 |
| ATsi610 | sense | ATs610 | mA*fC*mCmCfAmAfUmAfGfCmUmUfAmAfCmAmAfGmC*C*T-GA3 | ACCCAAUAGCUUAACAAGCCT | 16 |
|  | Antisense | ATa610 | (5p)mA*G*mGfCmUfUmGmUfUmAmAfGmCfUmUmAfUmUmGfGmGT*mA*mG | AGGCUUGUUAAGCUAUUGGGTAG | 17 |
| ATsi611 | sense | ATs483 | mC*fC*mAmA*rU*mA*rG*mCfUfUmAmA*rC*mA*rA*mGmCfCmU*T*T-GA3 | CCAAUAGCUUAACAAGCCUTT | 18 |
|  | Antisense | ATa609 | (5p)mA*G*mGfCmUfUmGmUfUmAmAfGmCfUmUmAfUmUmGfG*mU*mU | AGGCUUGUUAAGCUAUUGGUU | 15 |
| ATsi612 | sense | ATs612 or ATs603 | mU*fG*mCmAfAmGfAmCfUfUmGmAfCmAfCmCmGfAmA*T*T-GA3 | UGCAAGACUUGACACCGAATT | 8 |
|  | Antisense | ATa612 or ATa787 | (5p)mU*T*mCfGmGfUmGmUfCmAmAfGmUfCmUfUmGmCfA*mG*mC | UCGGUGUCAAGUCUUGCAGC | 19 |
| ATsi613 | sense | AT&613 | mA*fG*mCmUfCmAfAmCfAfAmGmCfCmUfGmAmGfGmU*T*T-GA3 | AGCUCAACAAGCCUGAGGUUT | 20 |

TABLE 2-continued

AGT siRNAs with Modifications to Both Strands

| siRNA Name | Sense or Antisense | Strand Name | Sequence + Chemistry (5' to 3') | Sequence | SEQ ID NO: |
|---|---|---|---|---|---|
| | Antisense | ATa613 | (5p)mA*C*mCfUmCfAmGmG fCmUmUfGmUfUmGfAmGm CfU*mG*mU | ACCUCAGGCUU GUUGAGCUGU | 21 |

TABLE 2A

Reference siRNA

| siRNA Name | Sense or Antisense | Strand Name | Sequence + Chemistry (5' to 3') | Sequence | SEQ ID NO: |
|---|---|---|---|---|---|
| ATXL-G | sense | ATXL-Gs | mG*mU*mCmAmU mCfCmAfCfAfAmUmGmAm GmAmGmUmAmCmA- GalNAc | GUCAUCCACAA UGAGAGUACA | 22 |
| | Antisense | ATXL-Ga | mU*fG*mUmAmC(gnaT)mCm UmCmAmUmUmGfUmGfGm AmUmGmAmC*mG*mA | UGUACUCUCAU UGUGGAUGACG A | 23 |

In Vitro Screening of siRNAs Targeting Human AGT mRNA in Cells

The siRNAs were incubated with human primary hepatocytes (HPH) and taken up by the cells through free uptake, i.e., siRNAs were incubated with cells in the absence of transfection reagents and enter cells through endocytosis via GalNAc conjugate and ASGR receptor interactions. Cells were incubated at different final concentrations for 41-48 hr and total RNA prepared using AcroPrep Advance 96-well Filter Plates (Pall Corporation, Port Washington, New York) and Qiagen's RLT, RW1 and RPE buffers. AGT mRNA levels were determined through qRT-PCR using AGT specific primer probe sets as listed in Table 3. qRT-PCR was performed using AgPath-ID™ One-Step RT-PCR Reagents in QS3 real-time PCR system (ThenmoFisher Scientific, Waltham, MA, USA). The AGT target RNA levels detected in qRT-PCR assay were normalized to total RNA levels measured with RiboGreen™ (ThermoFisher Scientific, Waltham, MA, USA). The results are shown in FIG. 1. The IC50s are calculated and shown in Table 4.

TABLE 3

Sequences of Primer Probe Set for human AGT

| Name | SEQ ID NO: | Sequence |
|---|---|---|
| hsAGT-F | CTGATCCAGCCTCACTATGC | 24 |
| hsAGT-R | AGGTCATAAGATCCTTGCAGC | 25 |
| hsAGT-P | AGGGTCTCACTTTCCAGCAAAACTCC | 26 |

TABLE 4

AGT siRNA Inhibition in HPH Cells after 48 hrs

| AGT siRNAs | IC50 (uM) |
|---|---|
| ATsi603 | 0.0009 |
| ATsi600# | 0.0015 |

TABLE 4-continued

AGT siRNA Inhibition in HPH Cells after 48 hrs

| AGT siRNAs | IC50 (uM) |
|---|---|
| ATsi609 | 0.0025 |
| ATsi481 | 0.0027 |
| ATsi489 | 0.0031 |
| ATsi606 | 0.0042 |
| ATXL-G (old)* | 0.0058 |
| ATsi484# | 0.0071 |
| ATsi483# | 0.0074 |
| ATXL-G (DR)* | 0.0136 |
| ATsi480 | 0.0213 |
| ATsi610 | 0.0254 |
| ATsi611 | 0.0255 |
| ATsi612 | 0.0269 |
| ATsi605 | 0.032 |
| ATsi613 | 1.672 |

*ATXL-G was synthesized in 2 batches: "old" and "DR"
The sequence and chemistry of these siRNAs are listed in Table 7

The results indicated that some ARNATAR designed siRNAs appeared to be more potent than reference siRNA ATXL-G targeting AGT.

Example 2: In Vitro Comparison of ARNATAR Modifications with ESC/ESC+ Modifications for Different siRNA Sequences The above results suggest that ARNATAR chemical modification motifs produced potent AGT siRNAs. To further determine the effects of different siRNA modification motifs, siRNAs were designed targeting 5 different regions of human AGT. For comparison, the siRNAs were designed with ARNATAR motifs, or with a third party's structure and modification design (ESC or ESC+ as described in Hu et al., Therapeutic siRNA: State of the Art, Signal Transduction and Targeted Therapy, 2020, 5:101; Zilebesiran uses the ESC+ modification motif). Since the ESC/ESC+ motif differed in strand length from ARNATAR's motif, the AGT siRNA antisense sequences were matched from the 5' end, to keep a consistent seed sequence. In addition, the siRNAs were made without GalNAc conjugates in order to only compare the chemical modification motifs. The ARNATAR designed siRNAs have a 5'-phosphate on the antisense strand. The AGT siRNA sequences and chemistry are listed in Table 5. The third party's design is represented by letters "AL" or "AL1".

TABLE 5

Oligomeric Compounds Targeting Different Regions of AGT mRNA.

| siRNA Name | Strand Name | Sense or Antisense | Sequence + Chemistry (5' to 3') | Sequence | SEQ ID NO: |
|---|---|---|---|---|---|
| ATsi-365m | ATs365m | sense | mU*fA*mOmUrC*mGrC*mUfGfC mAmArA*mArC*mUmUfGmA*T*T | UAGUCGCUGCAA AACUUGATT | 27 |
| | ATa365m | Antisense | (5p)mU*C*mAfAmGfUT*mUfUm GmCfAmGfCmGfAmCmUA*mG*mC | UCAAGUUUGCA GCGACUAGC | 28 |
| 643-AN | ATsi-643s1 | sense | mU*fA*mGmUfCmGfCmUfGfCm GmAfAmfCmUmUfOmA*T*T | UAGUCGCUGCGA AACUUGATT | 29 |
| | ATa643 | Antisense | (5p)mU*C*mAfAmGfUmUmUfCm GmCfAmGfCmGfAmCmUfA*mG*mC | UCAAGUUUCGCA GCGACUAGC | 30 |
| 643-AL | 643-Als | sense | mG*mC*mUmAmGmUfCmGfCfUf GmCmGmAmAmAmCmUmUmGmA | GCUAGUCGCUGC GAAACUUGA | 31 |
| | 643-Ala | Antisense | mU*fC*mAmAmGfUgnaTfUfCmG mCmAmGfCmGfAmCmUmAmGm C*mA*mC | UCAAGUUUCGCA GCGACUAGCAC | 32 |
| ATsi565 | ATs565 | sense | mU*fG*mCmAfAmGfAmCfUfUm GmAfCmAfCmCmGfAmA*T*T | UGCAAGACUUGA CACCGAATT | 33 |
| | ATa565, ATa603 or ATa786 | Antisense | (5p)mU*T*mCfGmGfUG*mUfCm AmAfGmUfCmUfUmGmCA*mG*mC | UCGGUGUCAAG UCUUGCAGC | 9 |
| 612-AN | ATs565 | sense | mU*fG*mCmAfAmGfAmCfUfUm GmAfCmAfCmCmGfAmA*T*T | UGCAAGACUUGA CACCGAATT | 33 |
| | ATa612 or ATa787 | Antisense | (5p)mU*T*mCfGmGfUmGmUfCm AmAfGmUfCmUfUmGmCfA*mG*mC | UCGGUGUCAAG UCUUGCAGC | 19 |
| 612-AL | 612-Als | sense | mG*mC*mUmGmCmAfAmGfAfCf UmUmGmAmCmAmCmCmGmAmA | GCUGCAAGACUU GACACCGAA | 34 |
| | 612-Ala++ | Antisense | mU*fU*mCmGmGgnaTmGfUfCm AmAmGmUfCmUfUmGmCmAmG mC*mG*mA | UUCGGUGUCAAG UCUUGCAGCGA | 35 |
| ATsiS79 | ATs579 | sense | mG*fA*mCmCfCmUfAmCfCfUm UmCfAmUfAmCmCfUmG*T*T | GACCCUACCUUC AUACCUGTT | 36 |
| | ATa579 | Antisense | (5p)mC*A*mGfGmUfAT*mGfAm AmGfGmUfAmGfGmGmUC*mU*mU | CAGGUAUGAAGG UAGGGUCUU | 37 |
| 579-AL1 | 579s-AL1 | sense | mA*mA*mGmAmCmCfCmUfAfCf CmUmUmCmAmUmAmCmCmUmG | AAGACCCUACCU UCAUACCUG | 38 |
| | 579a-AL | Antisense | mC*fA*mGmGmUfAgnaTfGfAmA mGmGmUfAmGfGmGmUCmUm U*mU*mG | CAGGUAUGAAGG UAGGGUCUUUG | 39 |
| ATsi597 | ATs597 | sense | mU*fU*mAmAfCmAfAmGfCfCm UmAfAmGfGmUmCfUmU*T*T | UUAACAAGCCUA AGGUCUUTT | 40 |
| | ATa597 | Antisense | (5p)mA*A*mGfAmCfCT*mUfAm GmGfCmUfUmGfUmUmAA*mG*mC | AAGACCUAGGC UUGUUAAGC | 7 |

TABLE 5-continued

Oligomeric Compounds Targeting Different Regions of AGT mRNA.

| siRNA Name | Strand Name | Sense or Antisense | Sequence + Chemistry (5' to 3') | Sequence | SEQ ID NO: |
|---|---|---|---|---|---|
| 597-AL1 | 597s-AL1 | sense | mG*mC*mUmUmAmAfCmAfAfGf CmCmUmAmAmGmGmUmCmUm U | GCUUAACAAGCC UAAGGUCUU | 41 |
|  | 597a-AL | Antisense | mA*fA*mGmAmCfCgnaTfUfAmG mGmCmUfUmGfUmUmAmAmGm C*mU*mG | AAGACCUUAGGC UUGUUAAGCUG | 42 |
| ATsi598 | ATs598 | sense | mC*fC*mAmAfUmAfGmCfUfUm AmAfCmAfAmGmCfCmU*T*T | CCAAUAGCUUAA CAAGCCUTT | 43 |
|  | ATa598 or ATa484 | Antisense | (5p)mA*G*mGfCmUfUG*mUfUm AmAfGmCfUmAfUmUmGG*mG* mU | AGGCUUGUUAAG CUAUUGGGU | 44 |
| 598-AL1 | 598s-AL1 | sense | mA*mC*mCmCmAmAfUmAfGfCf UmUmAmAmCmAmAmGmCmCm U | ACCCAAUAGCUU AACAAGCCU | 45 |
|  | 598a-AL⁺⁺⁺ | Antisense | mA*fG*mGmCmUfUmGfUfUmAm AmGmCfUmAfUmUmGmGmGmU *mA*mG | AGGCUUGUUAAG CUAUUGGGUAG | 46 |

⁺⁺Since gnaG was not available, 612-Ala differs from the normal ESC+ chemistry in placement of the gna modification, however, gna at position 6 has also been widely used in drug discovery (see PCT/US2019/032150).
⁺⁺⁺Since gnaG is not available, 598a-AL does not contain gna at position 7, similar to the BSC chemistry.

In Vitro Assays—Comparison of ARNATAR Motifs to Third Party Motifs

AGT siRNAs without GalNAc conjugate were transfected at 0-10 nM into Hep3B cells with RNAiMAX (Invitrogen, Waltham, MA) and the cells further cultured for 24 hr. siRNA activity was determined by qRT-PCR using the primer probe sets as listed in Table 3. The IC50 of the siRNAs targeting AGT are shown in Table 6 and the dose response curve of siRNA on AGT mRNA levels in Hep3B cells are shown in FIG. 2.

TABLE 6 siRNA Activity Targeting AGT in Hep3B cells

| siRNAs | IC50 (nM) |
|---|---|
| 579AL | 15.06 |
| ATsi-579 | 0.0947 |
| 597AL | 1.105 |
| ATsi-597 | 0.087 |
| 598-AL | 0.3776 |
| ATsi-598 | 0.0604 |
| 612-AL | 1233 |
| 612-AN | 0.1821 |
| ATsi-565 | 0.0284 |
| 643-AL | 1172.3 |
| ATsi-365m | 0.04887 |
| 643-AN | 0.01122 |

The results indicate that for all these different sequences, the optimized ARNATAR designs are more potent than the third-party design (P<0.0001), indicating that the optimized ARNATAR motifs are generalizable and the increased activity applies to different sequences.

Example 3: ARNATAR AGT siRNAs Showed Better Activity and Longer Duration Compared with the Reference siRNA in Animals To compare the activity and duration of siRNAs in vitro and in vivo with reference siRNA ATXL-G, selected ARNATAR siRNAs with different chemistry were designed and synthesized, using GalNAc3 (Table 7).

TABLE 7

AGT Oligomeric Compounds with Modifications to Both Strands

| siRNA Name | Strand Name | Sense or Antisense | Sequence + Chemistry (5' to 3') | Sequence | SEQ ID NO: |
|---|---|---|---|---|---|
| ATsi483 | ATs483 | sense |  | mC*fC*mAmA*rU*mA*G* mCfUfUmAmA*rC*mA*rA* mGmCfCmU*T*T-GA3 | CCAAUAGCUU AACAAGCCUTT | 18 |
|  | ATa483 | Antisense |  | (5p)mA*G*mGfCmUfUmGm UfUmAmAfGmCfUmAfUmU mGfG*mG*mU | AGGCUUGUUA AGCUAUUGGG U | 47 |

TABLE 7-continued

AGT Oligomeric Compounds with Modifications to Both Strands

| siRNA Name | Strand Name | Sense or Antisense | Sequence + Chemistry (5' to 3') | Sequence | SEQ ID NO: |
|---|---|---|---|---|---|
| ATsi484 | sense | ATs484 or ATs600 | mC*fC*mAmAfUmAfGmCf UfUmAmAfCmAfAmGmCfC mU*T*T-GA3 | CCAAUAGCUU AACAAGCCUTT | 14 |
|  | Antisense | ATa484 or ATa598 | (5p)mA*G*mGfCmUfUG*m UfUmAmAfGmCfUmAfUmU mGG*mG*mU | AGGCUUGUUA AGCUAUUGGG U | 44 |
| ATsi600 | sense | ATs484 or ATs600 | mC*fC*mAmAfUmAfGmCf UfUmAmAfCmAfAmGmCfC mU*T*T-GA3 | CCAAUAGCUU AACAAGCCUTT | 14 |
|  | Antisense | ATa483 | (5p)mA*G*mGfCmUfUmGm UfUmAmAfGmCfUmAfUmU mGfG*mG*mU | AGGCUUGUUA AGCUAUUGGG U | 47 |

In Vitro Assay siRNAs were delivered at different final concentrations to human primary hepatocytes (HPH) through free uptake, i.e., siRNAs are incubated with cells in the absence of transfection reagents and enter cells through endocytosis via GalNAc conjugate and ASGR receptor interactions. Cells were incubated for 42 hr and total RNA prepared using AcroPrep Advance 96-well Filter Plates (Pall Corporation, Port Washington, New York) and Qiagen's RLT, RW1 and RPE buffers. AGT mRNA levels were determined through qRT-PCR using AGT specific primer probe sets as listed in Table 3. qRT-PCR was performed using AgPath-ID™ One-Step RT-PCR Reagents in QS3 real-time PCR system (ThermoFisher Scientific, Waltham, MA, USA). The AGT RNA levels detected in qRT-PCR assay were normalized to total RNA levels as measured with RiboGreen™ (ThermoFisher Scientific, Waltham, MA, USA). The results are shown in FIG. 3. The IC50s are calculated and shown in Table 8.

TABLE 8

| IC50 of siRNA inhibition of AGT mRNA in HPH | | | | |
|---|---|---|---|---|
|  | ATsi483 | ATsi600 | ATsi484 | ATXL-G |
| IC50 (uM) | 0.00258 | 0.00956 | 0.01543 | 0.00259 |

The results showed that ARNATAR siRNA compounds, such as ATsi483, showed comparable activity with reference siRNA ATXL-G.

In Vivo Study 1

To assess human AGT siRNA activity in vivo, a mouse model expressing human AGT was made. Seven week old BALB/c mice were injected intravenously with adeno-associated virus (AAV) serotype AAV8 expressing human AGT mRNA (GenBank NM_001382817.3; Sands MS, AAV-Mediated Liver-Directed Gene Therapy, 2014, Methods Mol Biol, 807:141-157). At least 3 weeks later after virus administration, blood was collected from mice using lithium heparin as an anticoagulant, and plasma prepared by centrifugation of the blood samples at 2000×g for 10 min at 4° C. Plasma AGT protein levels were then determined using an ELISA kit specific to human AGT (IBL, Minneapolis, MN. Catalog. No 27412). The AGT levels of individual animals at this time point were used as base lines of the AGT (protein) expression.

To determine siRNA activity in vivo, the next day after baseline blood collection, siRNAs were dosed subcutaneously at 1 mg/kg (ATsi483, ATsi484 and ATXL-G) or 3 mg/kg (ATsi483, ATsi484, ATsi600 and ATXL-G) in the AGT transgenic mice (N=4-6 for each siRNA dose cohort). Blood samples were then collected at indicated times after siRNA dosing, and AGT protein levels in plasma were measured by ELISA. Average AGT protein levels relative to baseline levels (measured at Day −1 before dosing) are shown in FIG. 4.

The results showed that ARNATAR siRNAs showed comparable (ATsi483 and ATsi484) or better (ATsi600) activity in vivo compared with reference siRNA ATXL-G, with similar duration in the over 6-weeks time frame tested. Interestingly, several siRNAs, e.g., ATsi484 and ATsi600, appear slightly less active than the reference siRNA in cell culture by free uptake, however, similar or better activity than the reference siRNA was observed in animals. These results suggest that some difference exists in activity between cell culture and in vivo systems.

Example 4. Evaluation of Different Sequences and Modifications In Vivo

To further evaluate the effects of sequences and chemical motifs on AGT siRNA activity, new ARNATAR siRNAs were synthesized that contain either different sequences, different modification motifs, or different lengths. The siRNAs were conjugated with GalNAc3 (GA3 from Gene Link, Elmsford, NY, USA). The siRNAs are listed in Table 9.

TABLE 9

AGT Oligomeric Compounds with Modifications to Both Strands

| siRNA Name | Sense or Antisense | Strand Name | Sequence + Chemistry (5' to 3') | Sequence | SEQ ID NO: |
|---|---|---|---|---|---|
| ATsi610 | sense | ATs610 | mA*fC*mCmCfAmAfUmAfGf CmUmUfAmAfCmAmAfGmC *C*T-GA3 | ACCCAAUAGCU UAACAAGCCT | 16 |
| | Antisense | ATa610 | (5p)mA*G*mGfCmUfUmGmU fUmAmAfGmCfUmAfUmUm GfGmGT*mA*mG | AGGCUUGUUA AGCUAUUGGGT AG | 17 |
| ATsi643 | sense | ATs643 | mU*fA*mGmUfCmGfCmUfGf CmGmAfAmAfCmUmUfGmA *T*T-GA3 | UAGUCGCUGCG AAACUUGATT | 48 |
| | Antisense | ATa643 | (5p)mU*C*mAfAmGfUmUmU fCmGmCfAmGfCmGfAmCm UfA*mG*mC | UCAAGUUUCGC AGCGACUAGC | 30 |
| ATsi644 | sense | ATs644 | mG*fC*mUmUfAmAfCmAfAf GmCmCfUmAfAmGmGfUmC *mU*mU-GA3 | GCUUAACAAGC CUAAGGUCUU | 49 |
| | Antisense | ATa644 | (5p)mA*A*mGfAmCfCmUmU fAmGmGfCmUfUmGfUmUm AfAmGmC*mU*mG | AAGACCUUAG GCUUGUUAAG CUG | 50 |
| ATsi648 | sense | ATs648 | mG*fA*mCmCfCmUfAmCfCf UmUmCfAmUfAmCmCfUmG *T*T-GA3 | GACCCUACCUU CAUACCUGTT | 51 |
| | Antisense | ATa648 | (5p)mC*A*mGfGmUfAmUmG fAmAmGfGmUfAmGfOmGm UfC*mU*mU | CAGGUAUGAA GGUAGGGUCU U | 52 |

To produce a mouse model expressing human AGT, 7 weeks BALB/c mice were injected intravenously with adeno-associated virus (AAV) serotype AAV8 expressing human AGT mRNA (GenBank NM_001382817.3; Sands MS, AAV-Mediated Liver-Directed Gene Therapy, 2014, Methods Mol Biol, 807:141-157). At least 3 weeks later after virus administration, blood was collected from mice, and plasma prepared by centrifugation of the blood samples at 2000×g for 10 min at 4° C. Plasma AGT protein levels were then determined using an ELISA kit specific to human AGT (IBL, Minneapolis, MN. Catalog. No 27412). The AGT levels of individual animals at this time point were used as base lines of the AGT (protein) expression.

To determine siRNA activity in vivo, the next day after baseline blood collection, siRNAs were dosed subcutaneously at 3 mg/kg (N=3-4). Blood samples were then collected at indicated times after siRNA dosing, and AGT protein levels in plasma were measured by ELISA. Average AGT protein levels relative to baseline levels (measured at Day −1 before dosing) are shown in FIG. 5. In the previous experiment (Example 3, FIG. 4) for the reference compound ATXL-G at the last time point (31 days), the AGT level was ~40%, similar here to ATsi610 and ATsi643. The results showed that certain siRNA compounds, such as ATsi643 and ATsi610, are comparable to the reference siRNA in terms of both activity and duration.

Example 5: Evaluation of Additional Sequences and Modifications In Vitro and In Vivo To further evaluate the effects of sequences and chemical motifs on siRNA activity, new ARNATAR siRNAs were synthesized that contain either different sequences, different modification motifs, different lengths or with natural or TT overhangs. For example, the sequence for ATsi603 and ATsi612 contains a mismatched mutation to SEQ ID NO: 1. The siRNAs were conjugated with GalNAc3 (GA3 from Gene Link, Elmsford, NY, USA). The siRNAs are listed in Table 10.

TABLE 10

AGT Oligomeric Compounds with Modifications to Both Strands

| siRNA Name | Sense or Antisense | Strand Name | Sequence + Chemistry (5' to 3*) | Sequence | SEQ ID NO: |
|---|---|---|---|---|---|
| ATsi603 | sense | ATs603 or ATs612 | mU*fG*mCmAfAmGfAm CfUfUmGmAfCmAfCmC mGfAmA*T*T-GA3 | UGCAAGACUUG ACACCGAATT | 8 |
| | Antisense | ATa603, ATa565 or ATa786 | (5p)mU*T*mCfGmGfUG* mUfCmAmAfGmUfCmUf UmGmCA*mG*mC | UCGGUGUCAA GUCUUGCAGC | 9 |
| ATsi612 | sense | ATs612 of ATs603 | mU*fG*mCmAfAmGfAm CfUfUmGmAfCmAfCmC mGfAmA*T*T-GA3 | UGCAAGACUUG ACACCGAATT | 8 |

TABLE 10-continued

AGT Oligomeric Compounds with Modifications to Both Strands

| siRNA Name | Sense or Antisense | Strand Name | Sequence + Chemistry (5' to 3*) | Sequence | SEQ ID NO: |
|---|---|---|---|---|---|
| | Antisense | ATa612 or ATa787 | (5p)mU*T*mCfGmGfUmG mUfCmAmAfGmUfCmUf UmGmCfA*mG*mC | UTCGGUGUCAA GUCUUGCAGC | 19 |
| ATsi633 | sense | ATs633 | mA*fC*mCmCfAmAfUm AfGfCmUmUfAmAfCmA mAfGmCmCfU*T*T-GA3 | ACCCAAUAGCU UAACAAGCCUT T | 53 |
| | Antisense | ATa633 | (5p)mA*G*mGfCmUfUmG mUfUmAmAfGmCfUmAf UmUmGfGmGmU*T*T | AGGCUUGUUAA GCUAUUGGGUT T | 54 |
| ATsi665 | sense | ATs633 | mA*fC*mCmCfAmAfUm AfGfCmUmUfAmAfCmA mAfGmCmCfU*T*T-GA3 | ACCCAAUAGCU UAACAAGCCUT T | 53 |
| | Antisense | ATa610 | (5p)mA*G*mGfCmUfUmG mUfUmAmAfGmCfUmAf UmUmGfGmGT*mA*mG | AGGCUUGUUAA GCUAUUGGGTA G | 17 |

In Vitro Assay

For a better comparison, two siRNAs (ATsi600 and ATsi610) evaluated above were also included in this assessment of additional ARNATAR siRNAs.

siRNAs were delivered at different final concentrations to human primary hepatocytes (HPH) through free uptake, i.e., siRNAs are incubated with cells in the absence of transfection reagents and enter cells through endocytosis via GalNAc conjugate and ASGR receptor interactions. Cells were incubated for 42 hr and total RNA prepared using AcroPrep Advance 96-well Filter Plates (Pall Corporation, Port Washington, New York) and Qiagen's RLT, RW1 and RPE buffers. AGT mRNA levels were determined through qRT-PCR using AGT specific primer probe sets as listed in Table 3. qRT-PCR was performed using AgPath-ID™ One-Step RT-PCR Reagents in QS3 real-time PCR system (ThermoFisher Scientific, Waltham, MA, USA). The AGT RNA levels detected in qRT-PCR assay were normalized to total RNA levels as measured with RiboGreen™ (ThermoFisher Scientific, Waltham, MA, USA). The results are shown in FIG. 6. The IC50s are calculated and shown in Table 11.

TABLE 11

IC50 of siRNA Inhibition of AGT mRNA in Human Primary Hepatocytes

| | ATsi603 | ATsi610 | ATsi612 | ATsi633 | ATsi600 | ATXL-G |
|---|---|---|---|---|---|---|
| IC50 (uM) | 0.101 | 0.267 | 0.201 | 1.617 | 0.137 | 0.043 |

In Vivo Study

To produce a mouse model expressing human AGT, 7 weeks BALB/c mice were injected intravenously with adeno-associated virus (AAV) serotype AAV8 expressing human AGT mRNA (GenBank NM_001382817.3; Sands MS, AAV-Mediated Liver-Directed Gene Therapy, 2014, Methods Mol Biol, 807:141-157). At least 3 weeks later after virus administration, blood was collected from mice, and plasma prepared by centrifugation of the blood samples at 2000×g for 10 min at 4° C. Plasma AGT protein levels were then determined using an ELISA kit specific to human AGT (IBL, Minneapolis, MN. Catalog. No 27412). The AGT levels of individual animals at this time point were used as baselines of the AGT (protein) expression.

To determine siRNA activity in vivo, the next day after baseline blood collection, selected siRNAs ATsi603, ATsi612, ATsi665 and benchmark siRNA ATXL-G were dosed subcutaneously at 3 mg/kg (N=2-4). Blood samples were then collected at indicated times after siRNA dosing, plasma prepared, and AGT protein levels in plasma were measured by ELISA. Average AGT protein levels relative to baseline levels (measured at Day −1 before dosing) are shown in FIG. 7 and Table 12.

TABLE 12

Plasma AGT protein level in percentage relative to base line AGT protein level

| | ATsi665 | ATXL-G | ATsi612 | ATsi603 |
|---|---|---|---|---|
| Week 1 | 46.38 | 17.03 | 12.77 | 18.00 |
| Week 2 | 46.8 | 18.7 | 18.6 | 17.9 |

The results indicate that, again, although certain siRNAs, such as ATsi612, showed slightly lower activity in vitro, however, in vivo, this siRNA compound showed slightly better or comparable to the reference siRNA in terms of both activity and duration.

Example 6: Evaluation of Selected Oligomeric Compounds In Vitro and In Vivo

To further evaluate the effects of GalNAc conjugates on siRNA activity, new ARNATAR siRNAs were designed that contain the sequence and chemical motif of ATsi603 or ATsi612 (see Table 10), but, were conjugated to a different GalNAc-comprising moiety (GalNAc-AN also known as GA-AN or GA4, see supra for a description of GA4). The new siRNAs are listed in Table 13.

TABLE 13

AGT Oligomeric Compounds with Modifications to Both Strands

| siRNA Name | Sense or Antisense | Strand Name | Sequence + Chemistry (5' to 3') | Sequence | SEQ ID NO: |
|---|---|---|---|---|---|
| ATsi786 | Sense | ATs786 or ATs787 | mU*fG*mCmAfAmGfAm CfUfUmGmAfCmAfCmC mGfAmA*T*T-GA4 | UGCAAGACUUG ACACCGAATT | 55 |
| | Antisense | ATa786, ATa565 or ATa603 | (5p)mU*T*mCfGmGfUG* mUfCmAmAfGmUfCmUf UmGmCA*mG*mC | UTCGGUGUCAA GUCUUGCAGC | 9 |
| ATsi787 | Sense | ATs787 or ATs786 | mU*fG*mCmAfAmGfAm CfUfUmGmAfCmAfCmC mGfAmA*T*T-GA4 | UGCAAGACUUG ACACCGAATT | 55 |
| | Antisense | ATa787 or ATa612 | (5p)mU*T*mCfGmGfUmG mUfCmAmAfGmUfCmUf UmGmCfA*mG*mC | UTCGGUGUCAA GUCUUGCAGC | 19 |

In Vitro Assay: Time Course in Hep3B Cells

AGT targeting siRNAs ATsi603, ATsi786, ATsi787 and benchmark siRNA ATXL-G were transfected at 0 nM, 0.008 nM, 0.04 nM, 0.2 nM, 1 nM and 5 nM into Hep3B cells with RNAiMAX (Invitrogen, Waltham, MA) and the cells further cultured for 8 hr or 13 hr. siRNA activity was determined by qRT-PCR using the primer probe sets as listed in Table 3.

The AGT RNA levels detected in qRT-PCR assay were normalized to total RNA levels as measured with RiboGreen™ (ThermoFisher Scientific, Waltham, MA, USA). The percent of AGT mRNA levels are shown in FIG. 8. ATsi786 and ATsi603 are more potent than ATXL-G, with P=0.0047 and 0.0033 at 8 hrs; P=0.0019 and 0.0385 at 12 hrs.

In Vivo Assay

To produce a mouse model expressing human AGT, 7 weeks BALB/c mice were injected intravenously with adeno-associated virus (AAV) serotype AAV8 expressing human AGT mRNA (GenBank NM_001382817.3; Sands MS, AAV-Mediated Liver-Directed Gene Therapy, 2014, Methods Mol Biol, 807:141-157). At least 3 weeks later after virus administration, blood was collected from mice, and plasma prepared by centrifugation of the blood samples at 2000×g for 10 min at 4° C. Plasma AGT protein levels were then determined using an ELISA kit specific to human AGT (IBL, Minneapolis, MN. Catalog. No 27412). The AGT levels of individual animals at this time point were used as baselines of the AGT (protein) expression.

To determine siRNA activity in vivo, the next day after baseline blood collection, AGT targeting siRNAs ATsi786, ATsi787 and benchmark siRNA ATXL-G were dosed subcutaneously at 3 mg/kg (N=3-4). Blood samples were then collected weekly for up to 6 or 7 weeks after siRNA dosing, plasma prepared, and AGT protein levels in plasma were measured by ELISA. Average AGT protein levels relative to baseline levels (measured at Day −1 before dosing) are shown in FIG. 9. As shown in FIG. 9, ATsi786 was slightly more potent at several time points than benchmark ATXL-G in reducing AGT expression.

Example 7: Evaluation of Selected Oligomeric Compounds in AGT Transgenic Mice

To assess the early kinetics of human AGT siRNA activity in vivo, a mouse model expressing human AGT was made. 7-8 week old BALB/c mice were injected intravenously with adeno-associated virus (AAV) serotype AAV8 expressing human AGT mRNA (GenBank NM_001382817.3; Sands MS, AAV-Mediated Liver-Directed Gene Therapy, 2014, Methods Mol Biol, 807:141-157) at $2.5 \times 10^{11}$ virus genome per animal. About 3 weeks after virus administration, blood was collected from mice using lithium heparin as an anti-coagulant, and plasma prepared by centrifugation of the blood samples at 2000×g for 10 min at 4° C. Plasma AGT protein levels were then determined using an ELISA kit specific to human AGT (IBL, Minneapolis, MN. Catalog. No 27412). The AGT levels of individual animals at this time point were used as base lines of the AGT (protein) expression.

To determine siRNA activity in vivo, human AGT siRNA ATsi786 or benchmark ATXL-G was administered at 3 mg/kg through subcutaneous (SC) injection on Day 0 (N=3 for each group). Approximately 50 µl blood was collected through cheek bleeding on day −1 (base line) and on day 3, 5, 7 and 10 into Microvette® CB 300 Lithium heparin LH tubes (Sarstedtstr, NUmbrecht Germany) and kept on ice for over 20 mins. Plasma was prepared by centrifugation of the blood sample at 2000×g for 20 minutes at 4° C., using a 5425R centrifuge (Eppendorf, Hamburg, Germany), and supernatant was collected. Human AGT protein levels in plasma (1:1000 dilution) from day −1 and day 10 were determined using Human Total Angiotensinogen Assay Kit (product number 27412; IBL-America, Minneapolis, MN, USA), based on the manufacturer's protocol. The relative AGT protein levels at different times were calculated in Excel as percentage of the AGT protein levels at day −1 of the individual animals. The average percentage in each group was calculated in Excel as shown in Table 14 and plotted as shown in FIG. 10.

TABLE 14

Mean Expression of AGT Protein Levels at Various Time Points

| Treatment | Mean Expression % | | | | |
|---|---|---|---|---|---|
| | Day-1 | Day 3 | Day 5 | Day 7 | Day 10 |
| ATsi786 | 100.0 | 14.9 | 10.3 | 9.9 | 3.4 |
| ATXL-G | 100.0 | 34.4 | 24.2 | 19.6 | 17.3 |

The results show that the level of human AGT protein in plasma was quickly reduced upon ATsi786 siRNA administration in animals. ATsi786 reduced human AGT protein faster than benchmark ATXL-G (P=0.0201).

TABLE 15

Sequences

| SEQ ID NO: | SEQUENCE | DESCRIPTION |
|---|---|---|
| 1 | AGAAAGTAGACCCTCACCAGGCATGGAATCTGCCAGTG<br>CCTTGATCTTGGACTTCCAGCTTCCAGAACTGGTATGCG<br>GAAGCCAGCACCCCAGTCTGAGATGGCTCCTGCCGGTG<br>TGAGCCTGAGGGCCACCATCCTCTGCCTCCTGGCCTGG<br>GCTGGCCTGGCTGCAGGTGACCGGGTGTACATACACCC<br>CTTCCACCTCGTCATCCACAATGAGAGTACCTGTGAGC<br>AGCTGGCAAAGGCCAATGCCGGGAAGCCCAAAGACCC<br>CACCTTCATACCTGCTCCAATTCAGGCCAAGACATCCCC<br>TGTGGATGAAAAGGCCCTACAGGACCAGCTGGTGCTAG<br>TCGCTGCAAAACTTGACACCGAAGACAAGTTGAGGGCC<br>GCAATGGTCGGGATGCTGGCCAACTTCTTGGGCTTCCGT<br>ATATATGGCATGCACAGTGAGCTATGGGGCGTGGTCCA<br>TGGGGCCACCGTCCTCTCCCCAACGGCTGTCTTTGGCAC<br>CCTGGCCTCTCTATCTGGGAGCCTTGGACCACACAGC<br>TGACAGGCTACAGGCAATCCTGGGTGTTCCTTGGAAGG<br>ACAAGAACTGCACCTCCCGGCTGGATGCGCACAAGGTC<br>CTGTCTGCCCTGCAGGCTGTACAGGGCCTGCTAGTGGC<br>CCAGGGCAGGGCTGATAGCCAGGCCCAGCTGCTGCTGT<br>CCACGGTGGTGGGCGTGTTCACAGCCCCAGGCCTGCAC<br>CTGAAGCAGCCGTTTGTGCAGGGCCTGGCTCTCTATACC<br>CCTGTGGTCCTCCCACGCTCTCTGGACTTCACAGAACTG<br>GATGTTGCTGCTGAGAAGATTGACAGGTTCATGCAGGC<br>TGTGACAGGATGGAAGACTGGCTGCTCCCTGATGGGAG<br>CCAGTGTGGACAGCACCCTGGCTTTCAACACCTACGTC<br>CACTTCCAAGGGAAGATGAAGGGCTTCTCCCTGCTGGC<br>CGAGCCCCAGGAGTTCTGGGTGGACAACAGCACCTCAG<br>TGTCTGTTCCCATGCTCTCTGGCATGGGCACCTTCCAGC<br>ACTGGAGTGACATCCAGGACAACTTCTCGGTGACTCAA<br>GTGCCCTTCACTGAGAGCGCCTGCCTGCTGCTGATCCAG<br>CCTCACTATGCCTCTGACCTGGACAAGGTGGAGGGTCT<br>CACTTTCCAGCAAAACTCCCTCAACTGGATGAAGAAAC<br>TATCTCCCCGGACCATCCACCTGACCATGCCCCAACTGG<br>TGCTGCAAGGATCTTATGACCTGCAGGACCTGCTCGCC<br>CAGGCTGAGCTGCCCGCCATTCTGCACACCGAGCTGAA<br>CCTGCAAAAATTGAGCAATGACCGCATCAGGGTGGGGG<br>AGGTGCTGAACAGCATTTTTTTTGAGCTTGAAGCGGAT<br>GAGAGAGAGCCCACAGAGTCTACCCAACAGCTTAACAA<br>GCCTGAGGTCTTGGAGGTGACCCTGAACCGCCCATTCC<br>TGTTTGCTGTGTATGATCAAAGCGCCACTGCCCTGCACT<br>TCCTGGGCCGCGTGGCCAACCCGCTGAGCACAGCATGA<br>GGCCAGGGCCCCAGAACACAGTGCCTGGCAAGGCCTCT<br>GCCCCTGGCCTTTGAGGCAAAGGCCAGCAGCAGATAAC<br>AACCCCGGACAAATCGACGATGTGTCACCCCCAGTCTC<br>CCACCTTTTCTTCTAATGAGTCGACTTTGAGCTGGAAAG<br>CAGCCGTTTCTCCTTGGTCTAAGTGTGCTGCATGGAGTG<br>AGCAGTAGAAGCCTGCAGCGGCACAAATGCACCTCCCA<br>GTTTGCTGGGTTTATTTTAGAGAATGGGGGTGGGGAGG<br>CAAGAACCAGTGTTTAGCGCGGGACTACTGTTCCAAAA<br>AGAATTCCAACCGACCAGCTTGTTTGTGAAACAAAAAA<br>GTGTTCCCTTTTCAAGTTGAGAACAAAAATTGGGTTTTA<br>AAATTAAAGTATACATTTTTGCATTGCCTTCGGTTTGTA<br>TTTAGTGTCTTGAATGTAAGAACATGACCTCCGTGTAGT<br>GTCTGTAATACCTTAGTTTTTTCCACAGATGCTTGTGAT<br>TTTTGAACAATACGTGAAAGATGCAAGCACCTGAATTT<br>CTGTTTGAATGCGGAACCATAGCTGGTTATTTCTCCCTT<br>GTGTTAGTAATAAACGTCTTGCCACAATAAGCCTCCAA<br>AAA | AGT sequence GenBank NM_001382817.3 |
| 56 | CCAACAGCUUACCAAGCCUTT | Sense strand ATs480 |
| 57 | AGGCUUGGUAAGCUGUUGGGU | Antisense strand ATa480 |
| 58 | UUAACAAGCCUAAGGUCUUTT | Sense strand ATs481, ATs489, ATs597 |
| 59 | AAGACCUUAGGCUUGUUAAGC | Antisense strand ATa481 |
| 60 | AAGACCTUAGGCUUGUUAAGC | Antisense strand ATa489, ATa597 |

TABLE 15-continued

Sequences

| SEQ ID NO: | SEQUENCE | DESCRIPTION |
|---|---|---|
| 61 | UGCAAGACUUGACACCGAATT | Sense strand ATs565, ATs603 ATs612, ATs786, ATs787 |
| 62 | UTCGGUGUCAAGUCUUGCAGG | Antisense strand ATa565, ATa603, ATa612, ATa786, ATa787 |
| 63 | GCUGCAAGACUUGACACCGAA | Sense strand 612-Als |
| 64 | UUCGGUGUCAAGUCUUGCAGCGA | Antisense strand 612-Ala |
| 65 | GACCCUACCUUCAUACCUGTT | Sense strand ATs579, ATs648 |
| 66 | CAGGUATGAAGGUAGGGUCUU | Antisense strand ATa579 |
| 67 | AAGACCCUACCUUCAUACCUG | Sense strand 579s-AL1 |
| 68 | CAGGUAUGAAGGUAGGGUCUUUG | Antisense strand 579a-AL |
| 69 | GCUUAACAAGCCUAAGGUCUU | Sense strand 597s-AL1 |
| 70 | AAGACCUUAGGCUUGUUAAGCUG | Antisense strand 597a-AL |
| 71 | CCAAUAGCUUAACAAGCCUTT | Sense strand ATs483, ATs484, ATs598, ATs600 |
| 72 | AGGCUUGUUAAGCUAUUGGGU | Antisense strand ATa483, ATa484, ATa598 |
| 73 | UGCAAAACUUGACACCGAATT | Sense strand ATs605 |
| 74 | UTCGGUGUCAAGUUUUGCAGC | Antisense strand ATa605 |
| 75 | CCAACAGCUUAACAAGCCUTT | Sense strand ATs606 |
| 76 | AGGCUUGUUAAGCUGUUGGGU | Antisense strand ATa606 |
| 77 | AGGCUUGUUAAGCUAUUGGUU | Antisense strand ATa609 |
| 78 | ACCCAAUAGCUUAACAAGCCT | Sense strand ATs610 |
| 79 | AGGCUUGUUAAGCUAUUGGGTAG | Antisense strand ATa610 |
| 80 | ACCUCAACAAGCCUGAGGUTT | Sense strand ATs613 |
| 81 | ACCUCAGGCUUGUUGAGCUGU | Antisense strand ATa613 |
| 82 | GUCAUCCACAAUGAGAGUACA | Sense strand ATXL-Gs |
| 83 | UGUACUCUCAUUGUGGAUGACGA | Antisense strand ATXL-Ga |
| 84 | CTGATCCAGCCTCACTATGC | Human AGT forward primer hsAGT-F |
| 85 | AGGTCATAAGATCCTTGCAGC | Human AGT reverse primer hsAGT-R |
| 86 | AGGGTCTCACTTTCCAGCAAAACTCC | Human AGT probe hsAGT-P |
| 87 | UAGUCGCUGCAAAACUUGATT | Sense strand ATs365m |
| 88 | UCAAGUUUUGCAGCGACUAGC | Antisense strand ATa365m |
| 89 | UAGUCGCUGCGAAACUUGATT | Sense strand ATs643, ATsi-643s1 |
| 90 | UCAAGUUUCGCAGCGACUAGC | Antisense strand ATa643 |
| 91 | GCUAGUCGCUGCGAAACUUGA | Sense strand 643-Als |
| 92 | UCAAGUUUCGCAGCGACUAGCAC | Antisense strand 643-Ala |
| 93 | ACCCAAUAGCUUAACAAGCCU | Sense strand 598s-AL1 |

TABLE 15-continued

Sequences

| SEQ ID NO: | SEQUENCE | DESCRIPTION |
|---|---|---|
| 94 | AGGCUUGUUAAGCUAUUGGGUAG | Antisense strand 598a-AL |
| 95 | GCUUAACAAGCCUAAGGUCUU | Sense strand ATs644 |
| 96 | AAGACCUUAGGCUUGUUAAGCUG | Antisense strand ATa644 |
| 97 | CAGGUAUGAAGGUAGGGUCUU | Antisense strand ATa648 |
| 98 | ACCCAAUAGCUUAACAAGCCUTT | Sense strand ATs633 |
| 99 | AGGCUUGUUAAGCUAUUGGGUTT | Antisense strand ATa633 |

What is claimed:

1. A compound comprising an siRNA compound for inhibiting expression of angiotensinogen (AGT) in a cell, wherein the siRNA compound comprises a sense strand and an antisense strand forming a duplex, wherein the sense strand comprises SEQ ID NO: 55 and a GalNAc moiety as shown in the formula:

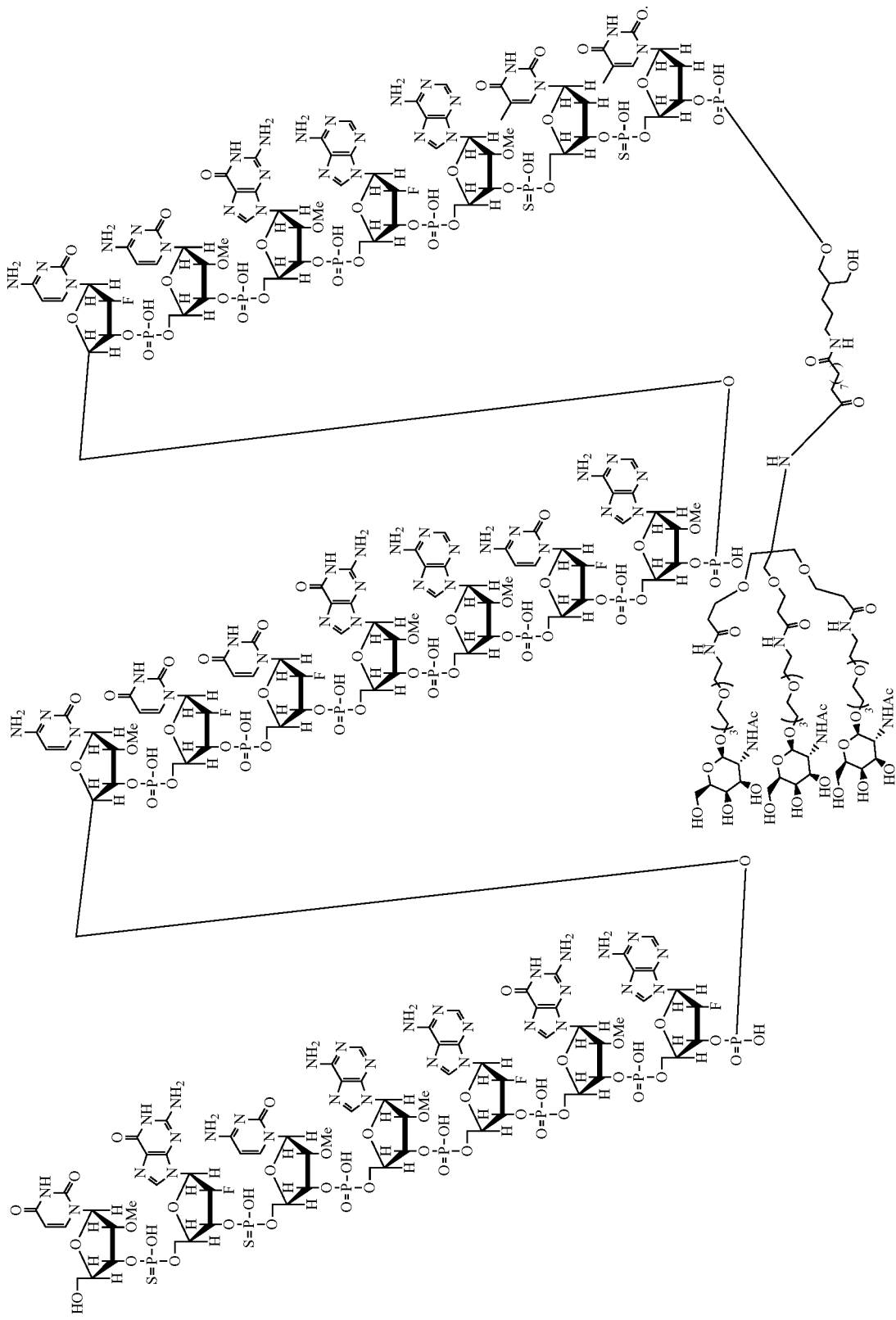

2. A compound comprising an siRNA compound for inhibiting expression of angiotensinogen (AGT) in a cell, wherein the siRNA compound comprises a sense strand and an antisense strand forming a duplex, wherein the antisense strand comprises SEQ ID NO: 9 as shown in the formula:

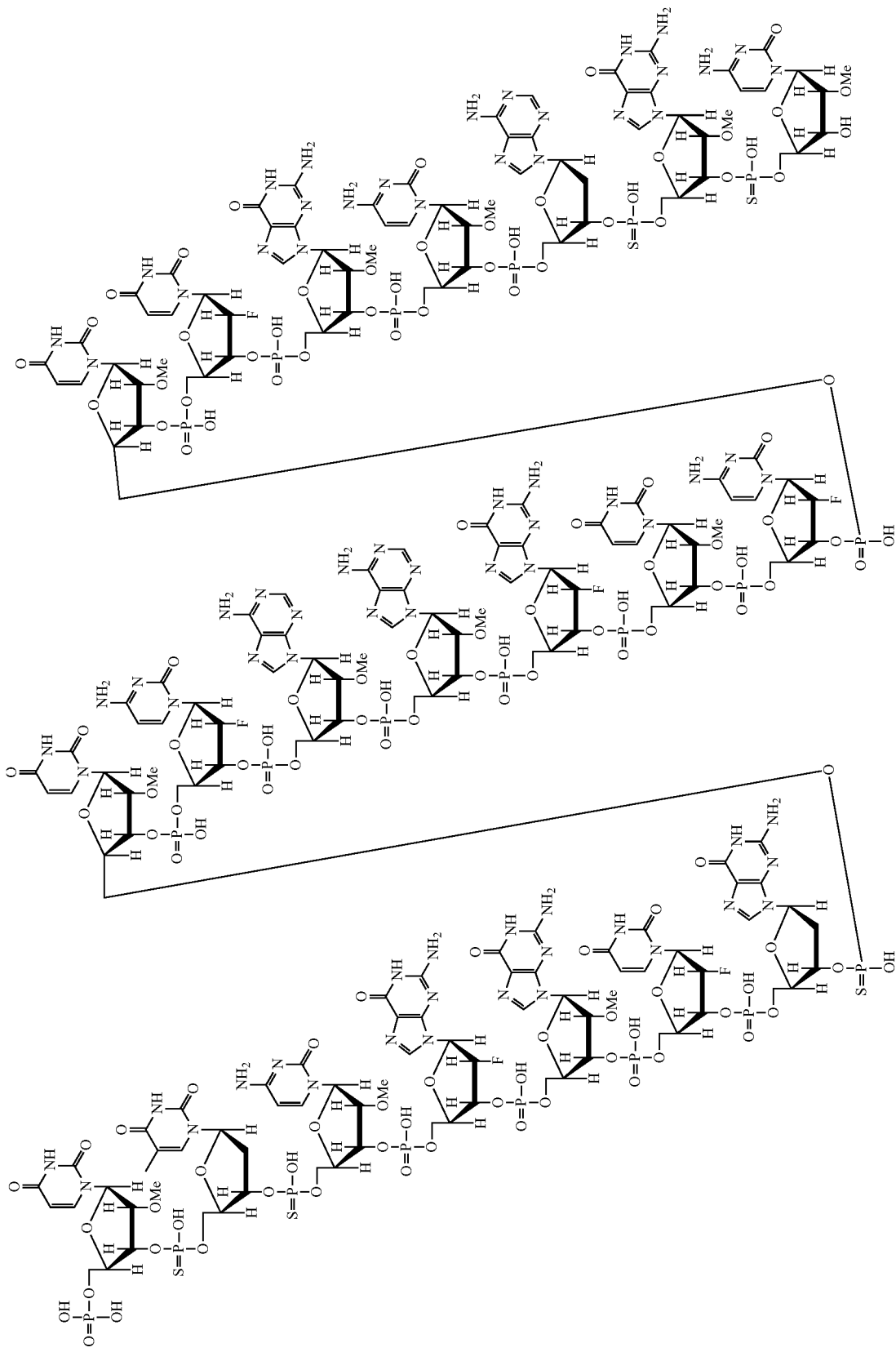

or SEQ ID NO: 19 as shown in the formula:

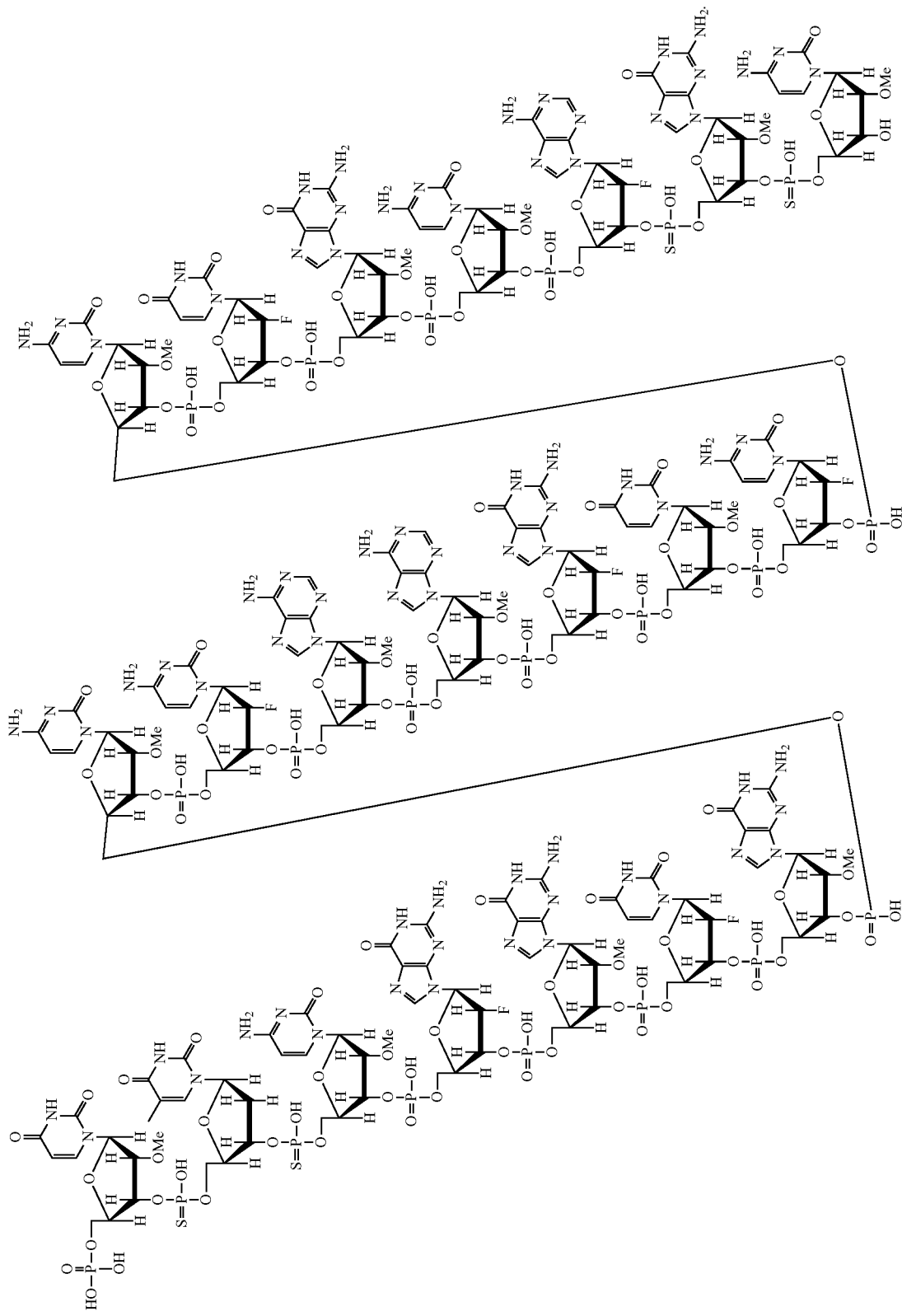

3. A compound comprising an siRNA compound for inhibiting expression of angiotensinogen (AGT) in a cell, wherein the siRNA compound comprises a sense strand and an antisense strand forming a duplex, wherein the sense strand comprises SEQ ID NO: 55 and a GalNAc moiety as shown in the formula:

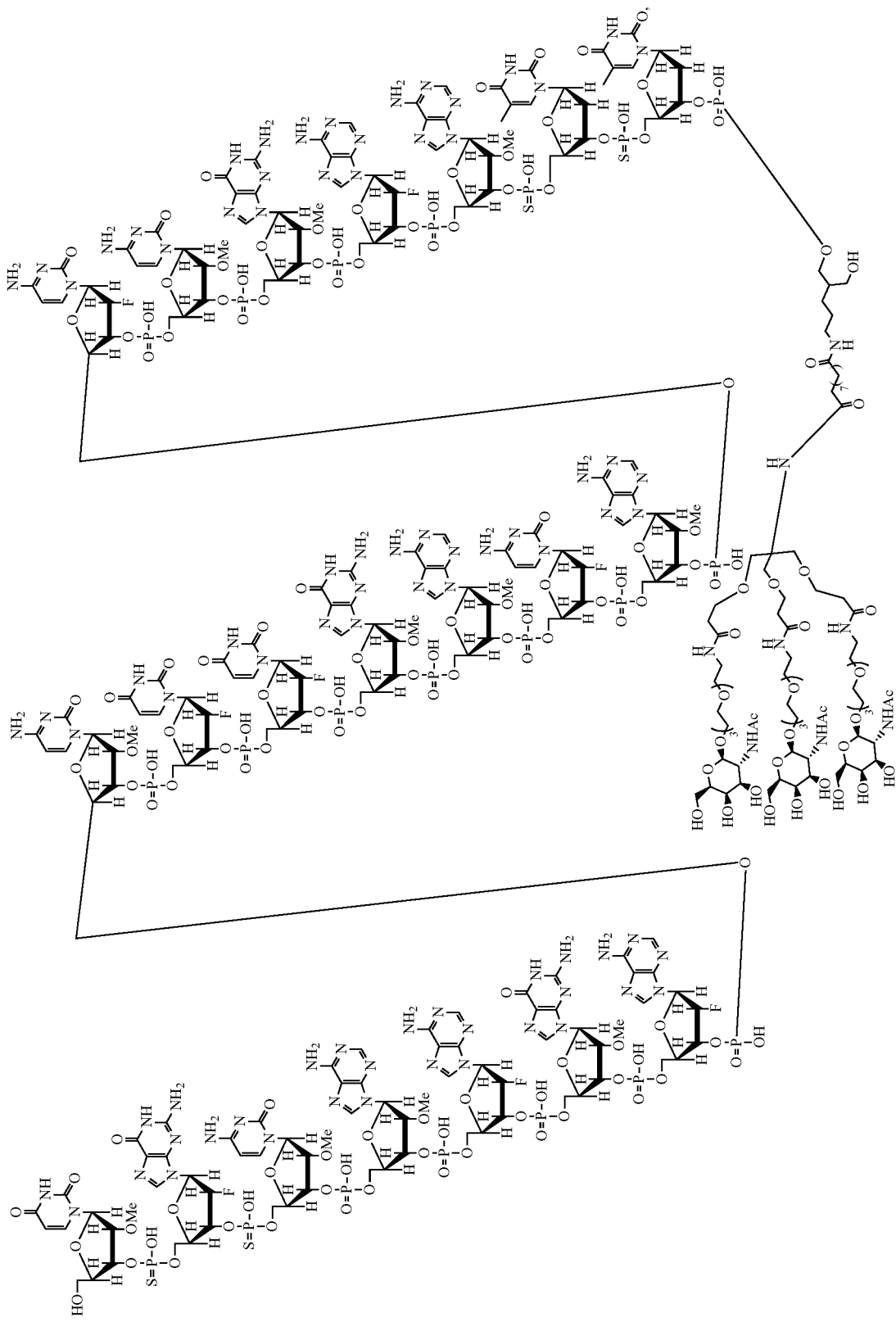

and wherein the antisense strand comprises SEQ ID NO: 9 as shown in the formula:

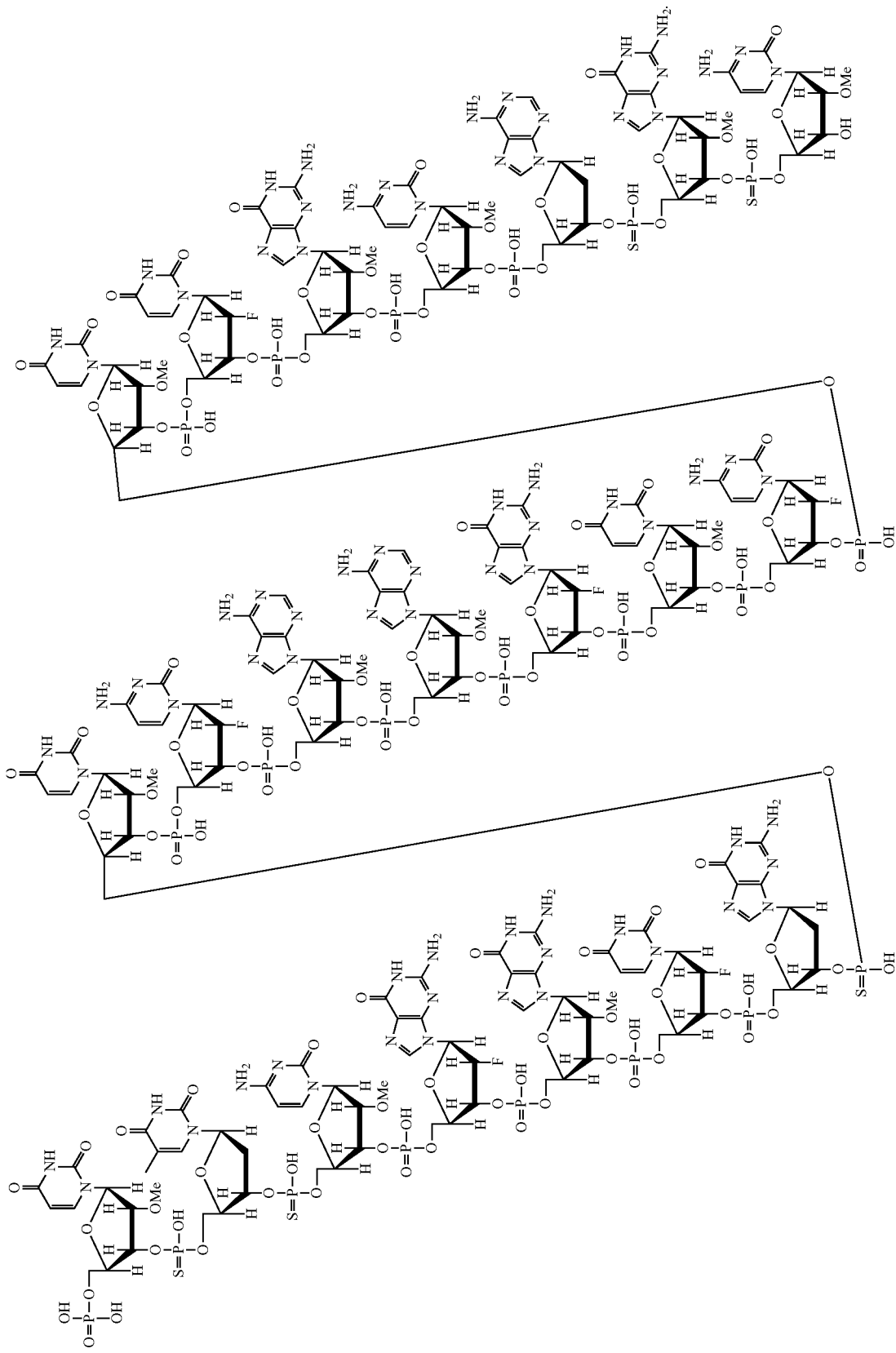

4. A compound comprising an siRNA compound for inhibiting expression of angiotensinogen (AGT) in a cell, wherein the siRNA compound comprises a sense strand and an antisense strand forming a duplex, wherein the sense strand comprises SEQ ID NO: 55 and a GalNAc moiety as shown in the formula:

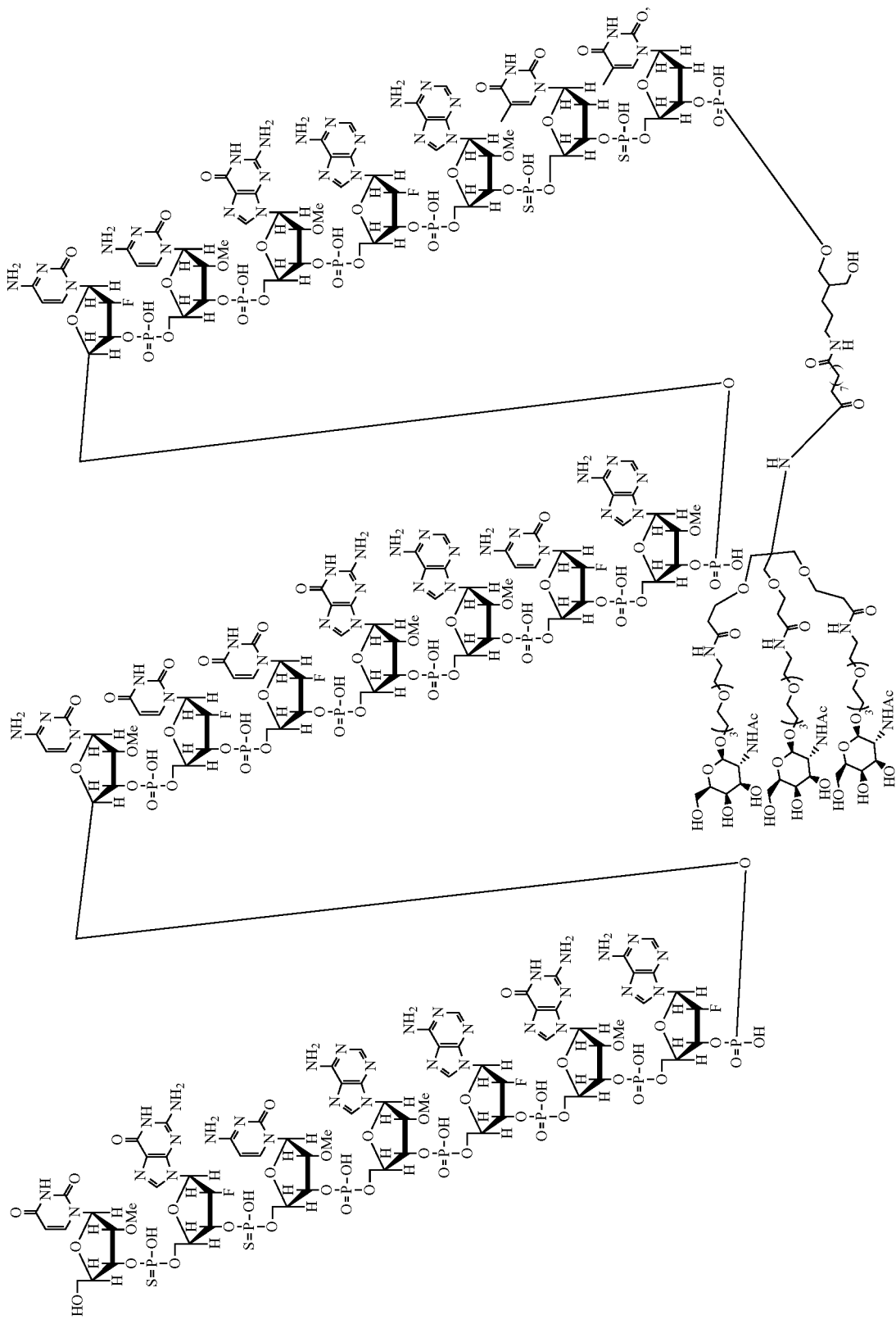

and wherein the antisense strand comprises SEQ ID NO: 19 as shown in the formula:

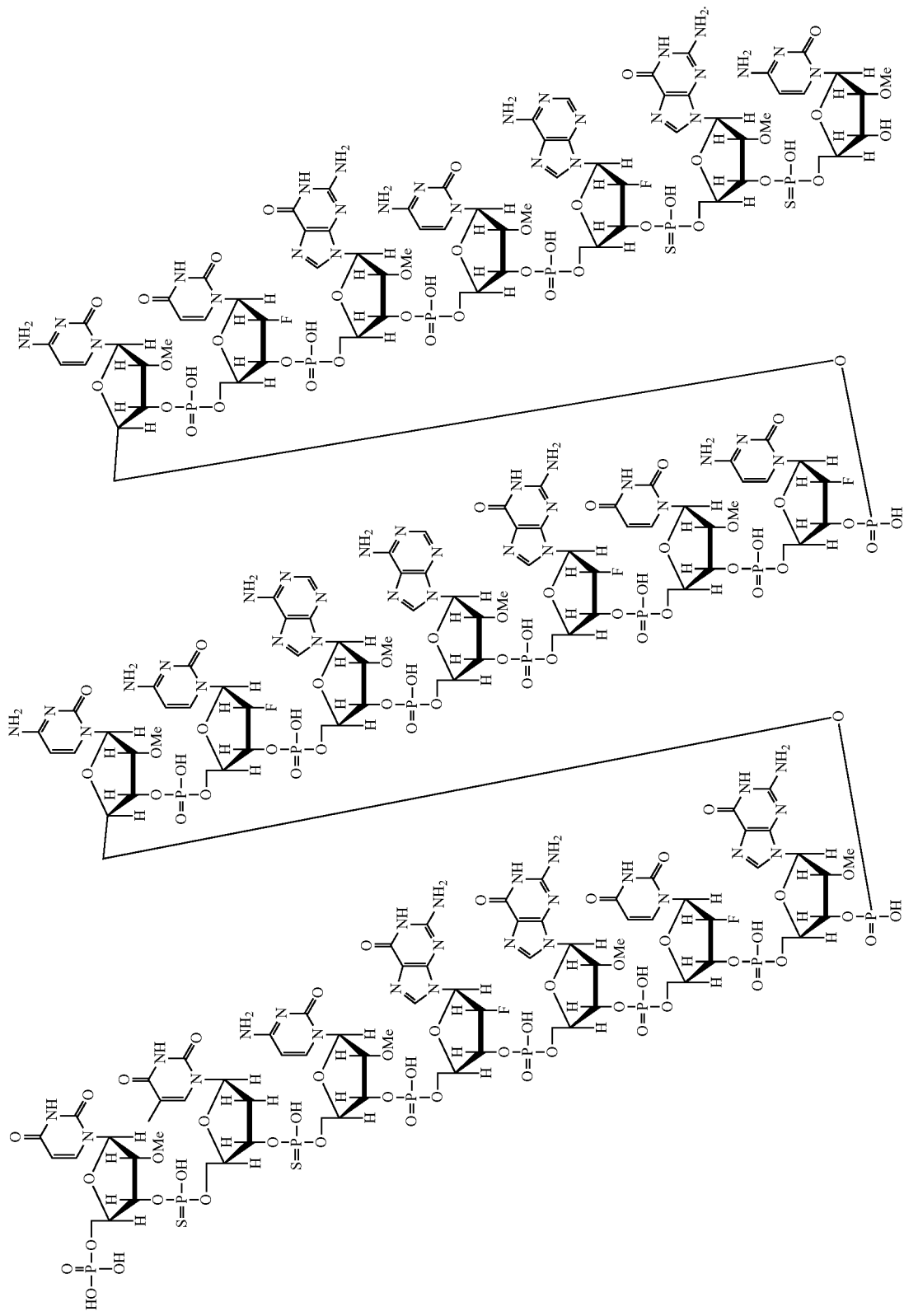

5. The compound of claim 1, wherein the compound inhibits expression of angiotensinogen (AGT) by at least about 70%, 75%, 80%, 85%, 90%, 95%, 98% or 99%.

6. The compound of claim 2, wherein the compound inhibits expression of angiotensinogen (AGT) by at least about 70%, 75%, 80%, 85%, 90%, 95%, 98% or 99%.

7. The compound of claim 3, wherein the compound inhibits expression of angiotensinogen (AGT) by at least about 70%, 75%, 80%, 85%, 90%, 95%, 98% or 99%.

8. The compound of claim 4, wherein the compound inhibits expression of angiotensinogen (AGT) by at least about 70%, 75%, 80%, 85%, 90%, 95%, 98% or 99%.

9. A method of inhibiting angiotensinogen (AGT) expression in a cell comprising contacting the cell with the compound of claim 1 in an amount sufficient to inhibit expression of AGT, thereby inhibiting expression of AGT in the cell.

10. A method of inhibiting angiotensinogen (AGT) expression in a cell comprising contacting the cell with the compound of claim 2 in an amount sufficient to inhibit expression of AGT, thereby inhibiting expression of AGT in the cell.

11. A method of inhibiting angiotensinogen (AGT) expression in a cell comprising contacting the cell with the compound of claim 3 in an amount sufficient to inhibit expression of AGT, thereby inhibiting expression of AGT in the cell.

12. A method of inhibiting angiotensinogen (AGT) expression in a cell comprising contacting the cell with the compound of claim 4 in an amount sufficient to inhibit expression of AGT, thereby inhibiting expression of AGT in the cell.

13. A pharmaceutical composition for inhibiting angiotensinogen (AGT) expression in a cell comprising the double-stranded ribonucleic acid (dsRNA) compound of claim 1, alone or in combination with a pharmaceutically acceptable carrier or excipient.

14. A pharmaceutical composition for inhibiting angiotensinogen (AGT) expression in a cell comprising the double-stranded ribonucleic acid (dsRNA) compound of claim 2, alone or in combination with a pharmaceutically acceptable carrier or excipient.

15. A pharmaceutical composition for inhibiting angiotensinogen (AGT) expression in a cell comprising the double-stranded ribonucleic acid (dsRNA) compound of claim 3, alone or in combination with a pharmaceutically acceptable carrier or excipient.

16. A pharmaceutical composition for inhibiting angiotensinogen (AGT) expression in a cell comprising the double-stranded ribonucleic acid (dsRNA) compound of claim 4, alone or in combination with a pharmaceutically acceptable carrier or excipient.

17. A kit comprising the compound of claim 1, and a label.

18. A kit comprising the compound of claim 2, and a label.

19. A kit comprising the compound of claim 3, and a label.

20. A kit comprising the compound of claim 4, and a label.

21. A process for preparing the sense strand of the double stranded ribonucleic acid (dsRNA) compound of claim 1, wherein the process comprises the steps of:
   a. coupling a GalNAc-comprising moiety to a solid support via a phosphoramidite oligonucleotide synthesis,
   b. coupling a modified and/or unmodified nucleotide by the phosphoramidite oligonucleotide synthesis to the GalNAc-comprising moiety on the solid support;
   c. sequentially coupling additional modified and/or unmodified nucleotides via the phosphoramidite oligonucleotide synthesis to prepare the sense strand; and
   d. detaching the sense strand from the solid support and removing the solid support.

22. A process for preparing the antisense strand of the double stranded ribonucleic acid (dsRNA) compound of claim 2, wherein the process comprises the steps of:
   a. preparing the antisense strand by sequential coupling of modified and/or unmodified nucleotides via the phosphoramidite oligonucleotide synthesis on a solid support;
   b. optionally, coupling a GalNAc-comprising moiety to the antisense strand on the solid support via the phosphoramidite oligonucleotide synthesis; and
   c. detaching the antisense strand from the solid support and removing the solid support.

* * * * *

SEQUENCE LISTING

```
Sequence total quantity: 99
SEQ ID NO: 1            moltype = DNA  length = 2148
FEATURE                 Location/Qualifiers
source                  1..2148
                        mol_type = other DNA
                        organism = synthetic construct
SEQUENCE: 1
agaaagtaga ccctcaccag gcatggaatc tgccagtgcc ttgatcttgg acttccagct    60
tccagaactg gtatgcggaa gcgagccacc cagtctgaga tggctcctgc cggtgtgagc   120
ctgagggcca ccatcctctg cctcctggcc tgggctggcc tggctgcagg tgaccgggtg   180
tacatacacc ccttccacct cgtcatccac aatgagagta cctgtgagca gctggcaaag   240
gccaatgccg ggaagcccaa agaccccacc ttcatacctg ctccaattca ggccaagaca   300
tcccctgtgg atgaaaaggc cctacaggac cagctggtgc tagtcgctgc aaaacttgac   360
accgaagaca agttgagggc cgcaatggtc gggatgctgg ccaacttctt gggcttccgt   420
atatatggca tgcacagtga gctatggggc gtggtccatg gggccaccgt cctctcccca   480
acggctgtct ttggcaccct ggcctctctc tatctgggag ccttggacca cacagctgac   540
aggctacagg caatcctggg tgttccttgg aaggacaaga actgcacctc ccggctggat   600
gcgcacaagg tcctgtctgc cctgcaggct gtacagggcc tgcagtggcc cagggcagg   660
gctgatagcc aggcccagct gctgctgtcc acggtggtgg gcgtgttcac agccccaggc   720
ctgcacctga agcagccgtt tgtgcaggcc ctggctctct atacccctgt ggtcctccca   780
cgctctctgg acttcacaga actggatgtt gctgctgaga agattgacag gttcatgcag   840
gctgtgacag gatggaagac tggctgctcc ctgatgggag ccagtgtgga cagcaccctg   900
gctttcaaca cctacgtcca cttccaaggg aagatgaagg gcttctcct gctggccgag   960
ccccaggagt tctgggtgga caacagcacc tcagtgtctg ttcccatgct ctctggcatg  1020
ggcaccttcc agcactggag tgacatccag gacaacttct cggtgactca agtgcccttc  1080
actgagagcg cctgcctgct gctgatccag cctcactatg cctctgacct ggacaaggtg  1140
gagggtctca ctttccagca aaactccctc aactggatga agaactatc tccccggacc  1200
atccacctga ccatgcccca actggtgctg caaggatctt atgacctgca ggacctgctc  1260
gcccaggctg agctgcccgc cattctgcac accgagctga cctgcaaaa attgagcaat  1320
gaccgcatca gggtgggga ggtgctgaac agcatttttt ttgagcttga agcggatgag  1380
agagagccca cagagtctac ccaacagctt aacaagcctg aggtcttgga ggtgaccctg  1440
aaccgcccat tcctgtttgc tgtgtatgat caaagcgcca ctgccctgca cttcctgggc  1500
cgcgtggcca acccgctgag cacagcatga ggccagggcc ccagaacaca gtgcctggca  1560
aggcctctgc ccctggcctt tgaggcaaag gccagcagca gataacaacc ccggacaaat  1620
cagcgatgtg tcaccccag tctcccacct tttcttctaa tgagtcgact ttgagctgga  1680
aagcagccgt ttctccttgg tctaagtgtg ctgcatggag tgagcagtag aagcctgcag  1740
cggcacaaat gcacctccca gtttgctggg tttattttag agaatggggg tggggaggca  1800
agaaccagtg tttagcgcgg gactactgtt ccaaaaagaa ttccaaccga ccagcttgtt  1860
tgtgaaacaa aaaagtgttc ccttttcaag ttgagaacaa aaattgggtt ttaaaattaa  1920
agtatacatt tttgcattgc cttcggtttg tatttagtgt cttgaatgta agaacatgac  1980
ctccgtgtag tgtctgtaat accttagttt tttccacaga tgcttgtgat ttttgaacaa  2040
tacgtgaaag tcaagcac ctgaatttct gtttgaatgc ggaaccatag ctggttattt  2100
ctcccttgtg ttagtaataa acgtcttgcc acaataagcc tccaaaaa                2148

SEQ ID NO: 2            moltype = RNA  length = 21
FEATURE                 Location/Qualifiers
source                  1..21
                        mol_type = other RNA
                        organism = synthetic construct
modified_base           1
                        mod_base = OTHER
                        note = 2'-O-methyl cytidine
modified_base           2
                        mod_base = OTHER
```

```
                              note = 2'-fluoro cytidine 5'-thiophosphate
modified_base                 3
                              mod_base = OTHER
                              note = 2'-O-methyl adenosine 5'-thiophosphate
modified_base                 4
                              mod_base = OTHER
                              note = 2'-O-methyl adenosine
modified_base                 6
                              mod_base = OTHER
                              note = 2'-O-methyl adenosine 5'-thiophosphate
modified_base                 8
                              mod_base = OTHER
                              note = 2'-O-methyl cytidine 5'-thiophosphate
modified_base                 9
                              mod_base = OTHER
                              note = 2'-fluoro uridine
modified_base                 10
                              mod_base = OTHER
                              note = 2'-fluoro uridine
modified_base                 11
                              mod_base = OTHER
                              note = 2'-O-methyl adenosine
modified_base                 12
                              mod_base = OTHER
                              note = 2'-O-methyl cytidine
modified_base                 14
                              mod_base = OTHER
                              note = 2'-O-methyl adenosine 5'-thiophosphate
modified_base                 16
                              mod_base = OTHER
                              note = 2'-O-methyl guanosine 5'-thiophosphate
modified_base                 17
                              mod_base = OTHER
                              note = 2'-O-methyl cytidine
modified_base                 18
                              mod_base = OTHER
                              note = 2'-fluoro cytidine
modified_base                 19
                              mod_base = OTHER
                              note = 2'-O-methyl uridine
modified_base                 20
                              mod_base = OTHER
                              note = 2'-deoxy thymidine 5'-thiophosphate
modified_base                 21
                              mod_base = OTHER
                              note = 2'-deoxy thymidine 5'-thiophosphate
misc_feature                  21
                              note = 3'-O attached to a GalNAc-comprising compound via a
                               linker
SEQUENCE: 2
ccaacagctt accaagccttt t                                                21

SEQ ID NO: 3                  moltype = RNA   length = 21
FEATURE                       Location/Qualifiers
source                        1..21
                              mol_type = other RNA
                              organism = synthetic construct
modified_base                 1
                              mod_base = OTHER
                              note = 2'-O-methyl adenosine
modified_base                 2
                              mod_base = OTHER
                              note = 2'-deoxy guanosine 5'-thiophosphate
modified_base                 3
                              mod_base = OTHER
                              note = 2'-O-methyl guanosine 5'-thiophosphate
modified_base                 4
                              mod_base = OTHER
                              note = 2'-fluoro cytidine
modified_base                 5
                              mod_base = OTHER
                              note = 2'-O-methyl uridine
modified_base                 6
                              mod_base = OTHER
                              note = 2'-fluoro uridine
modified_base                 7
                              mod_base = OTHER
                              note = 2'-O-methyl guanosine
modified_base                 8
```

```
                         mod_base = OTHER
                         note = 2'-O-methyl guanosine
modified_base            9
                         mod_base = OTHER
                         note = 2'-fluoro uridine
modified_base            10
                         mod_base = OTHER
                         note = 2'-O-methyl adenosine
modified_base            11
                         mod_base = OTHER
                         note = 2'-O-methyl adenosine
modified_base            12
                         mod_base = OTHER
                         note = 2'-fluoro guanosine
modified_base            13
                         mod_base = OTHER
                         note = 2'-O-methyl cytidine
modified_base            14
                         mod_base = OTHER
                         note = 2'-fluoro uridine
modified_base            15
                         mod_base = OTHER
                         note = 2'-O-methyl guanosine
modified_base            16
                         mod_base = OTHER
                         note = 2'-fluoro uridine
modified_base            17
                         mod_base = OTHER
                         note = 2'-O-methyl uridine
modified_base            18
                         mod_base = OTHER
                         note = 2'-O-methyl guanosine
modified_base            19
                         mod_base = OTHER
                         note = 2'-fluoro guanosine
modified_base            20
                         mod_base = OTHER
                         note = 2'-O-methyl guanosine 5'-thiophosphate
modified_base            21
                         mod_base = OTHER
                         note = 2'-O-methyl uridine 5'-thiophosphate
SEQUENCE: 3
aggcttggta agctgttggg t                                            21

SEQ ID NO: 4             moltype = RNA   length = 21
FEATURE                  Location/Qualifiers
source                   1..21
                         mol_type = other RNA
                         organism = synthetic construct
modified_base            1
                         mod_base = OTHER
                         note = 2'-O-methyl uridine
modified_base            2
                         mod_base = OTHER
                         note = 2'-fluoro uridine 5'-thiophosphate
modified_base            3
                         mod_base = OTHER
                         note = 2'-O-methyl adenosine 5'-thiophosphate
modified_base            4
                         mod_base = OTHER
                         note = 2'-O-methyl adenosine
modified_base            5
                         mod_base = OTHER
                         note = cytidine 5'-thiophosphate
modified_base            6
                         mod_base = OTHER
                         note = 2'-O-methyl adenosine 5'-thiophosphate
modified_base            7
                         mod_base = OTHER
                         note = adenosine 5'-thiophosphate
modified_base            8
                         mod_base = OTHER
                         note = 2'-O-methyl guanosine 5'-thiophosphate
modified_base            9
                         mod_base = OTHER
                         note = 2'-fluoro cytidine
modified_base            10
                         mod_base = OTHER
                         note = 2'-fluoro cytidine
```

```
modified_base       11
                    mod_base = OTHER
                    note = 2'-O-methyl uridine
modified_base       12
                    mod_base = OTHER
                    note = 2'-O-methyl adenosine
modified_base       13
                    mod_base = OTHER
                    note = adenosine 5'-thiophosphate
modified_base       14
                    mod_base = OTHER
                    note = 2'-O-methyl guanosine 5'-thiophosphate
modified_base       15
                    mod_base = OTHER
                    note = guanosine 5'-thiophosphate
modified_base       16
                    mod_base = OTHER
                    note = 2'-O-methyl uridine 5'-thiophosphate
modified_base       17
                    mod_base = OTHER
                    note = 2'-O-methyl cytidine
modified_base       18
                    mod_base = OTHER
                    note = 2'-fluoro uridine
modified_base       19
                    mod_base = OTHER
                    note = 2'-O-methyl uridine
modified_base       20
                    mod_base = OTHER
                    note = 2'-deoxy thymidine 5'-thiophosphate
modified_base       21
                    mod_base = OTHER
                    note = 2'-deoxy thymidine 5'-thiophosphate
misc_feature        21
                    note = 3'-O attached to a GalNAc-comprising compound via a
                    linker
SEQUENCE: 4
ttaacaagcc taaggtctttt t                                            21

SEQ ID NO: 5        moltype = RNA  length = 21
FEATURE             Location/Qualifiers
source              1..21
                    mol_type = other RNA
                    organism = synthetic construct
modified_base       1
                    mod_base = OTHER
                    note = 2'-O-methyl adenosine
modified_base       2
                    mod_base = OTHER
                    note = 2'-deoxy adenosine 5'-thiophosphate
modified_base       3
                    mod_base = OTHER
                    note = 2'-O-methyl guanosine 5'-thiophosphate
modified_base       4
                    mod_base = OTHER
                    note = 2'-fluoro adenosine
modified_base       5
                    mod_base = OTHER
                    note = 2'-O-methyl cytidine
modified_base       6
                    mod_base = OTHER
                    note = 2'-fluoro cytidine
modified_base       7
                    mod_base = OTHER
                    note = 2'-O-methyl uridine
modified_base       8
                    mod_base = OTHER
                    note = 2'-O-methyl uridine
modified_base       9
                    mod_base = OTHER
                    note = 2'-fluoro adenosine
modified_base       10
                    mod_base = OTHER
                    note = 2'-O-methyl guanosine
modified_base       11
                    mod_base = OTHER
                    note = 2'-O-methyl guanosine
modified_base       12
                    mod_base = OTHER
```

```
                        note = 2'-fluoro cytidine
modified_base           13
                        mod_base = OTHER
                        note = 2'-O-methyl uridine
modified_base           14
                        mod_base = OTHER
                        note = 2'-fluoro uridine
modified_base           15
                        mod_base = OTHER
                        note = 2'-O-methyl guanosine
modified_base           16
                        mod_base = OTHER
                        note = 2'-fluoro uridine
modified_base           17
                        mod_base = OTHER
                        note = 2'-O-methyl uridine
modified_base           18
                        mod_base = OTHER
                        note = 2'-O-methyl adenosine
modified_base           19
                        mod_base = OTHER
                        note = 2'-fluoro adenosine
modified_base           20
                        mod_base = OTHER
                        note = 2'-O-methyl guanosine 5'-thiophosphate
modified_base           21
                        mod_base = OTHER
                        note = 2'-O-methyl cytidine 5'-thiophosphate
SEQUENCE: 5
aagaccttag gcttgttaag c                                              21

SEQ ID NO: 6            moltype = RNA  length = 21
FEATURE                 Location/Qualifiers
source                  1..21
                        mol_type = other RNA
                        organism = synthetic construct
modified_base           1
                        mod_base = OTHER
                        note = 2'-O-methyl uridine
modified_base           2
                        mod_base = OTHER
                        note = 2'-fluoro uridine 5'-thiophosphate
modified_base           3
                        mod_base = OTHER
                        note = 2'-O-methyl adenosine 5'-thiophosphate
modified_base           4
                        mod_base = OTHER
                        note = 2'-O-methyl adenosine
modified_base           5
                        mod_base = OTHER
                        note = 2'-fluoro cytidine
modified_base           6
                        mod_base = OTHER
                        note = 2'-O-methyl adenosine
modified_base           7
                        mod_base = OTHER
                        note = 2'-fluoro adenosine
modified_base           8
                        mod_base = OTHER
                        note = 2'-O-methyl guanosine
modified_base           9
                        mod_base = OTHER
                        note = 2'-fluoro cytidine
modified_base           10
                        mod_base = OTHER
                        note = 2'-fluoro cytidine
modified_base           11
                        mod_base = OTHER
                        note = 2'-O-methyl uridine
modified_base           12
                        mod_base = OTHER
                        note = 2'-O-methyl adenosine
modified_base           13
                        mod_base = OTHER
                        note = 2'-fluoro adenosine
modified_base           14
                        mod_base = OTHER
                        note = 2'-O-methyl guanosine
modified_base           15
```

```
                            mod_base = OTHER
                            note = 2'-fluoro guanosine
modified_base               16
                            mod_base = OTHER
                            note = 2'-O-methyl uridine
modified_base               17
                            mod_base = OTHER
                            note = 2'-O-methyl cytidine
modified_base               18
                            mod_base = OTHER
                            note = 2'-fluoro uridine
modified_base               19
                            mod_base = OTHER
                            note = 2'-O-methyl uridine
modified_base               20
                            mod_base = OTHER
                            note = 2'-deoxy thymidine 5'-thiophosphate
modified_base               21
                            mod_base = OTHER
                            note = 2'-deoxy thymidine 5'-thiophosphate
misc_feature                21
                            note = 3'-O attached to a GalNAc-comprising compound via a
                             linker
SEQUENCE: 6
ttaacaagcc taaggtctttt t                                            21

SEQ ID NO: 7                moltype = RNA  length = 21
FEATURE                     Location/Qualifiers
source                      1..21
                            mol_type = other RNA
                            organism = synthetic construct
modified_base               1
                            mod_base = OTHER
                            note = 2'-O-methyl adenosine
modified_base               2
                            mod_base = OTHER
                            note = 2'-deoxy adenosine 5'-thiophosphate
modified_base               3
                            mod_base = OTHER
                            note = 2'-O-methyl guanosine 5'-thiophosphate
modified_base               4
                            mod_base = OTHER
                            note = 2'-fluoro adenosine
modified_base               5
                            mod_base = OTHER
                            note = 2'-O-methyl cytidine
modified_base               6
                            mod_base = OTHER
                            note = 2'-fluoro cytidine
modified_base               7
                            mod_base = OTHER
                            note = 2'-deoxy thymidine
modified_base               8
                            mod_base = OTHER
                            note = 2'-O-methyl uridine 5'-thiophosphate
modified_base               9
                            mod_base = OTHER
                            note = 2'-fluoro adenosine
modified_base               10
                            mod_base = OTHER
                            note = 2'-O-methyl guanosine
modified_base               11
                            mod_base = OTHER
                            note = 2'-O-methyl guanosine
modified_base               12
                            mod_base = OTHER
                            note = 2'-fluoro cytidine
modified_base               13
                            mod_base = OTHER
                            note = 2'-O-methyl uridine
modified_base               14
                            mod_base = OTHER
                            note = 2'-fluoro uridine
modified_base               15
                            mod_base = OTHER
                            note = 2'-O-methyl guanosine
modified_base               16
                            mod_base = OTHER
                            note = 2'-fluoro uridine
```

```
modified_base         17
                      mod_base = OTHER
                      note = 2'-O-methyl uridine
modified_base         18
                      mod_base = OTHER
                      note = 2'-O-methyl adenosine
modified_base         19
                      mod_base = OTHER
                      note = 2'-deoxy adenosine
modified_base         20
                      mod_base = OTHER
                      note = 2'-O-methyl guanosine 5'-thiophosphate
modified_base         21
                      mod_base = OTHER
                      note = 2'-O-methyl cytidine 5'-thiophosphate
SEQUENCE: 7
aagaccttag gcttgttaag c                                              21

SEQ ID NO: 8          moltype = RNA  length = 21
FEATURE               Location/Qualifiers
source                1..21
                      mol_type = other RNA
                      organism = synthetic construct
modified_base         1
                      mod_base = OTHER
                      note = 2'-O-methyl uridine
modified_base         2
                      mod_base = OTHER
                      note = 2'-fluoro guanosine 5'-thiophosphate
modified_base         3
                      mod_base = OTHER
                      note = 2'-O-methyl cytidine 5'-thiophosphate
modified_base         4
                      mod_base = OTHER
                      note = 2'-O-methyl adenosine
modified_base         5
                      mod_base = OTHER
                      note = 2'-fluoro adenosine
modified_base         6
                      mod_base = OTHER
                      note = 2'-O-methyl guanosine
modified_base         7
                      mod_base = OTHER
                      note = 2'-fluoro adenosine
modified_base         8
                      mod_base = OTHER
                      note = 2'-O-methyl cytidine
modified_base         9
                      mod_base = OTHER
                      note = 2'-fluoro uridine
modified_base         10
                      mod_base = OTHER
                      note = 2'-fluoro uridine
modified_base         11
                      mod_base = OTHER
                      note = 2'-O-methyl guanosine
modified_base         12
                      mod_base = OTHER
                      note = 2'-O-methyl adenosine
modified_base         13
                      mod_base = OTHER
                      note = 2'-fluoro cytidine
modified_base         14
                      mod_base = OTHER
                      note = 2'-O-methyl adenosine
modified_base         15
                      mod_base = OTHER
                      note = 2'-fluoro cytidine
modified_base         16
                      mod_base = OTHER
                      note = 2'-O-methyl cytidine
modified_base         17
                      mod_base = OTHER
                      note = 2'-O-methyl guanosine
modified_base         18
                      mod_base = OTHER
                      note = 2'-fluoro adenosine
modified_base         19
                      mod_base = OTHER
```

```
                         note = 2'-O-methyl adenosine
modified_base            20
                         mod_base = OTHER
                         note = 2'-deoxy thymidine 5'-thiophosphate
modified_base            21
                         mod_base = OTHER
                         note = 2'-deoxy thymidine 5'-thiophosphate
misc_feature             21
                         note = 3'-O attached to a GalNAc-comprising compound via a
                          linker
SEQUENCE: 8
tgcaagactt gacaccgaat t                                               21

SEQ ID NO: 9             moltype = RNA  length = 21
FEATURE                  Location/Qualifiers
source                   1..21
                         mol_type = other RNA
                         organism = synthetic construct
modified_base            1
                         mod_base = OTHER
                         note = 2'-O-methyl uridine
modified_base            2
                         mod_base = OTHER
                         note = 2'-deoxy thymidine 5'-thiophosphate
modified_base            3
                         mod_base = OTHER
                         note = 2'-O-methyl cytidine 5'-thiophosphate
modified_base            4
                         mod_base = OTHER
                         note = 2'-fluoro guanosine
modified_base            5
                         mod_base = OTHER
                         note = 2'-O-methyl guanosine
modified_base            6
                         mod_base = OTHER
                         note = 2'-fluoro uridine
modified_base            7
                         mod_base = OTHER
                         note = 2'-deoxy guanosine
modified_base            8
                         mod_base = OTHER
                         note = 2'-O-methyl uridine 5'-thiophosphate
modified_base            9
                         mod_base = OTHER
                         note = 2'-fluoro cytidine
modified_base            10
                         mod_base = OTHER
                         note = 2'-O-methyl adenosine
modified_base            11
                         mod_base = OTHER
                         note = 2'-O-methyl adenosine
modified_base            12
                         mod_base = OTHER
                         note = 2'-fluoro guanosine
modified_base            13
                         mod_base = OTHER
                         note = 2'-O-methyl uridine
modified_base            14
                         mod_base = OTHER
                         note = 2'-fluoro cytidine
modified_base            15
                         mod_base = OTHER
                         note = 2'-O-methyl uridine
modified_base            16
                         mod_base = OTHER
                         note = 2'-fluoro uridine
modified_base            17
                         mod_base = OTHER
                         note = 2'-O-methyl guanosine
modified_base            18
                         mod_base = OTHER
                         note = 2'-O-methyl cytidine
modified_base            19
                         mod_base = OTHER
                         note = 2'-deoxy adenosine
modified_base            20
                         mod_base = OTHER
                         note = 2'-O-methyl guanosine 5'-thiophosphate
modified_base            21
```

|   |   |
|---|---|
|   | mod_base = OTHER |
|   | note = 2'-O-methyl cytidine 5'-thiophosphate |
| SEQUENCE: 9 | |
| ttcggtgtca agtcttgcag c | 21 |
| | |
| SEQ ID NO: 10 | moltype = RNA length = 21 |
| FEATURE | Location/Qualifiers |
| source | 1..21 |
|   | mol_type = other RNA |
|   | organism = synthetic construct |
| modified_base | 1 |
|   | mod_base = OTHER |
|   | note = 2'-O-methyl uridine |
| modified_base | 2 |
|   | mod_base = OTHER |
|   | note = 2'-fluoro guanosine 5'-thiophosphate |
| modified_base | 3 |
|   | mod_base = OTHER |
|   | note = 2'-O-methyl cytidine 5'-thiophosphate |
| modified_base | 4 |
|   | mod_base = OTHER |
|   | note = 2'-O-methyl adenosine |
| modified_base | 5 |
|   | mod_base = OTHER |
|   | note = 2'-fluoro adenosine |
| modified_base | 6 |
|   | mod_base = OTHER |
|   | note = 2'-O-methyl adenosine |
| modified_base | 7 |
|   | mod_base = OTHER |
|   | note = 2'-fluoro adenosine |
| modified_base | 8 |
|   | mod_base = OTHER |
|   | note = 2'-O-methyl cytidine |
| modified_base | 9 |
|   | mod_base = OTHER |
|   | note = 2'-fluoro uridine |
| modified_base | 10 |
|   | mod_base = OTHER |
|   | note = 2'-fluoro uridine |
| modified_base | 11 |
|   | mod_base = OTHER |
|   | note = 2'-O-methyl guanosine |
| modified_base | 12 |
|   | mod_base = OTHER |
|   | note = 2'-O-methyl adenosine |
| modified_base | 13 |
|   | mod_base = OTHER |
|   | note = 2'-fluoro cytidine |
| modified_base | 14 |
|   | mod_base = OTHER |
|   | note = 2'-O-methyl adenosine |
| modified_base | 15 |
|   | mod_base = OTHER |
|   | note = 2'-fluoro cytidine |
| modified_base | 16 |
|   | mod_base = OTHER |
|   | note = 2'-O-methyl cytidine |
| modified_base | 17 |
|   | mod_base = OTHER |
|   | note = 2'-O-methyl guanosine |
| modified_base | 18 |
|   | mod_base = OTHER |
|   | note = 2'-fluoro adenosine |
| modified_base | 19 |
|   | mod_base = OTHER |
|   | note = 2'-O-methyl adenosine |
| modified_base | 20 |
|   | mod_base = OTHER |
|   | note = 2'-deoxy thymidine 5'-thiophosphate |
| modified_base | 21 |
|   | mod_base = OTHER |
|   | note = 2'-deoxy thymidine 5'-thiophosphate |
| misc_feature | 21 |
|   | note = 3'-O attached to a GalNAc-comprising compound via a linker |
| SEQUENCE: 10 | |
| tgcaaaactt gacaccgaat t | 21 |

| | | |
|---|---|---|
| SEQ ID NO: 11 | moltype = RNA   length = 21 | |
| FEATURE | Location/Qualifiers | |
| source | 1..21 | |
| | mol_type = other RNA | |
| | organism = synthetic construct | |
| modified_base | 1 | |
| | mod_base = OTHER | |
| | note = 2'-O-methyl uridine | |
| modified_base | 2 | |
| | mod_base = OTHER | |
| | note = 2'-deoxy thymidine 5'-thiophosphate | |
| modified_base | 3 | |
| | mod_base = OTHER | |
| | note = 2'-O-methyl cytidine 5'-thiophosphate | |
| modified_base | 4 | |
| | mod_base = OTHER | |
| | note = 2'-fluoro guanosine | |
| modified_base | 5 | |
| | mod_base = OTHER | |
| | note = 2'-O-methyl guanosine | |
| modified_base | 6 | |
| | mod_base = OTHER | |
| | note = 2'-fluoro uridine | |
| modified_base | 7 | |
| | mod_base = OTHER | |
| | note = 2'-deoxy guanosine | |
| modified_base | 8 | |
| | mod_base = OTHER | |
| | note = 2'-O-methyl uridine 5'-thiophosphate | |
| modified_base | 9 | |
| | mod_base = OTHER | |
| | note = 2'-fluoro cytidine | |
| modified_base | 10 | |
| | mod_base = OTHER | |
| | note = 2'-O-methyl adenosine | |
| modified_base | 11 | |
| | mod_base = OTHER | |
| | note = 2'-O-methyl adenosine | |
| modified_base | 12 | |
| | mod_base = OTHER | |
| | note = 2'-fluoro guanosine | |
| modified_base | 13 | |
| | mod_base = OTHER | |
| | note = 2'-O-methyl uridine | |
| modified_base | 14 | |
| | mod_base = OTHER | |
| | note = 2'-fluoro uridine | |
| modified_base | 15 | |
| | mod_base = OTHER | |
| | note = 2'-O-methyl uridine | |
| modified_base | 16 | |
| | mod_base = OTHER | |
| | note = 2'-fluoro uridine | |
| modified_base | 17 | |
| | mod_base = OTHER | |
| | note = 2'-O-methyl guanosine | |
| modified_base | 18 | |
| | mod_base = OTHER | |
| | note = 2'-O-methyl cytidine | |
| modified_base | 19 | |
| | mod_base = OTHER | |
| | note = 2'-deoxy adenosine | |
| modified_base | 20 | |
| | mod_base = OTHER | |
| | note = 2'-O-methyl guanosine 5'-thiophosphate | |
| modified_base | 21 | |
| | mod_base = OTHER | |
| | note = 2'-O-methyl cytidine 5'-thiophosphate | |
| SEQUENCE: 11 | | |
| ttcggtgtca agttttgcag c | | 21 |
| SEQ ID NO: 12 | moltype = RNA   length = 21 | |
| FEATURE | Location/Qualifiers | |
| source | 1..21 | |
| | mol_type = other RNA | |
| | organism = synthetic construct | |
| modified_base | 1 | |
| | mod_base = OTHER | |
| | note = 2'-O-methyl cytidine | |

```
modified_base            2
                         mod_base = OTHER
                         note = 2'-fluoro cytidine 5'-thiophosphate
modified_base            3
                         mod_base = OTHER
                         note = 2'-O-methyl adenosine 5'-thiophosphate
modified_base            4
                         mod_base = OTHER
                         note = 2'-O-methyl adenosine
modified_base            5
                         mod_base = OTHER
                         note = 2'-fluoro cytidine
modified_base            6
                         mod_base = OTHER
                         note = 2'-O-methyl adenosine
modified_base            7
                         mod_base = OTHER
                         note = 2'-fluoro guanosine
modified_base            8
                         mod_base = OTHER
                         note = 2'-O-methyl cytidine
modified_base            9
                         mod_base = OTHER
                         note = 2'-fluoro uridine
modified_base            10
                         mod_base = OTHER
                         note = 2'-fluoro uridine
modified_base            11
                         mod_base = OTHER
                         note = 2'-O-methyl adenosine
modified_base            12
                         mod_base = OTHER
                         note = 2'-O-methyl adenosine
modified_base            13
                         mod_base = OTHER
                         note = 2'-fluoro cytidine
modified_base            14
                         mod_base = OTHER
                         note = 2'-O-methyl adenosine
modified_base            15
                         mod_base = OTHER
                         note = 2'-fluoro adenosine
modified_base            16
                         mod_base = OTHER
                         note = 2'-O-methyl guanosine
modified_base            17
                         mod_base = OTHER
                         note = 2'-O-methyl cytidine
modified_base            18
                         mod_base = OTHER
                         note = 2'-fluoro cytidine
modified_base            19
                         mod_base = OTHER
                         note = 2'-O-methyl uridine
modified_base            20
                         mod_base = OTHER
                         note = 2'-deoxy thymidine 5'-thiophosphate
modified_base            21
                         mod_base = OTHER
                         note = 2'-deoxy thymidine 5'-thiophosphate
misc_feature             21
                         note = 3'-O attached to a GalNAc-comprising compound via a
                         linker
SEQUENCE: 12
ccaacagctt aacaagcctt t                                                          21

SEQ ID NO: 13            moltype = RNA  length = 21
FEATURE                  Location/Qualifiers
source                   1..21
                         mol_type = other RNA
                         organism = synthetic construct
modified_base            1
                         mod_base = OTHER
                         note = 2'-O-methyl adenosine
modified_base            2
                         mod_base = OTHER
                         note = 2'-deoxy guanosine 5'-thiophosphate
modified_base            3
                         mod_base = OTHER
```

|                | note = 2'-O-methyl guanosine 5'-thiophosphate |
| --- | --- |
| modified_base  | 4 |
|                | mod_base = OTHER |
|                | note = 2'-fluoro cytidine |
| modified_base  | 5 |
|                | mod_base = OTHER |
|                | note = 2'-O-methyl uridine |
| modified_base  | 6 |
|                | mod_base = OTHER |
|                | note = 2'-fluoro uridine |
| modified_base  | 7 |
|                | mod_base = OTHER |
|                | note = 2'-deoxy guanosine |
| modified_base  | 8 |
|                | mod_base = OTHER |
|                | note = 2'-O-methyl uridine 5'-thiophosphate |
| modified_base  | 9 |
|                | mod_base = OTHER |
|                | note = 2'-fluoro uridine |
| modified_base  | 10 |
|                | mod_base = OTHER |
|                | note = 2'-O-methyl adenosine |
| modified_base  | 11 |
|                | mod_base = OTHER |
|                | note = 2'-O-methyl adenosine |
| modified_base  | 12 |
|                | mod_base = OTHER |
|                | note = 2'-fluoro guanosine |
| modified_base  | 13 |
|                | mod_base = OTHER |
|                | note = 2'-O-methyl cytidine |
| modified_base  | 14 |
|                | mod_base = OTHER |
|                | note = 2'-fluoro uridine |
| modified_base  | 15 |
|                | mod_base = OTHER |
|                | note = 2'-O-methyl guanosine |
| modified_base  | 16 |
|                | mod_base = OTHER |
|                | note = 2'-fluoro uridine |
| modified_base  | 17 |
|                | mod_base = OTHER |
|                | note = 2'-O-methyl uridine |
| modified_base  | 18 |
|                | mod_base = OTHER |
|                | note = 2'-O-methyl guanosine |
| modified_base  | 19 |
|                | mod_base = OTHER |
|                | note = 2'-deoxy guanosine |
| modified_base  | 20 |
|                | mod_base = OTHER |
|                | note = 2'-O-methyl guanosine 5'-thiophosphate |
| modified_base  | 21 |
|                | mod_base = OTHER |
|                | note = 2'-O-methyl uridine 5'-thiophosphate |
| SEQUENCE: 13   | | aggcttgtta agctgttggg t                                                     21

| SEQ ID NO: 14  | moltype = RNA   length = 21 |
| --- | --- |
| FEATURE        | Location/Qualifiers |
| source         | 1..21 |
|                | mol_type = other RNA |
|                | organism = synthetic construct |
| modified_base  | 1 |
|                | mod_base = OTHER |
|                | note = 2'-O-methyl cytidine |
| modified_base  | 2 |
|                | mod_base = OTHER |
|                | note = 2'-fluoro cytidine 5'-thiophosphate |
| modified_base  | 3 |
|                | mod_base = OTHER |
|                | note = 2'-O-methyl adenosine 5'-thiophosphate |
| modified_base  | 4 |
|                | mod_base = OTHER |
|                | note = 2'-O-methyl adenosine |
| modified_base  | 5 |
|                | mod_base = OTHER |
|                | note = 2'-fluoro uridine |
| modified_base  | 6 |

|                 |                                                                    |
|-----------------|--------------------------------------------------------------------|
|                 | mod_base = OTHER                                                   |
|                 | note = 2'-O-methyl adenosine                                       |
| modified_base   | 7                                                                  |
|                 | mod_base = OTHER                                                   |
|                 | note = 2'-fluoro guanosine                                         |
| modified_base   | 8                                                                  |
|                 | mod_base = OTHER                                                   |
|                 | note = 2'-O-methyl cytidine                                        |
| modified_base   | 9                                                                  |
|                 | mod_base = OTHER                                                   |
|                 | note = 2'-fluoro uridine                                           |
| modified_base   | 10                                                                 |
|                 | mod_base = OTHER                                                   |
|                 | note = 2'-fluoro uridine                                           |
| modified_base   | 11                                                                 |
|                 | mod_base = OTHER                                                   |
|                 | note = 2'-O-methyl adenosine                                       |
| modified_base   | 12                                                                 |
|                 | mod_base = OTHER                                                   |
|                 | note = 2'-O-methyl adenosine                                       |
| modified_base   | 13                                                                 |
|                 | mod_base = OTHER                                                   |
|                 | note = 2'-fluoro cytidine                                          |
| modified_base   | 14                                                                 |
|                 | mod_base = OTHER                                                   |
|                 | note = 2'-O-methyl adenosine                                       |
| modified_base   | 15                                                                 |
|                 | mod_base = OTHER                                                   |
|                 | note = 2'-fluoro adenosine                                         |
| modified_base   | 16                                                                 |
|                 | mod_base = OTHER                                                   |
|                 | note = 2'-O-methyl guanosine                                       |
| modified_base   | 17                                                                 |
|                 | mod_base = OTHER                                                   |
|                 | note = 2'-O-methyl cytidine                                        |
| modified_base   | 18                                                                 |
|                 | mod_base = OTHER                                                   |
|                 | note = 2'-fluoro cytidine                                          |
| modified_base   | 19                                                                 |
|                 | mod_base = OTHER                                                   |
|                 | note = 2'-O-methyl uridine                                         |
| modified_base   | 20                                                                 |
|                 | mod_base = OTHER                                                   |
|                 | note = 2'-deoxy thymidine 5'-thiophosphate                         |
| modified_base   | 21                                                                 |
|                 | mod_base = OTHER                                                   |
|                 | note = 2'-deoxy thymidine 5'-thiophosphate                         |
| misc_feature    | 21                                                                 |
|                 | note = 3'-O attached to a GalNAc-comprising compound via a         |
|                 |  linker                                                            |
| SEQUENCE: 14    |                                                                    |
| ccaatagctt aacaagcctt t                                        21  |                                                                    |
|                 |                                                                    |
| SEQ ID NO: 15   | moltype = RNA  length = 21                                         |
| FEATURE         | Location/Qualifiers                                                |
| source          | 1..21                                                              |
|                 | mol_type = other RNA                                               |
|                 | organism = synthetic construct                                     |
| modified_base   | 1                                                                  |
|                 | mod_base = OTHER                                                   |
|                 | note = 2'-O-methyl adenosine                                       |
| modified_base   | 2                                                                  |
|                 | mod_base = OTHER                                                   |
|                 | note = 2'-deoxy guanosine 5'-thiophosphate                         |
| modified_base   | 3                                                                  |
|                 | mod_base = OTHER                                                   |
|                 | note = 2'-O-methyl guanosine 5'-thiophosphate                      |
| modified_base   | 4                                                                  |
|                 | mod_base = OTHER                                                   |
|                 | note = 2'-fluoro cytidine                                          |
| modified_base   | 5                                                                  |
|                 | mod_base = OTHER                                                   |
|                 | note = 2'-O-methyl uridine                                         |
| modified_base   | 6                                                                  |
|                 | mod_base = OTHER                                                   |
|                 | note = 2'-fluoro uridine                                           |
| modified_base   | 7                                                                  |
|                 | mod_base = OTHER                                                   |
|                 | note = 2'-O-methyl guanosine                                       |

```
modified_base       8
                    mod_base = OTHER
                    note = 2'-O-methyl uridine
modified_base       9
                    mod_base = OTHER
                    note = 2'-fluoro uridine
modified_base       10
                    mod_base = OTHER
                    note = 2'-O-methyl adenosine
modified_base       11
                    mod_base = OTHER
                    note = 2'-O-methyl adenosine
modified_base       12
                    mod_base = OTHER
                    note = 2'-fluoro guanosine
modified_base       13
                    mod_base = OTHER
                    note = 2'-O-methyl cytidine
modified_base       14
                    mod_base = OTHER
                    note = 2'-fluoro uridine
modified_base       15
                    mod_base = OTHER
                    note = 2'-O-methyl adenosine
modified_base       16
                    mod_base = OTHER
                    note = 2'-fluoro uridine
modified_base       17
                    mod_base = OTHER
                    note = 2'-O-methyl uridine
modified_base       18
                    mod_base = OTHER
                    note = 2'-O-methyl guanosine
modified_base       19
                    mod_base = OTHER
                    note = 2'-fluoro guanosine
modified_base       20
                    mod_base = OTHER
                    note = 2'-O-methyl uridine 5'-thiophosphate
modified_base       21
                    mod_base = OTHER
                    note = 2'-O-methyl uridine 5'-thiophosphate
SEQUENCE: 15
aggcttgtta agctattggt t                                            21

SEQ ID NO: 16       moltype = RNA  length = 21
FEATURE             Location/Qualifiers
source              1..21
                    mol_type = other RNA
                    organism = synthetic construct
modified_base       1
                    mod_base = OTHER
                    note = 2'-O-methyl adenosine
modified_base       2
                    mod_base = OTHER
                    note = 2'-fluoro cytidine 5'-thiophosphate
modified_base       3
                    mod_base = OTHER
                    note = 2'-O-methyl cytidine 5'-thiophosphate
modified_base       4
                    mod_base = OTHER
                    note = 2'-O-methyl cytidine
modified_base       5
                    mod_base = OTHER
                    note = 2'-fluoro adenosine
modified_base       6
                    mod_base = OTHER
                    note = 2'-O-methyl adenosine
modified_base       7
                    mod_base = OTHER
                    note = 2'-fluoro uridine
modified_base       8
                    mod_base = OTHER
                    note = 2'-O-methyl adenosine
modified_base       9
                    mod_base = OTHER
                    note = 2'-fluoro guanosine
modified_base       10
                    mod_base = OTHER
```

```
                              note = 2'-fluoro cytidine
modified_base                 11
                              mod_base = OTHER
                              note = 2'-O-methyl uridine
modified_base                 12
                              mod_base = OTHER
                              note = 2'-O-methyl uridine
modified_base                 13
                              mod_base = OTHER
                              note = 2'-fluoro adenosine
modified_base                 14
                              mod_base = OTHER
                              note = 2'-O-methyl adenosine
modified_base                 15
                              mod_base = OTHER
                              note = 2'-fluoro cytidine
modified_base                 16
                              mod_base = OTHER
                              note = 2'-O-methyl adenosine
modified_base                 17
                              mod_base = OTHER
                              note = 2'-O-methyl adenosine
modified_base                 18
                              mod_base = OTHER
                              note = 2'-fluoro guanosine
modified_base                 19
                              mod_base = OTHER
                              note = 2'-O-methyl cytidine
modified_base                 20
                              mod_base = OTHER
                              note = 2'-deoxy cytidine 5'-thiophosphate
modified_base                 21
                              mod_base = OTHER
                              note = 2'-deoxy thymidine 5'-thiophosphate
misc_feature                  21
                              note = 3'-O attached to a GalNAc-comprising compound via a
                               linker
SEQUENCE: 16
acccaatagc ttaacaagcc t                                               21

SEQ ID NO: 17                 moltype = RNA   length = 23
FEATURE                       Location/Qualifiers
source                        1..23
                              mol_type = other RNA
                              organism = synthetic construct
modified_base                 1
                              mod_base = OTHER
                              note = 2'-O-methyl adenosine
modified_base                 2
                              mod_base = OTHER
                              note = 2'-deoxy guanosine 5'-thiophosphate
modified_base                 3
                              mod_base = OTHER
                              note = 2'-O-methyl guanosine 5'-thiophosphate
modified_base                 4
                              mod_base = OTHER
                              note = 2'-fluoro cytidine
modified_base                 5
                              mod_base = OTHER
                              note = 2'-O-methyl uridine
modified_base                 6
                              mod_base = OTHER
                              note = 2'-fluoro uridine
modified_base                 7
                              mod_base = OTHER
                              note = 2'-O-methyl guanosine
modified_base                 8
                              mod_base = OTHER
                              note = 2'-O-methyl uridine
modified_base                 9
                              mod_base = OTHER
                              note = 2'-fluoro uridine
modified_base                 10
                              mod_base = OTHER
                              note = 2'-O-methyl adenosine
modified_base                 11
                              mod_base = OTHER
                              note = 2'-O-methyl adenosine
modified_base                 12
```

```
                          mod_base = OTHER
                          note = 2'-fluoro guanosine
modified_base             13
                          mod_base = OTHER
                          note = 2'-O-methyl cytidine
modified_base             14
                          mod_base = OTHER
                          note = 2'-fluoro uridine
modified_base             15
                          mod_base = OTHER
                          note = 2'-O-methyl adenosine
modified_base             16
                          mod_base = OTHER
                          note = 2'-fluoro uridine
modified_base             17
                          mod_base = OTHER
                          note = 2'-O-methyl uridine
modified_base             18
                          mod_base = OTHER
                          note = 2'-O-methyl guanosine
modified_base             19
                          mod_base = OTHER
                          note = 2'-fluoro guanosine
modified_base             20
                          mod_base = OTHER
                          note = 2'-O-methyl guanosine
modified_base             21
                          mod_base = OTHER
                          note = 2'-deoxy thymidine
modified_base             22
                          mod_base = OTHER
                          note = 2'-O-methyl adenosine 5'-thiophosphate
modified_base             23
                          mod_base = OTHER
                          note = 2'-O-methyl guanosine 5'-thiophosphate
SEQUENCE: 17
aggcttgtta agctattggg tag                                              23

SEQ ID NO: 18             moltype = RNA   length = 21
FEATURE                   Location/Qualifiers
source                    1..21
                          mol_type = other RNA
                          organism = synthetic construct
modified_base             1
                          mod_base = OTHER
                          note = 2'-O-methyl cytidine
modified_base             2
                          mod_base = OTHER
                          note = 2'-fluoro cytidine 5'-thiophosphate
modified_base             3
                          mod_base = OTHER
                          note = 2'-O-methyl adenosine 5'-thiophosphate
modified_base             4
                          mod_base = OTHER
                          note = 2'-O-methyl adenosine
modified_base             5
                          mod_base = OTHER
                          note = uridine 5'-thiophosphate
modified_base             6
                          mod_base = OTHER
                          note = 2'-O-methyl adenosine 5'-thiophosphate
modified_base             7
                          mod_base = OTHER
                          note = guanosine 5'-thiophosphate
modified_base             8
                          mod_base = OTHER
                          note = 2'-O-methyl cytidine 5'-thiophosphate
modified_base             9
                          mod_base = OTHER
                          note = 2'-fluoro uridine
modified_base             10
                          mod_base = OTHER
                          note = 2'-fluoro uridine
modified_base             11
                          mod_base = OTHER
                          note = 2'-O-methyl adenosine
modified_base             12
                          mod_base = OTHER
                          note = 2'-O-methyl adenosine
```

|               |                                                           |
|---------------|-----------------------------------------------------------|
| modified_base | 13                                                        |
|               | mod_base = OTHER                                          |
|               | note = cytidine 5'-thiophosphate                          |
| modified_base | 14                                                        |
|               | mod_base = OTHER                                          |
|               | note = 2'-O-methyl adenosine 5'-thiophosphate             |
| modified_base | 15                                                        |
|               | mod_base = OTHER                                          |
|               | note = adenosine 5'-thiophosphate                         |
| modified_base | 16                                                        |
|               | mod_base = OTHER                                          |
|               | note = 2'-O-methyl guanosine 5'-thiophosphate             |
| modified_base | 17                                                        |
|               | mod_base = OTHER                                          |
|               | note = 2'-O-methyl cytidine                               |
| modified_base | 18                                                        |
|               | mod_base = OTHER                                          |
|               | note = 2'-fluoro cytidine                                 |
| modified_base | 19                                                        |
|               | mod_base = OTHER                                          |
|               | note = 2'-O-methyl uridine                                |
| modified_base | 20                                                        |
|               | mod_base = OTHER                                          |
|               | note = 2'-deoxy thymidine 5'-thiophosphate                |
| modified_base | 21                                                        |
|               | mod_base = OTHER                                          |
|               | note = 2'-deoxy thymidine 5'-thiophosphate                |
| misc_feature  | 21                                                        |
|               | note = 3'-O attached to a GalNAc-comprising compound via a |
|               |  linker                                                   |
| SEQUENCE: 18  |                                                           |
| ccaatagctt aacaagcctt t              21                                  |
|               |                                                           |
| SEQ ID NO: 19 | moltype = RNA   length = 21                               |
| FEATURE       | Location/Qualifiers                                       |
| source        | 1..21                                                     |
|               | mol_type = other RNA                                      |
|               | organism = synthetic construct                            |
| modified_base | 1                                                         |
|               | mod_base = OTHER                                          |
|               | note = 2'-O-methyl uridine                                |
| modified_base | 2                                                         |
|               | mod_base = OTHER                                          |
|               | note = 2'-deoxy thymidine 5'-thiophosphate                |
| modified_base | 3                                                         |
|               | mod_base = OTHER                                          |
|               | note = 2'-O-methyl cytidine 5'-thiophosphate              |
| modified_base | 4                                                         |
|               | mod_base = OTHER                                          |
|               | note = 2'-fluoro guanosine                                |
| modified_base | 5                                                         |
|               | mod_base = OTHER                                          |
|               | note = 2'-O-methyl guanosine                              |
| modified_base | 6                                                         |
|               | mod_base = OTHER                                          |
|               | note = 2'-fluoro uridine                                  |
| modified_base | 7                                                         |
|               | mod_base = OTHER                                          |
|               | note = 2'-O-methyl guanosine                              |
| modified_base | 8                                                         |
|               | mod_base = OTHER                                          |
|               | note = 2'-O-methyl uridine                                |
| modified_base | 9                                                         |
|               | mod_base = OTHER                                          |
|               | note = 2'-fluoro cytidine                                 |
| modified_base | 10                                                        |
|               | mod_base = OTHER                                          |
|               | note = 2'-O-methyl adenosine                              |
| modified_base | 11                                                        |
|               | mod_base = OTHER                                          |
|               | note = 2'-O-methyl adenosine                              |
| modified_base | 12                                                        |
|               | mod_base = OTHER                                          |
|               | note = 2'-fluoro guanosine                                |
| modified_base | 13                                                        |
|               | mod_base = OTHER                                          |
|               | note = 2'-O-methyl uridine                                |
| modified_base | 14                                                        |
|               | mod_base = OTHER                                          |

|  |  |
|---|---|
|  | note = 2'-fluoro cytidine |
| modified_base | 15 |
|  | mod_base = OTHER |
|  | note = 2'-O-methyl uridine |
| modified_base | 16 |
|  | mod_base = OTHER |
|  | note = 2'-fluoro uridine |
| modified_base | 17 |
|  | mod_base = OTHER |
|  | note = 2'-O-methyl guanosine |
| modified_base | 18 |
|  | mod_base = OTHER |
|  | note = 2'-O-methyl cytidine |
| modified_base | 19 |
|  | mod_base = OTHER |
|  | note = 2'-fluoro adenosine |
| modified_base | 20 |
|  | mod_base = OTHER |
|  | note = 2'-O-methyl guanosine 5'-thiophosphate |
| modified_base | 21 |
|  | mod_base = OTHER |
|  | note = 2'-O-methyl cytidine 5'-thiophosphate |
| SEQUENCE: 19 |  |
| ttcggtgtca agtcttgcag c | 21 |
| SEQ ID NO: 20 | moltype = RNA   length = 21 |
| FEATURE | Location/Qualifiers |
| source | 1..21 |
|  | mol_type = other RNA |
|  | organism = synthetic construct |
| modified_base | 1 |
|  | mod_base = OTHER |
|  | note = 2'-O-methyl adenosine |
| modified_base | 2 |
|  | mod_base = OTHER |
|  | note = 2'-fluoro guanosine 5'-thiophosphate |
| modified_base | 3 |
|  | mod_base = OTHER |
|  | note = 2'-O-methyl cytidine 5'-thiophosphate |
| modified_base | 4 |
|  | mod_base = OTHER |
|  | note = 2'-O-methyl uridine |
| modified_base | 5 |
|  | mod_base = OTHER |
|  | note = 2'-fluoro cytidine |
| modified_base | 6 |
|  | mod_base = OTHER |
|  | note = 2'-O-methyl adenosine |
| modified_base | 7 |
|  | mod_base = OTHER |
|  | note = 2'-fluoro adenosine |
| modified_base | 8 |
|  | mod_base = OTHER |
|  | note = 2'-O-methyl cytidine |
| modified_base | 9 |
|  | mod_base = OTHER |
|  | note = 2'-fluoro adenosine |
| modified_base | 10 |
|  | mod_base = OTHER |
|  | note = 2'-fluoro adenosine |
| modified_base | 11 |
|  | mod_base = OTHER |
|  | note = 2'-O-methyl guanosine |
| modified_base | 12 |
|  | mod_base = OTHER |
|  | note = 2'-O-methyl cytidine |
| modified_base | 13 |
|  | mod_base = OTHER |
|  | note = 2'-fluoro cytidine |
| modified_base | 14 |
|  | mod_base = OTHER |
|  | note = 2'-O-methyl uridine |
| modified_base | 15 |
|  | mod_base = OTHER |
|  | note = 2'-fluoro guanosine |
| modified_base | 16 |
|  | mod_base = OTHER |
|  | note = 2'-O-methyl adenosine |
| modified_base | 17 |

```
                              mod_base = OTHER
                              note = 2'-O-methyl guanosine
modified_base                 18
                              mod_base = OTHER
                              note = 2'-fluoro guanosine
modified_base                 19
                              mod_base = OTHER
                              note = 2'-O-methyl uridine
modified_base                 20
                              mod_base = OTHER
                              note = 2'-deoxy thymidine 5'-thiophosphate
modified_base                 21
                              mod_base = OTHER
                              note = 2'-deoxy thymidine 5'-thiophosphate
misc_feature                  21
                              note = 3'-O attached to a GalNAc-comprising compound via a
                               linker
SEQUENCE: 20
agctcaacaa gcctgaggtt t                                              21

SEQ ID NO: 21                 moltype = RNA   length = 21
FEATURE                       Location/Qualifiers
source                        1..21
                              mol_type = other RNA
                              organism = synthetic construct
modified_base                 1
                              mod_base = OTHER
                              note = 2'-O-methyl adenosine
modified_base                 2
                              mod_base = OTHER
                              note = 2'-deoxy cytidine 5'-thiophosphate
modified_base                 3
                              mod_base = OTHER
                              note = 2'-O-methyl cytidine 5'-thiophosphate
modified_base                 4
                              mod_base = OTHER
                              note = 2'-fluoro uridine
modified_base                 5
                              mod_base = OTHER
                              note = 2'-O-methyl cytidine
modified_base                 6
                              mod_base = OTHER
                              note = 2'-fluoro adenosine
modified_base                 7
                              mod_base = OTHER
                              note = 2'-O-methyl guanosine
modified_base                 8
                              mod_base = OTHER
                              note = 2'-O-methyl guanosine
modified_base                 9
                              mod_base = OTHER
                              note = 2'-fluoro cytidine
modified_base                 10
                              mod_base = OTHER
                              note = 2'-O-methyl uridine
modified_base                 11
                              mod_base = OTHER
                              note = 2'-O-methyl uridine
modified_base                 12
                              mod_base = OTHER
                              note = 2'-fluoro guanosine
modified_base                 13
                              mod_base = OTHER
                              note = 2'-O-methyl uridine
modified_base                 14
                              mod_base = OTHER
                              note = 2'-fluoro uridine
modified_base                 15
                              mod_base = OTHER
                              note = 2'-O-methyl guanosine
modified_base                 16
                              mod_base = OTHER
                              note = 2'-fluoro adenosine
modified_base                 17
                              mod_base = OTHER
                              note = 2'-O-methyl guanosine
modified_base                 18
                              mod_base = OTHER
                              note = 2'-O-methyl cytidine
```

```
modified_base       19
                    mod_base = OTHER
                    note = 2'-fluoro uridine
modified_base       20
                    mod_base = OTHER
                    note = 2'-O-methyl guanosine 5'-thiophosphate
modified_base       21
                    mod_base = OTHER
                    note = 2'-O-methyl uridine 5'-thiophosphate
SEQUENCE: 21
acctcaggct tgttgagctg t                                         21

SEQ ID NO: 22       moltype = RNA  length = 21
FEATURE             Location/Qualifiers
source              1..21
                    mol_type = other RNA
                    organism = synthetic construct
modified_base       1
                    mod_base = OTHER
                    note = 2'-O-methyl guanosine
modified_base       2
                    mod_base = OTHER
                    note = 2'-O-methyl uridine 5'-thiophosphate
modified_base       3
                    mod_base = OTHER
                    note = 2'-O-methyl cytidine 5'-thiophosphate
modified_base       4
                    mod_base = OTHER
                    note = 2'-O-methyl adenosine
modified_base       5
                    mod_base = OTHER
                    note = 2'-O-methyl uridine
modified_base       6
                    mod_base = OTHER
                    note = 2'-O-methyl cytidine
modified_base       7
                    mod_base = OTHER
                    note = 2'-fluoro cytidine
modified_base       8
                    mod_base = OTHER
                    note = 2'-O-methyl adenosine
modified_base       9
                    mod_base = OTHER
                    note = 2'-fluoro cytidine
modified_base       10
                    mod_base = OTHER
                    note = 2'-fluoro adenosine
modified_base       11
                    mod_base = OTHER
                    note = 2'-fluoro adenosine
modified_base       12
                    mod_base = OTHER
                    note = 2'-O-methyl uridine
modified_base       13
                    mod_base = OTHER
                    note = 2'-O-methyl guanosine
modified_base       14
                    mod_base = OTHER
                    note = 2'-O-methyl adenosine
modified_base       15
                    mod_base = OTHER
                    note = 2'-O-methyl guanosine
modified_base       16
                    mod_base = OTHER
                    note = 2'-O-methyl adenosine
modified_base       17
                    mod_base = OTHER
                    note = 2'-O-methyl guanosine
modified_base       18
                    mod_base = OTHER
                    note = 2'-O-methyl uridine
modified_base       19
                    mod_base = OTHER
                    note = 2'-O-methyl adenosine
modified_base       20
                    mod_base = OTHER
                    note = 2'-O-methyl cytidine
modified_base       21
                    mod_base = OTHER
```

```
                        note = 2'-O-methyl adenosine
misc_feature            21
                        note = 3'-O attached to a GalNAc-comprising compound via a
                         linker
SEQUENCE: 22
gtcatccaca atgagagtac a                                                  21

SEQ ID NO: 23           moltype = RNA   length = 23
FEATURE                 Location/Qualifiers
source                  1..23
                        mol_type = other RNA
                        organism = synthetic construct
modified_base           1
                        mod_base = OTHER
                        note = 2'-O-methyl uridine
modified_base           2
                        mod_base = OTHER
                        note = 2'-fluoro guanosine 5'-thiophosphate
modified_base           3
                        mod_base = OTHER
                        note = 2'-O-methyl uridine 5'-thiophosphate
modified_base           4
                        mod_base = OTHER
                        note = 2'-O-methyl adenosine
modified_base           5
                        mod_base = OTHER
                        note = 2'-O-methyl cytidine
modified_base           6
                        mod_base = OTHER
                        note = 2,3-dihydroxypropyl thymidine
modified_base           7
                        mod_base = OTHER
                        note = 2'-O-methyl cytidine
modified_base           8
                        mod_base = OTHER
                        note = 2'-O-methyl uridine
modified_base           9
                        mod_base = OTHER
                        note = 2'-O-methyl cytidine
modified_base           10
                        mod_base = OTHER
                        note = 2'-O-methyl adenosine
modified_base           11
                        mod_base = OTHER
                        note = 2'-O-methyl uridine
modified_base           12
                        mod_base = OTHER
                        note = 2'-O-methyl uridine
modified_base           13
                        mod_base = OTHER
                        note = 2'-O-methyl guanosine
modified_base           14
                        mod_base = OTHER
                        note = 2'-fluoro uridine
modified_base           15
                        mod_base = OTHER
                        note = 2'-O-methyl guanosine
modified_base           16
                        mod_base = OTHER
                        note = 2'-fluoro guanosine
modified_base           17
                        mod_base = OTHER
                        note = 2'-O-methyl adenosine
modified_base           18
                        mod_base = OTHER
                        note = 2'-O-methyl uridine
modified_base           19
                        mod_base = OTHER
                        note = 2'-O-methyl guanosine
modified_base           20
                        mod_base = OTHER
                        note = 2'-O-methyl adenosine
modified_base           21
                        mod_base = OTHER
                        note = 2'-O-methyl cytidine
modified_base           22
                        mod_base = OTHER
                        note = 2'-O-methyl guanosine 5'-thiophosphate
modified_base           23
```

```
                        mod_base = OTHER
                        note = 2'-O-methyl adenosine 5'-thiophosphate
SEQUENCE: 23
tgtactctca ttgtggatga cga                                              23

SEQ ID NO: 24           moltype = DNA  length = 20
FEATURE                 Location/Qualifiers
source                  1..20
                        mol_type = other DNA
                        organism = synthetic construct
SEQUENCE: 24
ctgatccagc ctcactatgc                                                  20

SEQ ID NO: 25           moltype = DNA  length = 21
FEATURE                 Location/Qualifiers
source                  1..21
                        mol_type = other DNA
                        organism = synthetic construct
SEQUENCE: 25
aggtcataag atccttgcag c                                                21

SEQ ID NO: 26           moltype = DNA  length = 26
FEATURE                 Location/Qualifiers
source                  1..26
                        mol_type = other DNA
                        organism = synthetic construct
SEQUENCE: 26
agggtctcac tttccagcaa aactcc                                           26

SEQ ID NO: 27           moltype = RNA  length = 21
FEATURE                 Location/Qualifiers
source                  1..21
                        mol_type = other RNA
                        organism = synthetic construct
modified_base           1
                        mod_base = OTHER
                        note = 2'-O-methyl uridine
modified_base           2
                        mod_base = OTHER
                        note = 2'-fluoro adenosine 5'-thiophosphate
modified_base           3
                        mod_base = OTHER
                        note = 2'-O-methyl guanosine 5'-thiophosphate
modified_base           4
                        mod_base = OTHER
                        note = 2'-O-methyl uridine
modified_base           6
                        mod_base = OTHER
                        note = 2'-O-methyl guanosine 5'-thiophosphate
modified_base           8
                        mod_base = OTHER
                        note = 2'-O-methyl uridine 5'-thiophosphate
modified_base           9
                        mod_base = OTHER
                        note = 2'-fluoro guanosine
modified_base           10
                        mod_base = OTHER
                        note = 2'-fluoro cytidine
modified_base           11
                        mod_base = OTHER
                        note = 2'-O-methyl adenosine
modified_base           12
                        mod_base = OTHER
                        note = 2'-O-methyl adenosine
modified_base           14
                        mod_base = OTHER
                        note = 2'-O-methyl adenosine 5'-thiophosphate
modified_base           16
                        mod_base = OTHER
                        note = 2'-O-methyl uridine 5'-thiophosphate
modified_base           17
                        mod_base = OTHER
                        note = 2'-O-methyl uridine
modified_base           18
                        mod_base = OTHER
                        note = 2'-fluoro guanosine
modified_base           19
                        mod_base = OTHER
                        note = 2'-O-methyl adenosine
```

```
                        -continued modified_base          20
                       mod_base = OTHER
                       note = 2'-deoxy thymidine 5'-thiophosphate
modified_base          21
                       mod_base = OTHER
                       note = 2'-deoxy thymidine 5'-thiophosphate
SEQUENCE: 27
tagtcgctgc aaaacttgat t                                              21

SEQ ID NO: 28          moltype = RNA  length = 21
FEATURE                Location/Qualifiers
source                 1..21
                       mol_type = other RNA
                       organism = synthetic construct
modified_base          1
                       mod_base = OTHER
                       note = 2'-O-methyl uridine
modified_base          2
                       mod_base = OTHER
                       note = 2'-deoxy cytidine 5'-thiophosphate
modified_base          3
                       mod_base = OTHER
                       note = 2'-O-methyl adenosine 5'-thiophosphate
modified_base          4
                       mod_base = OTHER
                       note = 2'-fluoro adenosine
modified_base          5
                       mod_base = OTHER
                       note = 2'-O-methyl guanosine
modified_base          6
                       mod_base = OTHER
                       note = 2'-fluoro uridine
modified_base          7
                       mod_base = OTHER
                       note = 2'-deoxy thymidine
modified_base          8
                       mod_base = OTHER
                       note = 2'-O-methyl uridine 5'-thiophosphate
modified_base          9
                       mod_base = OTHER
                       note = 2'-fluoro uridine
modified_base          10
                       mod_base = OTHER
                       note = 2'-O-methyl guanosine
modified_base          11
                       mod_base = OTHER
                       note = 2'-O-methyl cytidine
modified_base          12
                       mod_base = OTHER
                       note = 2'-fluoro adenosine
modified_base          13
                       mod_base = OTHER
                       note = 2'-O-methyl guanosine
modified_base          14
                       mod_base = OTHER
                       note = 2'-fluoro cytidine
modified_base          15
                       mod_base = OTHER
                       note = 2'-O-methyl guanosine
modified_base          16
                       mod_base = OTHER
                       note = 2'-fluoro adenosine
modified_base          17
                       mod_base = OTHER
                       note = 2'-O-methyl cytidine
modified_base          18
                       mod_base = OTHER
                       note = 2'-O-methyl uridine
modified_base          19
                       mod_base = OTHER
                       note = 2'-deoxy adenosine
modified_base          20
                       mod_base = OTHER
                       note = 2'-O-methyl guanosine 5'-thiophosphate
modified_base          21
                       mod_base = OTHER
                       note = 2'-O-methyl cytidine 5'-thiophosphate
SEQUENCE: 28
tcaagttttg cagcgactag c                                              21
```

```
SEQ ID NO: 29              moltype = RNA  length = 21
FEATURE                    Location/Qualifiers
source                     1..21
                           mol_type = other RNA
                           organism = synthetic construct
modified_base              1
                           mod_base = OTHER
                           note = 2'-O-methyl uridine
modified_base              2
                           mod_base = OTHER
                           note = 2'-fluoro adenosine 5'-thiophosphate
modified_base              3
                           mod_base = OTHER
                           note = 2'-O-methyl guanosine 5'-thiophosphate
modified_base              4
                           mod_base = OTHER
                           note = 2'-O-methyl uridine
modified_base              5
                           mod_base = OTHER
                           note = 2'-fluoro cytidine
modified_base              6
                           mod_base = OTHER
                           note = 2'-O-methyl guanosine
modified_base              7
                           mod_base = OTHER
                           note = 2'-fluoro cytidine
modified_base              8
                           mod_base = OTHER
                           note = 2'-O-methyl uridine
modified_base              9
                           mod_base = OTHER
                           note = 2'-fluoro guanosine
modified_base              10
                           mod_base = OTHER
                           note = 2'-fluoro cytidine
modified_base              11
                           mod_base = OTHER
                           note = 2'-O-methyl guanosine
modified_base              12
                           mod_base = OTHER
                           note = 2'-O-methyl adenosine
modified_base              13
                           mod_base = OTHER
                           note = 2'-fluoro adenosine
modified_base              14
                           mod_base = OTHER
                           note = 2'-O-methyl adenosine
modified_base              15
                           mod_base = OTHER
                           note = 2'-fluoro cytidine
modified_base              16
                           mod_base = OTHER
                           note = 2'-O-methyl uridine
modified_base              17
                           mod_base = OTHER
                           note = 2'-O-methyl uridine
modified_base              18
                           mod_base = OTHER
                           note = 2'-fluoro guanosine
modified_base              19
                           mod_base = OTHER
                           note = 2'-O-methyl adenosine
modified_base              20
                           mod_base = OTHER
                           note = 2'-deoxy thymidine 5'-thiophosphate
modified_base              21
                           mod_base = OTHER
                           note = 2'-deoxy thymidine 5'-thiophosphate
SEQUENCE: 29
tagtcgctgc gaaacttgat t                                                    21

SEQ ID NO: 30              moltype = RNA  length = 21
FEATURE                    Location/Qualifiers
source                     1..21
                           mol_type = other RNA
                           organism = synthetic construct
modified_base              1
                           mod_base = OTHER
```

| | | |
|---|---|---|
| modified_base | | note = 2'-O-methyl uridine |
| | 2 | |
| | | mod_base = OTHER |
| | | note = 2'-deoxy cytidine 5'-thiophosphate |
| modified_base | 3 | |
| | | mod_base = OTHER |
| | | note = 2'-O-methyl adenosine 5'-thiophosphate |
| modified_base | 4 | |
| | | mod_base = OTHER |
| | | note = 2'-fluoro adenosine |
| modified_base | 5 | |
| | | mod_base = OTHER |
| | | note = 2'-O-methyl guanosine |
| modified_base | 6 | |
| | | mod_base = OTHER |
| | | note = 2'-fluoro uridine |
| modified_base | 7 | |
| | | mod_base = OTHER |
| | | note = 2'-O-methyl uridine |
| modified_base | 8 | |
| | | mod_base = OTHER |
| | | note = 2'-O-methyl uridine |
| modified_base | 9 | |
| | | mod_base = OTHER |
| | | note = 2'-fluoro cytidine |
| modified_base | 10 | |
| | | mod_base = OTHER |
| | | note = 2'-O-methyl guanosine |
| modified_base | 11 | |
| | | mod_base = OTHER |
| | | note = 2'-O-methyl cytidine |
| modified_base | 12 | |
| | | mod_base = OTHER |
| | | note = 2'-fluoro adenosine |
| modified_base | 13 | |
| | | mod_base = OTHER |
| | | note = 2'-O-methyl guanosine |
| modified_base | 14 | |
| | | mod_base = OTHER |
| | | note = 2'-fluoro cytidine |
| modified_base | 15 | |
| | | mod_base = OTHER |
| | | note = 2'-O-methyl guanosine |
| modified_base | 16 | |
| | | mod_base = OTHER |
| | | note = 2'-fluoro adenosine |
| modified_base | 17 | |
| | | mod_base = OTHER |
| | | note = 2'-O-methyl cytidine |
| modified_base | 18 | |
| | | mod_base = OTHER |
| | | note = 2'-O-methyl uridine |
| modified_base | 19 | |
| | | mod_base = OTHER |
| | | note = 2'-fluoro adenosine |
| modified_base | 20 | |
| | | mod_base = OTHER |
| | | note = 2'-O-methyl guanosine 5'-thiophosphate |
| modified_base | 21 | |
| | | mod_base = OTHER |
| | | note = 2'-O-methyl cytidine 5'-thiophosphate |
| SEQUENCE: 30 | | |
| tcaagtttcg cagcgactag c | | 21 |
| | | |
| SEQ ID NO: 31 | moltype = RNA length = 21 | |
| FEATURE | Location/Qualifiers | |
| source | 1..21 | |
| | mol_type = other RNA | |
| | organism = synthetic construct | |
| modified_base | 1 | |
| | | mod_base = OTHER |
| | | note = 2'-O-methyl guanosine |
| modified_base | 2 | |
| | | mod_base = OTHER |
| | | note = 2'-O-methyl cytidine 5'-thiophosphate |
| modified_base | 3 | |
| | | mod_base = OTHER |
| | | note = 2'-O-methyl uridine 5'-thiophosphate |
| modified_base | 4 | |

|  |  |
|---|---|
|  | mod_base = OTHER |
|  | note = 2'-O-methyl adenosine |
| modified_base | 5 |
|  | mod_base = OTHER |
|  | note = 2'-O-methyl guanosine |
| modified_base | 6 |
|  | mod_base = OTHER |
|  | note = 2'-O-methyl uridine |
| modified_base | 7 |
|  | mod_base = OTHER |
|  | note = 2'-fluoro cytidine |
| modified_base | 8 |
|  | mod_base = OTHER |
|  | note = 2'-O-methyl guanosine |
| modified_base | 9 |
|  | mod_base = OTHER |
|  | note = 2'-fluoro cytidine |
| modified_base | 10 |
|  | mod_base = OTHER |
|  | note = 2'-fluoro uridine |
| modified_base | 11 |
|  | mod_base = OTHER |
|  | note = 2'-fluoro guanosine |
| modified_base | 12 |
|  | mod_base = OTHER |
|  | note = 2'-O-methyl cytidine |
| modified_base | 13 |
|  | mod_base = OTHER |
|  | note = 2'-O-methyl guanosine |
| modified_base | 14 |
|  | mod_base = OTHER |
|  | note = 2'-O-methyl adenosine |
| modified_base | 15 |
|  | mod_base = OTHER |
|  | note = 2'-O-methyl adenosine |
| modified_base | 16 |
|  | mod_base = OTHER |
|  | note = 2'-O-methyl adenosine |
| modified_base | 17 |
|  | mod_base = OTHER |
|  | note = 2'-O-methyl cytidine |
| modified_base | 18 |
|  | mod_base = OTHER |
|  | note = 2'-O-methyl uridine |
| modified_base | 19 |
|  | mod_base = OTHER |
|  | note = 2'-O-methyl uridine |
| modified_base | 20 |
|  | mod_base = OTHER |
|  | note = 2'-O-methyl guanosine |
| modified_base | 21 |
|  | mod_base = OTHER |
|  | note = 2'-O-methyl adenosine |
| SEQUENCE: 31 |  |
| gctagtcgct gcgaaacttg a | 21 |
|  |  |
| SEQ ID NO: 32 | moltype = RNA  length = 23 |
| FEATURE | Location/Qualifiers |
| source | 1..23 |
|  | mol_type = other RNA |
|  | organism = synthetic construct |
| modified_base | 1 |
|  | mod_base = OTHER |
|  | note = 2'-O-methyl uridine |
| modified_base | 2 |
|  | mod_base = OTHER |
|  | note = 2'-fluoro cytidine 5'-thiophosphate |
| modified_base | 3 |
|  | mod_base = OTHER |
|  | note = 2'-O-methyl adenosine 5'-thiophosphate |
| modified_base | 4 |
|  | mod_base = OTHER |
|  | note = 2'-O-methyl adenosine |
| modified_base | 5 |
|  | mod_base = OTHER |
|  | note = 2'-O-methyl guanosine |
| modified_base | 6 |
|  | mod_base = OTHER |
|  | note = 2'-fluoro uridine |

```
modified_base      7
                   mod_base = OTHER
                   note = 2,3-dihydroxypropyl thymidine
modified_base      8
                   mod_base = OTHER
                   note = 2'-fluoro uridine
modified_base      9
                   mod_base = OTHER
                   note = 2'-fluoro cytidine
modified_base      10
                   mod_base = OTHER
                   note = 2'-O-methyl guanosine
modified_base      11
                   mod_base = OTHER
                   note = 2'-O-methyl cytidine
modified_base      12
                   mod_base = OTHER
                   note = 2'-O-methyl adenosine
modified_base      13
                   mod_base = OTHER
                   note = 2'-O-methyl guanosine
modified_base      14
                   mod_base = OTHER
                   note = 2'-fluoro cytidine
modified_base      15
                   mod_base = OTHER
                   note = 2'-O-methyl guanosine
modified_base      16
                   mod_base = OTHER
                   note = 2'-fluoro adenosine
modified_base      17
                   mod_base = OTHER
                   note = 2'-O-methyl cytidine
modified_base      18
                   mod_base = OTHER
                   note = 2'-O-methyl uridine
modified_base      19
                   mod_base = OTHER
                   note = 2'-O-methyl adenosine
modified_base      20
                   mod_base = OTHER
                   note = 2'-O-methyl guanosine
modified_base      21
                   mod_base = OTHER
                   note = 2'-O-methyl cytidine
modified_base      22
                   mod_base = OTHER
                   note = 2'-O-methyl adenosine 5'-thiophosphate
modified_base      23
                   mod_base = OTHER
                   note = 2'-O-methyl cytidine 5'-thiophosphate
SEQUENCE: 32
tcaagtttcg cagcgactag cac                                             23

SEQ ID NO: 33      moltype = RNA   length = 21
FEATURE            Location/Qualifiers
source             1..21
                   mol_type = other RNA
                   organism = synthetic construct
modified_base      1
                   mod_base = OTHER
                   note = 2'-O-methyl uridine
modified_base      2
                   mod_base = OTHER
                   note = 2'-fluoro guanosine 5'-thiophosphate
modified_base      3
                   mod_base = OTHER
                   note = 2'-O-methyl cytidine 5'-thiophosphate
modified_base      4
                   mod_base = OTHER
                   note = 2'-O-methyl adenosine
modified_base      5
                   mod_base = OTHER
                   note = 2'-fluoro adenosine
modified_base      6
                   mod_base = OTHER
                   note = 2'-O-methyl guanosine
modified_base      7
                   mod_base = OTHER
```

```
                         note = 2'-fluoro adenosine
modified_base            8
                         mod_base = OTHER
                         note = 2'-O-methyl cytidine
modified_base            9
                         mod_base = OTHER
                         note = 2'-fluoro uridine
modified_base            10
                         mod_base = OTHER
                         note = 2'-fluoro uridine
modified_base            11
                         mod_base = OTHER
                         note = 2'-O-methyl guanosine
modified_base            12
                         mod_base = OTHER
                         note = 2'-O-methyl adenosine
modified_base            13
                         mod_base = OTHER
                         note = 2'-fluoro cytidine
modified_base            14
                         mod_base = OTHER
                         note = 2'-O-methyl adenosine
modified_base            15
                         mod_base = OTHER
                         note = 2'-fluoro cytidine
modified_base            16
                         mod_base = OTHER
                         note = 2'-O-methyl cytidine
modified_base            17
                         mod_base = OTHER
                         note = 2'-O-methyl guanosine
modified_base            18
                         mod_base = OTHER
                         note = 2'-fluoro adenosine
modified_base            19
                         mod_base = OTHER
                         note = 2'-O-methyl adenosine
modified_base            20
                         mod_base = OTHER
                         note = 2'-deoxy thymidine 5'-thiophosphate
modified_base            21
                         mod_base = OTHER
                         note = 2'-deoxy thymidine 5'-thiophosphate
SEQUENCE: 33
tgcaagactt gacaccgaat t                                              21

SEQ ID NO: 34            moltype = RNA   length = 21
FEATURE                  Location/Qualifiers
source                   1..21
                         mol_type = other RNA
                         organism = synthetic construct
modified_base            1
                         mod_base = OTHER
                         note = 2'-O-methyl guanosine
modified_base            2
                         mod_base = OTHER
                         note = 2'-O-methyl cytidine 5'-thiophosphate
modified_base            3
                         mod_base = OTHER
                         note = 2'-O-methyl uridine 5'-thiophosphate
modified_base            4
                         mod_base = OTHER
                         note = 2'-O-methyl guanosine
modified_base            5
                         mod_base = OTHER
                         note = 2'-O-methyl cytidine
modified_base            6
                         mod_base = OTHER
                         note = 2'-O-methyl adenosine
modified_base            7
                         mod_base = OTHER
                         note = 2'-fluoro adenosine
modified_base            8
                         mod_base = OTHER
                         note = 2'-O-methyl guanosine
modified_base            9
                         mod_base = OTHER
                         note = 2'-fluoro adenosine
modified_base            10
```

|  |  |
|---|---|
|  | mod_base = OTHER |
|  | note = 2'-fluoro cytidine |
| modified_base | 11 |
|  | mod_base = OTHER |
|  | note = 2'-fluoro uridine |
| modified_base | 12 |
|  | mod_base = OTHER |
|  | note = 2'-O-methyl uridine |
| modified_base | 13 |
|  | mod_base = OTHER |
|  | note = 2'-O-methyl guanosine |
| modified_base | 14 |
|  | mod_base = OTHER |
|  | note = 2'-O-methyl adenosine |
| modified_base | 15 |
|  | mod_base = OTHER |
|  | note = 2'-O-methyl cytidine |
| modified_base | 16 |
|  | mod_base = OTHER |
|  | note = 2'-O-methyl adenosine |
| modified_base | 17 |
|  | mod_base = OTHER |
|  | note = 2'-O-methyl cytidine |
| modified_base | 18 |
|  | mod_base = OTHER |
|  | note = 2'-O-methyl cytidine |
| modified_base | 19 |
|  | mod_base = OTHER |
|  | note = 2'-O-methyl guanosine |
| modified_base | 20 |
|  | mod_base = OTHER |
|  | note = 2'-O-methyl adenosine |
| modified_base | 21 |
|  | mod_base = OTHER |
|  | note = 2'-O-methyl adenosine |
| SEQUENCE: 34 | |
| gctgcaagac ttgacaccga a | 21 |
|  |  |
| SEQ ID NO: 35 | moltype = RNA  length = 23 |
| FEATURE | Location/Qualifiers |
| source | 1..23 |
|  | mol_type = other RNA |
|  | organism = synthetic construct |
| modified_base | 1 |
|  | mod_base = OTHER |
|  | note = 2'-O-methyl uridine |
| modified_base | 2 |
|  | mod_base = OTHER |
|  | note = 2'-fluoro uridine 5'-thiophosphate |
| modified_base | 3 |
|  | mod_base = OTHER |
|  | note = 2'-O-methyl cytidine 5'-thiophosphate |
| modified_base | 4 |
|  | mod_base = OTHER |
|  | note = 2'-O-methyl guanosine |
| modified_base | 5 |
|  | mod_base = OTHER |
|  | note = 2'-O-methyl guanosine |
| modified_base | 6 |
|  | mod_base = OTHER |
|  | note = 2,3-dihydroxypropyl thymidine |
| modified_base | 7 |
|  | mod_base = OTHER |
|  | note = 2'-O-methyl guanosine |
| modified_base | 8 |
|  | mod_base = OTHER |
|  | note = 2'-fluoro uridine |
| modified_base | 9 |
|  | mod_base = OTHER |
|  | note = 2'-fluoro cytidine |
| modified_base | 10 |
|  | mod_base = OTHER |
|  | note = 2'-O-methyl adenosine |
| modified_base | 11 |
|  | mod_base = OTHER |
|  | note = 2'-O-methyl adenosine |
| modified_base | 12 |
|  | mod_base = OTHER |
|  | note = 2'-O-methyl guanosine |

```
modified_base          13
                       mod_base = OTHER
                       note = 2'-O-methyl uridine
modified_base          14
                       mod_base = OTHER
                       note = 2'-fluoro cytidine
modified_base          15
                       mod_base = OTHER
                       note = 2'-O-methyl uridine
modified_base          16
                       mod_base = OTHER
                       note = 2'-fluoro uridine
modified_base          17
                       mod_base = OTHER
                       note = 2'-O-methyl guanosine
modified_base          18
                       mod_base = OTHER
                       note = 2'-O-methyl cytidine
modified_base          19
                       mod_base = OTHER
                       note = 2'-O-methyl adenosine
modified_base          20
                       mod_base = OTHER
                       note = 2'-O-methyl guanosine
modified_base          21
                       mod_base = OTHER
                       note = 2'-O-methyl cytidine
modified_base          22
                       mod_base = OTHER
                       note = 2'-O-methyl guanosine 5'-thiophosphate
modified_base          23
                       mod_base = OTHER
                       note = 2'-O-methyl adenosine 5'-thiophosphate
SEQUENCE: 35
ttcggtgtca agtcttgcag cga                                              23

SEQ ID NO: 36          moltype = RNA   length = 21
FEATURE                Location/Qualifiers
source                 1..21
                       mol_type = other RNA
                       organism = synthetic construct
modified_base          1
                       mod_base = OTHER
                       note = 2'-O-methyl guanosine
modified_base          2
                       mod_base = OTHER
                       note = 2'-fluoro adenosine 5'-thiophosphate
modified_base          3
                       mod_base = OTHER
                       note = 2'-O-methyl cytidine 5'-thiophosphate
modified_base          4
                       mod_base = OTHER
                       note = 2'-O-methyl cytidine
modified_base          5
                       mod_base = OTHER
                       note = 2'-fluoro cytidine
modified_base          6
                       mod_base = OTHER
                       note = 2'-O-methyl uridine
modified_base          7
                       mod_base = OTHER
                       note = 2'-fluoro adenosine
modified_base          8
                       mod_base = OTHER
                       note = 2'-O-methyl cytidine
modified_base          9
                       mod_base = OTHER
                       note = 2'-fluoro cytidine
modified_base          10
                       mod_base = OTHER
                       note = 2'-fluoro uridine
modified_base          11
                       mod_base = OTHER
                       note = 2'-O-methyl uridine
modified_base          12
                       mod_base = OTHER
                       note = 2'-O-methyl cytidine
modified_base          13
                       mod_base = OTHER
```

```
                              note = 2'-fluoro adenosine
modified_base                 14
                              mod_base = OTHER
                              note = 2'-O-methyl uridine
modified_base                 15
                              mod_base = OTHER
                              note = 2'-fluoro adenosine
modified_base                 16
                              mod_base = OTHER
                              note = 2'-O-methyl cytidine
modified_base                 17
                              mod_base = OTHER
                              note = 2'-O-methyl cytidine
modified_base                 18
                              mod_base = OTHER
                              note = 2'-fluoro uridine
modified_base                 19
                              mod_base = OTHER
                              note = 2'-O-methyl guanosine
modified_base                 20
                              mod_base = OTHER
                              note = 2'-deoxy thymidine 5'-thiophosphate
modified_base                 21
                              mod_base = OTHER
                              note = 2'-deoxy thymidine 5'-thiophosphate
SEQUENCE: 36
gaccctacct tcatacctgt t                                                     21

SEQ ID NO: 37                 moltype = RNA   length = 21
FEATURE                       Location/Qualifiers
source                        1..21
                              mol_type = other RNA
                              organism = synthetic construct
modified_base                 1
                              mod_base = OTHER
                              note = 2'-O-methyl cytidine
modified_base                 2
                              mod_base = OTHER
                              note = 2'-deoxy adenosine 5'-thiophosphate
modified_base                 3
                              mod_base = OTHER
                              note = 2'-O-methyl guanosine 5'-thiophosphate
modified_base                 4
                              mod_base = OTHER
                              note = 2'-fluoro guanosine
modified_base                 5
                              mod_base = OTHER
                              note = 2'-O-methyl uridine
modified_base                 6
                              mod_base = OTHER
                              note = 2'-fluoro adenosine
modified_base                 7
                              mod_base = OTHER
                              note = 2'-deoxy thymidine
modified_base                 8
                              mod_base = OTHER
                              note = 2'-O-methyl guanosine 5'-thiophosphate
modified_base                 9
                              mod_base = OTHER
                              note = 2'-fluoro adenosine
modified_base                 10
                              mod_base = OTHER
                              note = 2'-O-methyl adenosine
modified_base                 11
                              mod_base = OTHER
                              note = 2'-O-methyl guanosine
modified_base                 12
                              mod_base = OTHER
                              note = 2'-fluoro guanosine
modified_base                 13
                              mod_base = OTHER
                              note = 2'-O-methyl uridine
modified_base                 14
                              mod_base = OTHER
                              note = 2'-fluoro adenosine
modified_base                 15
                              mod_base = OTHER
                              note = 2'-O-methyl guanosine
modified_base                 16
```

|                  |                                              |
|------------------|----------------------------------------------|
|                  | mod_base = OTHER                             |
|                  | note = 2'-fluoro guanosine                   |
| modified_base    | 17                                           |
|                  | mod_base = OTHER                             |
|                  | note = 2'-O-methyl guanosine                 |
| modified_base    | 18                                           |
|                  | mod_base = OTHER                             |
|                  | note = 2'-O-methyl uridine                   |
| modified_base    | 19                                           |
|                  | mod_base = OTHER                             |
|                  | note = 2'-deoxy cytidine                     |
| modified_base    | 20                                           |
|                  | mod_base = OTHER                             |
|                  | note = 2'-O-methyl uridine 5'-thiophosphate  |
| modified_base    | 21                                           |
|                  | mod_base = OTHER                             |
|                  | note = 2'-O-methyl uridine 5'-thiophosphate  |
| SEQUENCE: 37     |                                              |
| caggtatgaa ggtagggtct t                                         21 |

| SEQ ID NO: 38    | moltype = RNA  length = 21                   |
| FEATURE          | Location/Qualifiers                          |
| source           | 1..21                                        |
|                  | mol_type = other RNA                         |
|                  | organism = synthetic construct               |
| modified_base    | 1                                            |
|                  | mod_base = OTHER                             |
|                  | note = 2'-O-methyl adenosine                 |
| modified_base    | 2                                            |
|                  | mod_base = OTHER                             |
|                  | note = 2'-O-methyl adenosine 5'-thiophosphate|
| modified_base    | 3                                            |
|                  | mod_base = OTHER                             |
|                  | note = 2'-O-methyl guanosine 5'-thiophosphate|
| modified_base    | 4                                            |
|                  | mod_base = OTHER                             |
|                  | note = 2'-O-methyl adenosine                 |
| modified_base    | 5                                            |
|                  | mod_base = OTHER                             |
|                  | note = 2'-O-methyl cytidine                  |
| modified_base    | 6                                            |
|                  | mod_base = OTHER                             |
|                  | note = 2'-O-methyl cytidine                  |
| modified_base    | 7                                            |
|                  | mod_base = OTHER                             |
|                  | note = 2'-fluoro cytidine                    |
| modified_base    | 8                                            |
|                  | mod_base = OTHER                             |
|                  | note = 2'-O-methyl uridine                   |
| modified_base    | 9                                            |
|                  | mod_base = OTHER                             |
|                  | note = 2'-fluoro adenosine                   |
| modified_base    | 10                                           |
|                  | mod_base = OTHER                             |
|                  | note = 2'-fluoro cytidine                    |
| modified_base    | 11                                           |
|                  | mod_base = OTHER                             |
|                  | note = 2'-fluoro cytidine                    |
| modified_base    | 12                                           |
|                  | mod_base = OTHER                             |
|                  | note = 2'-O-methyl uridine                   |
| modified_base    | 13                                           |
|                  | mod_base = OTHER                             |
|                  | note = 2'-O-methyl uridine                   |
| modified_base    | 14                                           |
|                  | mod_base = OTHER                             |
|                  | note = 2'-O-methyl cytidine                  |
| modified_base    | 15                                           |
|                  | mod_base = OTHER                             |
|                  | note = 2'-O-methyl adenosine                 |
| modified_base    | 16                                           |
|                  | mod_base = OTHER                             |
|                  | note = 2'-O-methyl uridine                   |
| modified_base    | 17                                           |
|                  | mod_base = OTHER                             |
|                  | note = 2'-O-methyl adenosine                 |
| modified_base    | 18                                           |
|                  | mod_base = OTHER                             |
|                  | note = 2'-O-methyl cytidine                  |

-continued

```
modified_base       19
                    mod_base = OTHER
                    note = 2'-O-methyl cytidine
modified_base       20
                    mod_base = OTHER
                    note = 2'-O-methyl uridine
modified_base       21
                    mod_base = OTHER
                    note = 2'-O-methyl guanosine
SEQUENCE: 38
aagaccctac cttcatacct g                                      21

SEQ ID NO: 39       moltype = RNA  length = 23
FEATURE             Location/Qualifiers
source              1..23
                    mol_type = other RNA
                    organism = synthetic construct
modified_base       1
                    mod_base = OTHER
                    note = 2'-O-methyl cytidine
modified_base       2
                    mod_base = OTHER
                    note = 2'-fluoro adenosine 5'-thiophosphate
modified_base       3
                    mod_base = OTHER
                    note = 2'-O-methyl guanosine 5'-thiophosphate
modified_base       4
                    mod_base = OTHER
                    note = 2'-O-methyl guanosine
modified_base       5
                    mod_base = OTHER
                    note = 2'-O-methyl uridine
modified_base       6
                    mod_base = OTHER
                    note = 2'-fluoro adenosine
modified_base       7
                    mod_base = OTHER
                    note = 2,3-dihydroxypropyl thymidine
modified_base       8
                    mod_base = OTHER
                    note = 2'-fluoro guanosine
modified_base       9
                    mod_base = OTHER
                    note = 2'-fluoro adenosine
modified_base       10
                    mod_base = OTHER
                    note = 2'-O-methyl adenosine
modified_base       11
                    mod_base = OTHER
                    note = 2'-O-methyl guanosine
modified_base       12
                    mod_base = OTHER
                    note = 2'-O-methyl guanosine
modified_base       13
                    mod_base = OTHER
                    note = 2'-O-methyl uridine
modified_base       14
                    mod_base = OTHER
                    note = 2'-fluoro adenosine
modified_base       15
                    mod_base = OTHER
                    note = 2'-O-methyl guanosine
modified_base       16
                    mod_base = OTHER
                    note = 2'-fluoro guanosine
modified_base       17
                    mod_base = OTHER
                    note = 2'-O-methyl guanosine
modified_base       18
                    mod_base = OTHER
                    note = 2'-O-methyl uridine
modified_base       19
                    mod_base = OTHER
                    note = 2'-O-methyl cytidine
modified_base       20
                    mod_base = OTHER
                    note = 2'-O-methyl uridine
modified_base       21
                    mod_base = OTHER
```

|   |   |
|---|---|
|   | note = 2'-O-methyl uridine |
| modified_base | 22 |
|   | mod_base = OTHER |
|   | note = 2'-O-methyl uridine 5'-thiophosphate |
| modified_base | 23 |
|   | mod_base = OTHER |
|   | note = 2'-O-methyl guanosine 5'-thiophosphate |
| SEQUENCE: 39 |   |
| caggtatgaa ggtagggtct ttg | 23 |
|   |   |
| SEQ ID NO: 40 | moltype = RNA   length = 21 |
| FEATURE | Location/Qualifiers |
| source | 1..21 |
|   | mol_type = other RNA |
|   | organism = synthetic construct |
| modified_base | 1 |
|   | mod_base = OTHER |
|   | note = 2'-O-methyl uridine |
| modified_base | 2 |
|   | mod_base = OTHER |
|   | note = 2'-fluoro uridine 5'-thiophosphate |
| modified_base | 3 |
|   | mod_base = OTHER |
|   | note = 2'-O-methyl adenosine 5'-thiophosphate |
| modified_base | 4 |
|   | mod_base = OTHER |
|   | note = 2'-O-methyl adenosine |
| modified_base | 5 |
|   | mod_base = OTHER |
|   | note = 2'-fluoro cytidine |
| modified_base | 6 |
|   | mod_base = OTHER |
|   | note = 2'-O-methyl adenosine |
| modified_base | 7 |
|   | mod_base = OTHER |
|   | note = 2'-fluoro adenosine |
| modified_base | 8 |
|   | mod_base = OTHER |
|   | note = 2'-O-methyl guanosine |
| modified_base | 9 |
|   | mod_base = OTHER |
|   | note = 2'-fluoro cytidine |
| modified_base | 10 |
|   | mod_base = OTHER |
|   | note = 2'-fluoro cytidine |
| modified_base | 11 |
|   | mod_base = OTHER |
|   | note = 2'-O-methyl uridine |
| modified_base | 12 |
|   | mod_base = OTHER |
|   | note = 2'-O-methyl adenosine |
| modified_base | 13 |
|   | mod_base = OTHER |
|   | note = 2'-fluoro adenosine |
| modified_base | 14 |
|   | mod_base = OTHER |
|   | note = 2'-O-methyl guanosine |
| modified_base | 15 |
|   | mod_base = OTHER |
|   | note = 2'-fluoro guanosine |
| modified_base | 16 |
|   | mod_base = OTHER |
|   | note = 2'-O-methyl uridine |
| modified_base | 17 |
|   | mod_base = OTHER |
|   | note = 2'-O-methyl cytidine |
| modified_base | 18 |
|   | mod_base = OTHER |
|   | note = 2'-fluoro uridine |
| modified_base | 19 |
|   | mod_base = OTHER |
|   | note = 2'-O-methyl uridine |
| modified_base | 20 |
|   | mod_base = OTHER |
|   | note = 2'-deoxy thymidine 5'-thiophosphate |
| modified_base | 21 |
|   | mod_base = OTHER |
|   | note = 2'-deoxy thymidine 5'-thiophosphate |
| SEQUENCE: 40 |   |

```
ttaacaagcc taaggtctttt t                                                      21

SEQ ID NO: 41          moltype = RNA   length = 21
FEATURE                Location/Qualifiers
source                 1..21
                       mol_type = other RNA
                       organism = synthetic construct
modified_base          1
                       mod_base = OTHER
                       note = 2'-O-methyl guanosine
modified_base          2
                       mod_base = OTHER
                       note = 2'-O-methyl cytidine 5'-thiophosphate
modified_base          3
                       mod_base = OTHER
                       note = 2'-O-methyl uridine 5'-thiophosphate
modified_base          4
                       mod_base = OTHER
                       note = 2'-O-methyl uridine
modified_base          5
                       mod_base = OTHER
                       note = 2'-O-methyl adenosine
modified_base          6
                       mod_base = OTHER
                       note = 2'-O-methyl adenosine
modified_base          7
                       mod_base = OTHER
                       note = 2'-fluoro cytidine
modified_base          8
                       mod_base = OTHER
                       note = 2'-O-methyl adenosine
modified_base          9
                       mod_base = OTHER
                       note = 2'-fluoro adenosine
modified_base          10
                       mod_base = OTHER
                       note = 2'-fluoro guanosine
modified_base          11
                       mod_base = OTHER
                       note = 2'-fluoro cytidine
modified_base          12
                       mod_base = OTHER
                       note = 2'-O-methyl cytidine
modified_base          13
                       mod_base = OTHER
                       note = 2'-O-methyl uridine
modified_base          14
                       mod_base = OTHER
                       note = 2'-O-methyl adenosine
modified_base          15
                       mod_base = OTHER
                       note = 2'-O-methyl adenosine
modified_base          16
                       mod_base = OTHER
                       note = 2'-O-methyl guanosine
modified_base          17
                       mod_base = OTHER
                       note = 2'-O-methyl guanosine
modified_base          18
                       mod_base = OTHER
                       note = 2'-O-methyl uridine
modified_base          19
                       mod_base = OTHER
                       note = 2'-O-methyl cytidine
modified_base          20
                       mod_base = OTHER
                       note = 2'-O-methyl uridine
modified_base          21
                       mod_base = OTHER
                       note = 2'-O-methyl uridine
SEQUENCE: 41
gcttaacaag cctaaggtct t                                                       21

SEQ ID NO: 42          moltype = RNA   length = 23
FEATURE                Location/Qualifiers
source                 1..23
                       mol_type = other RNA
                       organism = synthetic construct
modified_base          1
```

|  |  |
|---|---|
| | mod_base = OTHER |
| | note = 2'-O-methyl adenosine |
| modified_base | 2 |
| | mod_base = OTHER |
| | note = 2'-fluoro adenosine 5'-thiophosphate |
| modified_base | 3 |
| | mod_base = OTHER |
| | note = 2'-O-methyl guanosine 5'-thiophosphate |
| modified_base | 4 |
| | mod_base = OTHER |
| | note = 2'-O-methyl adenosine |
| modified_base | 5 |
| | mod_base = OTHER |
| | note = 2'-O-methyl cytidine |
| modified_base | 6 |
| | mod_base = OTHER |
| | note = 2'-fluoro cytidine |
| modified_base | 7 |
| | mod_base = OTHER |
| | note = 2,3-dihydroxypropyl thymidine |
| modified_base | 8 |
| | mod_base = OTHER |
| | note = 2'-fluoro uridine |
| modified_base | 9 |
| | mod_base = OTHER |
| | note = 2'-fluoro adenosine |
| modified_base | 10 |
| | mod_base = OTHER |
| | note = 2'-O-methyl guanosine |
| modified_base | 11 |
| | mod_base = OTHER |
| | note = 2'-O-methyl guanosine |
| modified_base | 12 |
| | mod_base = OTHER |
| | note = 2'-O-methyl cytidine |
| modified_base | 13 |
| | mod_base = OTHER |
| | note = 2'-O-methyl uridine |
| modified_base | 14 |
| | mod_base = OTHER |
| | note = 2'-fluoro uridine |
| modified_base | 15 |
| | mod_base = OTHER |
| | note = 2'-O-methyl guanosine |
| modified_base | 16 |
| | mod_base = OTHER |
| | note = 2'-fluoro uridine |
| modified_base | 17 |
| | mod_base = OTHER |
| | note = 2'-O-methyl uridine |
| modified_base | 18 |
| | mod_base = OTHER |
| | note = 2'-O-methyl adenosine |
| modified_base | 19 |
| | mod_base = OTHER |
| | note = 2'-O-methyl adenosine |
| modified_base | 20 |
| | mod_base = OTHER |
| | note = 2'-O-methyl guanosine |
| modified_base | 21 |
| | mod_base = OTHER |
| | note = 2'-O-methyl cytidine |
| modified_base | 22 |
| | mod_base = OTHER |
| | note = 2'-O-methyl uridine 5'-thiophosphate |
| modified_base | 23 |
| | mod_base = OTHER |
| | note = 2'-O-methyl guanosine 5'-thiophosphate |
| SEQUENCE: 42 | |

```
aagaccttag gcttgttaag ctg                                              23
```

| | |
|---|---|
| SEQ ID NO: 43 | moltype = RNA   length = 21 |
| FEATURE | Location/Qualifiers |
| source | 1..21 |
| | mol_type = other RNA |
| | organism = synthetic construct |
| modified_base | 1 |
| | mod_base = OTHER |
| | note = 2'-O-methyl cytidine |

```
modified_base       2
                    mod_base = OTHER
                    note = 2'-fluoro cytidine 5'-thiophosphate
modified_base       3
                    mod_base = OTHER
                    note = 2'-O-methyl adenosine 5'-thiophosphate
modified_base       4
                    mod_base = OTHER
                    note = 2'-O-methyl adenosine
modified_base       5
                    mod_base = OTHER
                    note = 2'-fluoro uridine
modified_base       6
                    mod_base = OTHER
                    note = 2'-O-methyl adenosine
modified_base       7
                    mod_base = OTHER
                    note = 2'-fluoro guanosine
modified_base       8
                    mod_base = OTHER
                    note = 2'-O-methyl cytidine
modified_base       9
                    mod_base = OTHER
                    note = 2'-fluoro uridine
modified_base       10
                    mod_base = OTHER
                    note = 2'-fluoro uridine
modified_base       11
                    mod_base = OTHER
                    note = 2'-O-methyl adenosine
modified_base       12
                    mod_base = OTHER
                    note = 2'-O-methyl adenosine
modified_base       13
                    mod_base = OTHER
                    note = 2'-fluoro cytidine
modified_base       14
                    mod_base = OTHER
                    note = 2'-O-methyl adenosine
modified_base       15
                    mod_base = OTHER
                    note = 2'-fluoro adenosine
modified_base       16
                    mod_base = OTHER
                    note = 2'-O-methyl guanosine
modified_base       17
                    mod_base = OTHER
                    note = 2'-O-methyl cytidine
modified_base       18
                    mod_base = OTHER
                    note = 2'-fluoro cytidine
modified_base       19
                    mod_base = OTHER
                    note = 2'-O-methyl uridine
modified_base       20
                    mod_base = OTHER
                    note = 2'-deoxy thymidine 5'-thiophosphate
modified_base       21
                    mod_base = OTHER
                    note = 2'-deoxy thymidine 5'-thiophosphate
SEQUENCE: 43
ccaatagctt aacaagcctt t                                         21

SEQ ID NO: 44       moltype = RNA  length = 21
FEATURE             Location/Qualifiers
source              1..21
                    mol_type = other RNA
                    organism = synthetic construct
modified_base       1
                    mod_base = OTHER
                    note = 2'-O-methyl adenosine
modified_base       2
                    mod_base = OTHER
                    note = 2'-deoxy guanosine 5'-thiophosphate
modified_base       3
                    mod_base = OTHER
                    note = 2'-O-methyl guanosine 5'-thiophosphate
modified_base       4
                    mod_base = OTHER
```

| | |
|---|---|
| | note = 2'-fluoro cytidine |
| modified_base | 5 |
| | mod_base = OTHER |
| | note = 2'-O-methyl uridine |
| modified_base | 6 |
| | mod_base = OTHER |
| | note = 2'-fluoro uridine |
| modified_base | 7 |
| | mod_base = OTHER |
| | note = 2'-deoxy guanosine |
| modified_base | 8 |
| | mod_base = OTHER |
| | note = 2'-O-methyl uridine 5'-thiophosphate |
| modified_base | 9 |
| | mod_base = OTHER |
| | note = 2'-fluoro uridine |
| modified_base | 10 |
| | mod_base = OTHER |
| | note = 2'-O-methyl adenosine |
| modified_base | 11 |
| | mod_base = OTHER |
| | note = 2'-O-methyl adenosine |
| modified_base | 12 |
| | mod_base = OTHER |
| | note = 2'-fluoro guanosine |
| modified_base | 13 |
| | mod_base = OTHER |
| | note = 2'-O-methyl cytidine |
| modified_base | 14 |
| | mod_base = OTHER |
| | note = 2'-fluoro uridine |
| modified_base | 15 |
| | mod_base = OTHER |
| | note = 2'-O-methyl adenosine |
| modified_base | 16 |
| | mod_base = OTHER |
| | note = 2'-fluoro uridine |
| modified_base | 17 |
| | mod_base = OTHER |
| | note = 2'-O-methyl uridine |
| modified_base | 18 |
| | mod_base = OTHER |
| | note = 2'-O-methyl guanosine |
| modified_base | 19 |
| | mod_base = OTHER |
| | note = 2'-deoxy guanosine |
| modified_base | 20 |
| | mod_base = OTHER |
| | note = 2'-O-methyl guanosine 5'-thiophosphate |
| modified_base | 21 |
| | mod_base = OTHER |
| | note = 2'-O-methyl uridine 5'-thiophosphate |
| SEQUENCE: 44 | |
| aggcttgtta agctattggg t | 21 |
| | |
| SEQ ID NO: 45 | moltype = RNA   length = 21 |
| FEATURE | Location/Qualifiers |
| source | 1..21 |
| | mol_type = other RNA |
| | organism = synthetic construct |
| modified_base | 1 |
| | mod_base = OTHER |
| | note = 2'-O-methyl adenosine |
| modified_base | 2 |
| | mod_base = OTHER |
| | note = 2'-O-methyl cytidine 5'-thiophosphate |
| modified_base | 3 |
| | mod_base = OTHER |
| | note = 2'-O-methyl cytidine 5'-thiophosphate |
| modified_base | 4 |
| | mod_base = OTHER |
| | note = 2'-O-methyl cytidine |
| modified_base | 5 |
| | mod_base = OTHER |
| | note = 2'-O-methyl adenosine |
| modified_base | 6 |
| | mod_base = OTHER |
| | note = 2'-O-methyl adenosine |
| modified_base | 7 |

```
                         mod_base = OTHER
                         note = 2'-fluoro uridine
modified_base            8
                         mod_base = OTHER
                         note = 2'-O-methyl adenosine
modified_base            9
                         mod_base = OTHER
                         note = 2'-fluoro guanosine
modified_base            10
                         mod_base = OTHER
                         note = 2'-fluoro cytidine
modified_base            11
                         mod_base = OTHER
                         note = 2'-fluoro uridine
modified_base            12
                         mod_base = OTHER
                         note = 2'-O-methyl uridine
modified_base            13
                         mod_base = OTHER
                         note = 2'-O-methyl adenosine
modified_base            14
                         mod_base = OTHER
                         note = 2'-O-methyl adenosine
modified_base            15
                         mod_base = OTHER
                         note = 2'-O-methyl cytidine
modified_base            16
                         mod_base = OTHER
                         note = 2'-O-methyl adenosine
modified_base            17
                         mod_base = OTHER
                         note = 2'-O-methyl adenosine
modified_base            18
                         mod_base = OTHER
                         note = 2'-O-methyl guanosine
modified_base            19
                         mod_base = OTHER
                         note = 2'-O-methyl cytidine
modified_base            20
                         mod_base = OTHER
                         note = 2'-O-methyl cytidine
modified_base            21
                         mod_base = OTHER
                         note = 2'-O-methyl uridine
SEQUENCE: 45
acccaatagc ttaacaagcc t                                             21

SEQ ID NO: 46            moltype = RNA  length = 23
FEATURE                  Location/Qualifiers
source                   1..23
                         mol_type = other RNA
                         organism = synthetic construct
modified_base            1
                         mod_base = OTHER
                         note = 2'-O-methyl adenosine
modified_base            2
                         mod_base = OTHER
                         note = 2'-fluoro guanosine 5'-thiophosphate
modified_base            3
                         mod_base = OTHER
                         note = 2'-O-methyl guanosine 5'-thiophosphate
modified_base            4
                         mod_base = OTHER
                         note = 2'-O-methyl cytidine
modified_base            5
                         mod_base = OTHER
                         note = 2'-O-methyl uridine
modified_base            6
                         mod_base = OTHER
                         note = 2'-fluoro uridine
modified_base            7
                         mod_base = OTHER
                         note = 2'-O-methyl guanosine
modified_base            8
                         mod_base = OTHER
                         note = 2'-fluoro uridine
modified_base            9
                         mod_base = OTHER
                         note = 2'-fluoro uridine
```

```
modified_base      10
                   mod_base = OTHER
                   note = 2'-O-methyl adenosine
modified_base      11
                   mod_base = OTHER
                   note = 2'-O-methyl adenosine
modified_base      12
                   mod_base = OTHER
                   note = 2'-O-methyl guanosine
modified_base      13
                   mod_base = OTHER
                   note = 2'-O-methyl cytidine
modified_base      14
                   mod_base = OTHER
                   note = 2'-fluoro uridine
modified_base      15
                   mod_base = OTHER
                   note = 2'-O-methyl adenosine
modified_base      16
                   mod_base = OTHER
                   note = 2'-fluoro uridine
modified_base      17
                   mod_base = OTHER
                   note = 2'-O-methyl uridine
modified_base      18
                   mod_base = OTHER
                   note = 2'-O-methyl guanosine
modified_base      19
                   mod_base = OTHER
                   note = 2'-O-methyl guanosine
modified_base      20
                   mod_base = OTHER
                   note = 2'-O-methyl guanosine
modified_base      21
                   mod_base = OTHER
                   note = 2'-O-methyl uridine
modified_base      22
                   mod_base = OTHER
                   note = 2'-O-methyl adenosine 5'-thiophosphate
modified_base      23
                   mod_base = OTHER
                   note = 2'-O-methyl guanosine 5'-thiophosphate
SEQUENCE: 46
aggcttgtta agctattggg tag                                          23

SEQ ID NO: 47      moltype = RNA   length = 21
FEATURE            Location/Qualifiers
source             1..21
                   mol_type = other RNA
                   organism = synthetic construct
modified_base      1
                   mod_base = OTHER
                   note = 2'-O-methyl adenosine
modified_base      2
                   mod_base = OTHER
                   note = 2'-deoxy guanosine 5'-thiophosphate
modified_base      3
                   mod_base = OTHER
                   note = 2'-O-methyl guanosine 5'-thiophosphate
modified_base      4
                   mod_base = OTHER
                   note = 2'-fluoro cytidine
modified_base      5
                   mod_base = OTHER
                   note = 2'-O-methyl uridine
modified_base      6
                   mod_base = OTHER
                   note = 2'-fluoro uridine
modified_base      7
                   mod_base = OTHER
                   note = 2'-O-methyl guanosine
modified_base      8
                   mod_base = OTHER
                   note = 2'-O-methyl uridine
modified_base      9
                   mod_base = OTHER
                   note = 2'-fluoro uridine
modified_base      10
                   mod_base = OTHER
```

```
                            note = 2'-O-methyl adenosine
modified_base               11
                            mod_base = OTHER
                            note = 2'-O-methyl adenosine
modified_base               12
                            mod_base = OTHER
                            note = 2'-fluoro guanosine
modified_base               13
                            mod_base = OTHER
                            note = 2'-O-methyl cytidine
modified_base               14
                            mod_base = OTHER
                            note = 2'-fluoro uridine
modified_base               15
                            mod_base = OTHER
                            note = 2'-O-methyl adenosine
modified_base               16
                            mod_base = OTHER
                            note = 2'-fluoro uridine
modified_base               17
                            mod_base = OTHER
                            note = 2'-O-methyl uridine
modified_base               18
                            mod_base = OTHER
                            note = 2'-O-methyl guanosine
modified_base               19
                            mod_base = OTHER
                            note = 2'-fluoro guanosine
modified_base               20
                            mod_base = OTHER
                            note = 2'-O-methyl guanosine 5'-thiophosphate
modified_base               21
                            mod_base = OTHER
                            note = 2'-O-methyl uridine 5'-thiophosphate
SEQUENCE: 47
aggcttgtta agctattggg t                                                    21

SEQ ID NO: 48               moltype = RNA   length = 21
FEATURE                     Location/Qualifiers
source                      1..21
                            mol_type = other RNA
                            organism = synthetic construct
modified_base               1
                            mod_base = OTHER
                            note = 2'-O-methyl uridine
modified_base               2
                            mod_base = OTHER
                            note = 2'-fluoro adenosine 5'-thiophosphate
modified_base               3
                            mod_base = OTHER
                            note = 2'-O-methyl guanosine 5'-thiophosphate
modified_base               4
                            mod_base = OTHER
                            note = 2'-O-methyl uridine
modified_base               5
                            mod_base = OTHER
                            note = 2'-fluoro cytidine
modified_base               6
                            mod_base = OTHER
                            note = 2'-O-methyl guanosine
modified_base               7
                            mod_base = OTHER
                            note = 2'-fluoro cytidine
modified_base               8
                            mod_base = OTHER
                            note = 2'-O-methyl uridine
modified_base               9
                            mod_base = OTHER
                            note = 2'-fluoro guanosine
modified_base               10
                            mod_base = OTHER
                            note = 2'-fluoro cytidine
modified_base               11
                            mod_base = OTHER
                            note = 2'-O-methyl guanosine
modified_base               12
                            mod_base = OTHER
                            note = 2'-O-methyl adenosine
modified_base               13
```

```
                        mod_base = OTHER
                        note = 2'-fluoro adenosine
modified_base           14
                        mod_base = OTHER
                        note = 2'-O-methyl adenosine
modified_base           15
                        mod_base = OTHER
                        note = 2'-fluoro cytidine
modified_base           16
                        mod_base = OTHER
                        note = 2'-O-methyl uridine
modified_base           17
                        mod_base = OTHER
                        note = 2'-O-methyl uridine
modified_base           18
                        mod_base = OTHER
                        note = 2'-fluoro guanosine
modified_base           19
                        mod_base = OTHER
                        note = 2'-O-methyl adenosine
modified_base           20
                        mod_base = OTHER
                        note = 2'-deoxy thymidine 5'-thiophosphate
modified_base           21
                        mod_base = OTHER
                        note = 2'-deoxy thymidine 5'-thiophosphate
misc_feature            21
                        note = 3'-O attached to a GalNAc-comprising compound via a
                         linker
SEQUENCE: 48
tagtcgctgc gaaacttgat t                                             21

SEQ ID NO: 49           moltype = RNA   length = 21
FEATURE                 Location/Qualifiers
source                  1..21
                        mol_type = other RNA
                        organism = synthetic construct
modified_base           1
                        mod_base = OTHER
                        note = 2'-O-methyl guanosine
modified_base           2
                        mod_base = OTHER
                        note = 2'-fluoro cytidine 5'-thiophosphate
modified_base           3
                        mod_base = OTHER
                        note = 2'-O-methyl uridine 5'-thiophosphate
modified_base           4
                        mod_base = OTHER
                        note = 2'-O-methyl uridine
modified_base           5
                        mod_base = OTHER
                        note = 2'-fluoro adenosine
modified_base           6
                        mod_base = OTHER
                        note = 2'-O-methyl adenosine
modified_base           7
                        mod_base = OTHER
                        note = 2'-fluoro cytidine
modified_base           8
                        mod_base = OTHER
                        note = 2'-O-methyl adenosine
modified_base           9
                        mod_base = OTHER
                        note = 2'-fluoro adenosine
modified_base           10
                        mod_base = OTHER
                        note = 2'-fluoro guanosine
modified_base           11
                        mod_base = OTHER
                        note = 2'-O-methyl cytidine
modified_base           12
                        mod_base = OTHER
                        note = 2'-O-methyl cytidine
modified_base           13
                        mod_base = OTHER
                        note = 2'-fluoro 2'-deoxy thymidine
modified_base           14
                        mod_base = OTHER
                        note = 2'-O-methyl adenosine
```

```
modified_base       15
                    mod_base = OTHER
                    note = 2'-fluoro adenosine
modified_base       16
                    mod_base = OTHER
                    note = 2'-O-methyl guanosine
modified_base       17
                    mod_base = OTHER
                    note = 2'-O-methyl guanosine
modified_base       18
                    mod_base = OTHER
                    note = 2'-fluoro 2'-deoxy thymidine
modified_base       19
                    mod_base = OTHER
                    note = 2'-O-methyl cytidine
modified_base       20
                    mod_base = OTHER
                    note = 2'-O-methyl uridine 5'-thiophosphate
modified_base       21
                    mod_base = OTHER
                    note = 2'-O-methyl uridine 5'-thiophosphate
misc_feature        21
                    note = 3'-O attached to a GalNAc-comprising compound via a
                     linker
SEQUENCE: 49
gcttaacaag cctaaggtct t                                        21

SEQ ID NO: 50       moltype = RNA  length = 23
FEATURE             Location/Qualifiers
source              1..23
                    mol_type = other RNA
                    organism = synthetic construct
modified_base       1
                    mod_base = OTHER
                    note = 2'-O-methyl adenosine
modified_base       2
                    mod_base = OTHER
                    note = 2'-deoxy adenosine 5'-thiophosphate
modified_base       3
                    mod_base = OTHER
                    note = 2'-O-methyl guanosine 5'-thiophosphate
modified_base       4
                    mod_base = OTHER
                    note = 2'-fluoro adenosine
modified_base       5
                    mod_base = OTHER
                    note = 2'-O-methyl cytidine
modified_base       6
                    mod_base = OTHER
                    note = 2'-fluoro cytidine
modified_base       7
                    mod_base = OTHER
                    note = 2'-O-methyl uridine
modified_base       8
                    mod_base = OTHER
                    note = 2'-O-methyl uridine
modified_base       9
                    mod_base = OTHER
                    note = 2'-fluoro adenosine
modified_base       10
                    mod_base = OTHER
                    note = 2'-O-methyl guanosine
modified_base       11
                    mod_base = OTHER
                    note = 2'-O-methyl guanosine
modified_base       12
                    mod_base = OTHER
                    note = 2'-fluoro cytidine
modified_base       13
                    mod_base = OTHER
                    note = 2'-O-methyl uridine
modified_base       14
                    mod_base = OTHER
                    note = 2'-fluoro uridine
modified_base       15
                    mod_base = OTHER
                    note = 2'-O-methyl guanosine
modified_base       16
                    mod_base = OTHER
```

|   |   |
|---|---|
|   | note = 2'-fluoro uridine |
| modified_base | 17 |
|   | mod_base = OTHER |
|   | note = 2'-O-methyl uridine |
| modified_base | 18 |
|   | mod_base = OTHER |
|   | note = 2'-O-methyl adenosine |
| modified_base | 19 |
|   | mod_base = OTHER |
|   | note = 2'-fluoro adenosine |
| modified_base | 20 |
|   | mod_base = OTHER |
|   | note = 2'-O-methyl guanosine |
| modified_base | 21 |
|   | mod_base = OTHER |
|   | note = 2'-O-methyl cytidine |
| modified_base | 22 |
|   | mod_base = OTHER |
|   | note = 2'-O-methyl uridine 5'-thiophosphate |
| modified_base | 23 |
|   | mod_base = OTHER |
|   | note = 2'-O-methyl guanosine 5'-thiophosphate |
| SEQUENCE: 50 |   |
| aagaccttag gcttgttaag ctg | 23 |
|   |   |
| SEQ ID NO: 51 | moltype = RNA  length = 21 |
| FEATURE | Location/Qualifiers |
| source | 1..21 |
|   | mol_type = other RNA |
|   | organism = synthetic construct |
| modified_base | 1 |
|   | mod_base = OTHER |
|   | note = 2'-O-methyl guanosine |
| modified_base | 2 |
|   | mod_base = OTHER |
|   | note = 2'-fluoro adenosine 5'-thiophosphate |
| modified_base | 3 |
|   | mod_base = OTHER |
|   | note = 2'-O-methyl cytidine 5'-thiophosphate |
| modified_base | 4 |
|   | mod_base = OTHER |
|   | note = 2'-O-methyl cytidine |
| modified_base | 5 |
|   | mod_base = OTHER |
|   | note = 2'-fluoro cytidine |
| modified_base | 6 |
|   | mod_base = OTHER |
|   | note = 2'-O-methyl uridine |
| modified_base | 7 |
|   | mod_base = OTHER |
|   | note = 2'-fluoro adenosine |
| modified_base | 8 |
|   | mod_base = OTHER |
|   | note = 2'-O-methyl cytidine |
| modified_base | 9 |
|   | mod_base = OTHER |
|   | note = 2'-fluoro cytidine |
| modified_base | 10 |
|   | mod_base = OTHER |
|   | note = 2'-fluoro uridine |
| modified_base | 11 |
|   | mod_base = OTHER |
|   | note = 2'-O-methyl uridine |
| modified_base | 12 |
|   | mod_base = OTHER |
|   | note = 2'-O-methyl cytidine |
| modified_base | 13 |
|   | mod_base = OTHER |
|   | note = 2'-fluoro adenosine |
| modified_base | 14 |
|   | mod_base = OTHER |
|   | note = 2'-O-methyl uridine |
| modified_base | 15 |
|   | mod_base = OTHER |
|   | note = 2'-fluoro adenosine |
| modified_base | 16 |
|   | mod_base = OTHER |
|   | note = 2'-O-methyl cytidine |
| modified_base | 17 |

|                | mod_base = OTHER |
|                | note = 2'-O-methyl cytidine |
| modified_base | 18 |
|                | mod_base = OTHER |
|                | note = 2'-fluoro uridine |
| modified_base | 19 |
|                | mod_base = OTHER |
|                | note = 2'-O-methyl guanosine |
| modified_base | 20 |
|                | mod_base = OTHER |
|                | note = 2'-deoxy thymidine 5'-thiophosphate |
| modified_base | 21 |
|                | mod_base = OTHER |
|                | note = 2'-deoxy thymidine 5'-thiophosphate |
| misc_feature | 21 |
|                | note = 3'-O attached to a GalNAc-comprising compound via a linker |
| SEQUENCE: 51 | |
| gaccctacct tcatacctgt t | 21 |

| SEQ ID NO: 52 | moltype = RNA  length = 21 |
| FEATURE | Location/Qualifiers |
| source | 1..21 |
|        | mol_type = other RNA |
|        | organism = synthetic construct |
| modified_base | 1 |
|        | mod_base = OTHER |
|        | note = 2'-O-methyl cytidine |
| modified_base | 2 |
|        | mod_base = OTHER |
|        | note = 2'-deoxy adenosine 5'-thiophosphate |
| modified_base | 3 |
|        | mod_base = OTHER |
|        | note = 2'-O-methyl guanosine 5'-thiophosphate |
| modified_base | 4 |
|        | mod_base = OTHER |
|        | note = 2'-fluoro guanosine |
| modified_base | 5 |
|        | mod_base = OTHER |
|        | note = 2'-O-methyl uridine |
| modified_base | 6 |
|        | mod_base = OTHER |
|        | note = 2'-fluoro adenosine |
| modified_base | 7 |
|        | mod_base = OTHER |
|        | note = 2'-O-methyl uridine |
| modified_base | 8 |
|        | mod_base = OTHER |
|        | note = 2'-O-methyl guanosine |
| modified_base | 9 |
|        | mod_base = OTHER |
|        | note = 2'-fluoro adenosine |
| modified_base | 10 |
|        | mod_base = OTHER |
|        | note = 2'-O-methyl adenosine |
| modified_base | 11 |
|        | mod_base = OTHER |
|        | note = 2'-O-methyl guanosine |
| modified_base | 12 |
|        | mod_base = OTHER |
|        | note = 2'-fluoro guanosine |
| modified_base | 13 |
|        | mod_base = OTHER |
|        | note = 2'-O-methyl uridine |
| modified_base | 14 |
|        | mod_base = OTHER |
|        | note = 2'-fluoro adenosine |
| modified_base | 15 |
|        | mod_base = OTHER |
|        | note = 2'-O-methyl guanosine |
| modified_base | 16 |
|        | mod_base = OTHER |
|        | note = 2'-fluoro guanosine |
| modified_base | 17 |
|        | mod_base = OTHER |
|        | note = 2'-O-methyl guanosine |
| modified_base | 18 |
|        | mod_base = OTHER |
|        | note = 2'-O-methyl uridine |

```
modified_base       19
                    mod_base = OTHER
                    note = 2'-fluoro cytidine
modified_base       20
                    mod_base = OTHER
                    note = 2'-O-methyl uridine 5'-thiophosphate
modified_base       21
                    mod_base = OTHER
                    note = 2'-O-methyl uridine 5'-thiophosphate
SEQUENCE: 52
caggtatgaa ggtagggtct t                                           21

SEQ ID NO: 53       moltype = RNA  length = 23
FEATURE             Location/Qualifiers
source              1..23
                    mol_type = other RNA
                    organism = synthetic construct
modified_base       1
                    mod_base = OTHER
                    note = 2'-O-methyl adenosine
modified_base       2
                    mod_base = OTHER
                    note = 2'-fluoro cytidine 5'-thiophosphate
modified_base       3
                    mod_base = OTHER
                    note = 2'-O-methyl cytidine 5'-thiophosphate
modified_base       4
                    mod_base = OTHER
                    note = 2'-O-methyl cytidine
modified_base       5
                    mod_base = OTHER
                    note = 2'-fluoro adenosine
modified_base       6
                    mod_base = OTHER
                    note = 2'-O-methyl adenosine
modified_base       7
                    mod_base = OTHER
                    note = 2'-fluoro uridine
modified_base       8
                    mod_base = OTHER
                    note = 2'-O-methyl adenosine
modified_base       9
                    mod_base = OTHER
                    note = 2'-fluoro guanosine
modified_base       10
                    mod_base = OTHER
                    note = 2'-fluoro cytidine
modified_base       11
                    mod_base = OTHER
                    note = 2'-O-methyl uridine
modified_base       12
                    mod_base = OTHER
                    note = 2'-O-methyl uridine
modified_base       13
                    mod_base = OTHER
                    note = 2'-fluoro adenosine
modified_base       14
                    mod_base = OTHER
                    note = 2'-O-methyl adenosine
modified_base       15
                    mod_base = OTHER
                    note = 2'-fluoro cytidine
modified_base       16
                    mod_base = OTHER
                    note = 2'-O-methyl adenosine
modified_base       17
                    mod_base = OTHER
                    note = 2'-O-methyl adenosine
modified_base       18
                    mod_base = OTHER
                    note = 2'-fluoro guanosine
modified_base       19
                    mod_base = OTHER
                    note = 2'-O-methyl cytidine
modified_base       20
                    mod_base = OTHER
                    note = 2'-O-methyl cytidine
modified_base       21
                    mod_base = OTHER
```

```
                    note = 2'-fluoro uridine
modified_base       22
                    mod_base = OTHER
                    note = 2'-deoxy thymidine 5'-thiophosphate
modified_base       23
                    mod_base = OTHER
                    note = 2'-deoxy thymidine 5'-thiophosphate
misc_feature        23
                    note = 3'-O attached to a GalNAc-comprising compound via a
                     linker
SEQUENCE: 53
acccaatagc ttaacaagcc ttt                                                 23

SEQ ID NO: 54       moltype = RNA   length = 23
FEATURE             Location/Qualifiers
source              1..23
                    mol_type = other RNA
                    organism = synthetic construct
modified_base       1
                    mod_base = OTHER
                    note = 2'-O-methyl adenosine
modified_base       2
                    mod_base = OTHER
                    note = 2'-deoxy guanosine 5'-thiophosphate
modified_base       3
                    mod_base = OTHER
                    note = 2'-O-methyl guanosine 5'-thiophosphate
modified_base       4
                    mod_base = OTHER
                    note = 2'-fluoro cytidine
modified_base       5
                    mod_base = OTHER
                    note = 2'-O-methyl uridine
modified_base       6
                    mod_base = OTHER
                    note = 2'-fluoro uridine
modified_base       7
                    mod_base = OTHER
                    note = 2'-O-methyl guanosine
modified_base       8
                    mod_base = OTHER
                    note = 2'-O-methyl uridine
modified_base       9
                    mod_base = OTHER
                    note = 2'-fluoro uridine
modified_base       10
                    mod_base = OTHER
                    note = 2'-O-methyl adenosine
modified_base       11
                    mod_base = OTHER
                    note = 2'-O-methyl adenosine
modified_base       12
                    mod_base = OTHER
                    note = 2'-fluoro guanosine
modified_base       13
                    mod_base = OTHER
                    note = 2'-O-methyl cytidine
modified_base       14
                    mod_base = OTHER
                    note = 2'-fluoro uridine
modified_base       15
                    mod_base = OTHER
                    note = 2'-O-methyl adenosine
modified_base       16
                    mod_base = OTHER
                    note = 2'-fluoro uridine
modified_base       17
                    mod_base = OTHER
                    note = 2'-O-methyl uridine
modified_base       18
                    mod_base = OTHER
                    note = 2'-O-methyl guanosine
modified_base       19
                    mod_base = OTHER
                    note = 2'-fluoro guanosine
modified_base       20
                    mod_base = OTHER
                    note = 2'-O-methyl guanosine
modified_base       21
```

|  |  |
|---|---|
|  | mod_base = OTHER |
|  | note = 2'-O-methyl uridine |
| modified_base | 22 |
|  | mod_base = OTHER |
|  | note = 2'-deoxy thymidine 5'-thiophosphate |
| modified_base | 23 |
|  | mod_base = OTHER |
|  | note = 2'-deoxy thymidine 5'-thiophosphate |

SEQUENCE: 54
aggcttgtta agctattggg ttt                                    23

| SEQ ID NO: 55 | moltype = RNA  length = 21 |
|---|---|
| FEATURE | Location/Qualifiers |
| source | 1..21 |
|  | mol_type = other RNA |
|  | organism = synthetic construct |
| modified_base | 1 |
|  | mod_base = OTHER |
|  | note = 2'-O-methyl uridine |
| modified_base | 2 |
|  | mod_base = OTHER |
|  | note = 2'-fluoro guanosine 5'-thiophosphate |
| modified_base | 3 |
|  | mod_base = OTHER |
|  | note = 2'-O-methyl cytidine 5'-thiophosphate |
| modified_base | 4 |
|  | mod_base = OTHER |
|  | note = 2'-O-methyl adenosine |
| modified_base | 5 |
|  | mod_base = OTHER |
|  | note = 2'-fluoro adenosine |
| modified_base | 6 |
|  | mod_base = OTHER |
|  | note = 2'-O-methyl guanosine |
| modified_base | 7 |
|  | mod_base = OTHER |
|  | note = 2'-fluoro adenosine |
| modified_base | 8 |
|  | mod_base = OTHER |
|  | note = 2'-O-methyl cytidine |
| modified_base | 9 |
|  | mod_base = OTHER |
|  | note = 2'-fluoro uridine |
| modified_base | 10 |
|  | mod_base = OTHER |
|  | note = 2'-fluoro uridine |
| modified_base | 11 |
|  | mod_base = OTHER |
|  | note = 2'-O-methyl guanosine |
| modified_base | 12 |
|  | mod_base = OTHER |
|  | note = 2'-O-methyl adenosine |
| modified_base | 13 |
|  | mod_base = OTHER |
|  | note = 2'-fluoro cytidine |
| modified_base | 14 |
|  | mod_base = OTHER |
|  | note = 2'-O-methyl adenosine |
| modified_base | 15 |
|  | mod_base = OTHER |
|  | note = 2'-fluoro cytidine |
| modified_base | 16 |
|  | mod_base = OTHER |
|  | note = 2'-O-methyl cytidine |
| modified_base | 17 |
|  | mod_base = OTHER |
|  | note = 2'-O-methyl guanosine |
| modified_base | 18 |
|  | mod_base = OTHER |
|  | note = 2'-fluoro adenosine |
| modified_base | 19 |
|  | mod_base = OTHER |
|  | note = 2'-O-methyl adenosine |
| modified_base | 20 |
|  | mod_base = OTHER |
|  | note = 2'-deoxy thymidine 5'-thiophosphate |
| modified_base | 21 |
|  | mod_base = OTHER |
|  | note = 2'-deoxy thymidine 5'-thiophosphate |

```
                         misc_feature    21
                                         note = 3'-O attached to a GalNAc-comprising compound via a
                                             linker
SEQUENCE: 55
tgcaagactt gacaccgaat t                                                              21

SEQ ID NO: 56            moltype = RNA   length = 21
FEATURE                  Location/Qualifiers
source                   1..21
                         mol_type = other RNA
                         organism = synthetic construct
modified_base            20
                         mod_base = OTHER
                         note = 2'-deoxy thymidine
modified_base            21
                         mod_base = OTHER
                         note = 2'-deoxy thymidine
SEQUENCE: 56
ccaacagctt accaagcctt t                                                              21

SEQ ID NO: 57            moltype = RNA   length = 21
FEATURE                  Location/Qualifiers
source                   1..21
                         mol_type = other RNA
                         organism = synthetic construct
SEQUENCE: 57
aggcttggta agctgttggg t                                                              21

SEQ ID NO: 58            moltype = RNA   length = 21
FEATURE                  Location/Qualifiers
source                   1..21
                         mol_type = other RNA
                         organism = synthetic construct
modified_base            20
                         mod_base = OTHER
                         note = 2'-deoxy thymidine
modified_base            21
                         mod_base = OTHER
                         note = 2'-deoxy thymidine
SEQUENCE: 58
ttaacaagcc taaggtcttt t                                                              21

SEQ ID NO: 59            moltype = RNA   length = 21
FEATURE                  Location/Qualifiers
source                   1..21
                         mol_type = other RNA
                         organism = synthetic construct
SEQUENCE: 59
aagaccttag gcttgttaag c                                                              21

SEQ ID NO: 60            moltype = RNA   length = 21
FEATURE                  Location/Qualifiers
source                   1..21
                         mol_type = other RNA
                         organism = synthetic construct
modified_base            7
                         mod_base = OTHER
                         note = 2'-deoxy thymidine
SEQUENCE: 60
aagaccttag gcttgttaag c                                                              21

SEQ ID NO: 61            moltype = RNA   length = 21
FEATURE                  Location/Qualifiers
source                   1..21
                         mol_type = other RNA
                         organism = synthetic construct
modified_base            20
                         mod_base = OTHER
                         note = 2'-deoxy thymidine
modified_base            21
                         mod_base = OTHER
                         note = 2'-deoxy thymidine
SEQUENCE: 61
tgcaagactt gacaccgaat t                                                              21

SEQ ID NO: 62            moltype = RNA   length = 21
FEATURE                  Location/Qualifiers
source                   1..21
                         mol_type = other RNA
```

```
                        organism = synthetic construct
modified_base           2
                        mod_base = OTHER
                        note = 2'-deoxy thymidine
SEQUENCE: 62
ttcggtgtca agtcttgcag c                                              21

SEQ ID NO: 63           moltype = RNA  length = 21
FEATURE                 Location/Qualifiers
source                  1..21
                        mol_type = other RNA
                        organism = synthetic construct
SEQUENCE: 63
gctgcaagac ttgacaccga a                                              21

SEQ ID NO: 64           moltype = RNA  length = 23
FEATURE                 Location/Qualifiers
source                  1..23
                        mol_type = other RNA
                        organism = synthetic construct
SEQUENCE: 64
ttcggtgtca agtcttgcag cga                                            23

SEQ ID NO: 65           moltype = RNA  length = 21
FEATURE                 Location/Qualifiers
source                  1..21
                        mol_type = other RNA
                        organism = synthetic construct
modified_base           20
                        mod_base = OTHER
                        note = 2'-deoxy thymidine
modified_base           21
                        mod_base = OTHER
                        note = 2'-deoxy thymidine
SEQUENCE: 65
gaccctacct tcatacctgt t                                              21

SEQ ID NO: 66           moltype = RNA  length = 21
FEATURE                 Location/Qualifiers
source                  1..21
                        mol_type = other RNA
                        organism = synthetic construct
modified_base           7
                        mod_base = OTHER
                        note = 2'-deoxy thymidine
SEQUENCE: 66
caggtatgaa ggtagggtct t                                              21

SEQ ID NO: 67           moltype = RNA  length = 21
FEATURE                 Location/Qualifiers
source                  1..21
                        mol_type = other RNA
                        organism = synthetic construct
SEQUENCE: 67
aagaccctac cttcatacct g                                              21

SEQ ID NO: 68           moltype = RNA  length = 23
FEATURE                 Location/Qualifiers
source                  1..23
                        mol_type = other RNA
                        organism = synthetic construct
SEQUENCE: 68
caggtatgaa ggtagggtct ttg                                            23

SEQ ID NO: 69           moltype = RNA  length = 21
FEATURE                 Location/Qualifiers
source                  1..21
                        mol_type = other RNA
                        organism = synthetic construct
SEQUENCE: 69
gcttaacaag cctaaggtct t                                              21

SEQ ID NO: 70           moltype = RNA  length = 23
FEATURE                 Location/Qualifiers
source                  1..23
                        mol_type = other RNA
                        organism = synthetic construct
SEQUENCE: 70
aagaccttag gcttgttaag ctg                                            23
```

```
SEQ ID NO: 71            moltype = RNA   length = 21
FEATURE                  Location/Qualifiers
source                   1..21
                         mol_type = other RNA
                         organism = synthetic construct
modified_base            20
                         mod_base = OTHER
                         note = 2'-deoxy thymidine
modified_base            21
                         mod_base = OTHER
                         note = 2'-deoxy thymidine
SEQUENCE: 71
ccaatagctt aacaagcctt t                                             21

SEQ ID NO: 72            moltype = RNA   length = 21
FEATURE                  Location/Qualifiers
source                   1..21
                         mol_type = other RNA
                         organism = synthetic construct
SEQUENCE: 72
aggcttgtta agctattggg t                                             21

SEQ ID NO: 73            moltype = RNA   length = 21
FEATURE                  Location/Qualifiers
source                   1..21
                         mol_type = other RNA
                         organism = synthetic construct
modified_base            20
                         mod_base = OTHER
                         note = 2'-deoxy thymidine
modified_base            21
                         mod_base = OTHER
                         note = 2'-deoxy thymidine
SEQUENCE: 73
tgcaaaactt gacaccgaat t                                             21

SEQ ID NO: 74            moltype = RNA   length = 21
FEATURE                  Location/Qualifiers
source                   1..21
                         mol_type = other RNA
                         organism = synthetic construct
modified_base            2
                         mod_base = OTHER
                         note = 2'-deoxy thymidine
SEQUENCE: 74
ttcggtgtca agttttgcag c                                             21

SEQ ID NO: 75            moltype = RNA   length = 21
FEATURE                  Location/Qualifiers
source                   1..21
                         mol_type = other RNA
                         organism = synthetic construct
modified_base            20
                         mod_base = OTHER
                         note = 2'-deoxy thymidine
modified_base            21
                         mod_base = OTHER
                         note = 2'-deoxy thymidine
SEQUENCE: 75
ccaacagctt aacaagcctt t                                             21

SEQ ID NO: 76            moltype = RNA   length = 21
FEATURE                  Location/Qualifiers
source                   1..21
                         mol_type = other RNA
                         organism = synthetic construct
SEQUENCE: 76
aggcttgtta agctgttggg t                                             21

SEQ ID NO: 77            moltype = RNA   length = 21
FEATURE                  Location/Qualifiers
source                   1..21
                         mol_type = other RNA
                         organism = synthetic construct
SEQUENCE: 77
aggcttgtta agctattggt t                                             21

SEQ ID NO: 78            moltype = RNA   length = 21
```

```
FEATURE                 Location/Qualifiers
source                  1..21
                        mol_type = other RNA
                        organism = synthetic construct
modified_base           21
                        mod_base = OTHER
                        note = 2'-deoxy thymidine
SEQUENCE: 78
acccaatagc ttaacaagcc t                                              21

SEQ ID NO: 79           moltype = RNA   length = 23
FEATURE                 Location/Qualifiers
source                  1..23
                        mol_type = other RNA
                        organism = synthetic construct
modified_base           21
                        mod_base = OTHER
                        note = 2'-deoxy thymidine
SEQUENCE: 79
aggcttgtta agctattggg tag                                            23

SEQ ID NO: 80           moltype = RNA   length = 21
FEATURE                 Location/Qualifiers
source                  1..21
                        mol_type = other RNA
                        organism = synthetic construct
modified_base           20
                        mod_base = OTHER
                        note = 2'-deoxy thymidine
modified_base           21
                        mod_base = OTHER
                        note = 2'-deoxy thymidine
SEQUENCE: 80
agctcaacaa gcctgaggtt t                                              21

SEQ ID NO: 81           moltype = RNA   length = 21
FEATURE                 Location/Qualifiers
source                  1..21
                        mol_type = other RNA
                        organism = synthetic construct
SEQUENCE: 81
acctcaggct tgttgagctg t                                              21

SEQ ID NO: 82           moltype = RNA   length = 21
FEATURE                 Location/Qualifiers
source                  1..21
                        mol_type = other RNA
                        organism = synthetic construct
SEQUENCE: 82
gtcatccaca atgagagtac a                                              21

SEQ ID NO: 83           moltype = RNA   length = 23
FEATURE                 Location/Qualifiers
source                  1..23
                        mol_type = other RNA
                        organism = synthetic construct
SEQUENCE: 83
tgtactctca ttgtggatga cga                                            23

SEQ ID NO: 84           moltype = RNA   length = 20
FEATURE                 Location/Qualifiers
source                  1..20
                        mol_type = other RNA
                        organism = synthetic construct
modified_base           2
                        mod_base = OTHER
                        note = 2'-deoxy thymidine
modified_base           5
                        mod_base = OTHER
                        note = 2'-deoxy thymidine
modified_base           12
                        mod_base = OTHER
                        note = 2'-deoxy thymidine
modified_base           16
                        mod_base = OTHER
                        note = 2'-deoxy thymidine
modified_base           18
                        mod_base = OTHER
                        note = 2'-deoxy thymidine
```

```
SEQUENCE: 84
ctgatccagc ctcactatgc                                              20

SEQ ID NO: 85          moltype = RNA  length = 21
FEATURE                Location/Qualifiers
source                 1..21
                       mol_type = other RNA
                       organism = synthetic construct
modified_base          4
                       mod_base = OTHER
                       note = 2'-deoxy thymidine
modified_base          7
                       mod_base = OTHER
                       note = 2'-deoxy thymidine
modified_base          12
                       mod_base = OTHER
                       note = 2'-deoxy thymidine
modified_base          15
                       mod_base = OTHER
                       note = 2'-deoxy thymidine
modified_base          16
                       mod_base = OTHER
                       note = 2'-deoxy thymidine
SEQUENCE: 85
aggtcataag atccttgcag c                                            21

SEQ ID NO: 86          moltype = RNA  length = 26
FEATURE                Location/Qualifiers
source                 1..26
                       mol_type = other RNA
                       organism = synthetic construct
modified_base          5
                       mod_base = OTHER
                       note = 2'-deoxy thymidine
modified_base          7
                       mod_base = OTHER
                       note = 2'-deoxy thymidine
modified_base          11
                       mod_base = OTHER
                       note = 2'-deoxy thymidine
modified_base          12
                       mod_base = OTHER
                       note = 2'-deoxy thymidine
modified_base          13
                       mod_base = OTHER
                       note = 2'-deoxy thymidine
modified_base          24
                       mod_base = OTHER
                       note = 2'-deoxy thymidine
SEQUENCE: 86
agggtctcac tttccagcaa aactcc                                       26

SEQ ID NO: 87          moltype = RNA  length = 21
FEATURE                Location/Qualifiers
source                 1..21
                       mol_type = other RNA
                       organism = synthetic construct
modified_base          20
                       mod_base = OTHER
                       note = 2'-deoxy thymidine
modified_base          21
                       mod_base = OTHER
                       note = 2'-deoxy thymidine
SEQUENCE: 87
tagtcgctgc aaaacttgat t                                            21

SEQ ID NO: 88          moltype = RNA  length = 21
FEATURE                Location/Qualifiers
source                 1..21
                       mol_type = other RNA
                       organism = synthetic construct
modified_base          7
                       mod_base = OTHER
                       note = 2'-deoxy thymidine
SEQUENCE: 88
tcaagttttg cagcgactag c                                            21

SEQ ID NO: 89          moltype = RNA  length = 21
FEATURE                Location/Qualifiers
```

```
                   source            1..21
                                     mol_type = other RNA
                                     organism = synthetic construct
                   modified_base     20
                                     mod_base = OTHER
                                     note = 2'-deoxy thymidine
                   modified_base     21
                                     mod_base = OTHER
                                     note = 2'-deoxy thymidine
SEQUENCE: 89
tagtcgctgc gaaacttgat t                                                      21

SEQ ID NO: 90           moltype = RNA  length = 21
FEATURE                 Location/Qualifiers
source                  1..21
                        mol_type = other RNA
                        organism = synthetic construct
SEQUENCE: 90
tcaagtttcg cagcgactag c                                                      21

SEQ ID NO: 91           moltype = RNA  length = 21
FEATURE                 Location/Qualifiers
source                  1..21
                        mol_type = other RNA
                        organism = synthetic construct
SEQUENCE: 91
gctagtcgct gcgaaacttg a                                                      21

SEQ ID NO: 92           moltype = RNA  length = 23
FEATURE                 Location/Qualifiers
source                  1..23
                        mol_type = other RNA
                        organism = synthetic construct
SEQUENCE: 92
tcaagtttcg cagcgactag cac                                                    23

SEQ ID NO: 93           moltype = RNA  length = 21
FEATURE                 Location/Qualifiers
source                  1..21
                        mol_type = other RNA
                        organism = synthetic construct
SEQUENCE: 93
acccaatagc ttaacaagcc t                                                      21

SEQ ID NO: 94           moltype = RNA  length = 23
FEATURE                 Location/Qualifiers
source                  1..23
                        mol_type = other RNA
                        organism = synthetic construct
SEQUENCE: 94
aggcttgtta agctattggg tag                                                    23

SEQ ID NO: 95           moltype = RNA  length = 21
FEATURE                 Location/Qualifiers
source                  1..21
                        mol_type = other RNA
                        organism = synthetic construct
SEQUENCE: 95
gcttaacaag cctaaggtct t                                                      21

SEQ ID NO: 96           moltype = RNA  length = 23
FEATURE                 Location/Qualifiers
source                  1..23
                        mol_type = other RNA
                        organism = synthetic construct
SEQUENCE: 96
aagaccttag gcttgttaag ctg                                                    23

SEQ ID NO: 97           moltype = RNA  length = 21
FEATURE                 Location/Qualifiers
source                  1..21
                        mol_type = other RNA
                        organism = synthetic construct
SEQUENCE: 97
caggtatgaa ggtagggtct t                                                      21

SEQ ID NO: 98           moltype = RNA  length = 23
FEATURE                 Location/Qualifiers
source                  1..23
```

```
                        mol_type = other RNA
                        organism = synthetic construct
modified_base           22
                        mod_base = OTHER
                        note = 2'-deoxy thymidine
modified_base           23
                        mod_base = OTHER
                        note = 2'-deoxy thymidine
SEQUENCE: 98
acccaatagc ttaacaagcc ttt                                              23

SEQ ID NO: 99           moltype = RNA  length = 23
FEATURE                 Location/Qualifiers
source                  1..23
                        mol_type = other RNA
                        organism = synthetic construct
modified_base           22
                        mod_base = OTHER
                        note = 2'-deoxy thymidine
modified_base           23
                        mod_base = OTHER
                        note = 2'-deoxy thymidine
SEQUENCE: 99
aggcttgtta agctattggg ttt                                              23
```